(12) United States Patent
Kearney

(10) Patent No.: US 9,346,807 B2
(45) Date of Patent: May 24, 2016

(54) INHIBITORS OF PI3K-DELTA AND METHODS OF THEIR USE AND MANUFACTURE

(75) Inventor: Patrick Kearney, San Francisco, CA (US)

(73) Assignee: Exelixis, Inc., South San Francisco, CA (US)

( * ) Notice: Subject to any disclaimer, the term of this patent is extended or adjusted under 35 U.S.C. 154(b) by 12 days.

(21) Appl. No.: 13/822,840

(22) PCT Filed: Sep. 14, 2011

(86) PCT No.: PCT/US2011/051563
§ 371 (c)(1),
(2), (4) Date: Oct. 22, 2013

(87) PCT Pub. No.: WO2012/037226
PCT Pub. Date: Mar. 22, 2012

(65) Prior Publication Data
US 2014/0058103 A1    Feb. 27, 2014

Related U.S. Application Data

(60) Provisional application No. 61/382,884, filed on Sep. 14, 2010.

(51) Int. Cl.
*C07D 473/34* (2006.01)
*C07D 471/10* (2006.01)
*C07D 473/04* (2006.01)

(52) U.S. Cl.
CPC ............ *C07D 473/34* (2013.01); *C07D 471/10* (2013.01); *C07D 473/04* (2013.01)

(58) Field of Classification Search
CPC .................................................. C07D 473/34
See application file for complete search history.

(56) References Cited

U.S. PATENT DOCUMENTS 6,423,716 B1 * 7/2002 Matsuno et al. ...... C07D 239/94
514/242

FOREIGN PATENT DOCUMENTS

| JP | 2010522209 | 9/2008 |
|----|------------|--------|
| WO | 2008116129 | 9/2008 |
| WO | 2009045174 | 4/2009 |
| WO | 2009053716 | 4/2009 |
| WO | 2009146406 | 12/2009 |
| WO | 2009157880 | 12/2009 |
| WO | 2010005558 | 1/2010 |

OTHER PUBLICATIONS

Courtney, Kevin. JCO Feb 20, 2010 vol. 28 No. 6 1075-1083.*
MedicineNet.com <http://www.medterms.com> 2004.*
Ghigo, Alessandra. BioEssays Feb. 16, 2010, 32: 185-196.*
Database Chemcats Chemical Abstracts Service, Columbus, Ohio, US, Apr. 11, 2011, XP002663872, retrieved from STN accession No. 0022757892, Database accession No. STOCK6S-93767 abstract & "Ryan Scientific High Throughput Screening Compound Library." Apr. 11, 2011, Ryan Scientific Inc., Mt. Pleasant, SC 29465.
International Search Report for PCT/US2011/051563, mailed Dec. 5, 2011.

* cited by examiner

*Primary Examiner* — Golam M M Shameem
*Assistant Examiner* — Laura Daniel
(74) *Attorney, Agent, or Firm* — Honigman Miller Schwartz and Cohn, LLP; Heidi M. Berven; Jonathan P. O'Brien

(57) ABSTRACT

The invention is directed to Compounds of Formula I: and pharmaceutically acceptable salts or solvates thereof, as well as methods of making and using the compounds.

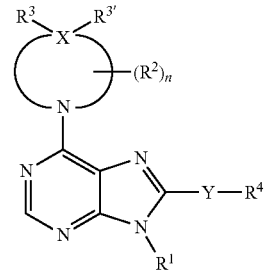

25 Claims, No Drawings

INHIBITORS OF PI3K-DELTA AND METHODS OF THEIR USE AND MANUFACTURE

CROSS-REFERENCE TO RELATED APPLICATIONS

This application is a U.S. National Phase filing of PCT/US2011/051563, filed Sep. 14, 2011, which claims priority to U.S. Provisional Application No. 61/382,884, filed Sep. 14, 2010, the entire contents of which are incorporated herein by reference.

FIELD OF THE INVENTION

This invention relates to the field of protein kinases and inhibitors thereof. In particular, the invention relates to inhibitors of PI3K delta, and methods of their use.

BACKGROUND OF THE INVENTION

Phosphoinositide 3-kinases (PI3Ks) are heterodimeric enzymes that utilize both lipid and protein kinase activity to regulate numerous lipid signaling pathways that are responsible for coordinating a broad range of cellular activities including cell survival, proliferation, and differentiation as well as inflammatory responses. The critical role of PI3Ks in these myriad important cellular processes make them a very attractive target for pharmaceutical intervention. The class of PI3Ks relevant to this disclosure catalyze the phosphorylation of phosphatilyl-inositol (4,5)-bisphosphate (PtIns(4,5)$P_2$ or $PIP_2$) on the 3-hydroxyl group of the inositol ring to produce the signaling molecule phosphatilyl-inositol (3,4,5)-triphosphate (PtIns(3,4,5)$P_3$ or $PIP_3$).

After extensive studies on the physiological role of the PI3K delta isoform in disease, PI3K delta has been implicated in a large number of immunological, inflammatory and cell regulation dysfunctions. Initial studies have focused on its role in immune and inflammatory pathologies. PI3K delta plays a significant role in the development, differentiation, proliferation and effector function of B-cells and T-cells. PI3K delta knock-in mice (D910A/D910A) have shown impaired or diminished proliferative T-cell responses and chemokine production when stimulated with T-cell receptor specific antigens. Moreover, these PI3K delta expressing animals demonstrate poor T-cell independent antibody responses concomitant with poor development of germinal centers in the spleen, lymph nodes and Peyer's patches and lymphoid hyperplasia after immunization. Inhibition of PI3K delta function also leads to dysfunctional homing by T-cells to sites of inflammation. PI3K delta activity has also been implicated in Treg cell control. PI3K delta$^{(D910A/D910A)}$ mice have Treg cells that fail to: 1.) suppress the proliferation of $CD4^+$ $CD25^-$ T-cells in vitro as well as Treg cells from wild-type animals; 2.) produce detectable levels of the anti-inflammatory cytokine IL-10; and 3.) protect against experimental colitis.

The effects of PI3K delta on B-cells are no less significant. Mice lacking p110 delta catalytic activity have reduced numbers of B1 and marginal zone (MZ) B cells, reduced levels of serum immunoglulins, and respond poorly to immunization with a thymus-independent antigen and are defective in their primary and secondary responses to thymus dependent antigens. Inhibition of PI3K delta via use of PI3K delta selective inhibitors have shown inhibition of B-cell receptor-induced B cell proliferation, and increased class-switch recombination. and defects in B-cell chemotaxis.

Experimental observations that PI3K delta may play a significant role in mediating the pro-inflammatory role of non-lymphoid hematopoetic cells have come from studies involving hematopoietic immune cells such as neutrophils, macrophages, dendritic cells, mast cells and eosinophils. For example, PI3K delta is required for neutrophil spreading and polarization, regulation of neutrophil migration, mast cell degranulation and among many others. A review of the important roles of PI3K delta in innate and adaptive immune responses, has generated intense investigation of the role of PI3K delta in immune diseases such as allergy, asthma, autoimmune diseases, and inflammation.

While a significant portion of the published scientific literature has focused on immune diseases, such as inflammation, autoimmune disease and the like, an attractive and productive area for investigation includes the role of PI3K delta in cancer. Experimental models have already provided for putative roles of PI3K alpha and PI3K beta in malignant cellular processes, including: (i) overexpression is capable of inducing transformation in experimental models; (ii) involvement in cell proliferation and tumor angiogenesis; (iii) involvement in Ras-induces transformation and oncogenesis (iv) activating mutations in the helical and kinase domains in breast and colon tumors; and (v) transformation induced by PTEN inactivation in vitro and in vivo As with PI3K alpha and PI3K beta, PI3K delta also induces oncogenic transformation in culture. When PI3K delta is introduced into chicken embryo fibroblasts (CEFs) with an avian retroviral vector, distinct foci form within ten days. When D910A kinase inactive PI3K delta is introduced into CEFs, no focus formation is observed indicating that transformation requires an active catalytic domain. As was observed for an oncogenic variant of PI3K alpha (H1047R), CEFs infected with PI3K delta showed constitutive activation of Akt at a level similar to PI3K alpha, even in serum starved conditions. For at least the reasons provided above, there is a need for selective PI3K delta inhibitors that can be used to prevent, treat or ameliorate PI3K delta mediated diseases, particularly in the fields of cancer, inflammation and autoimmune diseases.

SUMMARY OF THE INVENTION

The following only summarizes certain aspects of the invention and is not intended to be limiting in nature. These aspects and other aspects and embodiments are described more fully below. All references cited in this specification are hereby incorporated by reference in their entirety. In the event of a discrepancy between the express disclosure of this specification and the references incorporated by reference, the express disclosure of this specification shall control.

We recognized the important role of PI3K, particularly PI3K delta, in biological processes and disease states and, therefore, realized that inhibitors of these protein kinases would be desirable. Accordingly, the invention provides compounds that inhibit, regulate, and/or modulate PI3K delta that are useful in the treatment of various cancers, autoimmune diseases, inflammatory diseases in mammals. This invention also provides methods of making the compounds, methods of using such compounds in the treatment diseases, particularly hyperproliferative diseases, in mammals, especially humans, and to pharmaceutical compositions containing such compounds.

A first aspect of the invention provides a compound of Formula I:

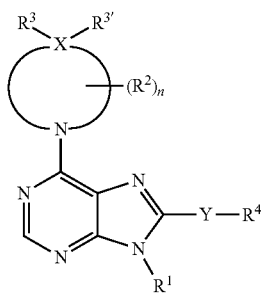
I or a stereoisomer or mixture of stereoisomers thereof, optionally as a pharmaceutically acceptable salt thereof, wherein:

$R^1$ is alkyl, haloalkyl, or optionally substituted cycloalkyl;

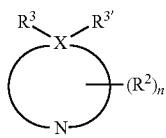

is a 4, 5, 6, or 7-membered ring, wherein:

$R^2$ at each occurrence is independently halo, hydroxy, alkyl, alkoxy, hydroxyalkyl, haloalkoxy, or —C(O)O-alkyl, or two $R^2$ groups may be joined together with the carbons to which they are attached to form a bridged or fused bicyclic ring;

n is 0, 1, 2, or 3;

X is C or N; wherein:

when X is N:
  $R^3$ is absent;
  $R^{3'}$ is aryl or heteroaryl optionally substituted with one or two groups independently selected from heteroarylalkyloxy; alkyl substituted with arylsulfonyalmino; alkyl substituted with cycloalkylcarbonylamino; or
  $R^{3'}$ is —SO$_2$—$R^a$, wherein $R^a$ is optionally substituted alkyl, optionally substituted phenyl, optionally substituted phenylalkyl, or optionally substituted heteroaryl;

when X is C:
  $R^3$ is cyano, aminoalkyl, alkoxycarbonyl, or hydroxy and $R^{3'}$ is a optionally substituted phenyl; or
  $R^3$ is hydrogen and $R^{3'}$ is phenyl, alkyl substituted with 1-phenyl-4,5,6,7-tetrahydro-1H-pyrazolo[3,4-c]pyridinyl, optionally substituted indolyl, optionally substituted 1H-benzo[d][1,2,3]triazolyl, optionally substituted oxoindolinyl, optionally substituted benzoimidazolyl, optionally substituted pyridinyl (oxadiazolyl substituted with furanyl), 2-oxo-3,4-dihydroquinazolinyl, —C(O)NR$^b$R$^c$, wherein R$^b$ is hydrogen or alkyl; and R$^c$ is optionally substituted heteroarylalkyl; or
  $R^3$ is hydrogen and $R^{3'}$ is a group of formula (a), (b), (c), (d), (e), or (f):

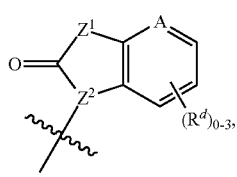
(a)

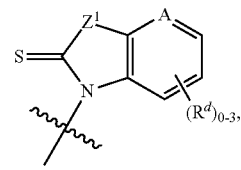
(b)

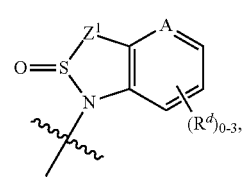
(c)

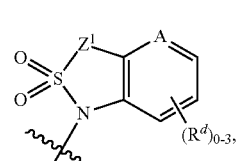
(d)

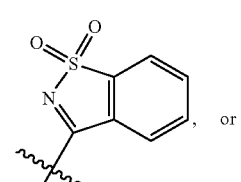
(e)

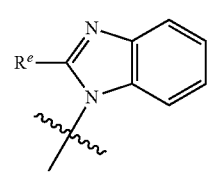
(f)

wherein:

$Z^1$ is O, NH, or N optionally substituted with aminoalkyl, alkylaminoalkyl, or dialkylaminoalkyl;

$Z^2$ is CH or N;

A is N, C—H, or C—$R^d$;

each $R^d$, when present, is independently halo, alkyl, optionally substituted alkoxy, or optionally substituted heterocycloalkyl and $R^e$ is amino or haloalkyl; or $R^3$ and $R^{3'}$ are taken together with the carbon to which they are attached to form an optionally substituted 5 or 6 membered ring (g), (h), (i), (j); (k), or (l)

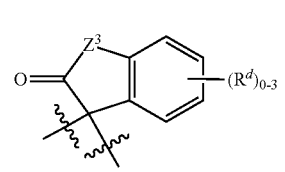
(g)

-continued (h)
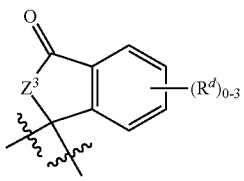

(i)
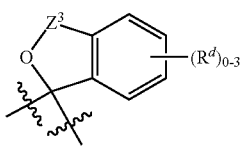

(j)
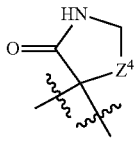

(k)
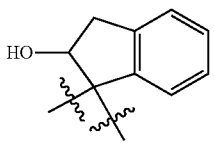

(l)
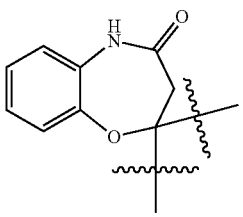

wherein $Z^3$ is $CH_2$ or NH; $Z^4$ is $NR^f$ or $CR^f$, and $R^f$ is optionally substituted phenyl;

Y is absent or is halo, alkyl, —(C=O)—, —$NR^x$—(C=O)—, or (C=O)$NR^x$—, —O—(C=O)—, (C=O)O—, —$NR^x$—(C=O)O—, or —O(C=O)$NR^x$—, wherein $R^x$ is hydrogen or optionally substituted alkyl;

$R^4$ is hydrogen, halo, optionally substituted alkyl, optionally substituted alkenyl, optionally substituted aryl, optionally substituted cycloalkyl, optionally substituted heterocycloalkyl, optionally substituted heteroaryl; and when Y is —N($R^x$)—(C=O)—, or —(C=O)—N($R^x$)—, $R^x$ and $R^4$ can be joined together along with the atoms to which they are attached to form a 4, 5, or 6 membered ring, optionally containing 1 or 2 additional heteroatoms selected from N, S, and O.

In a second aspect, the invention provides a pharmaceutical composition which comprises 1) a compound of Formula I or a single stereoisomer or mixture of isomers thereof, optionally as a pharmaceutically acceptable salt thereof and 2) a pharmaceutically acceptable carrier, excipient, or diluent.

In a third aspect, the invention provides a method of inhibiting the in vivo activity of PI3K delta, the method comprising administering to a patient an effective PI3K delta-inhibiting amount of a Compound of Formula I or a single stereoisomer or mixture of stereoisomers thereof, optionally as a pharmaceutically acceptable salt or solvate thereof or pharmaceutical composition thereof.

In a fourth aspect, the invention provides a method for treating a disease, disorder, or syndrome which method comprises administering to a patient a therapeutically effective amount of a compound of Formula I or a single stereoisomer or mixture of isomers thereof, optionally as a pharmaceutically acceptable salt or solvate thereof, or a pharmaceutical composition comprising a therapeutically effective amount of a compound of Formula I or a single stereoisomer or mixture of isomers thereof, optionally as a pharmaceutically acceptable salt or solvate thereof, and a pharmaceutically acceptable carrier, excipient, or diluent.

In a fifth aspect, the invention provides a process for making a compound of Formula I, comprising:

(a) treating a compound of formula 1 with a base and $R^1X^1$, to form a compound of formula 2, wherein X is halo, or OTf and X1 is halo, O-Ms, OTs;

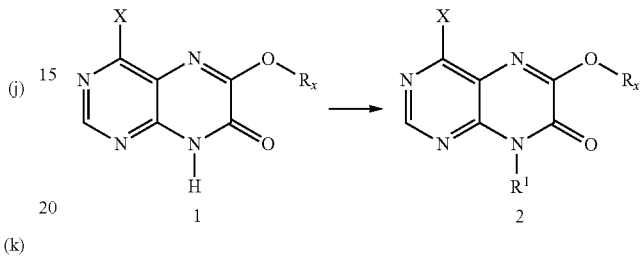

(b) heating a compound of formula 2 with compound 3 in the presence of base to form a compound of formula 3;

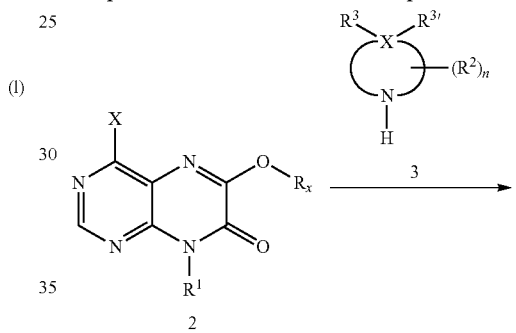

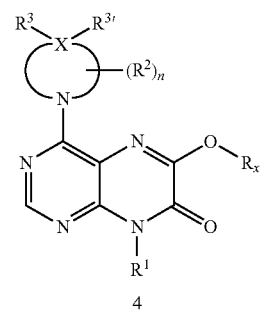

(c) heating a compound of formula 4 in a polar aprotic solvent in the presence of base to provide the carboxylic acid of formula 5;

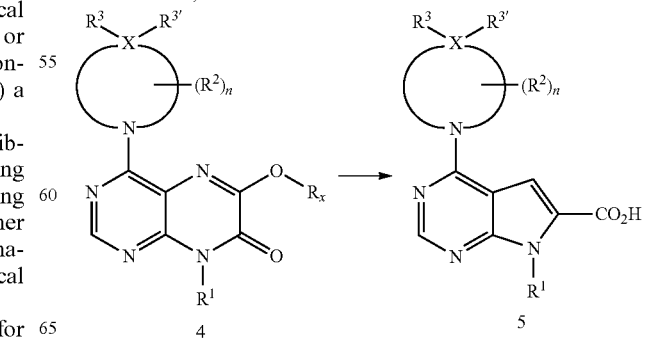

(d) amidating or esterifying the carboyxylic acid of formula 5 with $R^aR^bNH$ or $R^cOH$ to form a compound of formula I wherein $YR_4$ is $C(=O)-NR^aR^b$ or $C(=O)-OR^c$, wherein $R^a$ and $R^b$ are each independently H, $C_1$-$C_6$-alkyl, cycloalkyl, or alkylene-cycloalkyl or one of $R^a$ and $R^b$ is H, $C_1$-$C_6$-alkyl, cycloalkyl, alkylene-cycloalkyl and the other is $C_1$-$C_6$-alkyl or $NH^2$; and $R^c$ is $C_1$-$C_6$-alkyl.

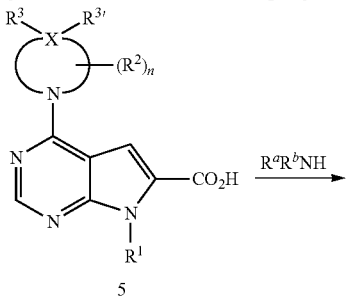

In a sixth aspect, the invention provides a process for making a compound of Formula I, comprising:

(a) treating a compound of formula 6 with a compound of formula 3 to form a compound of formula 7, wherein X is halo, or OTf and X1 is halo, O-Ms, OTs;

(b) reducing the compound of formula 7 to form the compound of formula 8;

(c) treating a compound of formula 8 with an aldehyde of formula 9 to form a compound of formula 1, wherein Y is absent and $R^4$ is alkyl, cycloalkyl, heterocycloalkyl, aryl, or heteroaryl.

In a seventh aspect, the invention provides a process for making a compound of Formula I, comprising:

(a) treating a compound of formula 10 with a acetic anhydride to form a compound of formula 10, wherein X is halo, or OTf and X1 is halo, O-Ms, OTs;

(b) treating the compound of formula 11 with a base and 1,2 dibromotetrachloroethane to form the compound of formula 12;

(c) treating a compound of formula 13 with $R^4$—H in the presence of base to form a compound of formula I wherein Y is absent and $R^4$ is alkyl, cycloalkyl, heterocycloalkyl, aryl, or heteroaryl.

DETAILED DESCRIPTION OF THE INVENTION

The following abbreviations and terms have the indicated meanings throughout:

| Abbreviation | Meaning |
| --- | --- |
| AcOH | acetic acid |
| br | broad |
| ° C. | degrees Celsius |
| conc | concentrated |
| d | doublet |
| dd | doublet of doublet |
| dt | doublet of triplet |
| DCM | dichloromethane |
| DIEA or DIPEA | N,N-di-isopropyl-N-ethylamine |
| DMA | N,N-dimethylacetamide |
| DME | 1,2-dimethoxyethane |
| DMF | N,N-dimethylformamide |
| DMSO | dimethyl sulfoxide |
| dppf | 1,1'-bis(diphenylphosphano)ferrocene |
| EI | Electron Impact ionization |
| equiv | equivalents |
| g | gram(s) |
| GC/MS | gas chromatography/mass spectrometry |
| h or hr | hour(s) |
| HATU | 2-(1H-7-azabenzotriazol-1-yl)-1,1,3,3-tetramethyl uronium hexafluorophosphate |
| HPLC | high pressure liquid chromatography |
| L | liter(s) |
| LC/MS | liquid chromatography/mass spectrometry |
| M | molar or molarity |
| m | Multiplet |
| MeOH | methanol |
| mg | milligram(s) |
| MHz | megahertz (frequency) |
| min | minute(s) |
| mL | milliliter(s) |
| µL | microliter(s) |
| µM | micromolar |
| µmol | micromole(s) |
| mM | Millimolar |
| mmol | millimole(s) |
| mol | mole(s) |
| MS | mass spectral analysis |
| Ms | mesyl |
| N | normal or normality |
| nM | Nanomolar |
| NMR | nuclear magnetic resonance spectroscopy |
| q | Quartet |
| quant | quantitative |
| rt | Room temperature |
| s | Singlet |
| t or tr | Triplet |
| THF | tetrahydrofuran |
| Ts | tosyl |

The symbol "—" means a single bond, "=" means a double bond, "≡" means a triple bond, "----" means a single or double bond. The symbol "⁓" refers to a group on a double-bond as occupying either position on the terminus of a double bond to which the symbol is attached; that is, the geometry, E- or Z-, of the double bond is ambiguous. When a group is depicted removed from its parent Formula, the "~" symbol will be used at the end of the bond which was theoretically cleaved in order to separate the group from its parent structural Formula.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual Formula as having a hydrogen or hydrogens as substitution (expressly defined hydrogen), for example, —CH$_2$CH$_2$—. It is understood by one of ordinary skill in the art that the aforementioned descriptive techniques are common in the chemical arts to provide brevity and simplicity to description of otherwise complex structures.

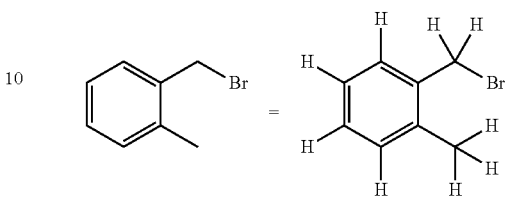

If a group "R" is depicted as "floating" on a ring system, as for example in the Formula:

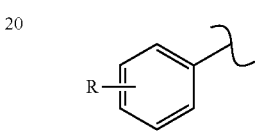

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused or bridged ring system, as for example in the Formula e:

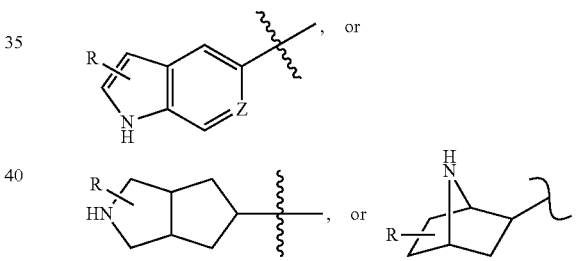

then, unless otherwise defined, a substituent "R" may reside on any atom of the fused or bridged ring system, assuming replacement of a depicted hydrogen (for example the —NH— in the Formula above), implied hydrogen (for example as in the Formula above, where the hydrogens are not shown but understood to be present), or expressly defined hydrogen (for example where in the Formula above, "Z" equals =CH—) from one of the ring atoms, so long as a stable structure is formed. In the example depicted, the "R" group may reside on either the 5-membered or the 6-membered ring of the fused or bridged ring system.

When a group "R" is depicted as existing on a ring system containing saturated carbons, as for example in the Formula:

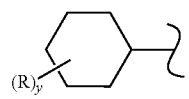

where, in this example, "y" can be more than one, assuming each replaces a currently depicted, implied, or expressly defined hydrogen on the ring; then, unless otherwise defined, where the resulting structure is stable, two "R's" may reside on the same carbon. In another example, two R's on the same carbon, including that carbon, may form a ring, thus creating a spirocyclic ring structure with the depicted ring as for example in the Formula:

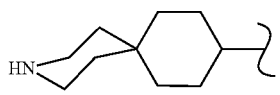

"Acyl" means a —C(O)R radical where R is alkyl, haloalkyl, alkenyl, cycloalkyl, cycloalkylalkyl, aryl, aralkyl, heteroaryl, heteroaralkyl, heterocycloalkyl, or heterocycloalkylalkyl, as defined herein, e.g., acetyl, trifluoromethylcarbonyl, or 2-methoxyethylcarbonyl, and the like.

"Acylamino" means a —NRR' radical where R is hydrogen, hydroxy, alkyl, or alkoxy and R' is acyl, as defined herein.

"Acyloxy" means an —OR radical where R is acyl, as defined herein, e.g. cyanomethylcarbonyloxy, and the like.

"Administration" and variants thereof (e.g., "administering" a compound) in reference to a compound of the invention means introducing the compound of the compound into the system of the animal in need of treatment. When a compound of the invention or prodrug thereof is provided in combination with one or more other active agents (e.g., surgery, radiation, and chemotherapy, etc.), "administration" and its variants are each understood to include concurrent and sequential introduction of the compound or prodrug thereof and other agents.

"Alkenyl" means a means a linear monovalent hydrocarbon radical of two to six carbon atoms or a branched monovalent hydrocarbon radical of three to 6 carbon atoms which radical contains at least one double bond, e.g., ethenyl, propenyl, 1-but-3-enyl, and 1-pent-3-enyl, and the like.

"Alkoxy" means an —OR group where R is alkyl group as defined herein. Examples include methoxy, ethoxy, propoxy, isopropoxy, and the like.

"Alkoxyalkyl" means an alkyl group, as defined herein, substituted with at least one, specifically one, two, or three, alkoxy groups as defined herein. Representative examples include methoxymethyl and the like.

"Alkoxycarbonyl" means a —C(O)R group where R is alkoxy, as defined herein.

"Alkyl" means a linear saturated monovalent hydrocarbon radical of one to six carbon atoms or a branched saturated monovalent hydrocarbon radical of three to 6 carbon atoms, e.g., methyl, ethyl, propyl, 2-propyl, butyl (including all isomeric forms), or pentyl (including all isomeric forms), and the like.

"Alkylamino" means an —NHR group where R is alkyl, as defined herein.

"Alkylaminoalkyl" means an alkyl group substituted with one or two alkylamino groups, as defined herein.

"Alkylaminoalkyloxy" means an —OR group where R is alkylaminoalkyl, as defined herein.

"Alkylcarbonyl" means a —C(O)R group where R is alkyl, as defined herein.

"Alkylsulfonyl" means an —S(O)$_2$R group where R is alkyl, as defined herein.

"Alkylsulfonylalkyl" means an alkyl group, as defined herein, substituted with at least one, preferably one or two, alkylsulfonyl groups, as defined herein.

"Alkynyl" means a linear monovalent hydrocarbon radical of two to six carbon atoms or a branched monovalent hydrocarbon radical of three to 6 carbon atoms which radical contains at least one triple bond, e.g., ethynyl, propynyl, butynyl, pentyn-2-yl and the like.

"Amino" means —NH$_2$.

"Aminoalkyl" means an alkyl group substituted with at least one, specifically one, two or three, amino groups.

"Aminoalkyloxy" means an —OR group where R is aminoalkyl, as defined herein.

"Aminocarbonyl" means a —C(O)NH$_2$ group.

"Alkylaminocarbonyl" means a —C(O)NHR group where R is alkyl as defined herein.

"Aryl" means a monovalent six- to fourteen-membered, mono- or bi-carbocyclic ring, wherein the monocyclic ring is aromatic and at least one of the rings in the bicyclic ring is aromatic. Unless stated otherwise, the valency of the group may be located on any atom of any ring within the radical, valency rules permitting. Representative examples include phenyl, naphthyl, and indanyl, and the like.

"Arylalkyl" means an alkyl radical, as defined herein, substituted with one or two aryl groups, as defined herein, e.g., benzyl and phenethyl, and the like.

"Arylalkyloxy" means an —OR group where R is arylakyl, as defined herein.

"Cyanoalkyl" means an alkyl group, as defined herein, substituted with one or two cyano groups.

"Cycloalkyl" means a monocyclic or fused or bridged bicyclic or tricyclic, saturated or partially unsaturated (but not aromatic), monovalent hydrocarbon radical of three to ten carbon ring atoms. Unless stated otherwise, the valency of the group may be located on any atom of any ring within the radical, valency rules permitting. One or two ring carbon atoms may be replaced by a —C(O)—, —C(S)—, or —C(=NH)— group. More specifically, the term cycloalkyl includes, but is not limited to, cyclopropyl, cyclobutyl, cyclopentyl, cyclohexyl, cyclohexyl, cyclohex-3-enyl, or (1r,3r,5R,7R)-tricyclo[3.3.1.1$^{3,7}$]decan-2-yl, and the like.

"Cycloalkylalkyl" means an alkyl group substituted with at least one, specifically one or two, cycloalkyl group(s) as defined herein.

"Dialkylamino" means a —NRR' radical where R and R' are alkyl as defined herein, or an N-oxide derivative, or a protected derivative thereof, e.g., dimethylamino, diethylamino, N,N-methylpropylamino or N,N-methylethylamino, and the like.

"Dialkylaminoalkyl" means an alkyl group substituted with one or two dialkylamino groups, as defined herein.

"Dialkylaminoalkyloxy" means an —OR group where R is dialkylaminoalkyl, as defined herein. Representative examples include 2-(N,N-diethylamino)-ethyloxy, and the like.

"Dialkylaminocarbonyl" means a —C(O)NRR' group where R and R' are alkyl as defined herein.

"Halogen" or "halo" refers to fluorine, chlorine, bromine and iodine.

"Haloalkoxy" means an —OR' group where R' is haloalkyl as defined herein, e.g., trifluoromethoxy or 2,2,2-trifluoroethoxy, and the like.

"Haloalkyl" mean an alkyl group substituted with one or more halogens, specifically 1, 2, 3, 4, 5, or 6 halo atoms, e.g., trifluoromethyl, 2-chloroethyl, and 2,2-difluoroethyl, and the like.

"Heteroaryl" means a monocyclic or fused or bridged bicyclic monovalent radical of 5 to 14 ring atoms containing one or more, specifically one, two, three, or four ring heteroatoms where each heteroatom is independently —O—, —S(O)$_n$— (n is 0, 1, or 2), —NH—, —N=, or N-oxide, with the remaining ring atoms being carbon, wherein the ring comprising a monocyclic radical is aromatic and wherein at least one of the fused rings comprising the bicyclic radical is aromatic. One or two ring carbon atoms of any nonaromatic rings comprising a bicyclic radical may be replaced by a —C(O)—, —C(S)—, or —C(=NH)— group. Unless stated otherwise, the valency may be located on any atom of any ring of the heteroaryl group, valency rules permitting. More specifically, the term heteroaryl includes, but is not limited to, 1,2,4-triazolyl, 1,3,5-triazolyl, phthalimidyl, pyridinyl, pyrrolyl, imidazolyl, thienyl, furanyl, indolyl, 2,3-dihydro-1H-indolyl (including, for example, 2,3-dihydro-1H-indol-2-yl or 2,3-dihydro-1H-indol-5-yl, and the like), isoindolyl, indolinyl, isoindolinyl, benzimidazolyl, benzodioxol-4-yl, benzofuranyl, cinnolinyl, indolizinyl, naphthyridin-3-yl, phthalazin-3-yl, phthalazin-4-yl, pteridinyl, purinyl, quinazolinyl, quinoxalinyl, tetrazoyl, pyrazolyl, pyrazinyl, pyrimidinyl, pyridazinyl, oxazolyl, isooxazolyl, oxadiazolyl, benzoxazolyl, quinolinyl, isoquinolinyl, tetrahydroisoquinolinyl (including, for example, tetrahydroisoquinolin-4-yl or tetrahydroisoquinolin-6-yl, and the like), pyrrolo[3,2-c]pyridinyl (including, for example, pyrrolo[3,2-c]pyridin-2-yl or pyrrolo[3,2-c]pyridin-7-yl, and the like), benzopyranyl, 2,3-dihydrobenzofuranyl, benzo[d][1,3]dioxolyl, 2,3-dihydrobenzo[b][1,4]dioxinyl, thiazolyl, isothiazolyl, thiadiazolyl, benzothiazolyl, benzothienyl, and the derivatives thereof, or N-oxide or a protected derivative thereof. The term "5- or 6-membered heteroaryl" describes a subset of the term "heteroaryl."

"Heteroarylalkyl" means an alkyl group, as defined herein, substituted with at least one, specifically one or two heteroaryl group(s), as defined herein.

"Heterocycloalkyl" means a saturated or partially unsaturated (but not aromatic) monovalent monocyclic group of 3 to 8 ring atoms or a saturated or partially unsaturated (but not aromatic) monovalent fused or bridged, bicyclic or tricyclic group of 5 to 12 ring atoms in which one or more, specifically one, two, three, or four ring heteroatoms where each heteroatom is independently O, S(O)$_n$ (n is 0, 1, or 2), —N=, or —NH—, the remaining ring atoms being carbon. One or two ring carbon atoms may be replaced by a —C(O)—, —C(S)—, or —C(=NH)— group. Unless otherwise stated, the valency of the group may be located on any atom of any ring within the radical, valency rules permitting. When the point of valency is located on a nitrogen atom, R$^y$ is absent. More specifically the term heterocycloalkyl includes, but is not limited to, azetidinyl, pyrrolidinyl, 2-oxopyrrolidinyl, 2,5-dihydro-1H-pyrrolyl, piperidinyl, 4-piperidonyl, morpholinyl, piperazinyl, 2-oxopiperazinyl, tetrahydropyranyl, 2-oxopiperidinyl, thiomorpholinyl, thiamorpholinyl, perhydroazepinyl, pyrazolidinyl, imidazolinyl, imidazolidinyl, dihydropyridinyl, tetrahydropyridinyl, oxazolinyl, oxazolidinyl, isoxazolidinyl, thiazolinyl, thiazolidinyl, quinuclidinyl, isothiazolidinyl, octahydrocyclopenta[c]pyrrolyl, octahydroindolyl, octahydroisoindolyl, decahydroisoquinolyl, tetrahydrofuryl, tetrahydropyranyl, (3aR,6aS)-5-methyloctahydrocyclopenta[c]pyffolyl, and (3aS,6aR)-5-methyl-1,2,3,3a,4,6a-hexahydrocyclopenta[c]pyrrolyl, and the derivatives thereof and N-oxide or a protected derivative thereof.

"Heterocycloalkylalkyl" means an alkyl radical, as defined herein, substituted with one or two heterocycloalkyl groups, as defined herein, e.g., morpholinylmethyl, N-pyrrolidinylethyl, and 3-(N-azetidinyl)propyl, and the like.

"Heterocycloalkyloxy" means an —OR group where R is heterocycloalkyl, as defined herein.

"Hydroxyalkyl" means an alkyl group, as defined herein, substituted with at least one, preferably 1, 2, 3, or 4, hydroxy groups.

"Phenylalkyl" means an alkyl group, as defined herein, substituted with one or two phenyl groups.

"Phenylalkyloxy" means an —OR group where R is phenylalkyl, as defined herein.

"Optional" or "optionally" means that the subsequently described event or circumstance may or may not occur, and that the description includes instances where said event or circumstance occurs and instances in which it does not. One of ordinary skill in the art would understand that with respect to any molecule described as containing one or more optional substituents, only sterically practical and/or synthetically feasible compounds are meant to be included. "Optionally substituted" refers to all subsequent modifiers in a term, unless stated otherwise. A list of exemplary optional substitutions is presented below in the definition of "substituted."

"Optionally substituted aryl" means an aryl group, as defined herein, optionally substituted with one, two, or three substituents independently acyl, acylamino, acyloxy, alkyl, haloalkyl, alkenyl, alkoxy, alkenyloxy, halo, hydroxy, alkoxycarbonyl, alkenyloxycarbonyl, amino, alkylamino, dialkylamino, nitro, aminocarbonyl, alkylaminocarbonyl, dialkylaminocarbonyl, carboxy, cyano, alkylthio, alkylsulfinyl, alkylsulfonyl, aminosulfonyl, alkylaminosulfonyl, dialkylaminosulfonyl, alkylsulfonylamino, or aminoalkoxy; or aryl is pentafluorophenyl. Within the optional substituents on "aryl", the alkyl and alkenyl, either alone or as part of another group (including, for example, the alkyl in alkoxycarbonyl), are independently optionally substituted with one, two, three, four, or five halo.

"Optionally substituted arylalkyl" means an alkyl group, as defined herein, substituted with optionally substituted aryl, as defined herein.

"Optionally substituted cycloalkyl" means a cycloalkyl group, as defined herein, substituted with one, two, or three groups independently acyl, acyloxy, acylamino, alkyl, haloalkyl, alkenyl, alkoxy, alkenyloxy, alkoxycarbonyl, alkenyloxycarbonyl, alkylthio, alkylsulfinyl, alkylsulfonyl, aminosulfonyl, alkylaminosulfonyl, dialkylaminosulfonyl, alkylsulfonylamino, halo, hydroxy, amino, alkylamino, dialkylamino, aminocarbonyl, alkylaminocarbonyl, dialkylaminocarbonyl, nitro, alkoxyalkyloxy, aminoalkoxy, alkylaminoalkoxy, dialkylaminoalkoxy, carboxy, or cyano. Within the above optional substitutents on "cycloalkyl", the alkyl and alkenyl either alone or as part of another substituent on the cycloalkyl ring, are independently optionally substituted with one, two, three, four, or five halo, e.g. haloalkyl, haloalkoxy, haloalkenyloxy, or haloalkylsulfonyl.

"Optionally substituted cycloalkylalkyl" means an alkyl group substituted with at least one, specifically one or two, optionally substituted cycloalkyl groups, as defined herein.

"Optionally substituted heteroaryl" means a heteroaryl group optionally substituted with one, two, or three substituents independently acyl, acylamino, acyloxy, alkyl, haloalkyl, alkenyl, alkoxy, alkenyloxy, halo, hydroxy, alkoxycarbonyl, alkenyloxycarbonyl, amino, alkylamino, dialkylamino, nitro, aminocarbonyl, alkylaminocarbonyl, dialkylaminocarbonyl, carboxy, cyano, alkylthio, alkylsulfinyl, alkylsulfonyl, aminosulfonyl, alkylaminosulfonyl, dialkylaminosulfonyl, alkylsulfonylamino, aminoalkoxy, alkylaminoalkoxy, or dialkylaminoalkoxy. Within the optional substituents on "heteroaryl", the alkyl and alkenyl, either alone or as part of another group (including, for example, the alkyl in alkoxycarbonyl), are independently optionally substituted with one, two, three, four, or five halo.

"Optionally substituted heteroarylalkyl" means an alkyl group, as defined herein, substituted with at least one, specifically one or two, optionally substituted heteroaryl group(s), as defined herein.

"Optionally substituted heterocycloalkyl" means a heterocycloalkyl group, as defined herein, optionally substituted with one, two, or three substituents independently acyl, acylamino, acyloxy, haloalkyl, alkyl, alkenyl, alkoxy, alkenyloxy, halo, hydroxy, alkoxycarbonyl, alkenyloxycarbonyl, amino, alkylamino, dialkylamino, nitro, aminocarbonyl, alkylaminocarbonyl, dialkylaminocarbonyl, carboxy, cyano, alkylthio, alkylsulfinyl, alkylsulfonyl, aminosulfonyl, alkylaminosulfonyl, dialkylaminosulfonyl, alkylsulfonylamino, aminoalkoxy, or phenylalkyl. Within the optional substituents on "heterocycloalkyl", the alkyl and alkenyl, either alone or as part of another group (including, for example, the alkyl in alkoxycarbonyl), are independently optionally substituted with one, two, three, four, or five halo.

"Optionally substituted heterocycloalkylalkyl" means an alkyl group, as defined herein, substituted with at least one, specifically one or two, optionally substituted heterocycloalkyl group(s) as defined herein.

"Optionally substituted phenyl" means a phenyl group optionally substituted with one, two, or three substituents independently acyl, acylamino, acyloxy, alkyl, haloalkyl, alkenyl, alkoxy, alkenyloxy, halo, hydroxy, alkoxycarbonyl, alkenyloxycarbonyl, amino, alkylamino, dialkylamino, nitro, aminocarbonyl, alkylaminocarbonyl, dialkylaminocarbonyl, carboxy, cyano, alkylthio, alkylsulfinyl, alkylsulfonyl, aminosulfonyl, alkylaminosulfonyl, dialkylaminosulfonyl, alkylsulfonylamino, or aminoalkoxy, or aryl is pentafluorophenyl. Within the optional substituents on "phenyl", the alkyl and alkenyl, either alone or as part of another group (including, for example, the alkyl in alkoxycarbonyl), are independently optionally substituted with one, two, three, four, or five halo.

"Optionally substituted phenylalkyl" means an alkyl group, as defined herein, substituted with one or two optionally substituted phenyl groups, as defined herein.

"Optionally substituted phenylsulfonyl" means an —S(O)$_2$R group where R is optionally substituted phenyl, as defined herein.

"Oxo" means an oxygen which is attached via a double bond.

"Yield" for each of the reactions described herein is expressed as a percentage of the theoretical yield.

"Patient" for the purposes of the present invention includes humans and other animals, particularly mammals, and other organisms. Thus the methods are applicable to both human therapy and veterinary applications. In a specific embodiment the patient is a mammal, and in a more specific embodiment the patient is human.

A "pharmaceutically acceptable salt" of a compound means a salt that is pharmaceutically acceptable and that possesses the desired pharmacological activity of the parent compound. It is understood that the pharmaceutically acceptable salts are non-toxic. Additional information on suitable pharmaceutically acceptable salts can be found in *Remington's Pharmaceutical Sciences*, 17$^{th}$ ed., Mack Publishing Company, Easton, Pa., 1985, which is incorporated herein by reference or S. M. Berge, et al., "Pharmaceutical Salts," J. Pharm. Sci., 1977; 66:1-19 both of which are incorporated herein by reference.

Examples of pharmaceutically acceptable acid addition salts include those formed with inorganic acids such as hydrochloric acid, hydrobromic acid, sulfuric acid, nitric acid, phosphoric acid, and the like; as well as organic acids such as acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, and salicylic acid and the like.

Examples of a pharmaceutically acceptable base addition salts include those formed when an acidic proton present in the parent compound is replaced by a metal ion, such as sodium, potassium, lithium, ammonium, calcium, magnesium, iron, zinc, copper, manganese, aluminum salts and the like. Specific salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins. Examples of organic bases include isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, tromethamine, N-methylglucamine, polyamine resins, and the like. Exemplary organic bases are isopropylamine, diethylamine, ethanolamine, trimethylamine, dicyclohexylamine, choline, and caffeine. "Platin(s)," and "platin-containing agent(s)" include, for example, cisplatin, carboplatin, and oxaliplatin.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to their knowledge and to this disclosure.

"Preventing" or "prevention" of a disease, disorder, or syndrome includes inhibiting the disease from occurring in a human, i.e. causing the clinical symptoms of the disease, disorder, or syndrome not to develop in an animal that may be exposed to or predisposed to the disease, disorder, or syndrome but does not yet experience or display symptoms of the disease, disorder, or syndrome.

"Treating" or "treatment" of a disease, disorder, or syndrome, as used herein, includes (i) inhibiting the disease, disorder, or syndrome, i.e., arresting its development; and (ii) relieving the disease, disorder, or syndrome, i.e., causing regression of the disease, disorder, or syndrome. As is known in the art, adjustments for systemic versus Localized delivery, age, body weight, general health, sex, diet, time of administration, drug interaction and the severity of the condition may be necessary, and will be ascertainable with routine experimentation by one of ordinary skill in the art.

Embodiments of the Invention

The following paragraphs present a number of embodiments of compounds of the invention. In each instance the embodiment includes both the recited compounds, as well as a single stereoisomer or mixture of stereoisomers thereof, as well as a pharmaceutically acceptable salt thereof.

Thus, as provided above, in one aspect, the invention provides a compound of Formula I.

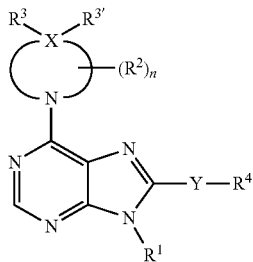

I

In one embodiment, two $R^2$ groups may be joined together with the carbons to which they are attached to form a bridged bicyclic ring;

In one embodiment, the compound of Formula I is a compound of Formula Ia, wherein

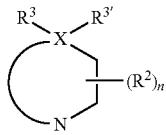

is a 5, 6, or 7-membered ring.

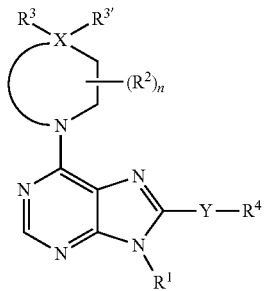

Ia

In another embodiment, the compound of Formula I is a compound of Formula Ib.

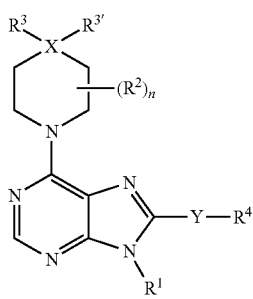

Ib

In these and other embodiments, $R^1$ is alkyl or cycloalkyl. More particularly, in these and other embodiments, $R^1$ is methyl, ethyl, or cyclopropyl.

In these and other embodiments, n is 0 or 1 and $R^2$ is hydroxy, carboxy, methyl, or hydroxymethyl.

In these and other embodiments, the compound of Formula I is a compound of Formula Ic or Id.

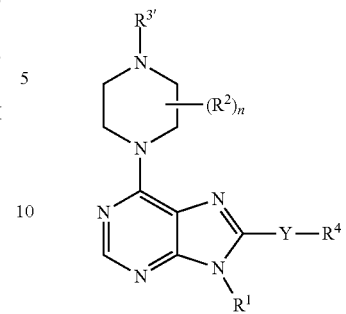

Ic

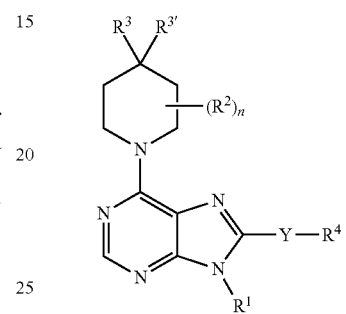

Id

In a further embodiment, the compound of Formula Ic is a compound of Formula Ic-1 or Ic-2 wherein R is heteroarylalkyloxy, alkyl substituted with arylsulfonylamino, or alkyl substituted with cycloalkylcarbonylamino.

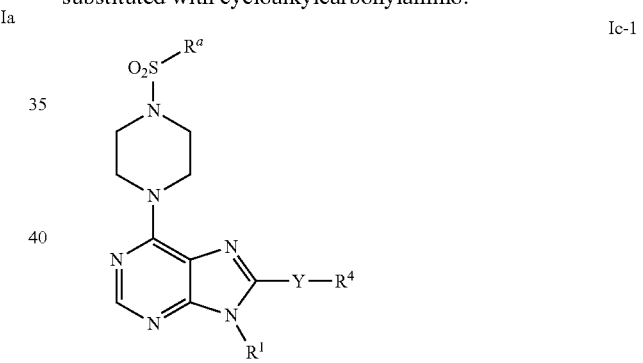

Ic-1

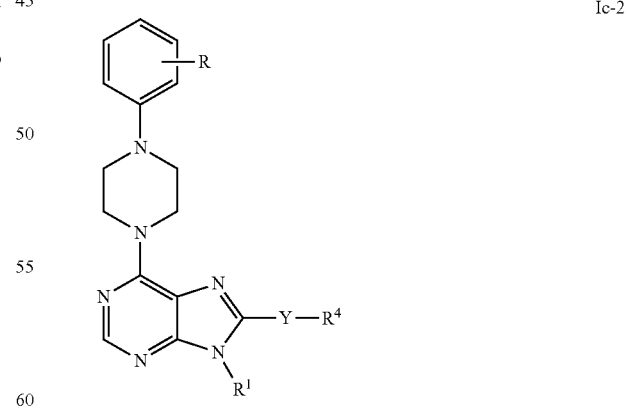

Ic-2

In a further embodiment, $R^1$ in the compounds of Formula Ic-1 and Ic-2 is alkyl.

In a further embodiment of a compound of Formula Id, $R^3$ is hydrogen, cyano, hydroxy, aminomethyl, optionally substituted alkoxy, or carboxymethyl, and $R^{3'}$ is optionally substituted phenyl, optionally substituted indolyl, optionally substituted 1H-benzo[d][1,2,3]triazolyl, optionally substituted oxoindolinyl, or optionally substituted benzoimidazolyl.

In a further embodiment, the compound of Formula Id is a compound of Formula Id-1 Id-2, Id-3, or Id-4.

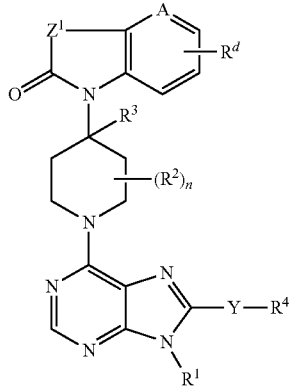

Id-1

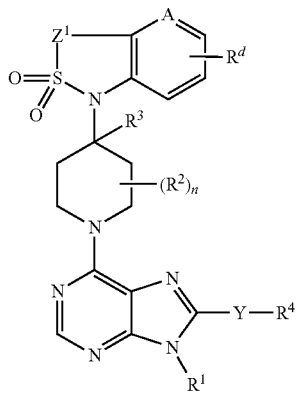

Id-2

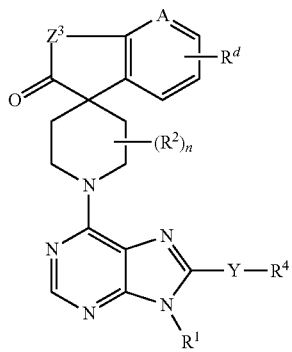

Id-3

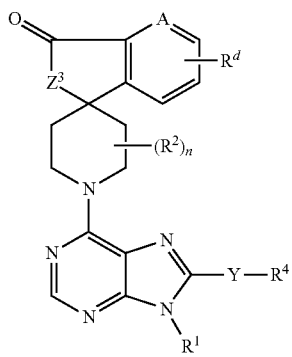

Id-4

In a further embodiment, the compound of Formula Id-1 or Id-2 is a compound of Formula Id-1(a), Id-1(b), or Id-2(a).

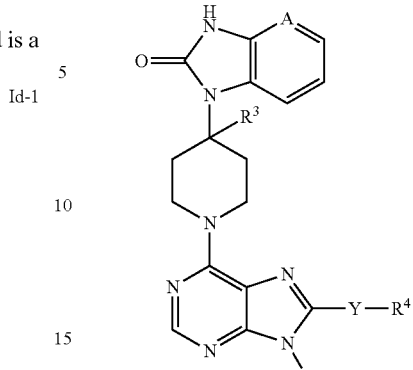

Id-1(a)

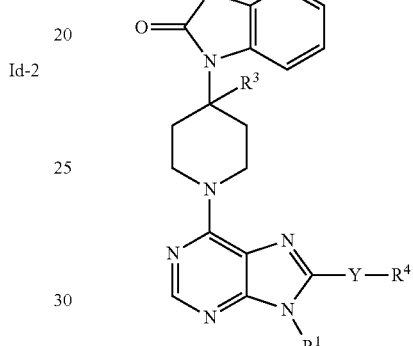

Id-1(b)

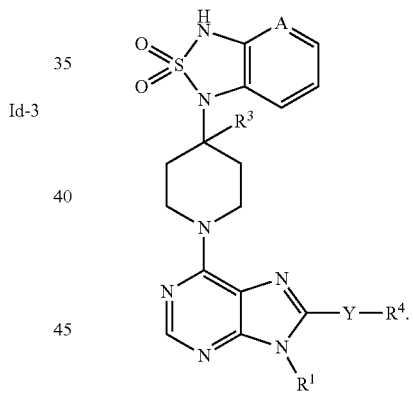

Id-2(a)

In a further embodiment, $R^1$ in the compounds of Formula Id-1(a), Id-1(b), and Id-2(a) is alkyl.

In a further embodiment, $R^1$ in the compounds of Formula Id-1(a), Id-1(b), and Id-2(a) is methyl.

In a further embodiment, $R^3$ in the compounds of Formula Id-1(a), Id-1(b), and Id-2(a) is H.

In a further embodiment, A in the compounds of Formula Id-1(a), Id-1(b), and Id-2(a) is N.

In a further embodiment, Y in the compounds of Formula Id-1(a), Id-1(b), and Id-2(a) is absent.

In a further embodiment, $R^4$ in the compounds of Formula Id-1(a), Id-1(b), and Id-2(a) is optionally substituted aryl, optionally substituted cycloalkyl, optionally substituted heterocycloalkyl, optionally substituted heteroaryl.

In a further embodiment, the compound of 1d-3 or Id-4 is a compound of Formula Id-3(a), Id-3(b), or Id-4(a).

Id-3(a)

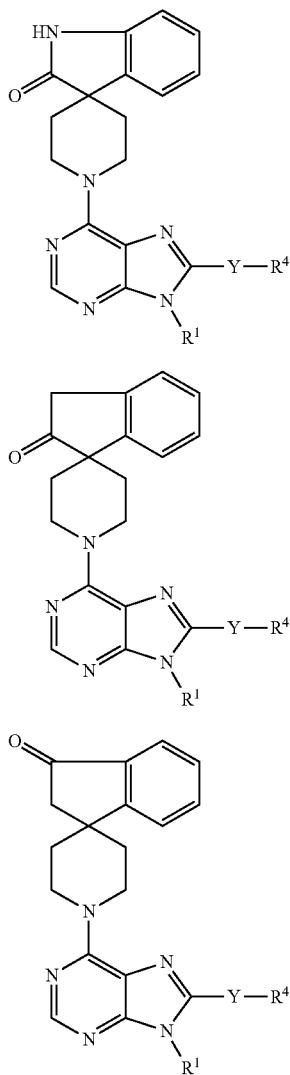

Id-3(b)

Id-4(a)

In a further embodiment, R¹ in the compounds of Formula Id-3(a), Id-3(b), and Id-4(a) is alkyl.

In a further embodiment, R¹ in the compounds of Formula Id-3(a), Id-3(b), and Id-4(a) is methyl.

In a further embodiment, Y in the compounds of Formula Id-3(a), Id-3(b), and Id-4(a) is absent.

In a further embodiment, Y in the compounds of Formula Id-3(a), Id-3(b), and Id-4(a) is —(C═O)—NH—.

In a further embodiment, R⁴ in the compounds of Formula Id-3(a), Id-3(b), and Id-4(a) is optionally substituted alkyl, optionally substituted aryl, optionally substituted cycloalkyl, optionally substituted heterocycloalkyl, optionally substituted heteroaryl.

In a further embodiment of a compound of Formula I:

R¹ is alkyl, haloalkyl, or optionally substituted cycloalkyl;

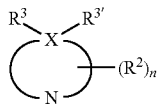

is a 4, 5, 6, or 7-membered ring, wherein:

X is C or N; wherein:

when X is N:

R³' is absent and R³ is phenyl optionally substituted with one or two groups independently selected from heteroarylalkyloxy; alkyl substituted with arylsulfonyalmino; alkyl substituted with cycloalkylcarbonylamino or R³ is —SO₂—Rᵃ, wherein Rᵃ is optionally substituted alkyl, optionally substituted phenyl, optionally substituted phenylalkyl, or optionally substituted heteroaryl;

when X is C:

R³ is cyano, aminoalkyl, alkoxycarbonyl, or hydroxy and R³' is a optionally substituted phenyl; or R³ is hydrogen and R³' is phenyl, alkyl substituted with 1-phenyl-4,5,6,7-tetrahydro-1H-pyrazolo[3,4-c]pyridinyl, 1H-indolyl, optionally substituted pyridinyl (oxadiazolyl substituted with furanyl), 2-oxo-3,4-dihydroquinazolinyl, —C(O)NRᵇRᶜ, wherein Rᵇ is hydrogen or alkyl; and Rᶜ is optionally substituted heteroarylalkyl; or R³ is a group of formula (a), (b), (c), (d), (e), or (f):

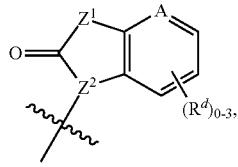
(a)

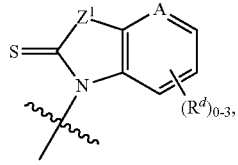
(b)

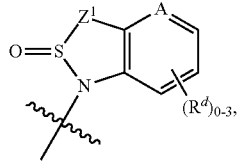
(c)

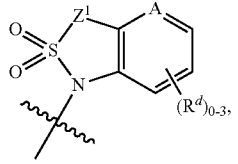
(d)

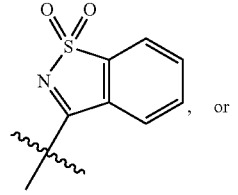
(e)

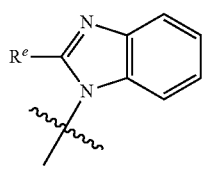
(f)

wherein Z¹ is O or NH or N optionally substituted with aminoalkyl, alkylaminoalkyl, or dialkylaminoalkyl, Z² is CH or N, and A is N or C and each $R^d$, when present, is independently halo, alkyl, optionally substituted alkoxy, or optionally substituted heterocycloalkyl and $R^e$ is amino or haloalkyl; or $R^3$ and $R^{3'}$ are taken together with the carbon to which they are attached to form an optionally substituted 5 or 6 membered ring (g), (h), (i), (j); or (k)

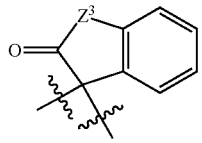
(g)

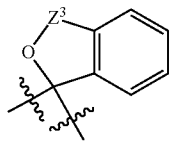
(h)

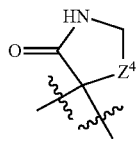
(i)

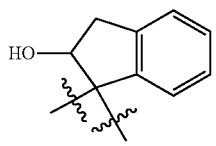
(j)

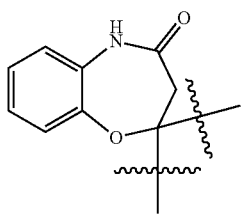
(k)

wherein $Z^3$ is $CH_2$ or NH; $Z^4$ is $NR^f$ or $CHR^f$, wherein $R^f$ is hydrogen or optionally substituted phenyl;

Y is absent or is halo, alkyl, —(C=O)—, $NR^x$—(C=O)—, or —(C=O)$NR^x$—, —O—(C=O)—, or —(C=O)O—, —$NR^x$—(C=O)O—, or —O(C=O)$NR^x$—, wherein $R^x$ is hydrogen or optionally substituted alkyl;

$R^4$ is hydrogen, halo, optionally substituted alkyl, optionally substituted alkenyl, optionally substituted aryl, optionally substituted heterocycloalkyl, optionally substituted heteroaryl; and when —$NR^x$—(C=O)—, or —(C=O)—$NR^x$—, $R^x$ and $R^4$ can be joined together along with the atoms to which they are attached to form a 4, 5, or 6 membered ring, optionally containing 1 or 2 additional heteroatoms selected from N, S, and O.

In a further embodiment of a compound of Formula I, $R^1$ is methyl.

In further embodiments, in the compounds of Formula I, Ia, Ib, Ic, and Id, Y is absent, or is halo, alkyl, haloallyl, —(C=O)—, or —(C=O)O—, or —(C=O)NH—.

In a further embodiments, in the compounds of Formula I, Ia, Ib, Ic, and Id, Y is absent and $R^4$ is ethyl, propenyl, or trifluoromethyl.

In a further embodiments, in the compounds of Formula I, Ia, Ib, Ic, and Id, $R^4$ is optionally substituted heteroaryl, optionally substituted alkyl, optionally substituted cycloalkyl, or optionally substituted heterocycloalkyl.

In a further embodiment, in the compounds of Formula I, Ia, Ib, Ic, and Id, Y is absent and $R^4$ is

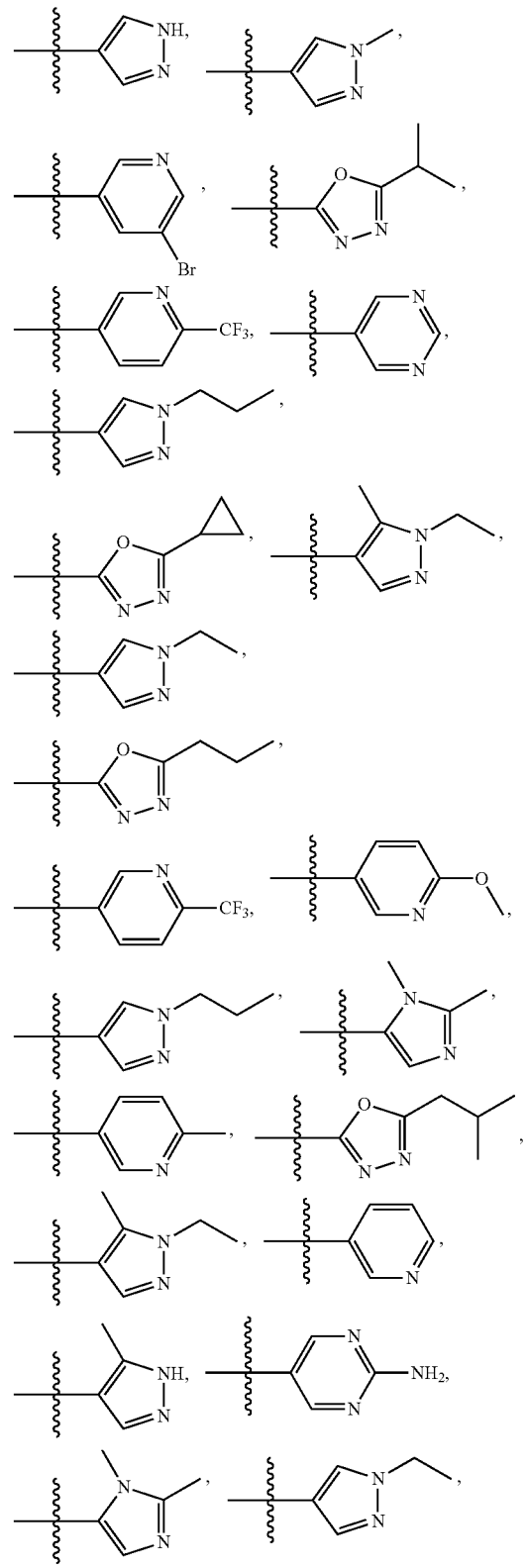

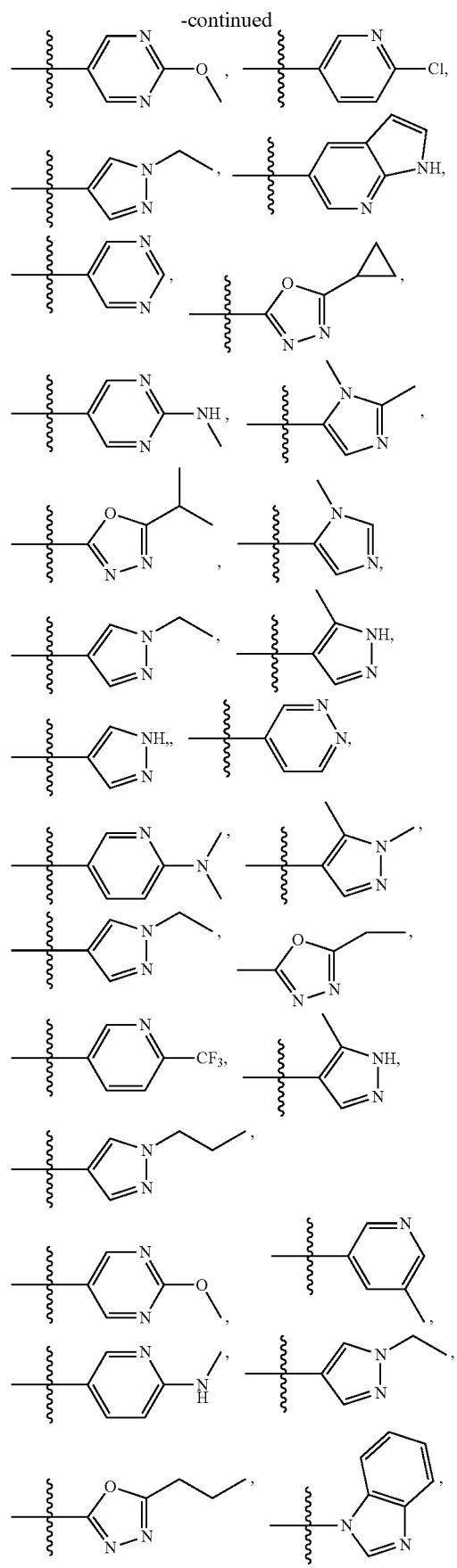
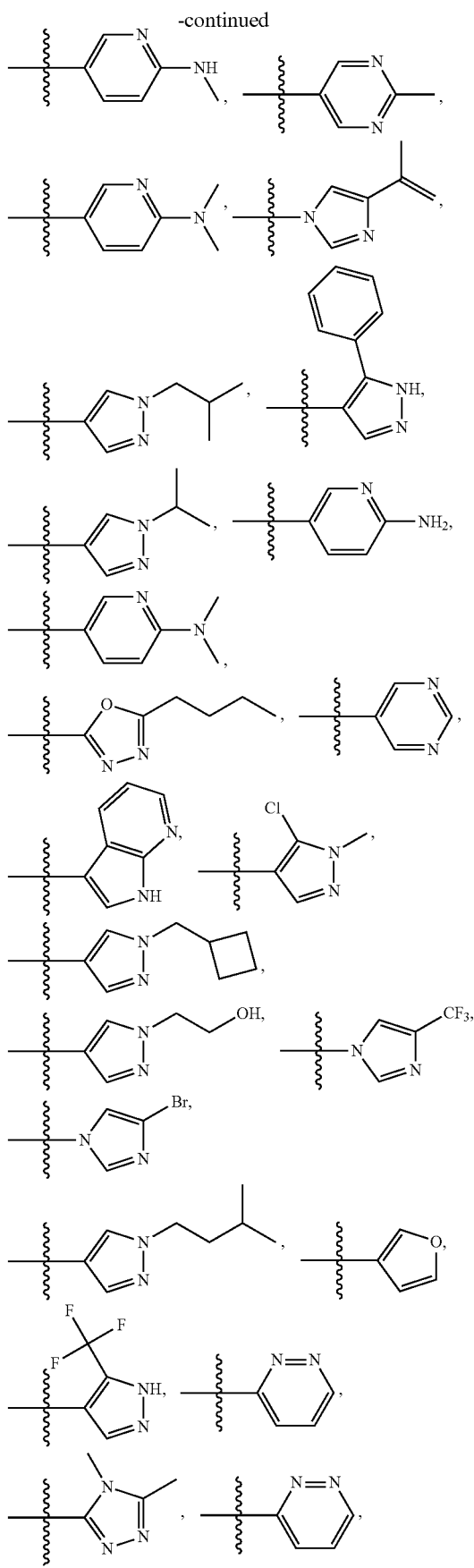

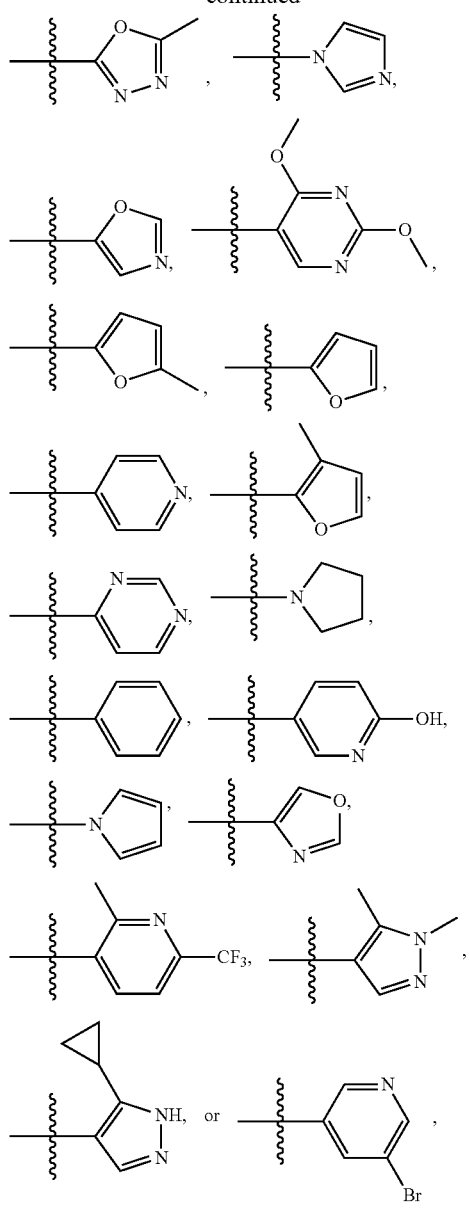
In a further embodiment, in the compounds of Formula I, Ia, Ib, Ic, and Id, Y is —(C=O)—, —(C=O)O—, or —(C=O)NH—.
In a further embodiment, in the compounds of Formula I, Ia, Ib, Ic, and Id, Y—R⁴ is
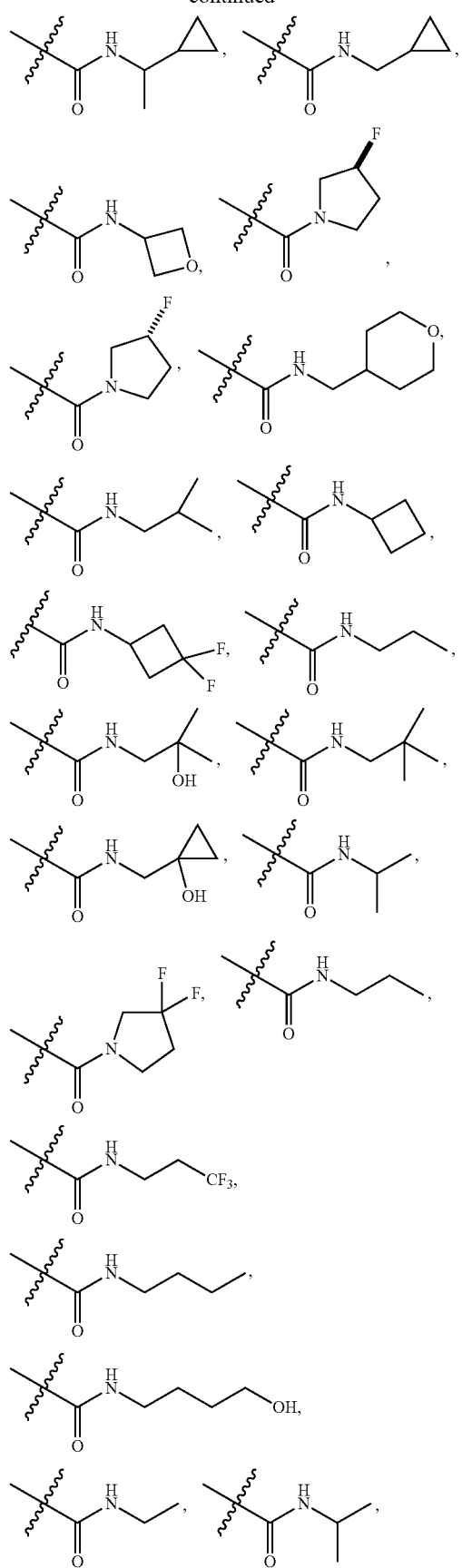

-continued
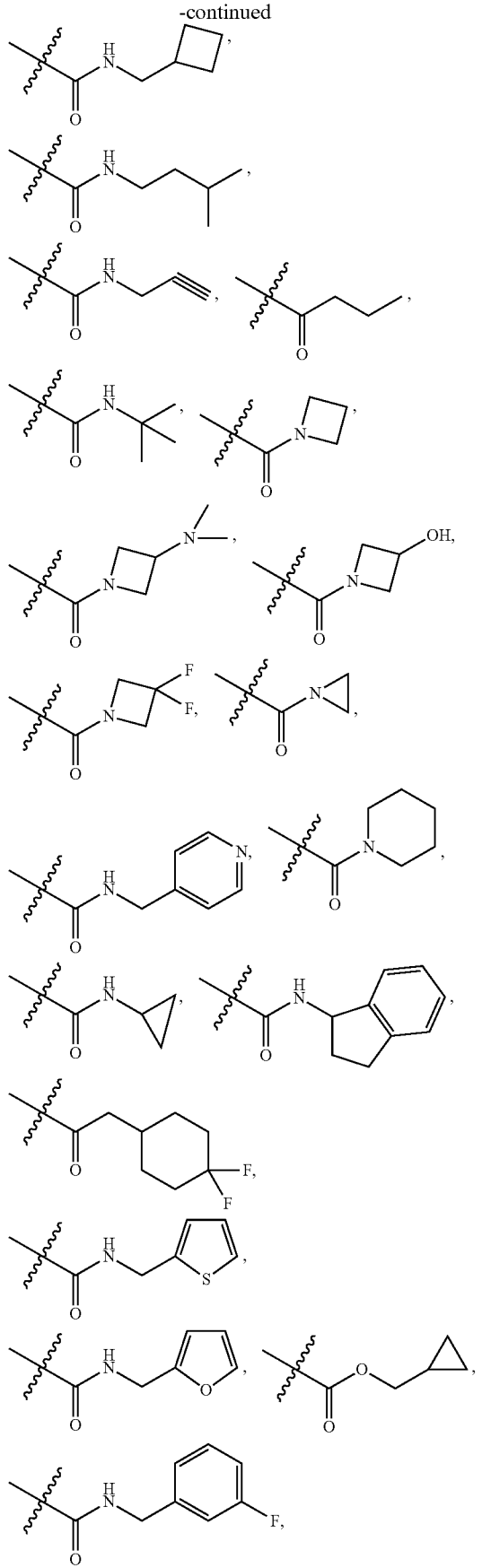
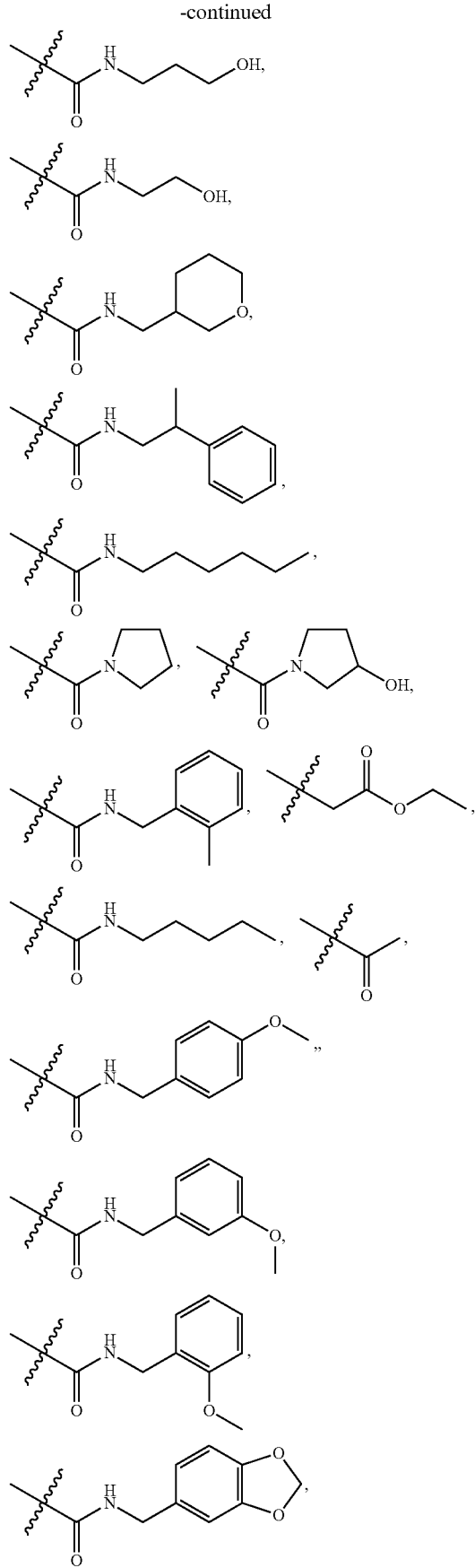

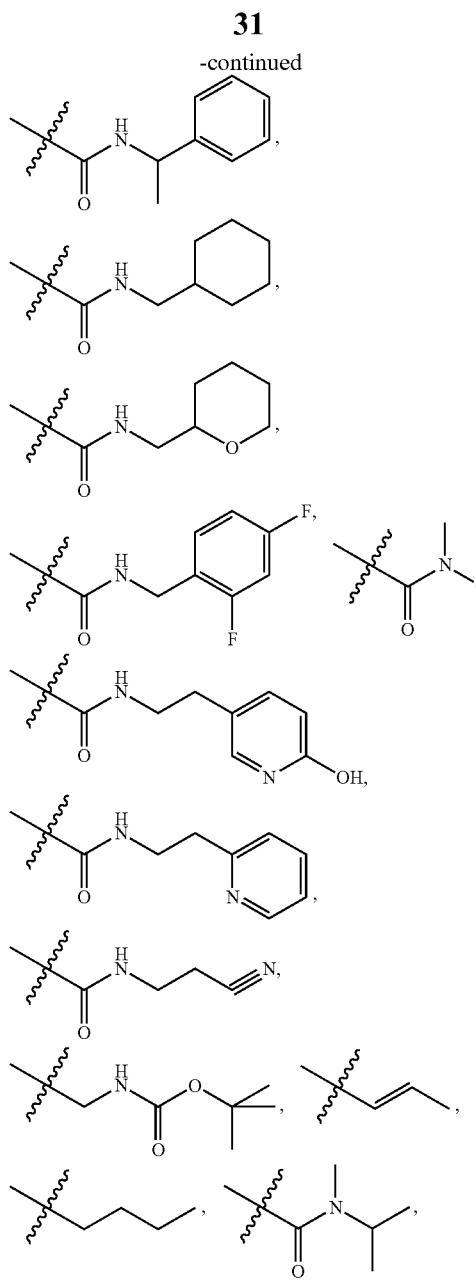
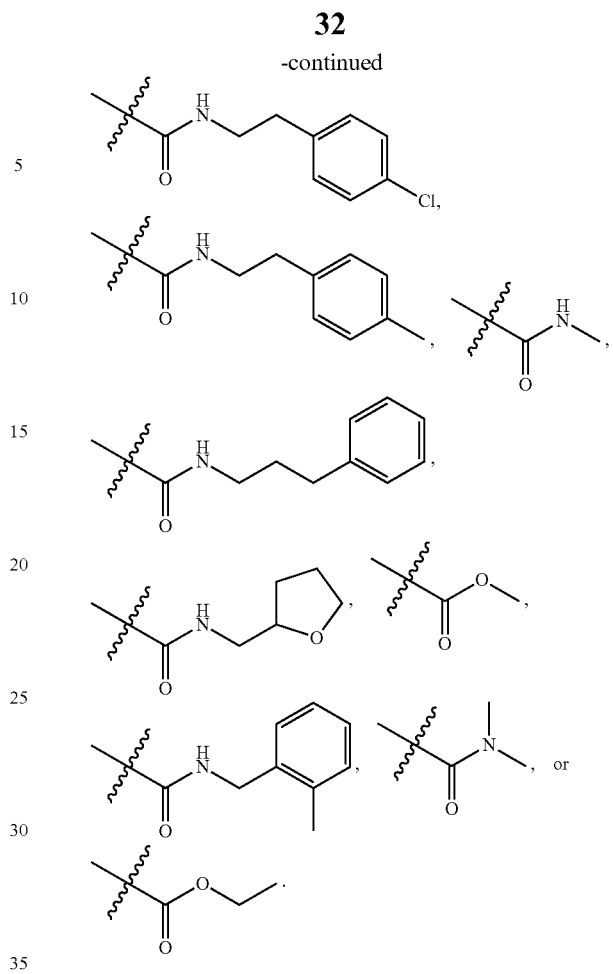

Representative Compounds

Representative compounds of Formula I are depicted below. The examples are merely illustrative and do not limit the scope of the invention in any way. Compounds of the invention are named according to systematic application of the nomenclature rules agreed upon by the International Union of Pure and Applied Chemistry (IUPAC), International Union of Biochemistry and Molecular Biology (IUBMB), and the Chemical Abstracts Service (CAS). Specifically, names in Table I were generated using ACD/Labs naming software 8.00 release, product version 8.08 or higher.

TABLE 1

| Compound Number | Structure | Name |
|---|---|---|
| 1 | 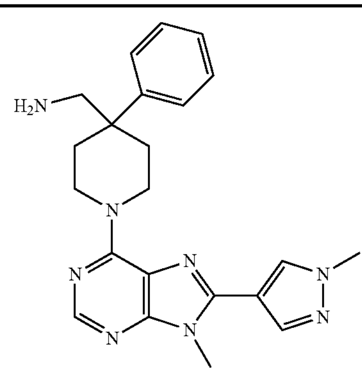 | 1-{1-[9-methyl-8-(1-methyl-1H-pyrazol-4-yl)-9H-purin-6-yl]-4-phenylpiperidin-4-yl}methenamine |

TABLE 1-continued

| Compound Number | Structure | Name |
|---|---|---|
| 2 | 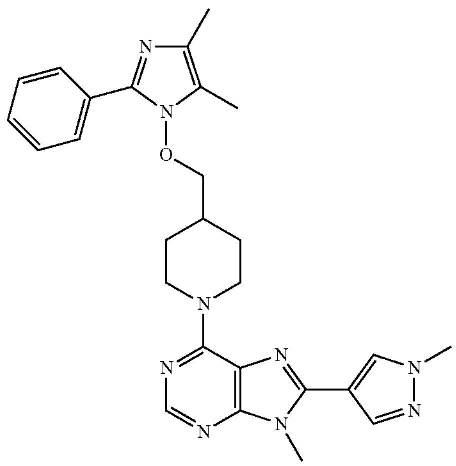 [SMILES: Cc1nc(-c2ccccc2)n(OCC2CCN(c3ncnc4c3nc(-c3cnn(C)c3)n4C)CC2)c1C] | 6-(4-(((4,5-dimethyl-2-phenyl-1H-imidazol-1-yl)oxy)methyl)piperidin-1-yl)-9-methyl-8-(1-methyl-1H-pyrazol-4-yl)-9H-purine |
| 3 | 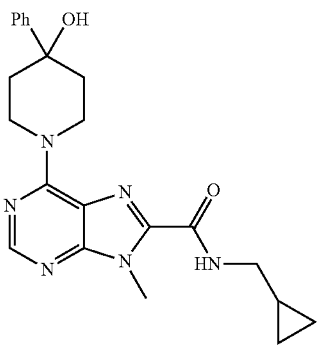 [SMILES: Cn1c(C(=O)NCC2CC2)nc2c(N3CCC(O)(c4ccccc4)CC3)ncnc21] | N-(cyclopropylmethyl)-6-(4-hydroxy-4-phenylpiperidin-1-yl)-9-methyl-9H-purine-8-carboxamide |
| 4 | 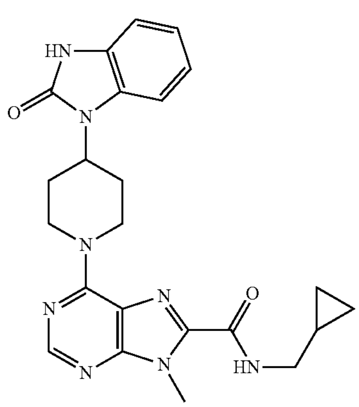 [SMILES: Cn1c(C(=O)NCC2CC2)nc2c(N3CCC(n4c(=O)[nH]c5ccccc54)CC3)ncnc21] | N-(cyclopropylmethyl)-9-methyl-6-[4-(2-oxo-2,3-dihydro-1H-benzimidazol-1-yl)piperidin-1-yl]-9H-purine-8-carboxamide |

TABLE 1-continued

| Compound Number | Structure | Name |
|---|---|---|
| 5 | 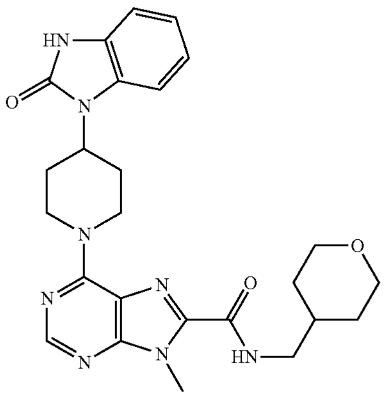 [SMILES: Cn1c(C(=O)NCC2CCOCC2)nc2c(N3CCC(n4c(=O)[nH]c5ccccc54)CC3)ncnc21] | 9-methyl-6-[4-(2-oxo-2,3-dihydro-1H-benzimidazol-1-yl)piperidin-1-yl]-N-(tetrahydro-2H-pyran-4-ylmethyl)-9H-purine-8-carboxamide |
| 6 | 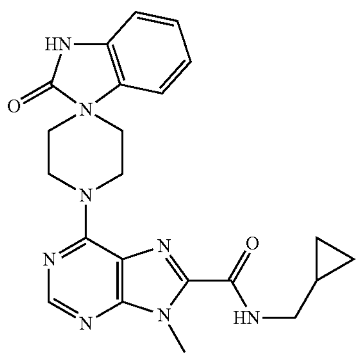 | N-(cyclopropylmethyl)-9-methyl-6-(2-oxo-1,2-dihydro-1'H-spiro[indole-3,4'-piperidin]-1'-yl)-9H-purine-8-carboxamide |
| 7 | 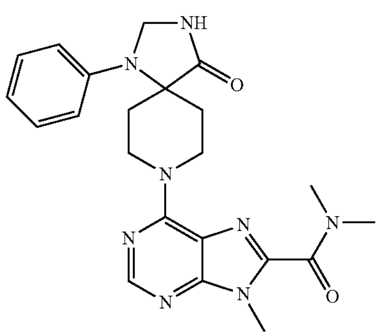 [SMILES: CN(C)C(=O)c1nc2c(N3CCC4(CC3)C(=O)NCN4c3ccccc3)ncnc2n1C] | N,N,9-trimethyl-6-(4-oxo-1-phenyl-1,3,8-triazaspiro[4.5]dec-8-yl)-9H-purine-8-carboxamide |
| 8 | 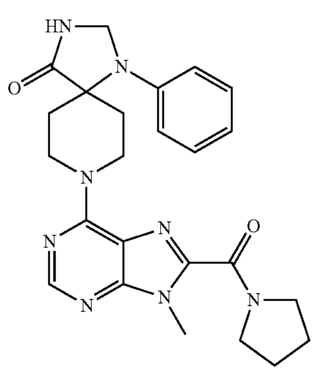 [SMILES: Cn1c(C(=O)N2CCCC2)nc2c(N3CCC4(CC3)C(=O)NCN4c3ccccc3)ncnc21] | 8-[9-methyl-8-(pyrrolidin-1-ylcarbonyl)-9H-purin-6-yl]-1-phenyl-1,3,8-triazaspiro[4.5]decan-4-one |

TABLE 1-continued

| Compound Number | Structure | Name |
|---|---|---|
| 9 | 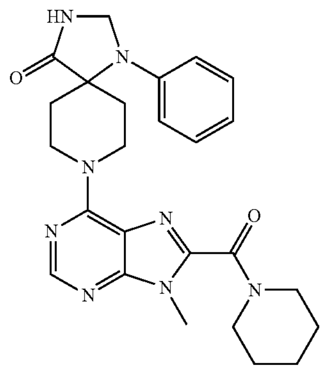 [SMILES: Cn1c(C(=O)N2CCCCC2)nc2c(N3CCC4(CC3)C(=O)NCN4c3ccccc3)ncnc21] | 8-[9-methyl-8-(piperidin-1-ylcarbonyl)-9H-purin-6-yl]-1-phenyl-1,3,8-triazaspiro[4.5]decan-4-one |
| 10 | 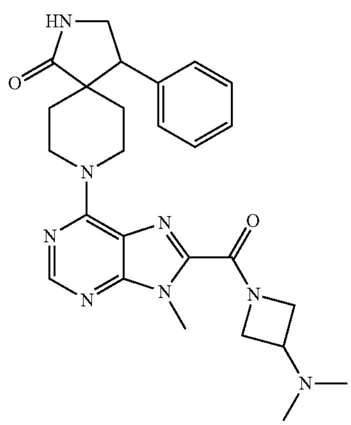 [SMILES: CN(C)C1CN(C(=O)c2nc3c(N4CCC5(CC4)C(=O)NCC5c4ccccc4)ncnc3n2C)C1] | 8-(8-{[3-(dimethylamino)azetidin-1-yl]carbonyl}-9-methyl-9H-purin-6-yl)-1-phenyl-1,3,8-triazaspiro[4.5]decan-4-one |
| 11 | 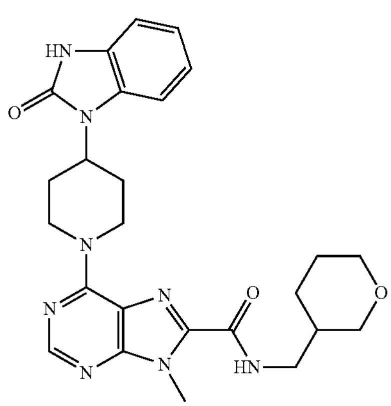 [SMILES: Cn1c(C(=O)NCC2CCCOC2)nc2c(N3CCC(n4c(=O)[nH]c5ccccc54)CC3)ncnc21] | 9-methyl-6-[4-(2-oxo-2,3-dihydro-1H-benzimidazol-1-yl)piperidin-1-yl]-N-(tetrahydro-2H-pyran-3-ylmethyl)-9H-purine-8-carboxamide |

TABLE 1-continued

| Compound Number | Structure | Name |
|---|---|---|
| 12 | 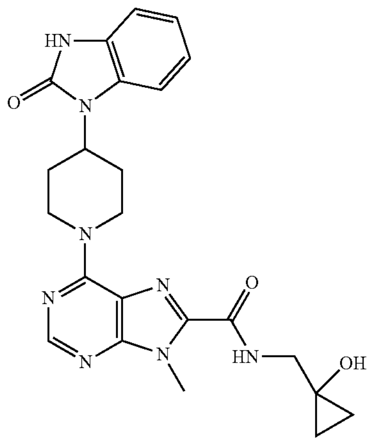 [SMILES: Cn1c(C(=O)NCC2(O)CC2)nc2c(N3CCC(n4c(=O)[nH]c5ccccc54)CC3)ncnc21] | N-[(1-hydroxycyclopropyl)methyl]-9-methyl-6-[4-(2-oxo-2,3-dihydro-1H-benzimidazol-1-yl)piperidin-1-yl]-9H-purine-8-carboxamide |
| 13 | 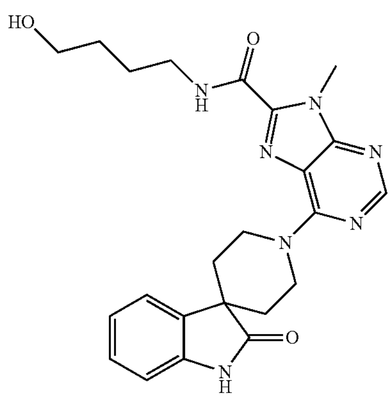 [SMILES: Cn1c(C(=O)NCCCCO)nc2c(N3CCC4(CC3)C(=O)Nc3ccccc34)ncnc21] | N-(4-hydroxybutyl)-9-methyl-6-(2-oxo-1,2-dihydro-1'H-spiro[indole-3,4'-piperidin]-1'-yl)-9H-purine-8-carboxamide |
| 14 | 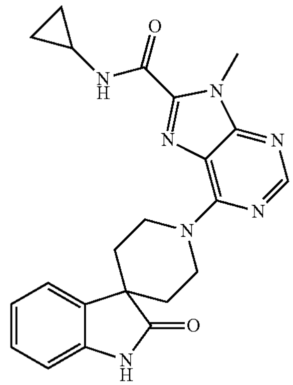 [SMILES: Cn1c(C(=O)NC2CC2)nc2c(N3CCC4(CC3)C(=O)Nc3ccccc34)ncnc21] | N-cyclopropyl-9-methyl-6-(2-oxo-1,2-dihydro-1'H-spiro[indole-3,4'-piperidin]-1'-yl)-9H-purine-8-carboxamide |

TABLE 1-continued

| Compound Number | Structure | Name |
|---|---|---|
| 15 | 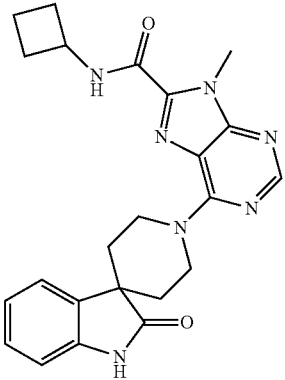 [SMILES: Cn1c(C(=O)NC2CCC2)nc2c(N3CCC4(CC3)C(=O)Nc3ccccc34)ncnc21] | N-cyclobutyl-9-methyl-6-(2-oxo-1,2-dihydro-1'H-spiro[indole-3,4'-piperidin]-1'-yl)-9H-purine-8-carboxamide |
| 16 | 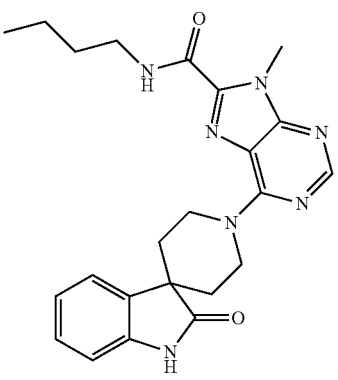 [SMILES: CCCCNC(=O)c1nc2c(N3CCC4(CC3)C(=O)Nc3ccccc34)ncnc2n1C] | N-butyl-9-methyl-6-(2-oxo-1,2-dihydro-1'H-spiro[indole-3,4'-piperidin]-1'-yl)-9H-purine-8-carboxamide |
| 17 | 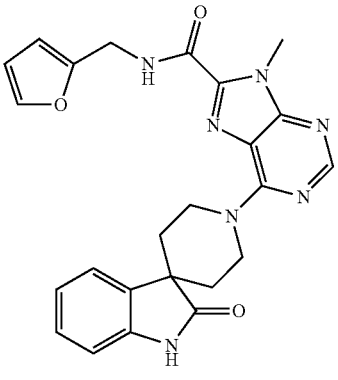 | N-(furan-2-ylmethyl)-9-methyl-6-(2-oxo-1,2-dihydro-1'H-spiro[indole-3,4'-piperidin]-1'-yl)-9H-purine-8-carboxamide |
| 18 | 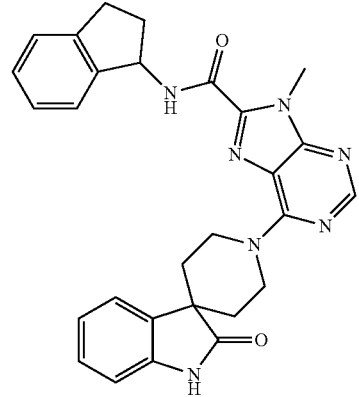 [SMILES: Cn1c(C(=O)NC2CCc3ccccc32)nc2c(N3CCC4(CC3)C(=O)Nc3ccccc34)ncnc21] | N-(2,3-dihydro-1H-inden-1-yl)-9-methyl-6-(2-oxo-1,2-dihydro-1'H-spiro[indole-3,4'-piperidin]-1'-yl)-9H-purine-8-carboxamide |

TABLE 1-continued

| Compound Number | Structure | Name |
| --- | --- | --- |
| 19 | 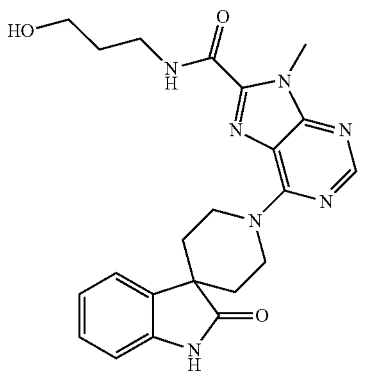 [SMILES: Cn1c(C(=O)NCCCO)nc2c(N3CCC4(CC3)C(=O)Nc3ccccc34)ncnc21] | N-(3-hydroxypropyl)-9-methyl-6-(2-oxo-1,2-dihydro-1'H-spiro[indole-3,4'-piperidin]-1'-yl)-9H-purine-8-carboxamide |
| 20 | 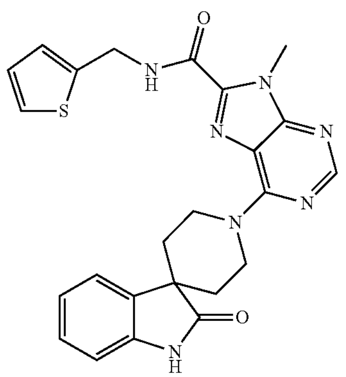 | 9-methyl-6-(2-oxo-1,2-dihydro-1'H-spiro[indole-3,4'-piperidin]-1'-yl)-N-(2-thienylmethyl)-9H-purine-8-carboxamide |
| 21 | 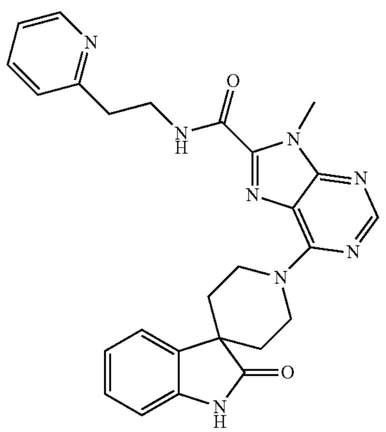 [SMILES: Cn1c(C(=O)NCCc2ccccn2)nc2c(N3CCC4(CC3)C(=O)Nc3ccccc34)ncnc21] | 9-methyl-6-(2-oxo-1,2-dihydro-1'H-spiro[indole-3,4'-piperidin]-1'-yl)-N-(2-pyridin-2-ylethyl)-9H-purine-8-carboxamide |
| 22 | 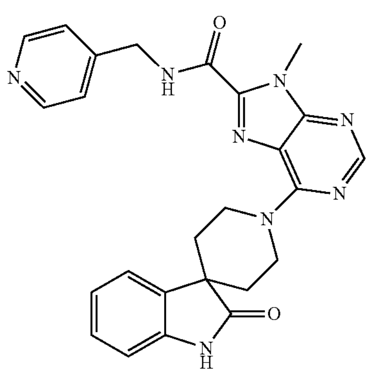 [SMILES: Cn1c(C(=O)NCc2ccncc2)nc2c(N3CCC4(CC3)C(=O)Nc3ccccc34)ncnc21] | 9-methyl-6-(2-oxo-1,2-dihydro-1'H-spiro[indole-3,4'-piperidin]-1'-yl)-N-(pyridin-4-ylmethyl)-9H-purine-8-carboxamide |

TABLE 1-continued

| Compound Number | Structure | Name |
|---|---|---|
| 23 | 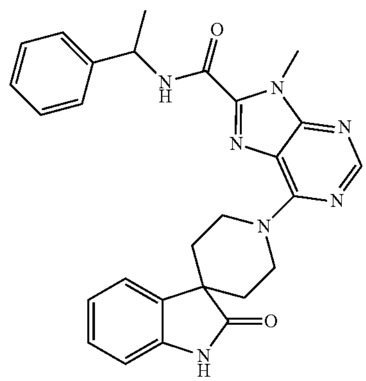 [SMILES: CC(NC(=O)c1nc2c(N3CCC4(CC3)C(=O)Nc3ccccc34)ncnc2n1C)c1ccccc1] | 9-methyl-6-(2-oxo-1,2-dihydro-1'H-spiro[indole-3,4'-piperidin]-1'-yl)-N-(1-phenylethyl)-9H-purine-8-carboxamide |
| 24 | 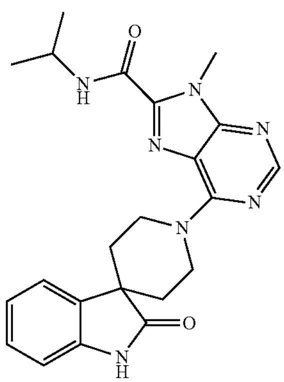 [SMILES: CC(C)NC(=O)c1nc2c(N3CCC4(CC3)C(=O)Nc3ccccc34)ncnc2n1C] | 9-methyl-N-(1-methylethyl)-6-(2-oxo-1,2-dihydro-1'H-spiro[indole-3,4'-piperidin]-1'-yl)-9H-purine-8-carboxamide |
| 25 | 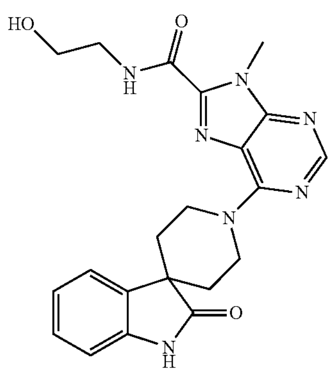 [SMILES: Cn1c(C(=O)NCCO)nc2c(N3CCC4(CC3)C(=O)Nc3ccccc34)ncnc21] | N-(2-hydroxyethyl)-9-methyl-6-(2-oxo-1,2-dihydro-1'H-spiro[indole-3,4'-piperidin]-1'-yl)-9H-purine-8-carboxamide |
| 26 | 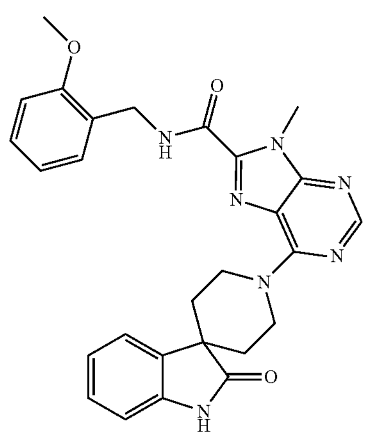 [SMILES: COc1ccccc1CNC(=O)c1nc2c(N3CCC4(CC3)C(=O)Nc3ccccc34)ncnc2n1C] | 9-methyl-N-{[2-(methyloxy)phenyl]methyl}-6-(2-oxo-1,2-dihydro-1'H-spiro[indole-3,4'-piperidin]-1'-yl)-9H-purine-8-carboxamide |

TABLE 1-continued

| Compound Number | Structure | Name |
|---|---|---|
| 27 | 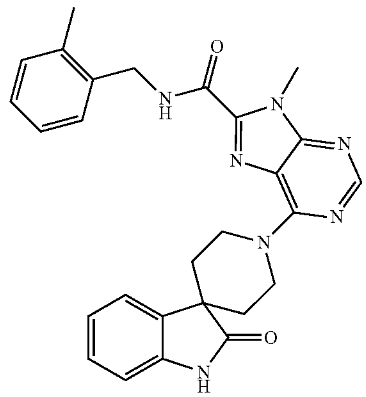 [SMILES: Cc1ccccc1CNC(=O)c1nc2c(N3CCC4(CC3)C(=O)Nc3ccccc34)ncnc2n1C] | 9-methyl-N-[(2-methylphenyl)methyl]-6-(2-oxo-1,2-dihydro-1'H-spiro[indole-3,4'-piperidin]-1'-yl)-9H-purine-8-carboxamide |
| 28 | 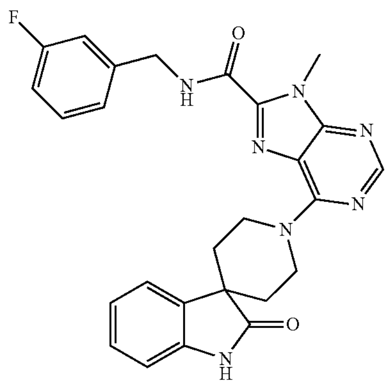 [SMILES: Cn1c(C(=O)NCc2cccc(F)c2)nc2c(N3CCC4(CC3)C(=O)Nc3ccccc34)ncnc21] | N-[(3-fluorophenyl)methyl]-9-methyl-6-(2-oxo-1,2-dihydro-1'H-spiro[indole-3,4'-piperidin]-1'-yl)-9H-purine-8-carboxamide |
| 29 | 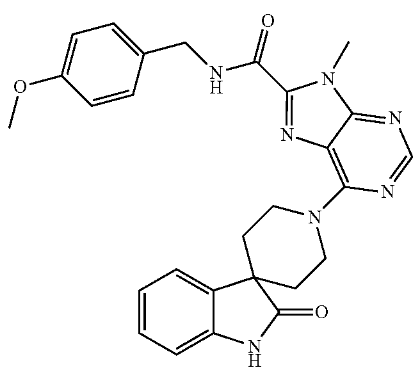 [SMILES: COc1ccc(CNC(=O)c2nc3c(N4CCC5(CC4)C(=O)Nc4ccccc45)ncnc3n2C)cc1] | 9-methyl-N-{[4-(methyloxy)phenyl]methyl}-6-(2-oxo-1,2-dihydro-1'H-spiro[indole-3,4'-piperidin]-1'-yl)-9H-purine-8-carboxamide |
| 30 | 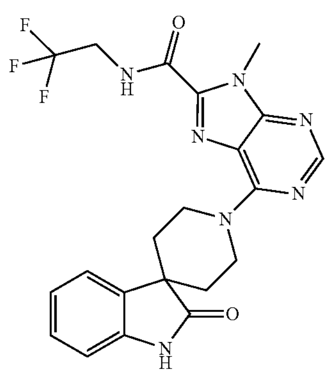 [SMILES: Cn1c(C(=O)NCC(F)(F)F)nc2c(N3CCC4(CC3)C(=O)Nc3ccccc34)ncnc21] | 9-methyl-6-(2-oxo-1,2-dihydro-1'H-spiro[indole-3,4'-piperidin]-1'-yl)-N-(2,2,2-trifluoroethyl)-9H-purine-8-carboxamide |

TABLE 1-continued

| Compound Number | Structure | Name |
|---|---|---|
| 31 | 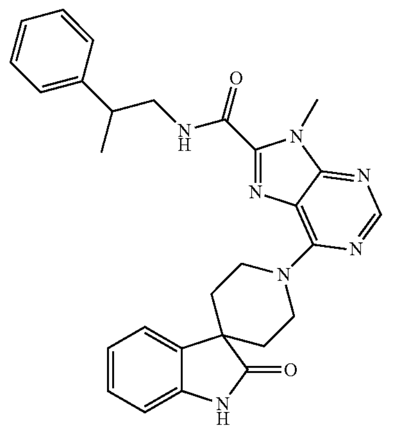 [SMILES: CC(CNC(=O)c1nc2c(N3CCC4(CC3)C(=O)Nc3ccccc34)ncnc2n1C)c1ccccc1] | 9-methyl-6-(2-oxo-1,2-dihydro-1'H-spiro[indole-3,4'-piperidin]-1'-yl)-N-(2-phenylpropyl)-9H-purine-8-carboxamide |
| 32 | 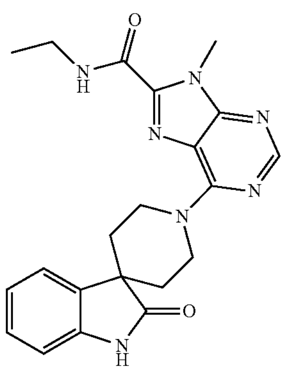 [SMILES: CCNC(=O)c1nc2c(N3CCC4(CC3)C(=O)Nc3ccccc34)ncnc2n1C] | N-ethyl-9-methyl-6-(2-oxo-1,2-dihydro-1'H-spiro[indole-3,4'-piperidin]-1'-yl)-9H-purine-8-carboxamide |
| 33 | 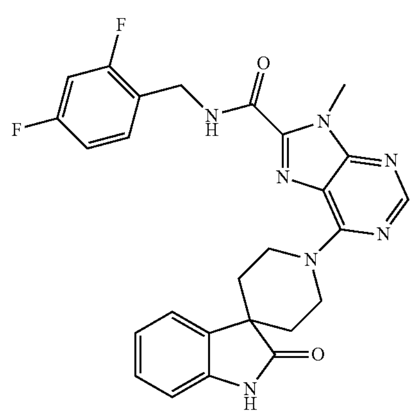 [SMILES: Cn1c(C(=O)NCc2ccc(F)cc2F)nc2c(N3CCC4(CC3)C(=O)Nc3ccccc34)ncnc21] | N-[(2,4-difluorophenyl)methyl]-9-methyl-6-(2-oxo-1,2-dihydro-1'H-spiro[indole-3,4'-piperidin]-1'-yl)-9H-purine-8-carboxamide |
| 34 | 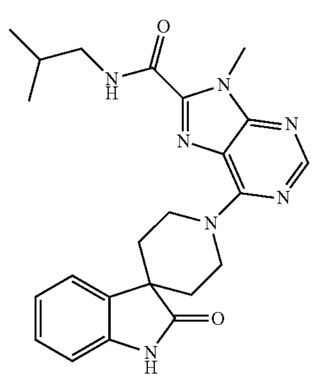 [SMILES: CC(C)CNC(=O)c1nc2c(N3CCC4(CC3)C(=O)Nc3ccccc34)ncnc2n1C] | 9-methyl-N-(2-methylpropyl)-6-(2-oxo-1,2-dihydro-1'H-spiro[indole-3,4'-piperidin]-1'-yl)-9H-purine-8-carboxamide |

TABLE 1-continued

| Compound Number | Structure | Name |
|---|---|---|
| 35 | 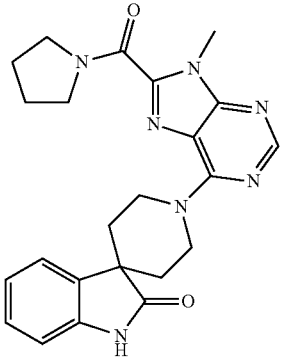 [SMILES: Cn1c(C(=O)N2CCCC2)nc2c(N3CCC4(CC3)C(=O)Nc3ccccc34)ncnc21] | 1'-[9-methyl-8-(pyrrolidin-1-ylcarbonyl)-9H-purin-6-yl]spiro[indole-3,4'-piperidin]-2(1H)-one |
| 36 | 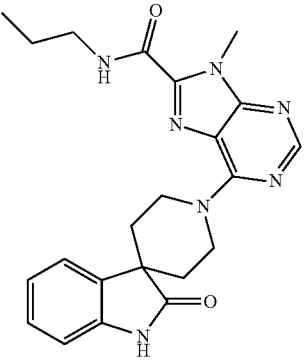 [SMILES: CCCNC(=O)c1nc2c(N3CCC4(CC3)C(=O)Nc3ccccc34)ncnc2n1C] | 9-methyl-6-(2-oxo-1,2-dihydro-1'H-spiro[indole-3,4'-piperidin]-1'-yl)-N-propyl-9H-purine-8-carboxamide |
| 37 | 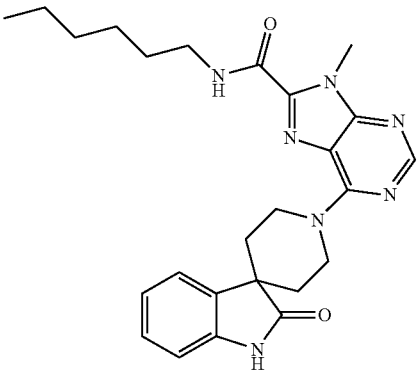 [SMILES: CCCCCCNC(=O)c1nc2c(N3CCC4(CC3)C(=O)Nc3ccccc34)ncnc2n1C] | N-hexyl-9-methyl-6-(2-oxo-1,2-dihydro-1'H-spiro[indole-3,4'-piperidin]-1'-yl)-9H-purine-8-carboxamide |
| 38 | 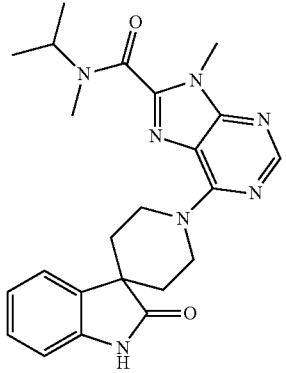 [SMILES: CC(C)N(C)C(=O)c1nc2c(N3CCC4(CC3)C(=O)Nc3ccccc34)ncnc2n1C] | N,9-dimethyl-N-(1-methylethyl)-6-(2-oxo-1,2-dihydro-1'H-spiro[indole-3,4'-piperidin]-1'-yl)-9H-purine-8-carboxamide |

TABLE 1-continued

| Compound Number | Structure | Name |
|---|---|---|
| 39 | 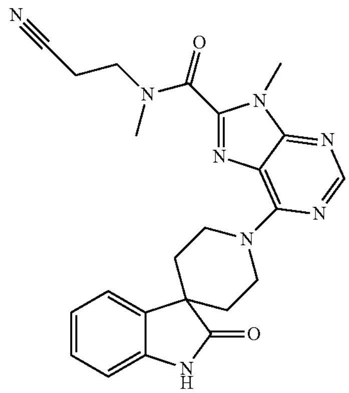 [SMILES: CN(CCC#N)C(=O)c1nc2c(N3CCC4(CC3)C(=O)Nc3ccccc34)ncnc2n1C] | N-(2-cyanoethyl)-N,9-dimethyl-6-(2-oxo-1,2-dihydro-1'H-spiro[indole-3,4'-piperidin]-1'-yl)-9H-purine-8-carboxamide |
| 40 | 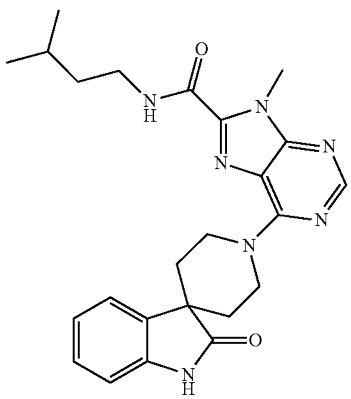 [SMILES: CC(C)CCNC(=O)c1nc2c(N3CCC4(CC3)C(=O)Nc3ccccc34)ncnc2n1C] | 9-methyl-N-(3-methylbutyl)-6-(2-oxo-1,2-dihydro-1'H-spiro[indole-3,4'-piperidin]-1'-yl)-9H-purine-8-carboxamide |
| 41 | 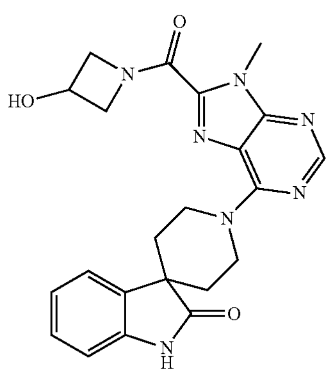 [SMILES: Cn1c(C(=O)N2CC(O)C2)nc2c(N3CCC4(CC3)C(=O)Nc3ccccc34)ncnc21] | 1'-{8-[(3-hydroxyazetidin-1-yl)carbonyl]-9-methyl-9H-purin-6-yl}spiro[indole-3,4'-piperidin]-2(1H)-one |
| 42 | 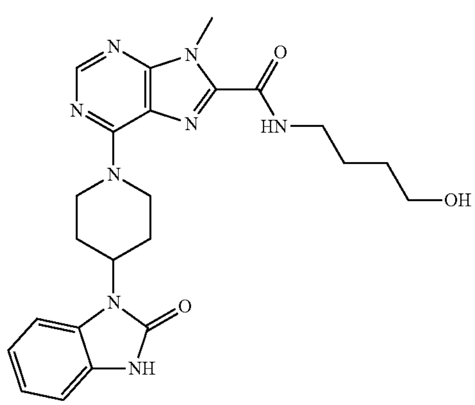 [SMILES: Cn1c(C(=O)NCCCCO)nc2c(N3CCC(n4c(=O)[nH]c5ccccc54)CC3)ncnc21] | N-(4-hydroxybutyl)-9-methyl-6-[4-(2-oxo-2,3-dihydro-1H-benzimidazol-1-yl)piperidin-1-yl]-9H-purine-8-carboxamide |

TABLE 1-continued

| Compound Number | Structure | Name |
|---|---|---|
| 43 | 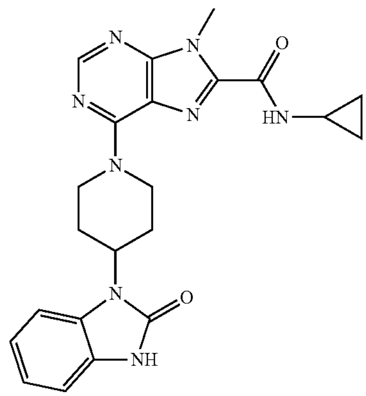 [SMILES: Cn1c(C(=O)NC2CC2)nc2c(N3CCC(n4c(=O)[nH]c5ccccc54)CC3)ncnc21] | N-cyclopropyl-9-methyl-6-[4-(2-oxo-2,3-dihydro-1H-benzimidazol-1-yl)piperidin-1-yl)-9H-purine-8-carboxamide |
| 44 | 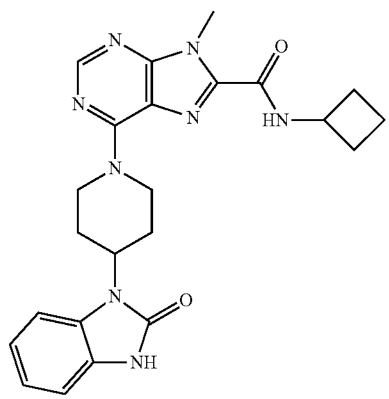 [SMILES: Cn1c(C(=O)NC2CCC2)nc2c(N3CCC(n4c(=O)[nH]c5ccccc54)CC3)ncnc21] | N-cyclobutyl-9-methyl-6[4-(2-oxo-2,3-dihydro-1H-benzimidazol-1-yl)piperidin-1-yl]-9H-purine-8-carboxamide |
| 45 | 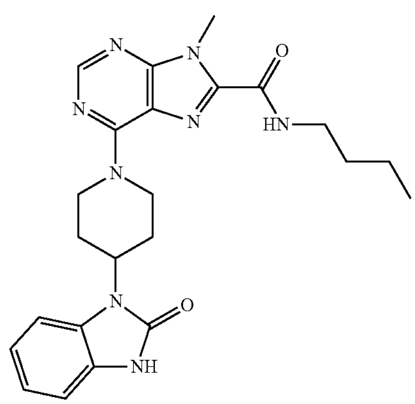 [SMILES: CCCCNC(=O)c1nc2c(N3CCC(n4c(=O)[nH]c5ccccc54)CC3)ncnc2n1C] | N-butyl-9-methyl-6-[4-(2-oxo-2,3-dihydro-1H-benzimidazol-1-yl)piperidin-1-yl]-9H-purine-8-carboxamide |
| 46 | 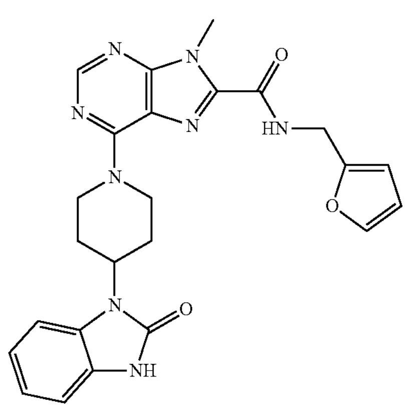 [SMILES: Cn1c(C(=O)NCc2ccco2)nc2c(N3CCC(n4c(=O)[nH]c5ccccc54)CC3)ncnc21] | N-(furan-2-ylmethyl)-9-methyl-6-[4-(2-oxo-2,3-dihydro-1H-benzimidazol-1-yl)piperidin-1-yl]-9H-purine-8-carboxamide |

TABLE 1-continued

| Compound Number | Structure | Name |
|---|---|---|
| 47 | 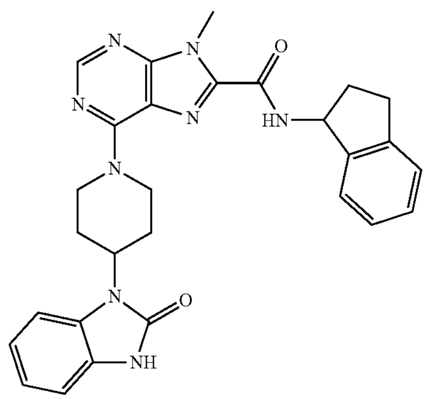 [SMILES: Cn1c(C(=O)NC2CCc3ccccc32)nc2c(N3CCC(n4c(=O)[nH]c5ccccc54)CC3)ncnc21] | N-(2,3-dihydro-1H-inden-1-yl)-9-methyl-6-[4-(2-oxo-2,3-dihydro-1H-benzimidazol-1-yl)piperidin-1-yl]-9H-purine-8-carboxamide |
| 48 | 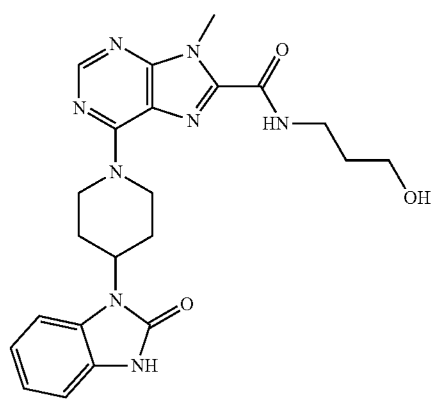 [SMILES: Cn1c(C(=O)NCCCO)nc2c(N3CCC(n4c(=O)[nH]c5ccccc54)CC3)ncnc21] | N-(3-hydroxypropyl)-9-methyl-6-[4-(2-oxo-2,3-dihydro-1H-benzimidazol-1-yl)piperidin-1-yl]-9H-purine-8-carboxamide |
| 49 | 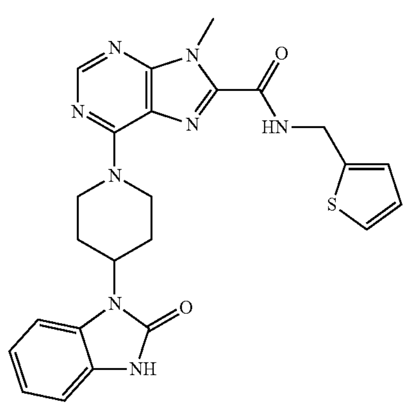 | 9-methyl-6-[4-(2-oxo-2,3-dihydro-1H-benzimidazol-1-yl)piperidin-1-yl]-N-(2-thienylmethyl)-9H-purine-8-carboxamide |

TABLE 1-continued

| Compound Number | Structure | Name |
|---|---|---|
| 50 | 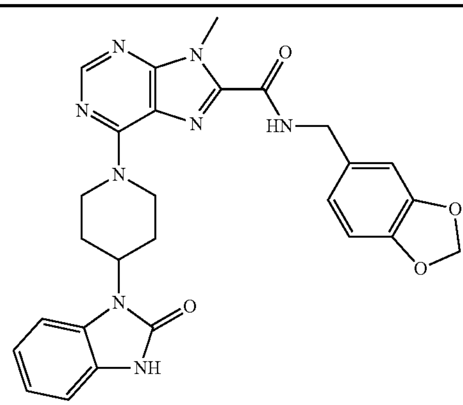 | N-(1,3-benzodioxol-5-ylmethyl)-9-methyl-6-[4-(2-oxo-2,3-dihydro-1H-benzimidazol-1-yl)piperidin-1-yl]-9H-purine-8-carboxamide |
| 51 | 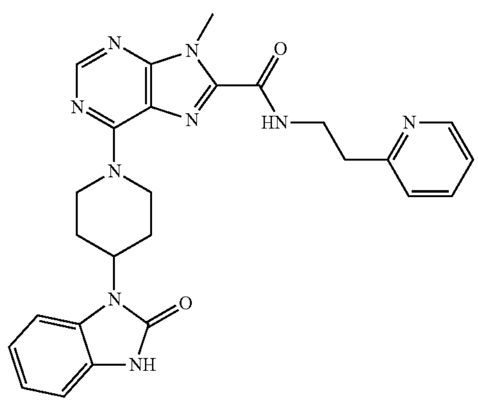 [SMILES: Cn1c(C(=O)NCCc2ccccn2)nc2c(N3CCC(n4c(=O)[nH]c5ccccc54)CC3)ncnc21] | 9-methyl-6-[4-(2-oxo-2,3-dihydro-1H-benzimidazol-1-yl)piperidin-1-yl]-N-(2-pyridin-2-ylethyl)-9H-purine-8-carboxamide |
| 52 | 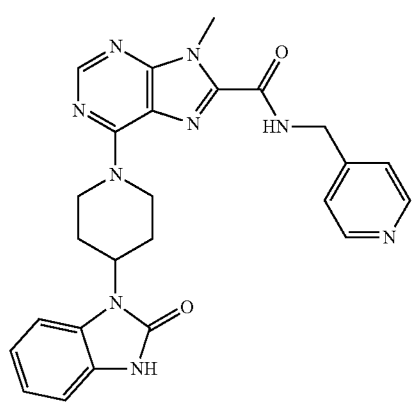 [SMILES: Cn1c(C(=O)NCc2ccncc2)nc2c(N3CCC(n4c(=O)[nH]c5ccccc54)CC3)ncnc21] | 9-methyl-6-[4-(2-oxo-2,3-dihydro-1H-benzimidazol-1-yl)piperidin-1-yl]-N-(pyridin-4-ylmethyl)-9H-purine-8-carboxamide |
| 53 | 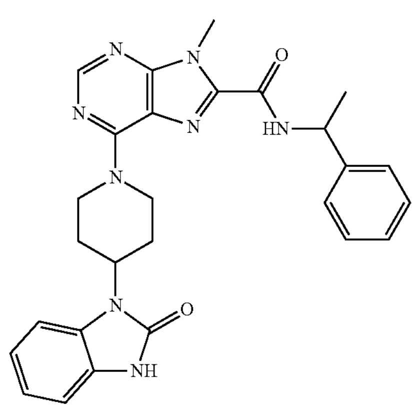 [SMILES: CC(NC(=O)c1nc2c(N3CCC(n4c(=O)[nH]c5ccccc54)CC3)ncnc2n1C)c1ccccc1] | 9-methyl-6-[4-(2-oxo-2,3-dihydro-1H-benzimidazol-1-yl)piperidin-1-yl]-N-(1-phenylethyl)-9H-purine-8-carboxamide |

TABLE 1-continued

| Compound Number | Structure | Name |
|---|---|---|
| 54 | 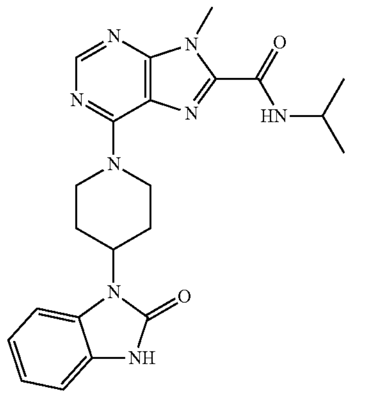 [SMILES: CC(C)NC(=O)c1nc2c(N3CCC(n4c(=O)[nH]c5ccccc54)CC3)ncnc2n1C] | 9-methyl-N-(1-methylethyl)-6-[4-(2-oxo-2,3-dihydro-1H-benzimidazol-1-yl)piperidin-1-yl]-9H-purine-8-carboxamide |
| 55 | 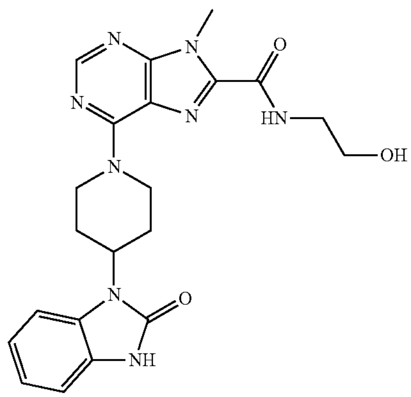 [SMILES: Cn1c(C(=O)NCCO)nc2c(N3CCC(n4c(=O)[nH]c5ccccc54)CC3)ncnc21] | N-(2-hydroxyethyl)-9-methyl-6-[4-(2-oxo-2,3-dihydro-1H-benzimidazol-1-yl)piperidin-1-yl]-9H-purine-8-carboxamide |
| 56 | 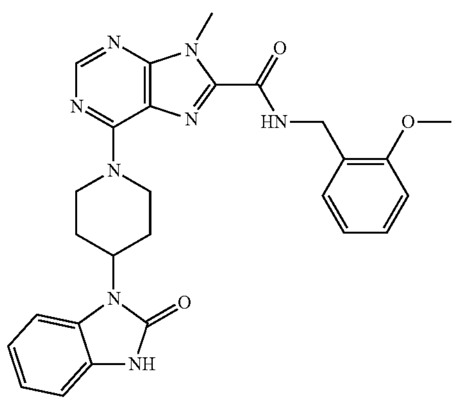 [SMILES: COc1ccccc1CNC(=O)c1nc2c(N3CCC(n4c(=O)[nH]c5ccccc54)CC3)ncnc2n1C] | 9-methyl-N-{[2-(methyloxy)phenyl]methyl}-6-[4-(2-oxo-2,3-dihydro-1H-benzimidazol-1-yl)piperidin-1-yl]-9H-purine-8-carboxamide |
| 57 | 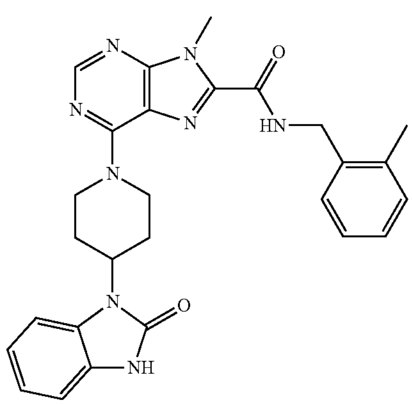 [SMILES: Cc1ccccc1CNC(=O)c1nc2c(N3CCC(n4c(=O)[nH]c5ccccc54)CC3)ncnc2n1C] | 9-methyl-N-[(2-methylphenypmethyl]-6-[4-(2-oxo-2,3-dihydro-1H-benzimidazol-1-yl)piperidin-1-yl]-9H-purine-8-carboxamide |

TABLE 1-continued

| Compound Number | Structure | Name |
|---|---|---|
| 58 | 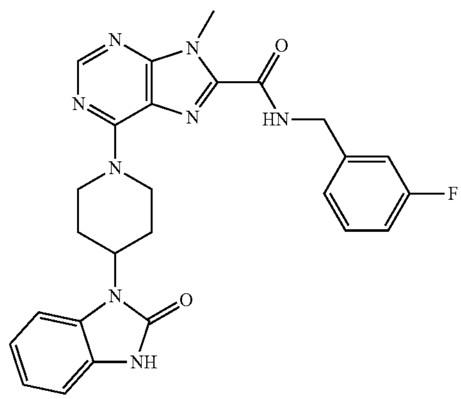 [SMILES: Cn1c(C(=O)NCc2cccc(F)c2)nc2c(N3CCC(n4c(=O)[nH]c5ccccc54)CC3)ncnc21] | N-[(3-fluorophenyl)methyl]-9-methyl-6-[4-(2-oxo-2,3-dihydro-1H-benzimidazol-1-yl)piperidin-1-yl]-9H-purine-8-carboxamide |
| 59 | 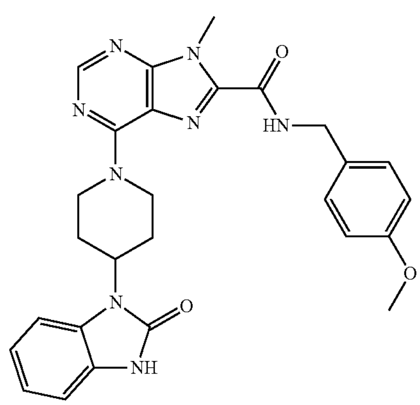 [SMILES: COc1ccc(CNC(=O)c2nc3c(N4CCC(n5c(=O)[nH]c6ccccc65)CC4)ncnc3n2C)cc1] | 9-methyl-N-{[4-(methyloxy)phenyl]methyl}-6-[4-(2-oxo-2,3-dihydro-1H-benzimidazol-1-yl)piperidin-1-yl]-9H-purine-8-carboxamide |
| 60 | 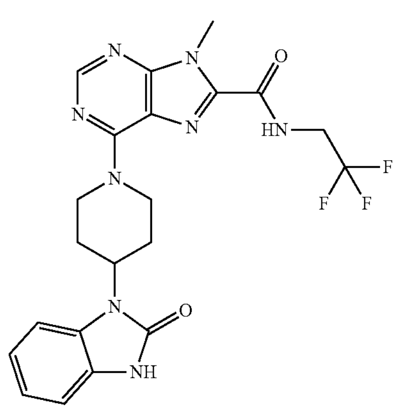 [SMILES: Cn1c(C(=O)NCC(F)(F)F)nc2c(N3CCC(n4c(=O)[nH]c5ccccc54)CC3)ncnc21] | 9-methyl-6-[4-(2-oxo-2,3-dihydro-1H-benzimidazol-1-yl)piperidin-1-yl]-N-(2,2,2-trifluoroethyl)-9H-purine-8-carboxamide |

TABLE 1-continued

| Compound Number | Structure | Name |
|---|---|---|
| 61 | 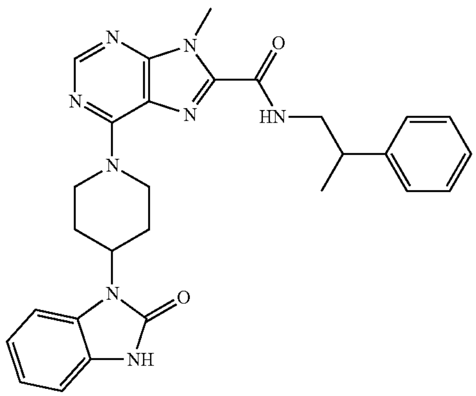 [SMILES: CC(CNC(=O)c1nc2c(N3CCC(n4c(=O)[nH]c5ccccc54)CC3)ncnc2n1C)c1ccccc1] | 9-methyl-6-[4-(2-oxo-2,3-dihydro-1H-benzimidazol-1-yl)piperidin-1-yl]-N-(2-phenylpropyl)-9H-purine-8-carboxamide |
| 62 | 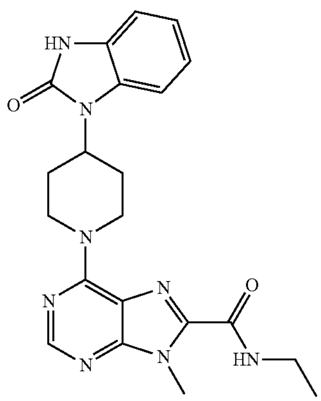 [SMILES: CCNC(=O)c1nc2c(N3CCC(n4c(=O)[nH]c5ccccc54)CC3)ncnc2n1C] | N-ethyl-9-methyl-6-[4-(2-oxo-2,3-dihydro-1H-benzimidazol-1-yl)piperidin-1-yl]-9H-purine-8-carboxamide |
| 63 | 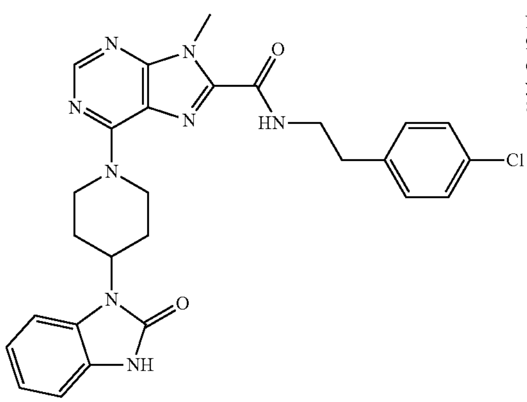 [SMILES: Cn1c(C(=O)NCCc2ccc(Cl)cc2)nc2c(N3CCC(n4c(=O)[nH]c5ccccc54)CC3)ncnc21] | N-[2-(4-chlorophenyl)ethyl]-9-methyl-6-[4-(2-oxo-2,3-dihydro-1H-benzimidazol-1-yl)piperidin-1-yl]-9H-purine-8-carboxamide |
| 64 | 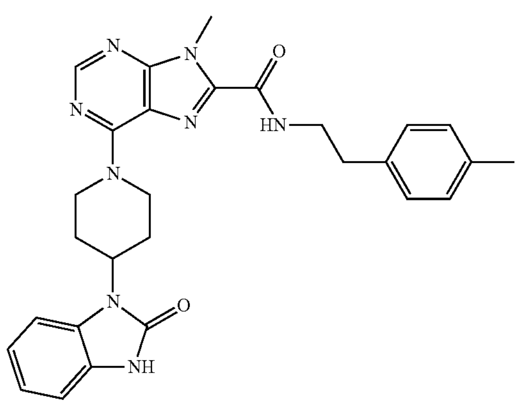 [SMILES: Cc1ccc(CCNC(=O)c2nc3c(N4CCC(n5c(=O)[nH]c6ccccc65)CC4)ncnc3n2C)cc1] | 9-methyl-N-[2-(4-methylphenyl)ethyl]-6-[4-(2-oxo-2,3-dihydro-1H-benzimidazol-1-yl)piperidin-1-yl]-9H-purine-8-carboxamide |

TABLE 1-continued

| Compound Number | Structure | Name |
|---|---|---|
| 65 | 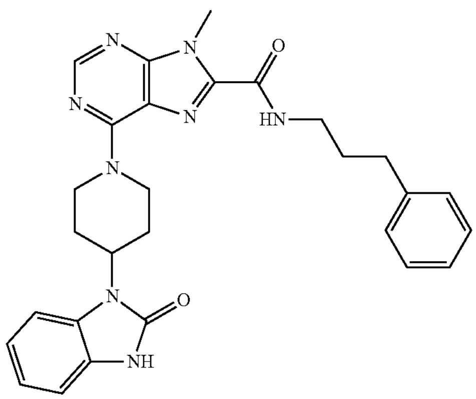 [SMILES: Cn1c(C(=O)NCCCc2ccccc2)nc2c(N3CCC(n4c(=O)[nH]c5ccccc54)CC3)ncnc21] | 9-methyl-6-[4-(2-oxo-2,3-dihydro-1H-benzimidazol-1-yl)piperidin-1-yl]-N-(3-phenylpropyl)-9H-purine-8-carboxamide |
| 66 | 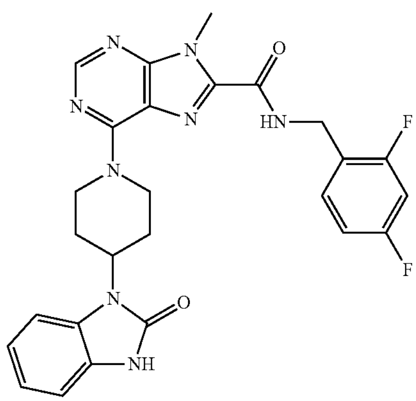 [SMILES: Cn1c(C(=O)NCc2ccc(F)cc2F)nc2c(N3CCC(n4c(=O)[nH]c5ccccc54)CC3)ncnc21] | N-[(2,4-difluorophenyp methyl]-9-methyl-6-[4-(2-oxo-2,3-dihydro-1H-benzimidazol-1-yl)piperidin-1-yl]-9H-purine-8-carboxamide |
| 67 | 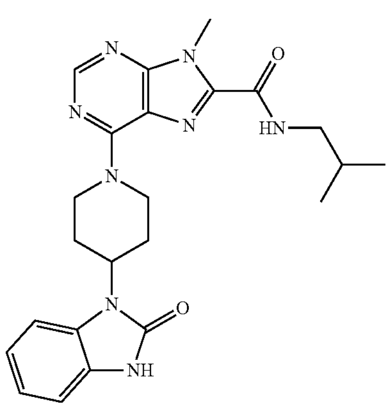 [SMILES: CC(C)CNC(=O)c1nc2c(N3CCC(n4c(=O)[nH]c5ccccc54)CC3)ncnc2n1C] | 9-methyl-N-(2-methylpropyl)-6-[4-(2-oxo-2,3-dihydro-1H-benzimidazol-1-yl)piperidin-1-yl]-9H-purine-8-carboxamide |

TABLE 1-continued

| Compound Number | Structure | Name |
|---|---|---|
| 68 | 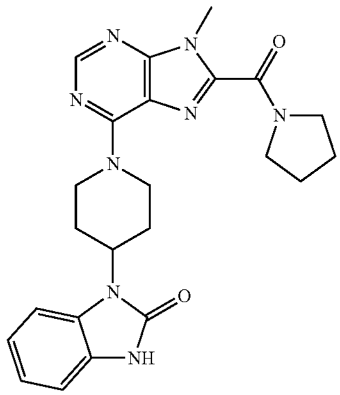 [SMILES: Cn1c(C(=O)N2CCCC2)nc2c(N3CCC(n4c(=O)[nH]c5ccccc54)CC3)ncnc21] | 1-{1-[9-methyl-8-(pyrrolidin-1-ylcarbonyl)-9H-purin-6-yl]piperidin-4-yl}-1,3-dihydro-2H-benzimidazol-2-one |
| 69 | 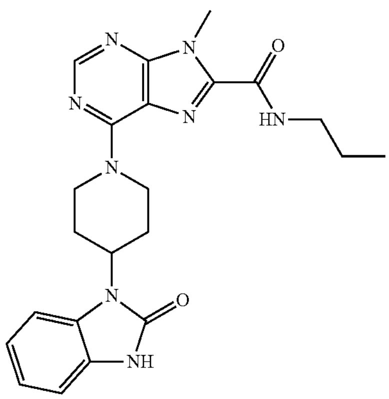 [SMILES: CCCNC(=O)c1nc2c(N3CCC(n4c(=O)[nH]c5ccccc54)CC3)ncnc2n1C] | 9-methyl-6-[4-(2-oxo-2,3-dihydro-1H-benzimidazol-1-yl)piperidin-1-yl]-N-propyl-9H-purine-8-carboxamide |
| 70 | 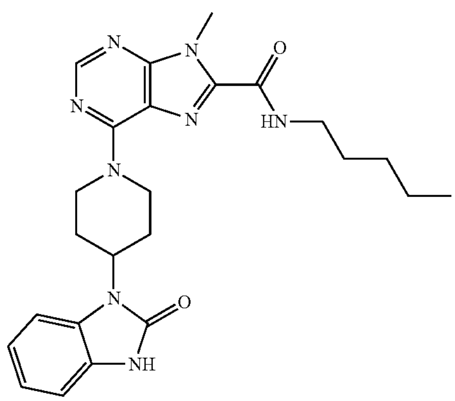 [SMILES: CCCCCNC(=O)c1nc2c(N3CCC(n4c(=O)[nH]c5ccccc54)CC3)ncnc2n1C] | 9-methyl-6-[4-(2-oxo-2,3-dihydro-1H-benzimidazol-1-yl)piperidin-1-yl]-N-pentyl-9H-purine-8-carboxamide |
| 71 | 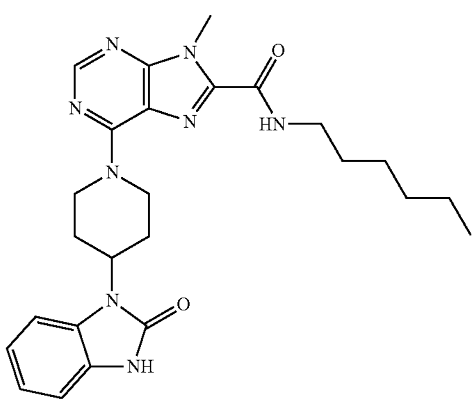 [SMILES: CCCCCCNC(=O)c1nc2c(N3CCC(n4c(=O)[nH]c5ccccc54)CC3)ncnc2n1C] | N-hexyl-9-methyl-6-[4-(2-oxo-2,3-dihydro-1H-benzimidazol-1-yl)piperidin-1-yl]-9H-purine-8-carboxamide |

TABLE 1-continued

| Compound Number | Structure | Name |
|---|---|---|
| 72 | 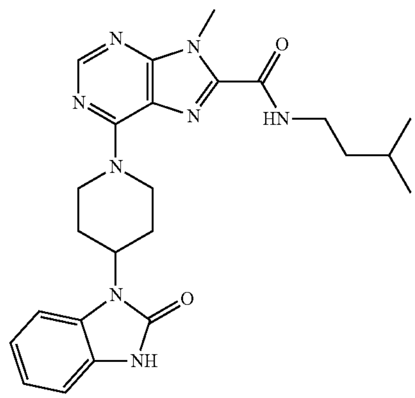 [SMILES: CC(C)CCNC(=O)c1nc2c(N3CCC(n4c(=O)[nH]c5ccccc54)CC3)ncnc2n1C] | 9-methyl-N-(3-methylbutyl)-6-[4-(2-oxo-2,3-dihydro-1H-benzimidazol-1-yl)piperidin-1-yl]-9H-purine-8-carboxamide |
| 73 | 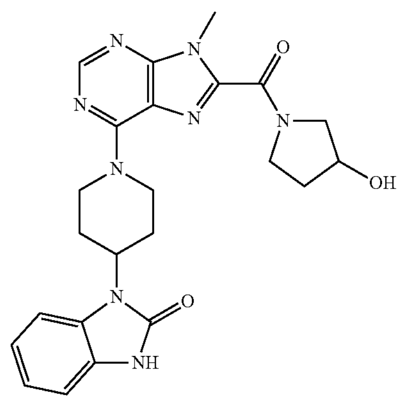 [SMILES: Cn1c(C(=O)N2CCC(O)C2)nc2c(N3CCC(n4c(=O)[nH]c5ccccc54)CC3)ncnc21] | 1-(1-{8-[(3-hydroxypyrrolidin-1-yl)carbonyl]-9-methyl-9H-purin-6-yl}piperidin-4-yl)-1,3-dihydro-2H-benzimidazol-2-one |
| 74 | 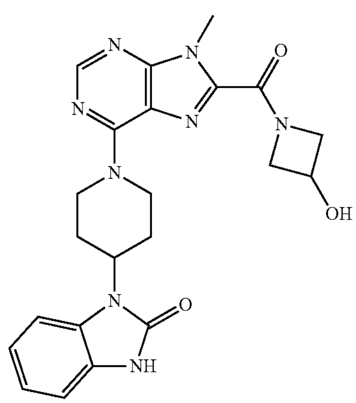 [SMILES: Cn1c(C(=O)N2CC(O)C2)nc2c(N3CCC(n4c(=O)[nH]c5ccccc54)CC3)ncnc21] | 1-(1-{8-[(3-hydroxyazetidin-1-yl)carbonyl]-9-methyl-9H-purin-6-yl}piperidin-4-yl)-1,3-dihydro-2H-benzimidazol-2-one |
| 75 | 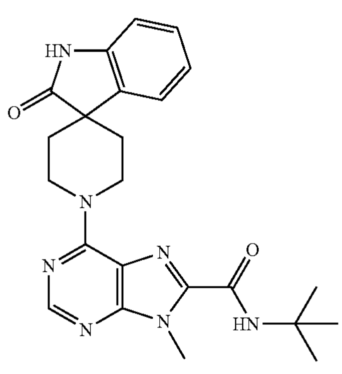 [SMILES: Cn1c(C(=O)NC(C)(C)C)nc2c(N3CCC4(CC3)C(=O)Nc3ccccc34)ncnc21] | N-(1,1-dimethylethyl)-9-methyl-6-(2-oxo-1,2-dihydro-1'H-spiro[indole-3,4'-piperidin]-1'-yl)-9H-purine-8-carboxamide |

TABLE 1-continued

| Compound Number | Structure | Name |
|---|---|---|
| 76 | 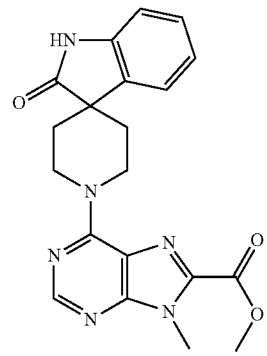 [SMILES: COC(=O)c1nc2c(N3CCC4(CC3)C(=O)Nc3ccccc34)ncnc2n1C] | methyl 9-methyl-6-(2-oxo-1,2-dihydro-1'H-spiro[indole-3,4'-piperidin]-1'-yl)-9H-purine-8-carboxylate |
| 77 | 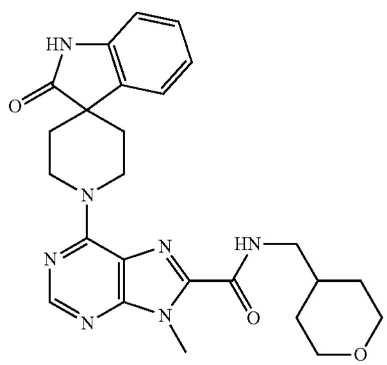 [SMILES: Cn1c(C(=O)NCC2CCOCC2)nc2c(N3CCC4(CC3)C(=O)Nc3ccccc34)ncnc21] | 9-methyl-6-(2-oxo-1,2-dihydro-1'H-spiro[indole-3,4'-piperidin]-1'-yl)-N-(tetrahydro-2H-pyran-4-ylmethyl)-9H-purine-8-carboxamide |
| 78 | 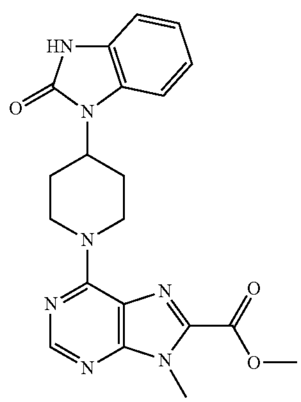 [SMILES: COC(=O)c1nc2c(N3CCC(n4c(=O)[nH]c5ccccc54)CC3)ncnc2n1C] | methyl 9-methyl-6-[4-(2-oxo-2,3-dihydro-1H-benzimidazol-1-yl)piperidin-1-yl]-9H-purine-8-carboxylate |
| 79 | 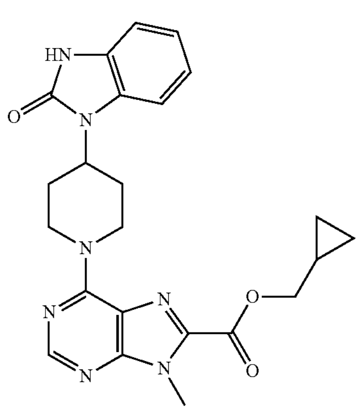 [SMILES: Cn1c(C(=O)OCC2CC2)nc2c(N3CCC(n4c(=O)[nH]c5ccccc54)CC3)ncnc21] | cyclopropylmethyl 9-methyl-6-[4-(2-oxo-2,3-dihydro-1H-benzimidazol-1-yl)piperidin-1-yl]-9H-purine-8-carboxylate |

TABLE 1-continued

| Compound Number | Structure | Name |
|---|---|---|
| 80 | 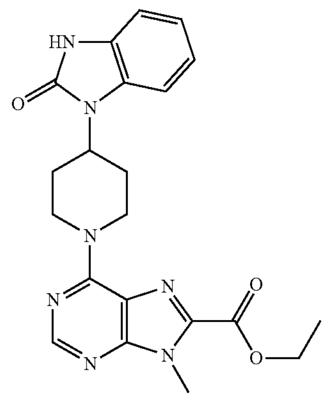 [SMILES: CCOC(=O)c1nc2c(N3CCC(n4c(=O)[nH]c5ccccc54)CC3)ncnc2n1C] | ethyl 9-methyl-6-[4-(2-oxo-2,3-dihydro-1H-benzimidazol-1-yl)piperidin-1-yl]-9H-purine-8-carboxylate |
| 81 | 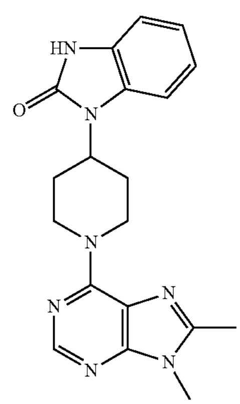 [SMILES: Cc1nc2c(N3CCC(n4c(=O)[nH]c5ccccc54)CC3)ncnc2n1C] | 1-[1-(8,9-dimethyl-9H-purin-6-yl)piperidin-4-yl]-1,3-dihydro-2H-benzimidazol-2-one |
| 82 | 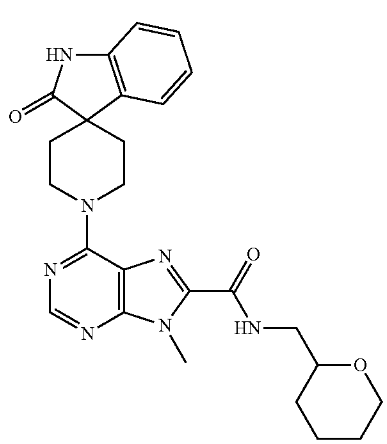 [SMILES: Cn1c(C(=O)NCC2CCCCO2)nc2c(N3CCC4(CC3)C(=O)Nc3ccccc34)ncnc21] | 9-methyl-6-(2-oxo-1,2-dihydro-1'H-spiro[indole-3,4'-piperidin]-1'-yl)-N-(tetrahydro-2H-pyran-2-ylmethyl)-9H-purine-8-carboxamide |

TABLE 1-continued

| Compound Number | Structure | Name |
|---|---|---|
| 83 | 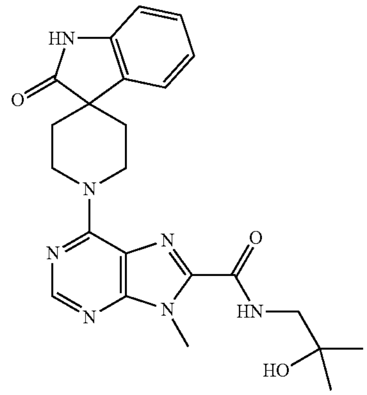 [SMILES: Cn1c(C(=O)NCC(C)(C)O)nc2c(N3CCC4(CC3)C(=O)Nc3ccccc34)ncnc21] | N-(2-hydroxy-2-methylpropyl)-9-methyl-6-(2-oxo-1,2-dihydro-1'H-spiro[indole-3,4'-piperidin]-1'-yl)-9H-purine-8-carboxamide |
| 84 | 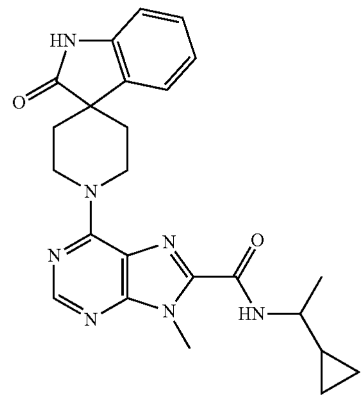 [SMILES: CC(NC(=O)c1nc2c(N3CCC4(CC3)C(=O)Nc3ccccc34)ncnc2n1C)C1CC1] | N-(1-cyclopropylethyl)-9-methyl-6-(2-oxo-1,2-dihydro-1'H-spiro[indole-3,4'-piperidin]-1'-yl)-9H-purine-8-carboxamide |
| 85 | 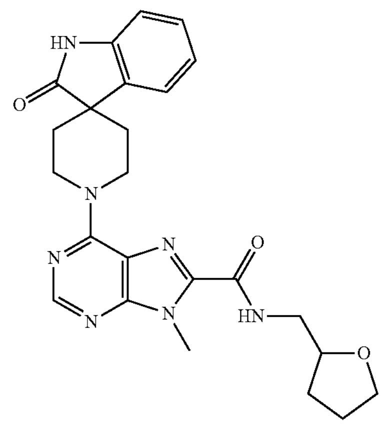 [SMILES: Cn1c(C(=O)NCC2CCCO2)nc2c(N3CCC4(CC3)C(=O)Nc3ccccc34)ncnc21] | 9-methyl-6-(2-oxo-1,2-dihydro-1'H-spiro[indole-3,4'-piperidin]-1'-yl)-N-(tetrahydrofuran-2-ylmethyl)-9H-purine-8-carboxamide |
| 86 | 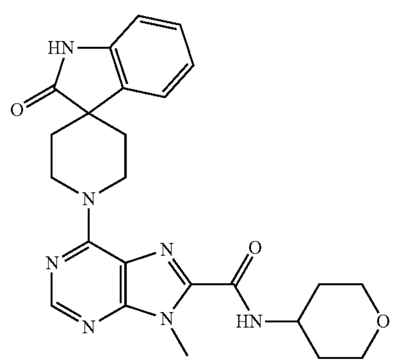 [SMILES: Cn1c(C(=O)NC2CCOCC2)nc2c(N3CCC4(CC3)C(=O)Nc3ccccc34)ncnc21] | 9-methyl-6-(2-oxo-1,2-dihydro-1'H-spiro[indole-3,4'-piperidin]-1'-yl)-N-(tetrahydro-2H-pyran-4-yl)-9H-purine-8-carboxamide |

TABLE 1-continued

| Compound Number | Structure | | Name |
|---|---|---|---|
| 87 | 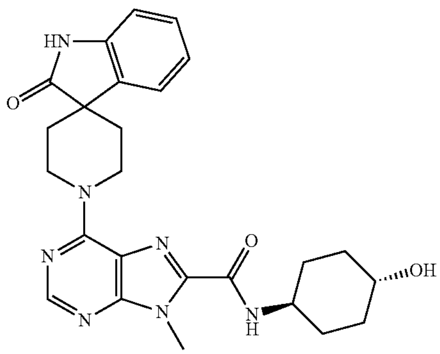 | Chiral | N-(trans-4-hydroxycyclohexyl)-9-methyl-6-(2-oxo-1,2-dihydro-1'H-spiro[indole-3,4'-piperidin]-1'-yl)-9H-purine-8-carboxamide |
| 88 | 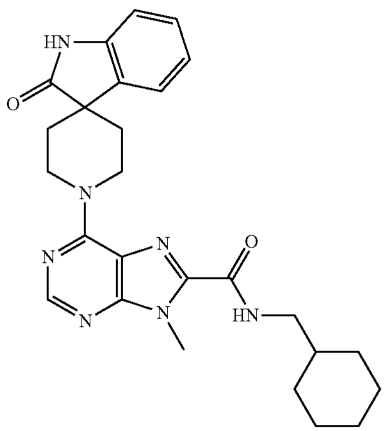 [SMILES: Cn1c(C(=O)NCC2CCCCC2)nc2c(N3CCC4(CC3)C(=O)Nc3ccccc34)ncnc21] | | N-(cyclohexylmethyl)-9-methyl-6-(2-oxo-1,2-dihydro-1'H-spiro[indole-3,4'-piperidin]-1'-yl)-9H-purine-8-carboxamide |
| 89 | 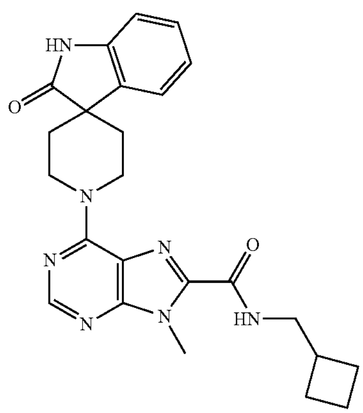 [SMILES: Cn1c(C(=O)NCC2CCC2)nc2c(N3CCC4(CC3)C(=O)Nc3ccccc34)ncnc21] | | N-(cyclobutylmethyl)-9-methyl-6-(2-oxo-1,2-dihydro-1'H-spiro[indole-3,4'-piperidin]-1'-yl)-9H-purine-8-carboxamide |
| 90 | 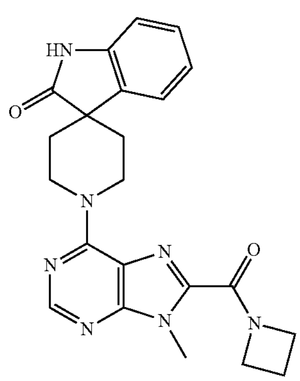 [SMILES: Cn1c(C(=O)N2CCC2)nc2c(N3CCC4(CC3)C(=O)Nc3ccccc34)ncnc21] | | 1'-[8-(azetidin-1-ylcarbonyl)-9-methyl-9H-purin-6-yl]spiro[indole-3,4'-piperidin]-2(1H)-one |

TABLE 1-continued

| Compound Number | Structure | Name |
|---|---|---|
| 91 | 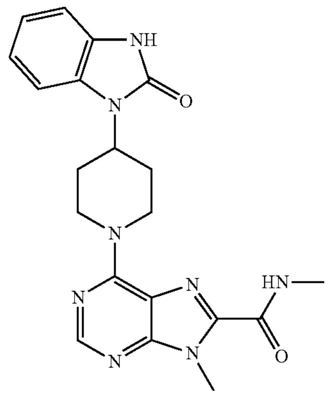 [SMILES: CNC(=O)c1nc2c(N3CCC(n4c(=O)[nH]c5ccccc54)CC3)ncnc2n1C] | N,9-dimethyl-6-[4-(2-oxo-2,3-dihydro-1H-benzimidazol-1-yl)piperidin-1-yl]-9H-purine-8-carboxamide |
| 92 | 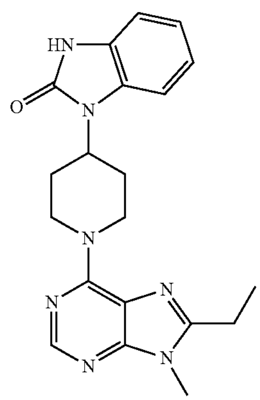 [SMILES: CCc1nc2c(N3CCC(n4c(=O)[nH]c5ccccc54)CC3)ncnc2n1C] | 1-[1-(8-ethyl-9-methyl-9H-purin-6-yl)piperidin-4-yl]-1,3-dihydro-2H-benzimidazol-2-one |
| 93 | 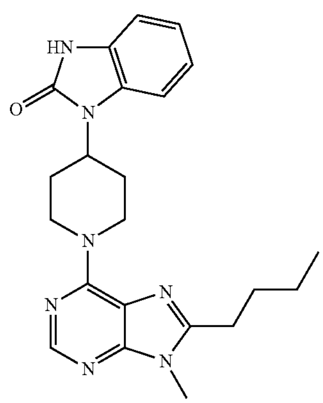 [SMILES: CCCCc1nc2c(N3CCC(n4c(=O)[nH]c5ccccc54)CC3)ncnc2n1C] | 1-[1-(8-butyl-9-methyl-9H-purin-6-yl)piperidin-4-yl]-1,3-dihydro-2H-benzimidazol-2-one |
| 94 | 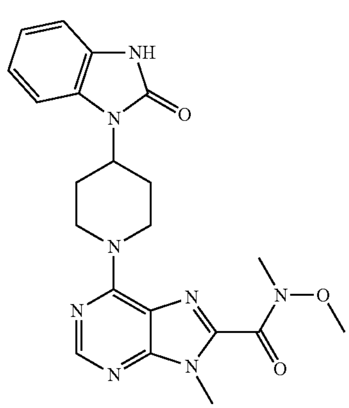 [SMILES: CON(C)C(=O)c1nc2c(N3CCC(n4c(=O)[nH]c5ccccc54)CC3)ncnc2n1C] | N,9-dimethyl-N-(methyloxy)-6-[4-(2-oxo-2,3-dihydro-1H-benzimidazol-1-yl)piperidin-1-yl]-9H-purine-8-carboxamide |

| Compound Number | Structure | Name |
|---|---|---|
| 95 | 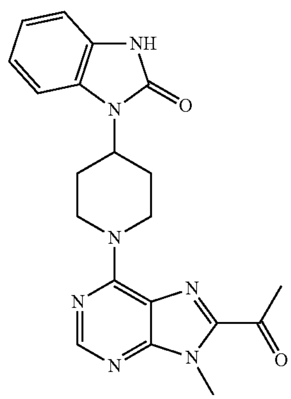 [SMILES: CC(=O)c1nc2c(N3CCC(n4c(=O)[nH]c5ccccc54)CC3)ncnc2n1C] | 1-[1-(8-acetyl-9-methyl-9H-purin-6-yl)piperidin-4-yl]-1,3-dihydro-2H-benzimidazol-2-one |
| 96 | 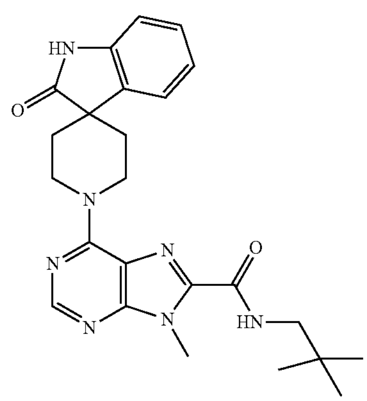 [SMILES: Cn1c(C(=O)NCC(C)(C)C)nc2c(N3CCC4(CC3)C(=O)Nc3ccccc34)ncnc21] | N-(2,2-dimethylpropyl)-9-methyl-6-(2-oxo-1,2-dihydro-1'H-spiro[indole-3,4'-piperidin]-1'-yl)-9H-purine-8-carboxamide |
| 97 | 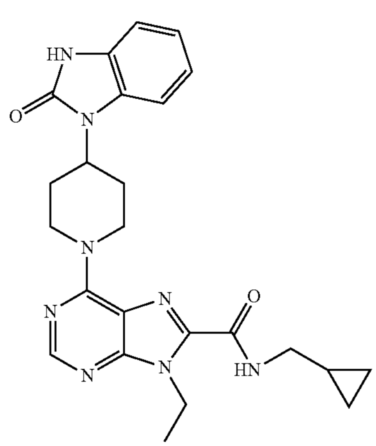 [SMILES: CCn1c(C(=O)NCC2CC2)nc2c(N3CCC(n4c(=O)[nH]c5ccccc54)CC3)ncnc21] | N-(cyclopropylmethyl)-9-ethyl-6-[4-(2-oxo-2,3-dihydro-1H-benzimidazol-1-yl)piperidin-1-yl]-9H-purine-8-carboxamide |

TABLE 1-continued
| Compound Number | Structure | Name |
|---|---|---|
| 98 | 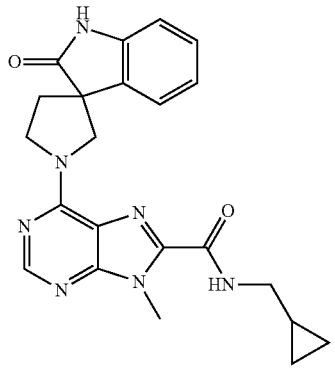 [SMILES: Cn1c(C(=O)NCC2CC2)nc2c(N3CCC4(C3)C(=O)Nc3ccccc34)ncnc21] | N-(cyclopropylmethyl)-9-methyl-6-(2-oxo-1,2-dihydro-1'H-spiro[indole-3,3'-pyrrolidin]-1'-yl)-9H-purine-8-carboxamide |
| 99 | 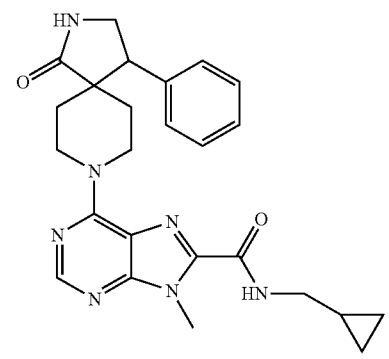 [SMILES: Cn1c(C(=O)NCC2CC2)nc2c(N3CCC4(CC3)C(=O)NCC4c3ccccc3)ncnc21] | N-(cyclopropylmethyl)-9-methyl-6-(1-oxo-4-phenyl-2,8-diazaspiro[4.5]dec-8-yl)-9H-purine-8-carboxamide |
| 100 | 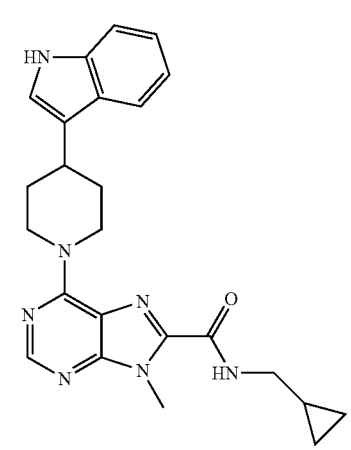 [SMILES: Cn1c(C(=O)NCC2CC2)nc2c(N3CCC(c4c[nH]c5ccccc45)CC3)ncnc21] | N-(cyclopropylmethyl)-6-[4-(1H-indol-3-yl)piperidin-1-yl]-9-methyl-9H-purine-8-carboxamide |

TABLE 1-continued
| Compound Number | Structure | Name |
| --- | --- | --- |
| 101 | 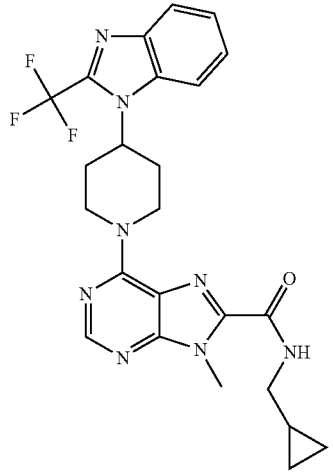 [SMILES: Cn1c(C(=O)NCC2CC2)nc2c(N3CCC(n4c(C(F)(F)F)nc5ccccc54)CC3)ncnc21] | N-(cyclopropylmethyl)-9-methyl-6-{4-[2-(trifluoromethyl)-1H-benzimidazol-1-yl]piperidin-1-yl]-9H-purine-8-carboxamide |
| 102 | 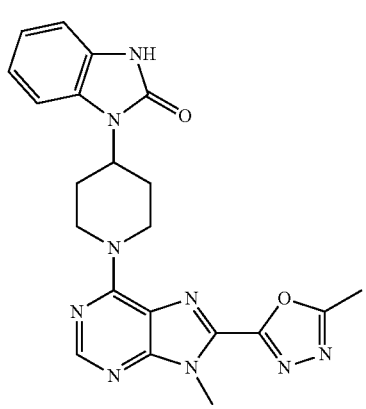 [SMILES: Cc1nnc(-c2nc3c(N4CCC(n5c(=O)[nH]c6ccccc65)CC4)ncnc3n2C)o1] | 1-{1-[9-methyl-8-(5-methyl-1,3,4-oxadiazol-2-yl)-9H-purin-6-yl]piperidin-4-yl}-1,3-dihydro-2H-benzimidazol-2-one |
| 103 | 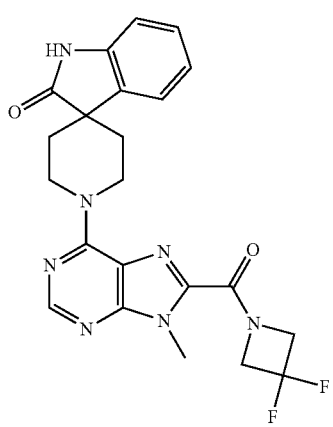 [SMILES: Cn1c(C(=O)N2CC(F)(F)C2)nc2c(N3CCC4(CC3)C(=O)Nc3ccccc34)ncnc21] | 1'{8-[(3,3-difluoroazetidin-1-yl)carbonyl]-9-methyl-9H-purin-6-yl}spiro[indole-3,4'-piperidin]-2(1H)-one |

TABLE 1-continued

| Compound Number | Structure | Name |
|---|---|---|
| 104 | 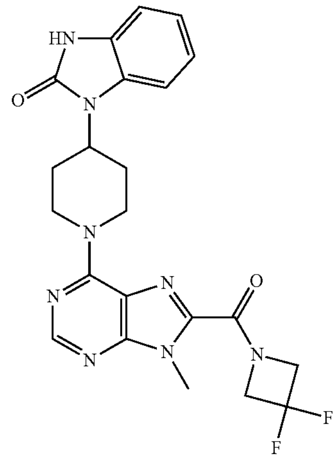 [SMILES: Cn1c(C(=O)N2CC(F)(F)C2)nc2c(N3CCC(n4c(=O)[nH]c5ccccc54)CC3)ncnc21] | 1-(1-{8-[(3,3-difluoroazetidin-1-yl)carbonyl]-9-methyl-9H-purin-6-yl}piperidin-4-yl)-1,3-dihydro-2H-benzimidazol-2-one |
| 105 | 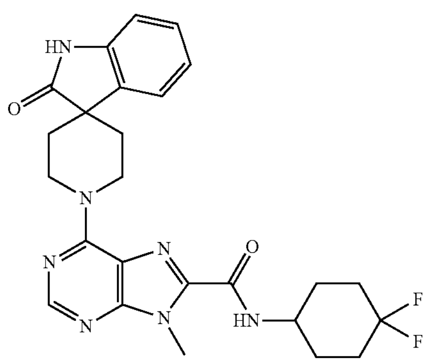 [SMILES: Cn1c(C(=O)NC2CCC(F)(F)CC2)nc2c(N3CCC4(CC3)C(=O)Nc3ccccc34)ncnc21] | N-(4,4-difluorocyclohexyl)-9-methyl-6-(2-oxo-1,2-dihydro-1'H-spiro[indole-3,4'-piperidin]-1'-yl)-9H-purine-8-carboxamide |
| 106 | 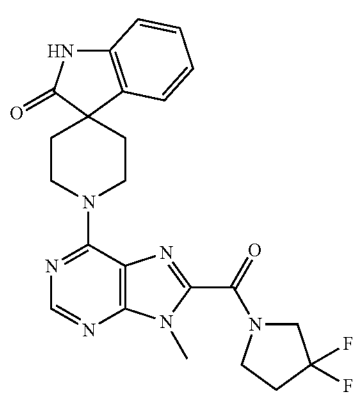 [SMILES: Cn1c(C(=O)N2CCC(F)(F)C2)nc2c(N3CCC4(CC3)C(=O)Nc3ccccc34)ncnc21] | 1'-{8-[(3,3-difluoropyrrolidin-1-yl)carbonyl]-9-methyl-9H-purin-6-yl}spiro[indole-3,4'-piperidin]-2(1H)-one |

TABLE 1-continued

| Compound Number | Structure | Name |
|---|---|---|
| 107 | 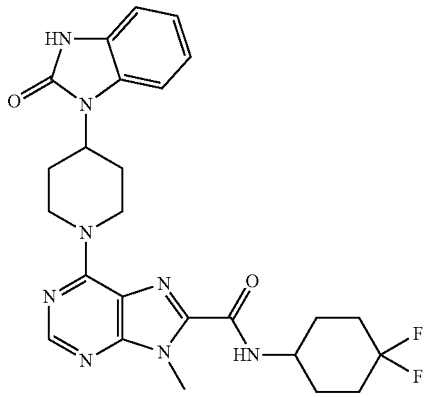 [SMILES: Cn1c(C(=O)NC2CCC(F)(F)CC2)nc2c(N3CCC(n4c(=O)[nH]c5ccccc54)CC3)ncnc21] | N-(4,4-difluorocyclohexyl)-9-methyl-6-[4-(2-oxo-2,3-dihydro-1H-benzimidazol-1-yl)piperidin-1-yl]-9H-purine-8-carboxamide |
| 108 | 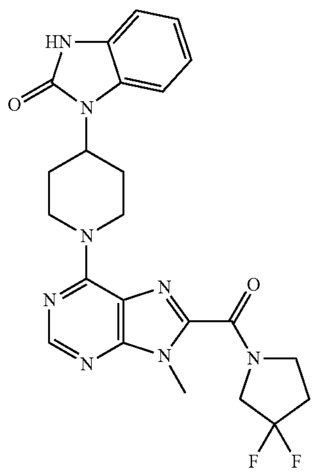 [SMILES: Cn1c(C(=O)N2CCC(F)(F)C2)nc2c(N3CCC(n4c(=O)[nH]c5ccccc54)CC3)ncnc21] | 1-(1-{8-[(3,3-difluoropyrrolidin-1-yl)carbonyl]-9-methyl-9H-purin-6-yl}piperidin-4-yl)-1,3-dihydro-2H-benzimidazol-2-one |
| 109 | Chiral | 1'-(8-{[(3S)-3-fluoropyrrolidin-1-yl]carbonyl}-9-methyl-9H-purin-6-yl)spiro[indole-3,4'-piperidin]-2(1H)-one |

TABLE 1-continued
| Compound Number | Structure | | Name |
|---|---|---|---|
| 110 | 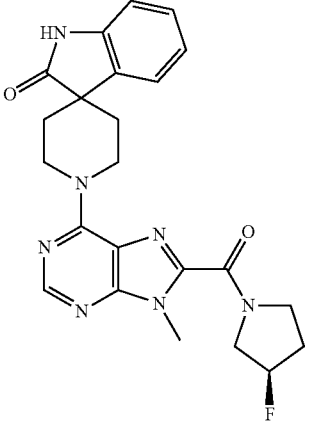 | Chiral | 1'-(8-{[(3R)-3-fluoropyrrolidin-1-yl]carbonyl}-9-methyl-9H-purin-6-yl)spiro[indole-3,4'-piperidin]-2(1H)-one |
| 111 | 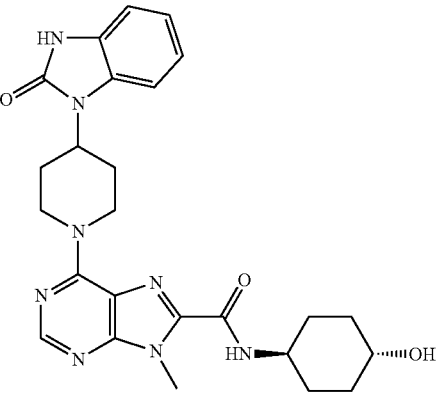 | Chiral | N-(trans-4-hydroxycyclohexyl)-9-methyl-6-[4-(2-oxo-2,3-dihydro-1H-benzimidazol-1-yl)piperidin-1-yl]-9H-purine-8-carboxamide |
| 112 | 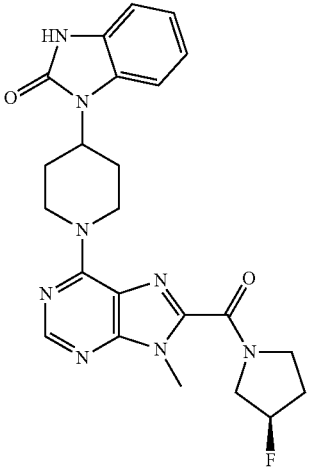 | Chiral | 1-[1-(8-{[(3R)-3-fluoropyrrolidin-1-yl]carbonyl}-9-methyl-9H-purin-6-yl)piperidin-4-yl]-1,3-dihydro-2H-benzimidazol-2-one |

TABLE 1-continued

| Compound Number | Structure | Name |
|---|---|---|
| 113 | 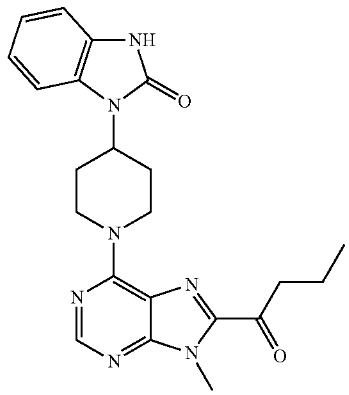 [SMILES: CCCC(=O)c1nc2c(N3CCC(n4c(=O)[nH]c5ccccc54)CC3)ncnc2n1C] | 1-[1-(8-butanoyl-9-methyl-9H-purin-6-yl)piperidin-4-yl]-1,3-dihydro-2H-benzimidazol-2-one |
| 114 | 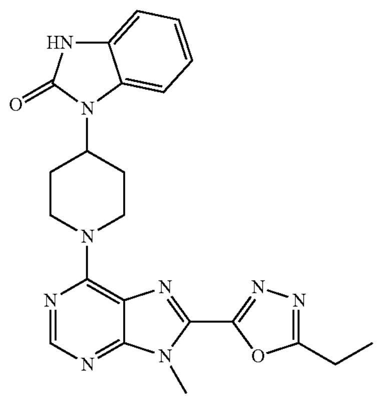 [SMILES: CCc1nnc(-c2nc3c(N4CCC(n5c(=O)[nH]c6ccccc65)CC4)ncnc3n2C)o1] | 1-{1-[8-(5-ethyl-1,3,4-oxadiazol-2-yl)-9-methyl-9H-purin-6-yl]piperidin-4-yl}-1,3-dihydro-2H-benzimidazol-2-one |
| 115 | 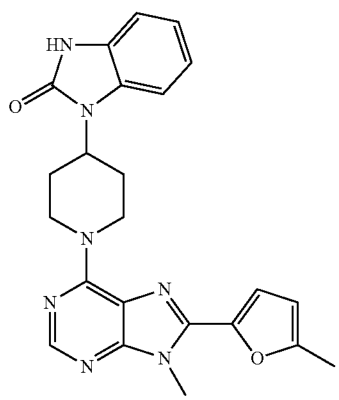 [SMILES: Cc1ccc(-c2nc3c(N4CCC(n5c(=O)[nH]c6ccccc65)CC4)ncnc3n2C)o1] | 1-{1-[9-methyl-8-(5-methylfuran-2-yl)-9H-purin-6-yl]piperidin-4-yl}-1,3-dihydro-2H-benzimidazol-2-one |
| 116 | 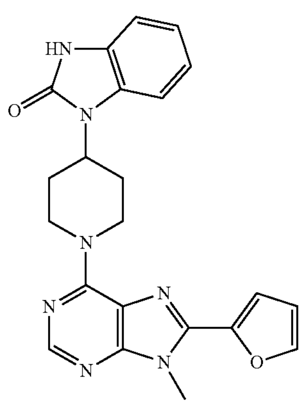 [SMILES: Cn1c(-c2ccco2)nc2c(N3CCC(n4c(=O)[nH]c5ccccc54)CC3)ncnc21] | 1-[1-(8-furan-2-yl-9-methyl-9H-purin-6-yl)piperidin-4-yl]-1,3-dihydro-2H-benzimidazol-2-one |

TABLE 1-continued

| Compound Number | Structure | Name |
|---|---|---|
| 117 | 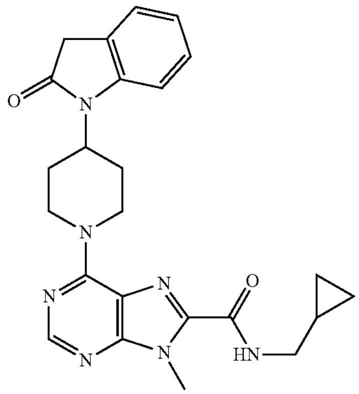 [SMILES: Cn1c(C(=O)NCC2CC2)nc2c(N3CCC(N4C(=O)Cc5ccccc54)CC3)ncnc21] | N-(cyclopropylmethyl)-9-methyl-6-[4-(2-oxo-2,3-dihydro-1H-indol-1-yl)piperidin-1-yl]-9H-purine-8-carboxamide |
| 118 | 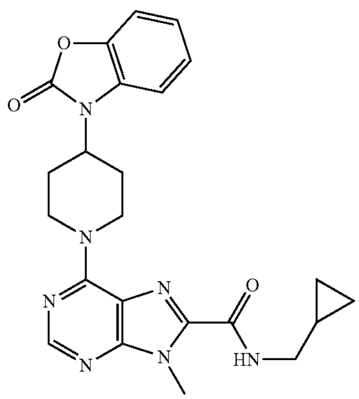 [SMILES: Cn1c(C(=O)NCC2CC2)nc2c(N3CCC(n4c(=O)oc5ccccc54)CC3)ncnc21] | N-(cyclopropylmethyl)-9-methyl-6-[4-(2-oxo-1,3-benzoxazol-3(2H)-yl)piperidin-1-yl]-9H-purine-8-carboxamide |
| 119 | 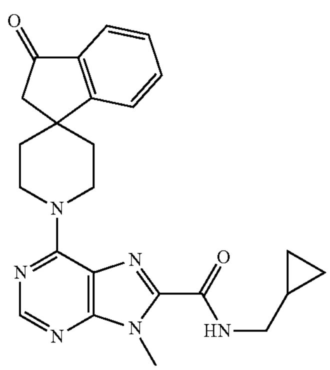 [SMILES: Cn1c(C(=O)NCC2CC2)nc2c(N3CCC4(CC3)CC(=O)c3ccccc34)ncnc21] | N-(cyclopropylmethyl)-9-methyl-6-(3-oxo-2,3-dihydro-1'H-spiro[indene-1,4'-piperidin]-1'-yl)-9H-purine-8-carboxamide |
| 120 | 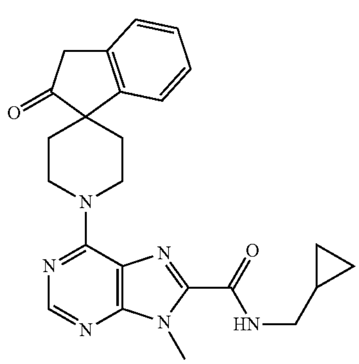 | N-(cyclopropylmethyl)-9-methyl-6-(2-oxo-2,3-dihydro-1'H-spiro[indene-1,4'-piperidin]-1'-yl)-9H-purine-8-carboxamide |

TABLE 1-continued

| Compound Number | Structure | Name |
|---|---|---|
| 121 | 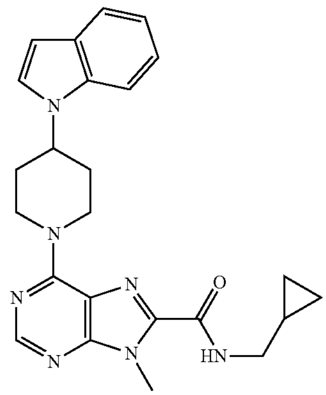 [SMILES: Cn1c(C(=O)NCC2CC2)nc2c(N3CCC(n4ccc5ccccc54)CC3)ncnc21] | N-(cyclopropylmethyl)-6-[4-(1H-indol-1-yl)piperidin-1-yl]-9-methyl-9H-purine-8-carboxamide |
| 122 | 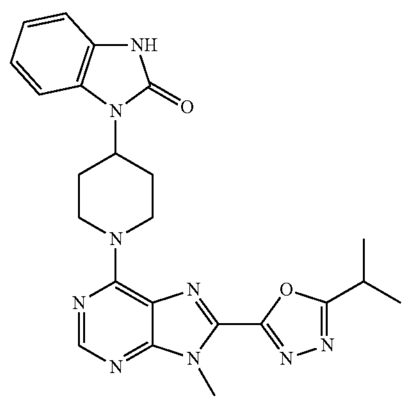 [SMILES: CC(C)c1nnc(-c2nc3c(N4CCC(n5c(=O)[nH]c6ccccc65)CC4)ncnc3n2C)o1] | 1-(1-{9-methyl-8-[5-(1-methylethyl)-1,3,4-oxadiazol-2-yl]-9H-purin-6-yl}piperidin-4-yl)-1,3-dihydro-2H-benzimidazol-2-one |
| 123 | 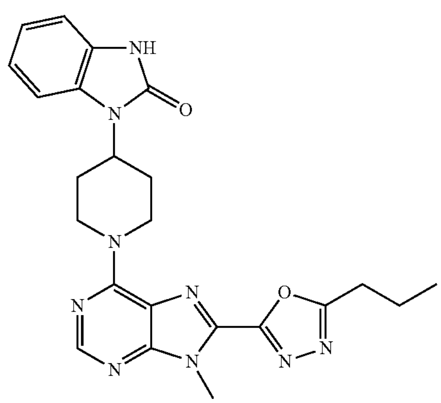 [SMILES: CCCc1nnc(-c2nc3c(N4CCC(n5c(=O)[nH]c6ccccc65)CC4)ncnc3n2C)o1] | 1-{1-[9-methyl-8-(5-propyl-1,3,4-oxadiazol-2-yl)-9H-purin-6-yl]piperidin-4-yl}-1,3-dihydro-2H-benzimidazol-2-one |
| 124 | 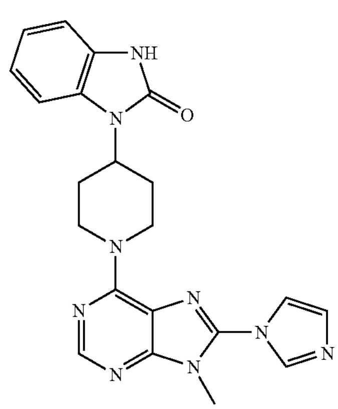 [SMILES: Cn1c(-n2ccnc2)nc2c(N3CCC(n4c(=O)[nH]c5ccccc54)CC3)ncnc21] | 1-{1-[8-(1H-imidazol-1-yl)-9-methyl-9H-purin-6-yl]piperidin-4-yl}-1,3-dihydro-2H-benzimidazol-2-one |

TABLE 1-continued

| Compound Number | Structure | Name |
|---|---|---|
| 125 | 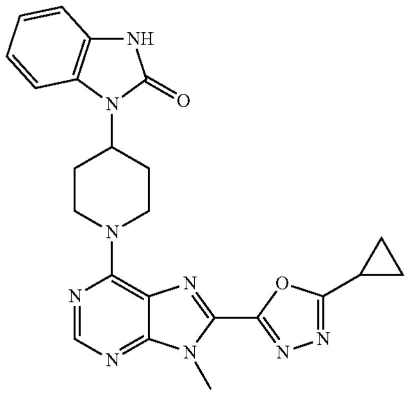 [SMILES: Cn1c(-c2nnc(C3CC3)o2)nc2c(N3CCC(n4c(=O)[nH]c5ccccc54)CC3)ncnc21] | 1-{1-[8-(5-cyclopropyl-1,3,4-oxadiazol-2-yl)-9-methyl-9H-purin-6-yl]piperidin-4-yl}-1,3-dihydro-2H-benzimidazol-2-one |
| 126 | 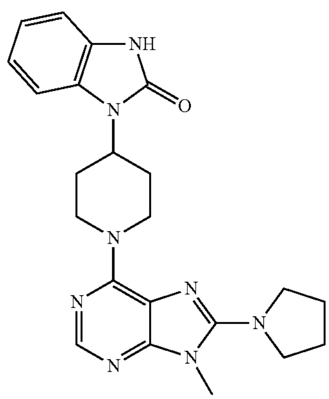 [SMILES: Cn1c(N2CCCC2)nc2c(N3CCC(n4c(=O)[nH]c5ccccc54)CC3)ncnc21] | 1-[1-(9-methyl-8-pyrrolidin-1-yl-9H-purin-6-yl)piperidin-4-yl]-1,3-dihydro-2H-benzimidazol-2-one |
| 127 | 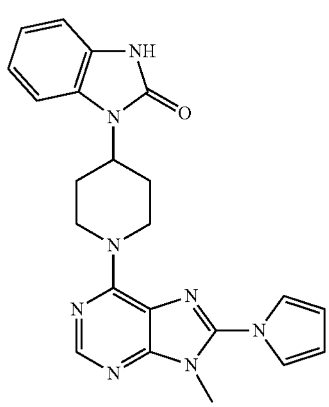 [SMILES: Cn1c(-n2cccc2)nc2c(N3CCC(n4c(=O)[nH]c5ccccc54)CC3)ncnc21] | 1-{1-[9-methyl-8-(1H-pyrrol-1-yl)-9H-purin-6-yl]piperidin-4-yl}-1,3-dihydro-2H-benzimidazol-2-one |

TABLE 1-continued

| Compound Number | Structure | Name |
|---|---|---|
| 128 | 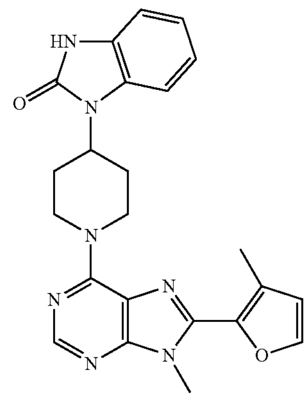 [SMILES: Cc1ccoc1-c1nc2c(N3CCC(n4c(=O)[nH]c5ccccc54)CC3)ncnc2n1C] | 1-{1-[9-methyl-8-(3-methylfuran-2-yl)-9H-purin-6-yl]piperidin-4-yl}-1,3-dihydro-2H-benzimidazol-2-one |
| 129 | 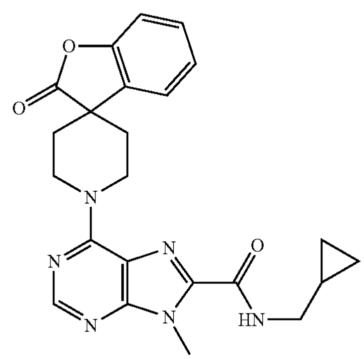 [SMILES: Cn1c(C(=O)NCC2CC2)nc2c(N3CCC4(CC3)C(=O)Oc3ccccc34)ncnc21] | N-(cyclopropylmethyl)-9-methyl-6-(2-oxo-1'H-spiro[1-benzofuran-3,4'-piperidin]-1'-yl)-9H-purine-8-carboxamide |
| 130 | 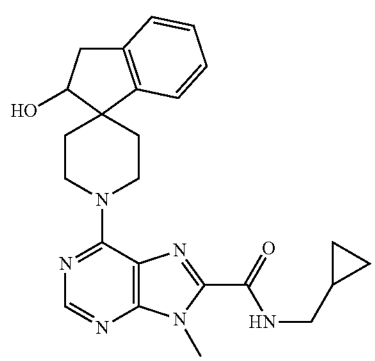 [SMILES: Cn1c(C(=O)NCC2CC2)nc2c(N3CCC4(CC3)c3ccccc3CC4O)ncnc21] | N-(cyclopropylmethyl)-6-(2-hydroxy-2,3-dihydro-1'H-spiro[indene-1,4'-piperidin]-1'-yl)-9-methyl-9H-purine-8-carboxamide |
| 131 | 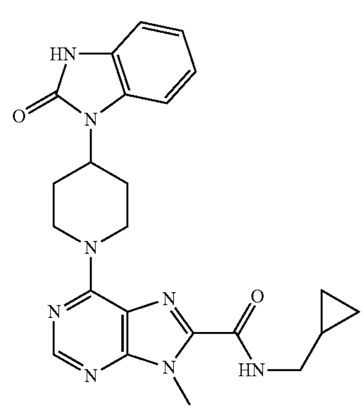 [SMILES: Cn1c(C(=O)NCC2CC2)nc2c(N3CCC(n4c(=O)[nH]c5ccccc54)CC3)ncnc21] | N-(cyclopropylmethyl)-9-methyl-6-[4-(2-oxo-2,3-dihydro-1H-indol-3-yl)piperidin-1-yl]-9H-purine-8-carboxamide |

TABLE 1-continued

| Compound Number | Structure | Name |
|---|---|---|
| 132 | 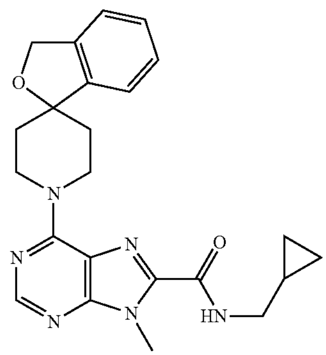 [SMILES: Cn1c(C(=O)NCC2CC2)nc2c(N3CCC4(CC3)OCc3ccccc34)ncnc21] | N-(cyclopropylmethyl)-9-methyl-6-(1'H,3H-spiro[2-benzofuran-1,4'-piperidin]-1'-yl)-9H-purine-8-carboxamide |
| 133 | 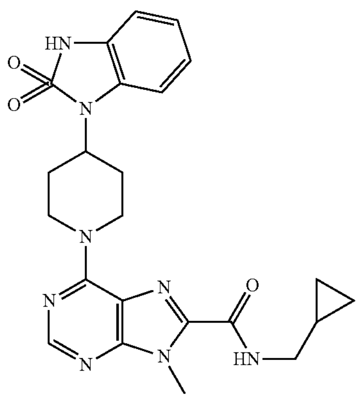 | N-(cyclopropylmethyl)-6-[4-(2,2-dioxido-2,1,3-benzothiadiazol-1(3H)-yl)piperidin-1-yl]-9-methyl-9H-purine-8-carboxamide |
| 134 | 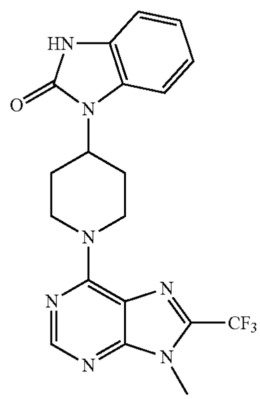 [SMILES: Cn1c(C(F)(F)F)nc2c(N3CCC(n4c(=O)[nH]c5ccccc54)CC3)ncnc21] | 1-{1-[9-methyl-8-(trifluoromethyl)-9H-purin-6-yl]piperidin-4-yl}-1,3-dihydro-2H-benzimidazol-2-one |
| 135 | 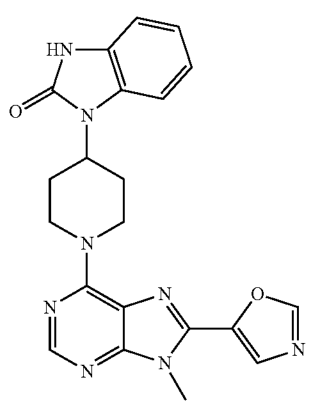 [SMILES: Cn1c(-c2cnco2)nc2c(N3CCC(n4c(=O)[nH]c5ccccc54)CC3)ncnc21] | 1-{1-[9-methyl-8-(1,3-oxazol-5-yl)-9H-purin-6-yl]piperidin-4-yl}-1,3-dihydro-2H-benzimidazol-2-one |

TABLE 1-continued

| Compound Number | Structure | Name |
|---|---|---|
| 136 | 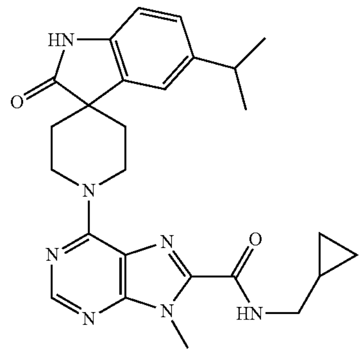 [SMILES: CC(C)c1ccc2c(c1)C1(CCN(c3ncnc4c3nc(C(=O)NCC3CC3)n4C)CC1)C(=O)N2] | N-(cyclopropylmethyl)-9-methyl-6-[5-(1-methylethyl)-2-oxo-1,2-dihydro-1'H-spiro[indole-3,4'-piperidin]-1'-yl]-9H-purine-8-carboxamide |
| 137 | 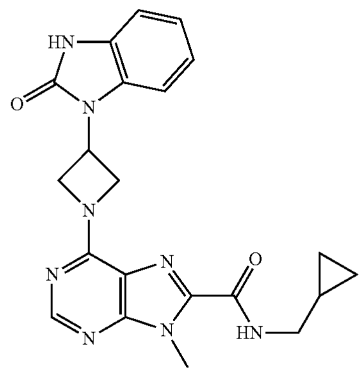 [SMILES: Cn1c(C(=O)NCC2CC2)nc2c(N3CC(n4c(=O)[nH]c5ccccc54)C3)ncnc21] | N-(cyclopropylmethyl)-9-methyl-6-[3-(2-oxo-2,3-dihydro-1H-benzimidazol-1-yl)azetidin-1-yl]-9H-purine-8-carboxamide |
| 138 | 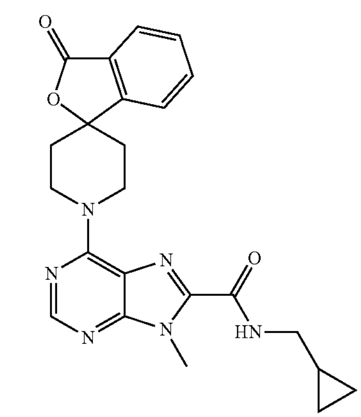 [SMILES: Cn1c(C(=O)NCC2CC2)nc2c(N3CCC4(CC3)OC(=O)c3ccccc34)ncnc21] | N-(cyclopropylmethyl)-9-methyl-6-(3-oxo-1'H,3H-spiro[2-benzofuran-1,4'-piperidin]-1'-yl)-9H-purine-8-carboxamide |
| 139 | 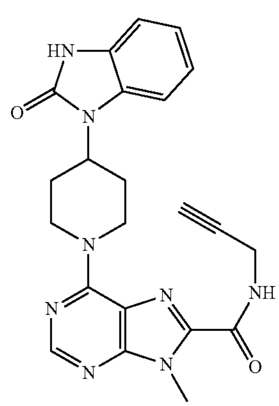 [SMILES: C#CCNC(=O)c1nc2c(N3CCC(n4c(=O)[nH]c5ccccc54)CC3)ncnc2n1C] | 9-methyl-6-[4-(2-oxo-2,3-dihydro-1H-benzimidazol-1-yl)piperidin-1-yl]-N-prop-2-yn-1-yl-9H-purine-8-carboxamide |

TABLE 1-continued

| Compound Number | Structure | Name |
|---|---|---|
| 140 | 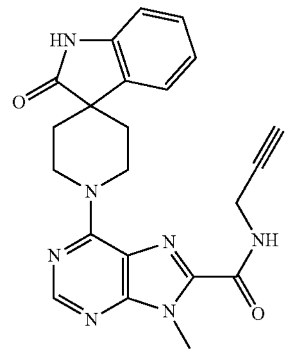 [SMILES: C#CCNC(=O)c1nc2c(N3CCC4(CC3)C(=O)Nc3ccccc34)ncnc2n1C] | 9-methyl-6-(2-oxo-1,2-dihydro-1'H-spiro[indole-3,4'-piperidin]-1'-yl)-N-prop-2-yn-1-yl-9H-purine-8-carboxamide |
| 141 | 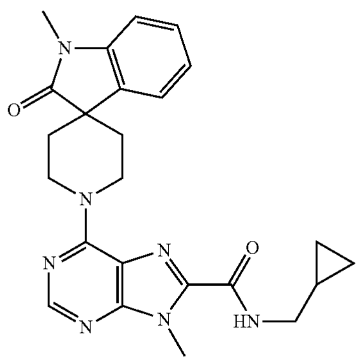 [SMILES: CN1C(=O)C2(CCN(c3ncnc4c3nc(C(=O)NCC3CC3)n4C)CC2)c2ccccc21] | N-(cyclopropylmethyl)-9-methyl-6-(1-methyl-2-oxo-1,2-dihydro-1'H-spiro[indole-3,4'-piperidin]-1'-yl)-9H-purine-8-carboxamide |
| 142 | 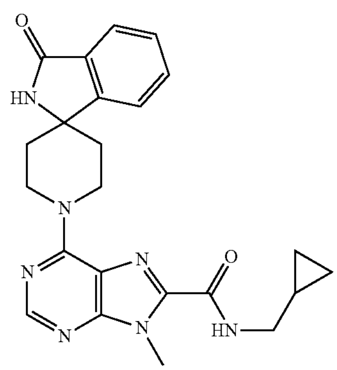 [SMILES: Cn1c(C(=O)NCC2CC2)nc2c(N3CCC4(CC3)NC(=O)c3ccccc34)ncnc21] | N-(cyclopropylmethyl)-9-methyl-6-(3-oxo-2,3-dihydro-1'H-spiro[isoindole-1,4'-piperidin]-1'-yl)-9H-purine-8-carboxamide |
| 143 | 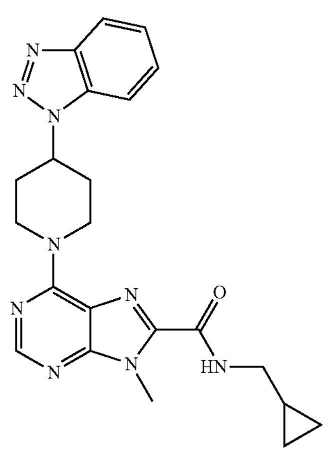 [SMILES: Cn1c(C(=O)NCC2CC2)nc2c(N3CCC(n4nnc5ccccc54)CC3)ncnc21] | 6-[4-(1H-1,2,3-benzotriazol-1-yl)piperidin-1-yl]-N-(cyclopropylmethyl)-9-methyl-9H-purine-8-carboxamide |

TABLE 1-continued

| Compound Number | Structure | Name |
|---|---|---|
| 144 | 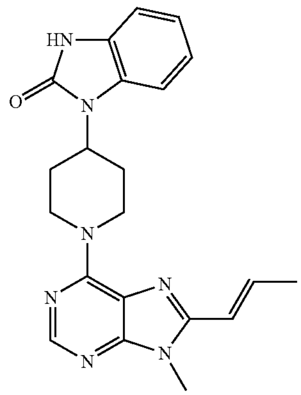 [SMILES: C/C=C/c1nc2c(N3CCC(n4c(=O)[nH]c5ccccc54)CC3)ncnc2n1C] | 1-(1-{9-methyl-8-[(1E)-prop-1-en-1-yl]-9H-purin-6-yl}piperidin-4-yl)-1,3-dihydro-2H-benzimidazol-2-one |
| 145 | 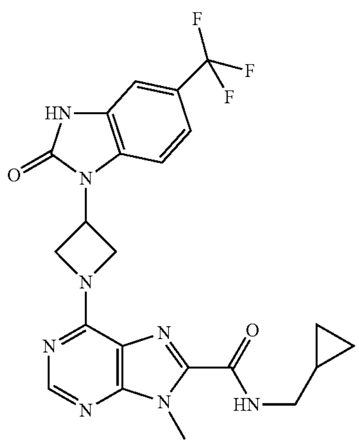 [SMILES: Cn1c(C(=O)NCC2CC2)nc2c(N3CC(n4c(=O)[nH]c5cc(C(F)(F)F)ccc54)C3)ncnc21] | N-(cyclopropylmethyl)-9-methyl-6-{3-[2-oxo-5-(trifluoromethyl)-2,3-dihydro-1H-benzimidazol-1-yl]azetidin-1-yl}-9H-purine-8-carboxamide |
| 146 | 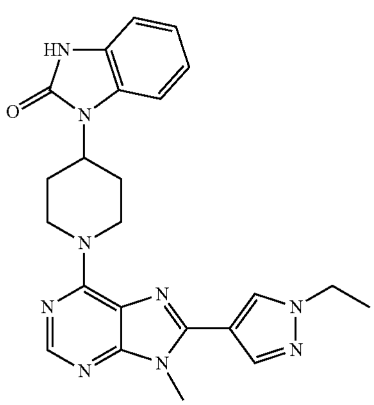 [SMILES: CCn1cc(-c2nc3c(N4CCC(n5c(=O)[nH]c6ccccc65)CC4)ncnc3n2C)cn1] | 1-{1-[8-(1-ethyl-1H-pyrazol-4-yl)-9-methyl-9H-purin-6-yl]piperidin-4-yl}-1,3-dihydro-2H-benzimidazol-2-one |

TABLE 1-continued

| Compound Number | Structure | Name |
|---|---|---|
| 147 | 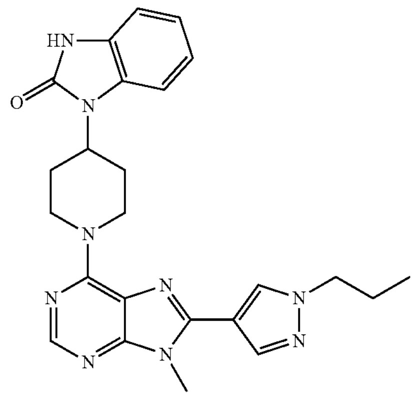 [SMILES: CCCn1cc(-c2nc3c(N4CCC(n5c(=O)[nH]c6ccccc65)CC4)ncnc3n2C)cn1] | 1-{1-[9-methyl-8-(1-propyl-1H-pyrazol-4-yl)-9H-purin-6-yl]piperidin-4-yl}-1,3-dihydro-2H-benzimidazol-2-one |
| 148 | 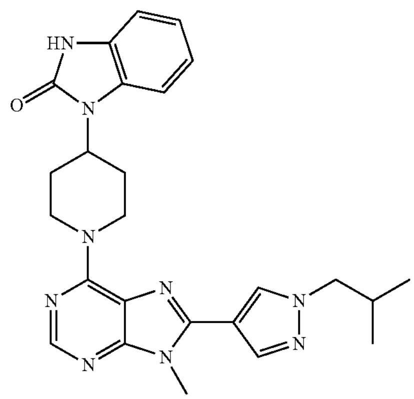 [SMILES: CC(C)Cn1cc(-c2nc3c(N4CCC(n5c(=O)[nH]c6ccccc65)CC4)ncnc3n2C)cn1] | 1-(1-{9-methyl-8-[1-(2-methylpropyl)-1H-pyrazol-4-yl]-9H-purin-6-yl}piperidin-4-yl)-1,3-dihydro-2H-benzimidazol-2-one |
| 149 | 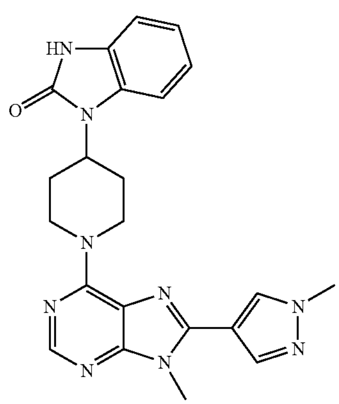 [SMILES: Cn1cc(-c2nc3c(N4CCC(n5c(=O)[nH]c6ccccc65)CC4)ncnc3n2C)cn1] | 1-{1-[9-methyl-8-(1-methyl-1H-pyrazol-4-yl)-9H-purin-6-yl]piperidin-4-yl}-1,3-dihydro-2H-benzimidazol-2-one |
| 150 | 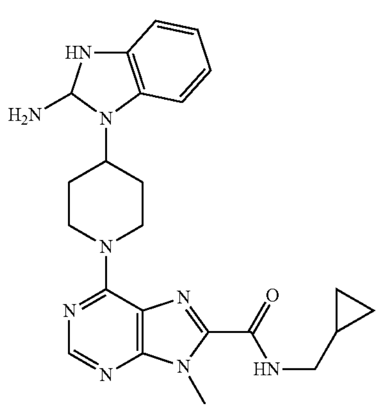 [SMILES: Cn1c(C(=O)NCC2CC2)nc2c(N3CCC(N4c5ccccc5NC4N)CC3)ncnc21] | 6-[4-(2-amino-1H-benzimidazol-1-yl)piperidin-1-yl]-N-(cyclopropylmethyl)-9-methyl-9H-purine-8-carboxamide |

TABLE 1-continued

| Compound Number | Structure | Name |
|---|---|---|
| 151 | 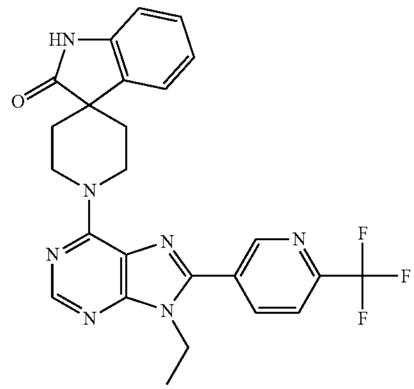 [SMILES: CCn1c(-c2ccc(C(F)(F)F)nc2)nc2c(N3CCC4(CC3)C(=O)Nc3ccccc34)ncnc21] | N-(cyclopropylmethyl)-9-methyl-6-(1-phenyl-1,4,6,7-tetrahydro-5H-pyrazolo[4,3-c]pyridin-5-yl)-9H-purine-8-carboxamide |
| 152 | 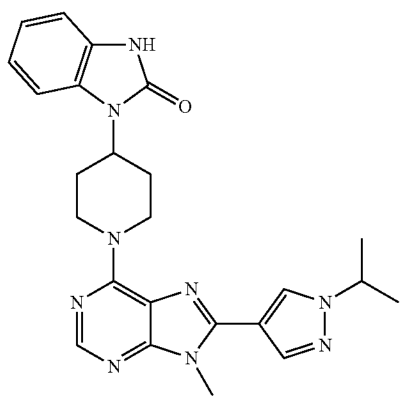 [SMILES: CC(C)n1cc(-c2nc3c(N4CCC(n5c(=O)[nH]c6ccccc65)CC4)ncnc3n2C)cn1] | 1-(1-{9-methyl-8-[1-(1-methylethyl)-1H-pyrazol-4-yl]-9H-purin-6-yl}piperidin-4-yl)-1,3-dihydro-2H-benzimidazol-2-one |
| 153 | 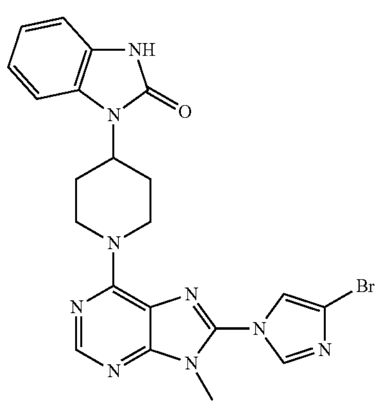 [SMILES: Cn1c(-n2cnc(Br)c2)nc2c(N3CCC(n4c(=O)[nH]c5ccccc54)CC3)ncnc21] | 1-{1-[8-(4-bromo-1H-imidazol-1-yl)-9-methyl-9H-purin-6-yl]piperidin-4-yl}-1,3-dihydro-2H-benzimidazol-2-one |

TABLE 1-continued

| Compound Number | Structure | | Name |
|---|---|---|---|
| 154 | 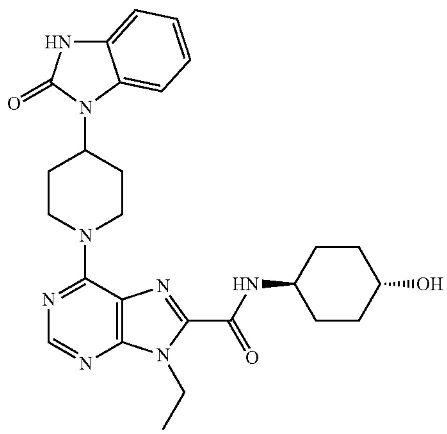 | Chiral | 9-ethyl-N-(trans-4-hydroxycyclohexyl)-6-[4-(2-oxo-2,3-dihydro-1H-benzimidazol-1-yl)piperidin-1-yl]-9H-purine-8-carboxamide |
| 155 | 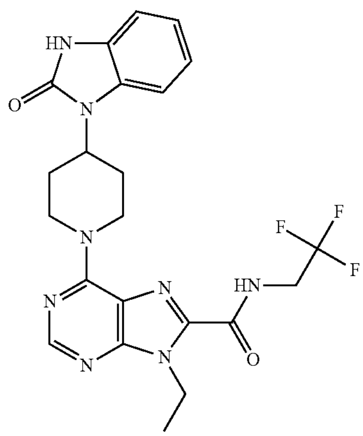 [SMILES: CCn1c(C(=O)NCC(F)(F)F)nc2c(N3CCC(n4c(=O)[nH]c5ccccc54)CC3)ncnc21] | | 9-ethyl-6-[4-(2-oxo-2,3-dihydro-1H-benzimidazol-1-yl)piperidin-1-yl]-N-(2,2,2-trifluoroethyl)-9H-purine-8-carboxamide |
| 156 | 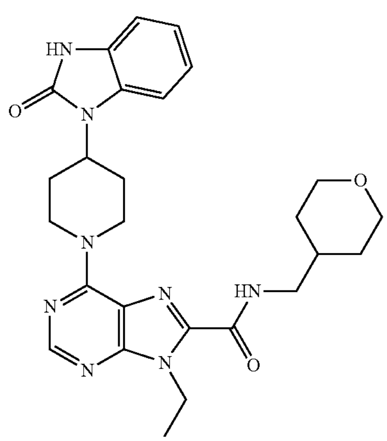 [SMILES: CCn1c(C(=O)NCC2CCOCC2)nc2c(N3CCC(n4c(=O)[nH]c5ccccc54)CC3)ncnc21] | | 9-ethyl-6-[4-(2-oxo-2,3-dihydro-1H-benzimidazol-1-yl)piperidin-1-yl]-N-(tetrahydro-2H-pyran-4-ylmethyl)-9H-purine-8-carboxamide |

TABLE 1-continued

| Compound Number | Structure | Name |
|---|---|---|
| 157 | 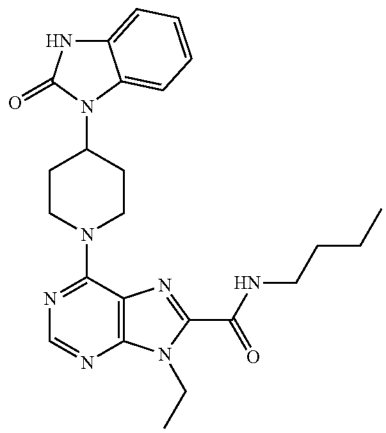 [SMILES: CCCCNC(=O)c1nc2c(N3CCC(n4c(=O)[nH]c5ccccc54)CC3)ncnc2n1CC] | N-butyl-9-ethyl-6-[4-(2-oxo-2,3-dihydro-1H-benzimidazol-1-yl)piperidin-1-yl]-9H-purine-8-carboxamide |
| 158 | 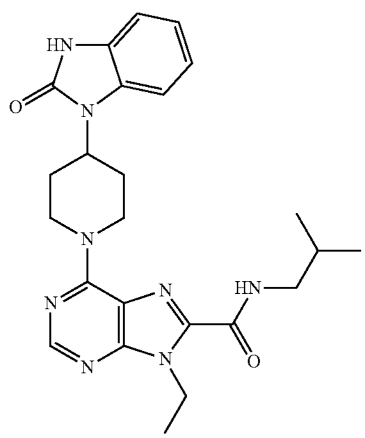 [SMILES: CCn1c(C(=O)NCC(C)C)nc2c(N3CCC(n4c(=O)[nH]c5ccccc54)CC3)ncnc21] | 9-ethyl-N-(2-methylpropyl)-6-[4-(2-oxo-2,3-dihydro-1H-benzimidazol-1-yl)piperidin-1-yl]-9H-purine-8-carboxamide |
| 159 | Chiral | 9-ethyl-N-(trans-4-hydroxycyclohexyl)-6-(2-oxo-1,2-dihydro-1'H-spiro[indole-3,4'-piperidin]-1'-yl)-9H-purine-8-carboxamide |

TABLE 1-continued

| Compound Number | Structure | Name |
|---|---|---|
| 160 | 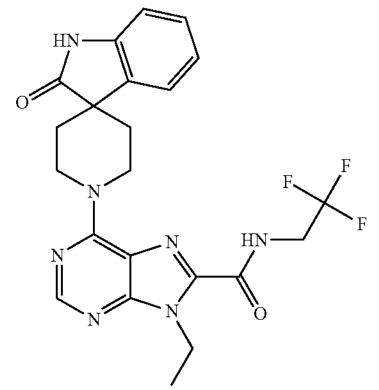 [SMILES: CCn1c(C(=O)NCC(F)(F)F)nc2c(N3CCC4(CC3)C(=O)Nc3ccccc34)ncnc21] | 9-ethyl-6-(2-oxo-1,2-dihydro-1'H-spiro[indole-3,4'-piperidin]-1'-yl)-N-(2,2,2-trifluoroethyl)-9H-purine-8-carboxamide |
| 161 | 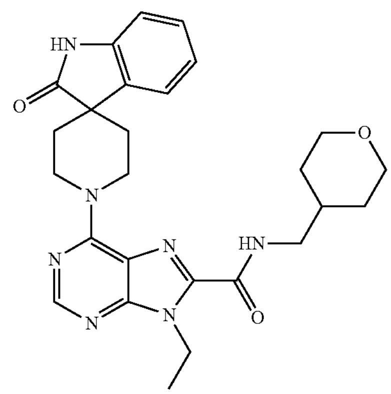 [SMILES: CCn1c(C(=O)NCC2CCOCC2)nc2c(N3CCC4(CC3)C(=O)Nc3ccccc34)ncnc21] | 9-ethyl-6-(2-oxo-1,2-dihydro-1'H-spiro[indole-3,4'-piperidin]-1'-yl)-N-(tetrahydro-2H-pyran-4-ylmethyl)-9H-purine-8-carboxamide |
| 162 | 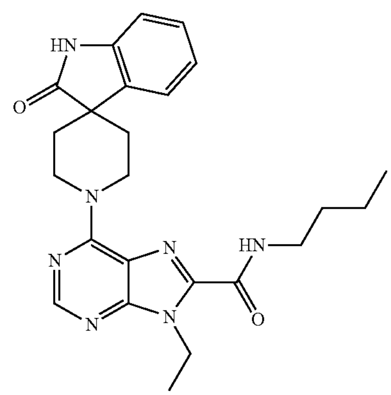 [SMILES: CCCCNC(=O)c1nc2c(N3CCC4(CC3)C(=O)Nc3ccccc34)ncnc2n1CC] | N-butyl-9-ethyl-6-(2-oxo-1,2-dihydro-1'H-spiro[indole-3,4'-piperidin]-1'-yl)-9H-purine-8-carboxamide |
| 163 | 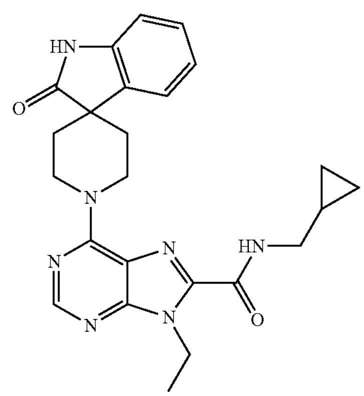 [SMILES: CCn1c(C(=O)NCC2CC2)nc2c(N3CCC4(CC3)C(=O)Nc3ccccc34)ncnc21] | N-(cyclopropylmethyl)-9-ethyl-6-(2-oxo-1,2-dihydro-1'H-spiro[indole-3,4'-piperidin]-1'-yl)-9H-purine-8-carboxamide |

TABLE 1-continued

| Compound Number | Structure | Name |
|---|---|---|
| 164 | 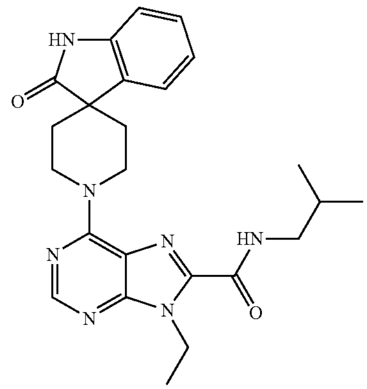 [SMILES: CCn1c(C(=O)NCC(C)C)nc2c(N3CCC4(CC3)C(=O)Nc3ccccc34)ncnc21] | 9-ethyl-N-(2-methylpropyl)-6-(2-oxo-1,2-dihydro-1'H-spiro[indole-3,4'-piperidin]-1'-yl)-9H-purine-8-carboxamide |
| 165 | 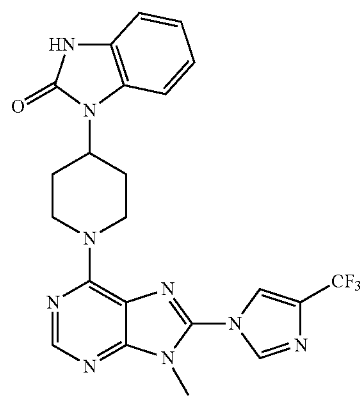 [SMILES: Cn1c(-n2cnc(C(F)(F)F)c2)nc2c(N3CCC(n4c(=O)[nH]c5ccccc54)CC3)ncnc21] | 1-(1-{9-methyl-8-[4-(trifluoromethyl)-1H-imidazol-1-yl]-9H-purin-6-yl}piperidin-4-yl)-1,3-dihydro-2H-benzimidazol-2-one |
| 166 | 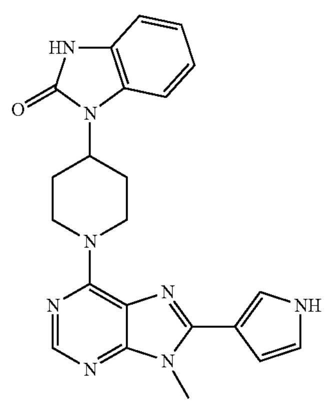 [SMILES: Cn1c(-c2cc[nH]c2)nc2c(N3CCC(n4c(=O)[nH]c5ccccc54)CC3)ncnc21] | 1-{1-[9-methyl-8-(1H-pyrrol-3-yl)-9H-purin-6-yl]piperidin-4-yl}-1,3-dihydro-2H-benzimidazol-2-one |
| 167 | 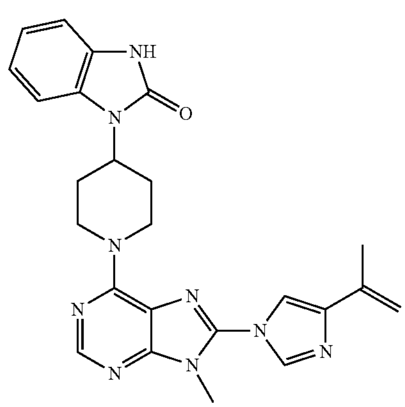 [SMILES: C=C(C)c1cn(-c2nc3c(N4CCC(n5c(=O)[nH]c6ccccc65)CC4)ncnc3n2C)cn1] | 1-(1-{9-methyl-8-[4-(1-methylethenyl)-1H-imidazol-1-yl]-9H-purin-6-yl}piperidin-4-yl)-1,3-dihydro-2H-benzimidazol-2-one |

TABLE 1-continued
| Compound Number | Structure | Name |
| --- | --- | --- |
| 168 | 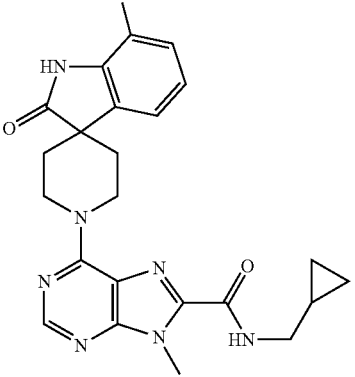 | 6-(7-bromo-2-oxo-1,2-dihydro-1'H-spiro[indole-3,4'-piperidin]-1'-yl)-N-(cyclopropylmethyl)-9-methyl-9H-purine-8-carboxamide |
| 169 | 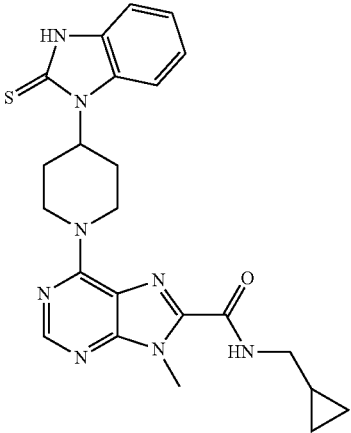 [SMILES: Cn1c(C(=O)NCC2CC2)nc2c(N3CCC(n4c(=S)[nH]c5ccccc54)CC3)ncnc21] | N-(cyclopropylmethyl)-9-methyl-6-[4-(2-thioxo-2,3-dihydro-1H-benzimidazol-1-yl)piperidin-1-yl]-9H-purine-8-carboxamide |
| 170 | 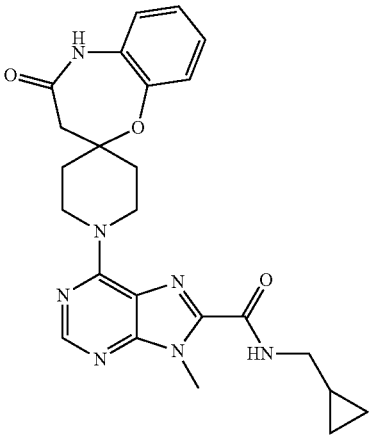 [SMILES: Cn1c(C(=O)NCC2CC2)nc2c(N3CCC4(CC3)CC(=O)Nc3ccccc3O4)ncnc21] | N-(cyclopropylmethyl)-9-methyl-6-(4-oxo-4,5-dihydro-1H,3H-spiro[1,5-benzoxazepine-2,4'-piperidin]-1'-yl)-9H-purine-8-carboxamide |

TABLE 1-continued

| Compound Number | Structure | Name |
|---|---|---|
| 171 | 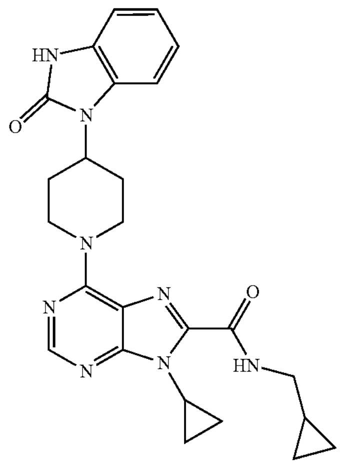 [SMILES: O=C(NCC1CC1)c1nc2c(N3CCC(n4c(=O)[nH]c5ccccc54)CC3)ncnc2n1C1CC1] | 9-cyclopropyl-N-(cyclopropylmethyl)-6-[4-(2-oxo-2,3-dihydro-1H-benzimidazol-1-yl)piperidin-1-yl]-9H-purine-8-carboxamide |
| 172 | 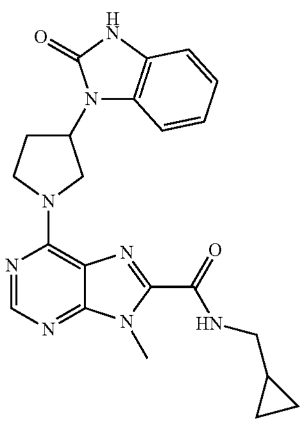 [SMILES: Cn1c(C(=O)NCC2CC2)nc2c(N3CCC(n4c(=O)[nH]c5ccccc54)C3)ncnc21] | N-(cyclopropylmethyl)-9-methyl-6-[3-(2-oxo-2,3-dihydro-1H-benzimidazol-1-yl)pyrrolidin-1-yl]-9H-purine-8-carboxamide |
| 173 | 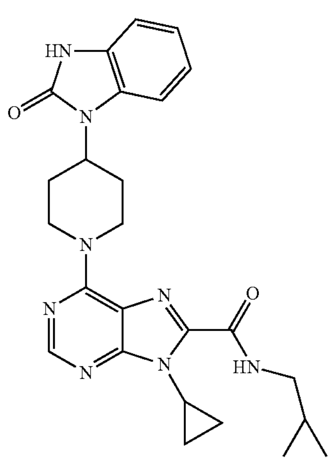 [SMILES: CC(C)CNC(=O)c1nc2c(N3CCC(n4c(=O)[nH]c5ccccc54)CC3)ncnc2n1C1CC1] | 9-cyclopropyl-N-(2-methylpropyl)-6-[4-(2-oxo-2,3-dihydro-1H-benzimidazol-1-yl)piperidin-1-yl]-9H-purine-8-carboxamide |

TABLE 1-continued

| Compound Number | Structure | Name |
|---|---|---|
| 174 | 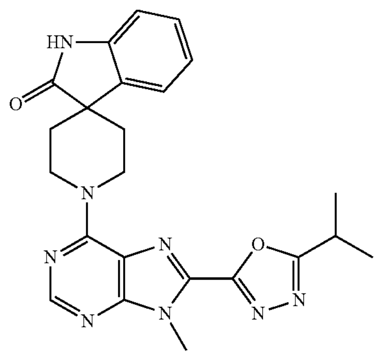 [SMILES: CC(C)c1nnc(-c2nc3c(N4CCC5(CC4)C(=O)Nc4ccccc45)ncnc3n2C)o1] | 1'-{9-methyl-8-[5-(1-methylethyl)-1,3,4-oxadiazol-2-yl]-9H-purin-6-yl}spiro[indole-3,4'-piperidin]-2(1H)-one |
| 175 | 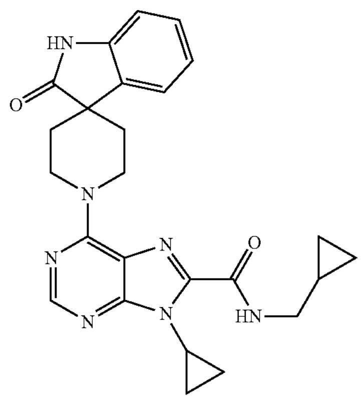 [SMILES: O=C(NCC1CC1)c1nc2c(N3CCC4(CC3)C(=O)Nc3ccccc34)ncnc2n1C1CC1] | 9-cyclopropyl-N-(cyclopropylmethyl)-6-(2-oxo-1,2-dihydro-1'H-spiro[indole-3,4'-piperidin]-1'-yl)-9H-purine-8-carboxamide |
| 176 | 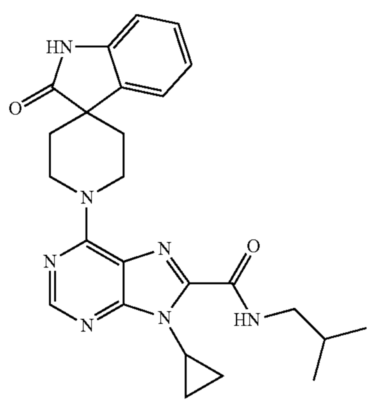 [SMILES: CC(C)CNC(=O)c1nc2c(N3CCC4(CC3)C(=O)Nc3ccccc34)ncnc2n1C1CC1] | 9-cyclopropyl-N-(2-methylpropyl)-6-(2-oxo-1,2-dihydro-1'H-spiro[indole-3,4'-piperidin]-1'-yl)-9H-purine-8-carboxamide |
| 177 | 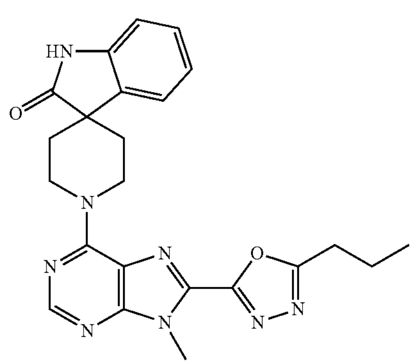 [SMILES: CCCc1nnc(-c2nc3c(N4CCC5(CC4)C(=O)Nc4ccccc45)ncnc3n2C)o1] | 1'-[9-methyl-8-(5-propyl-1,3,4-oxadiazol-2-yl)-9H-purin-6-yl]spiro[indole-3,4'-piperidin]-2(1H)-one |

TABLE 1-continued

| Compound Number | Structure | Name |
| --- | --- | --- |
| 178 | 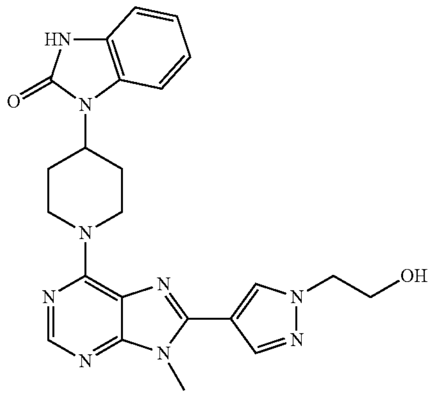 [SMILES: Cn1c(-c2cnn(CCO)c2)nc2c(N3CCC(n4c(=O)[nH]c5ccccc54)CC3)ncnc21] | 1-(1-{8-[1-(2-hydroxyethyl)-1H-pyrazol-4-yl)-9-methyl-9H-purin-6-yl)piperidin-4-yl)-1,3-dihydro-2H-benzimidazol-2-one |
| 179 | 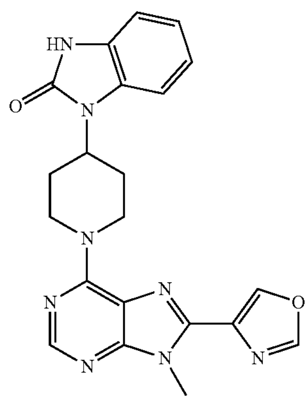 [SMILES: Cn1c(-c2cocn2)nc2c(N3CCC(n4c(=O)[nH]c5ccccc54)CC3)ncnc21] | 1-{1-[9-methyl-8-(1,3-oxazol-4-yl)-9H-purin-6-yl]piperidin-4-yl}-1,3-dihydro-2H-benzimidazol-2-one |
| 180 | 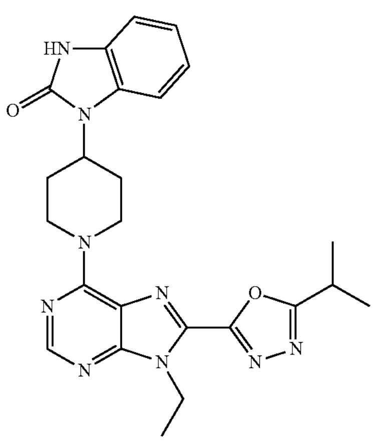 [SMILES: CCn1c(-c2nnc(C(C)C)o2)nc2c(N3CCC(n4c(=O)[nH]c5ccccc54)CC3)ncnc21] | 1-(1-{9-ethyl-8-[5-(1-methylethyl)-1,3,4-oxadiazol-2-yl]-9H-purin-6-yl}piperidin-4-yl)-1,3-dihydro-2H-benzimidazol-2-one |

TABLE 1-continued

| Compound Number | Structure | Name |
|---|---|---|
| 181 | 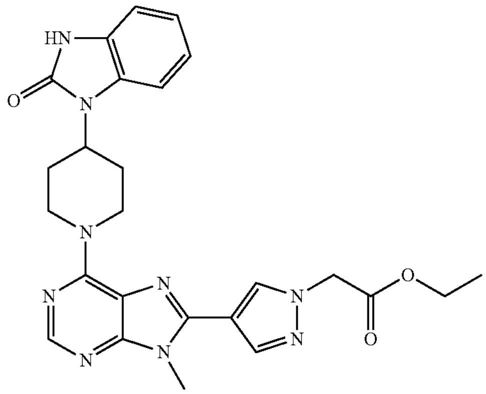 [SMILES: CCOC(=O)Cn1cc(-c2nc3c(N4CCC(n5c(=O)[nH]c6ccccc65)CC4)ncnc3n2C)cn1] | ethyl (4-{9-methyl-6-[4-(2-oxo-2,3-dihydro-1H-benzimidazol-1-yl)piperidin-1-yl]-9H-purin-8-yl}-1H-pyrazol-1-yl)acetate |
| 182 | 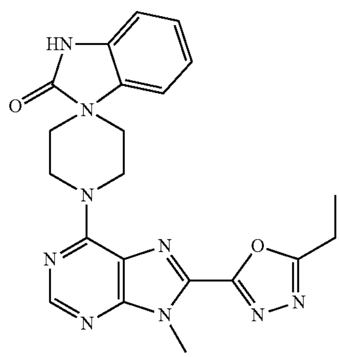 | 1'-[8-(5-ethyl-1,3,4-oxadiazol-2-yl)-9-methyl-9H-purin-6-yl]spiro[indole-3,4'-piperidin]-2(1H)-one |
| 183 | 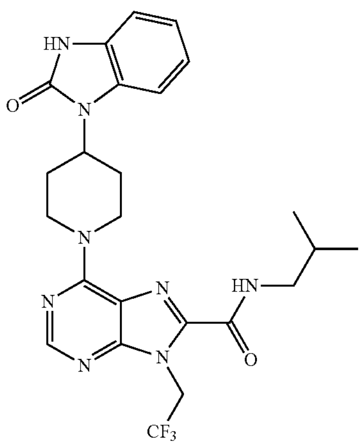 [SMILES: CC(C)CNC(=O)c1nc2c(N3CCC(n4c(=O)[nH]c5ccccc54)CC3)ncnc2n1CC(F)(F)F] | N-(2-methylpropyl)-6-[4-(2-oxo-2,3-dihydro-1H-benzimidazol-1-yl)piperidin-1-yl]-9-(2,2,2-trifluoroethyl)-9H-purine-8-carboxamide |
| 184 | 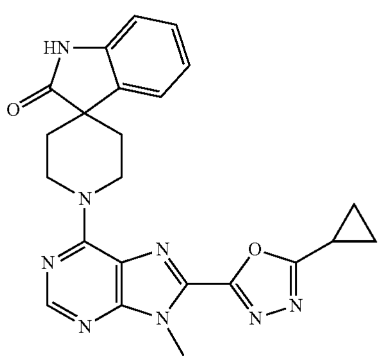 [SMILES: Cn1c(-c2nnc(C3CC3)o2)nc2c(N3CCC4(CC3)C(=O)Nc3ccccc34)ncnc21] | 1'-[8-(5-cyclopropyl-1,3,4-oxadiazol-2-yl)-9-methyl-9H-purin-6-yl]spiro[indole-3,4'-piperidin]-2(1H)-one |

TABLE 1-continued

| Compound Number | Structure | | Name |
|---|---|---|---|
| 185 | 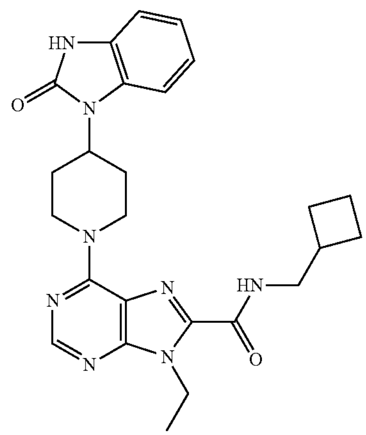 [SMILES: CCn1c(C(=O)NCC2CCC2)nc2c(N3CCC(n4c(=O)[nH]c5ccccc54)CC3)ncnc21] | | N-(cyclobutylmethyl)-9-ethyl-6-[4-(2-oxo-2,3-dihydro-1H-benzimidazol-1-yl)piperidin-1-yl]-9H-purine-8-carboxamide |
| 186 | 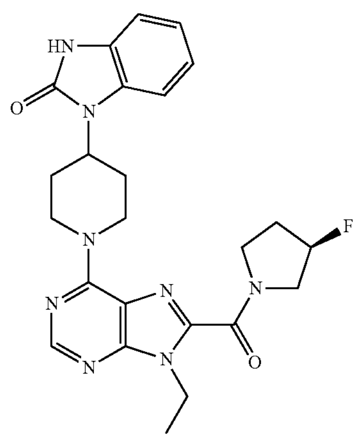 | Chiral | 1-[1-(9-ethyl-8-{[(3R)-3-fluoropyrrolidin-1-yl]carbonyl}-9H-purin-6-yl)piperidin-4-yl]-1,3-dihydro-2H-benzimidazol-2-one |
| 187 | 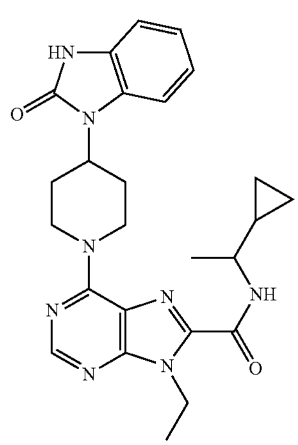 [SMILES: CCn1c(C(=O)NC(C)C2CC2)nc2c(N3CCC(n4c(=O)[nH]c5ccccc54)CC3)ncnc21] | | N-(1-cyclopropylethyl)-9-ethyl-6-[4-(2-oxo-2,3-dihydro-1H-benzimidazol-1-yl)piperidin-1-yl]-9H-purine-8-carboxamide |

TABLE 1-continued
| Compound Number | Structure | Name |
|---|---|---|
| 188 | 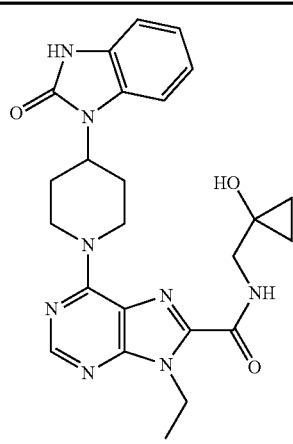 | 9-ethyl-N-[(1-hydroxycyclopropyl)methyl]-6-[4-(2-oxo-2,3-dihydro-1H-benzimidazol-1-yl)piperidin-1-yl]-9H-purine-8-carboxamide |
| 189 | 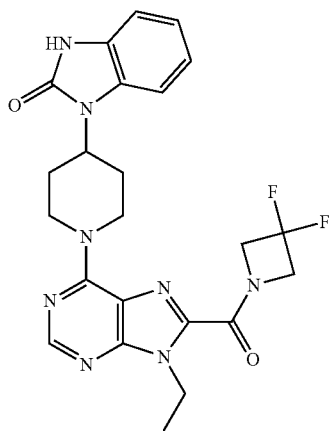 [SMILES: CCn1c(C(=O)N2CC(F)(F)C2)nc2c(N3CCC(n4c(=O)[nH]c5ccccc54)CC3)ncnc21] | 1-(1-{8-[(3,3-difluoroazetidin-1-yl)carbonyl]-9-ethyl-9H-purin-6-yl}piperidin-4-yl)-1,3-dihydro-2H-benzimidazol-2-one |
| 190 | 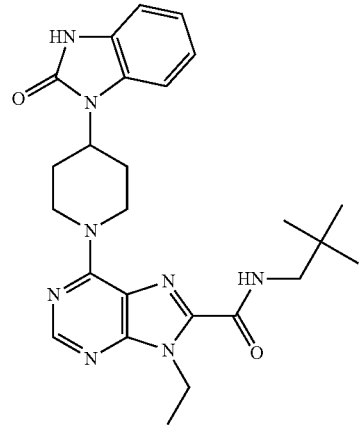 [SMILES: CCn1c(C(=O)NCC(C)(C)C)nc2c(N3CCC(n4c(=O)[nH]c5ccccc54)CC3)ncnc21] | N-(2,2-dimethylpropyl)-9-ethyl-6-[4-(2-oxo-2,3-dihydro-1H-benzimidazol-1-yl)piperidin-1-yl]-9H-purine-8-carboxamide |

TABLE 1-continued

| Compound Number | Structure | Name |
|---|---|---|
| 191 | 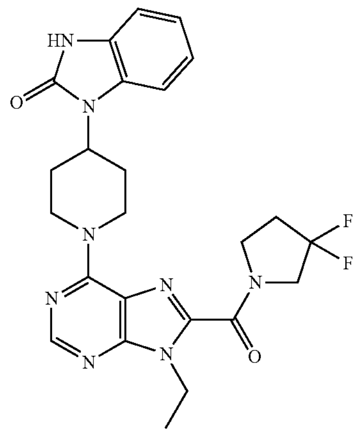 [SMILES: CCn1c(C(=O)N2CCC(F)(F)C2)nc2c(N3CCC(n4c(=O)[nH]c5ccccc54)CC3)ncnc21] | 1-(1-{8-[(3,3-difluoropyrrolidin-1-yl)carbonyl]-9-ethyl-9H-purin-6-yl}piperidin-4-yl)-1,3-dihydro-2H-benzimidazol-2-one |
| 192 | 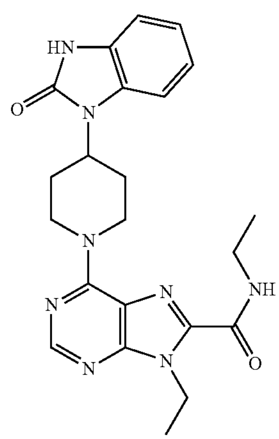 [SMILES: CCNC(=O)c1nc2c(N3CCC(n4c(=O)[nH]c5ccccc54)CC3)ncnc2n1CC] | N,9-diethyl-6-[4-(2-oxo-2,3-dihydro-1H-benzimidazol-1-yl)piperidin-1-yl]-9H-purine-8-carboxamide |
| 193 | 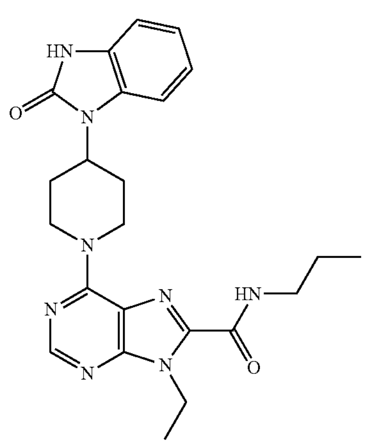 [SMILES: CCCNC(=O)c1nc2c(N3CCC(n4c(=O)[nH]c5ccccc54)CC3)ncnc2n1CC] | 9-ethyl-6-[4-(2-oxo-2,3-dihydro-1H-benzimidazol-1-yl)piperidin-1-yl]-N-propyl-9H-purine-8-carboxamide |

TABLE 1-continued
| Compound Number | Structure | Name |
|---|---|---|
| 194 | 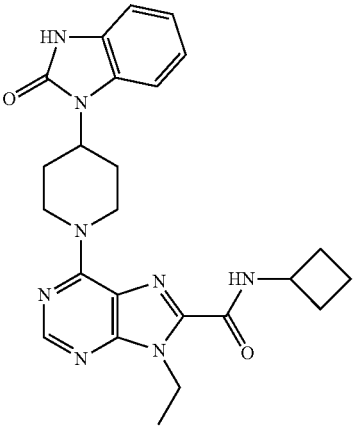 [SMILES: CCn1c(C(=O)NC2CCC2)nc2c(N3CCC(n4c(=O)[nH]c5ccccc54)CC3)ncnc21] | N-cyclobutyl-9-ethyl-6-[4-(2-oxo-2,3-dihydro-1H-benzimidazol-1-yl)piperidin-1-yl]-9H-purine-8-carboxamide |
| 195 | 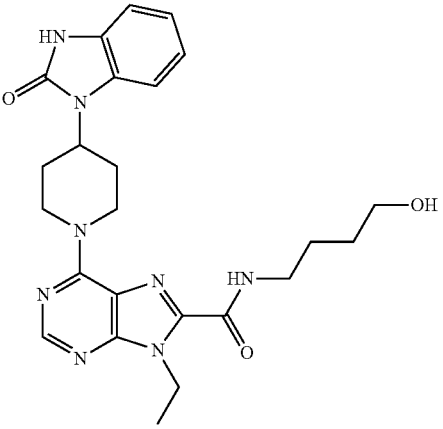 [SMILES: CCn1c(C(=O)NCCCCO)nc2c(N3CCC(n4c(=O)[nH]c5ccccc54)CC3)ncnc21] | 9-ethyl-N-(4-hydroxybutyl)-6-[4-(2-oxo-2,3-dihydro-1H-benzimidazol-1-yl)piperidin-1-yl]-9H-purine-8-carboxamide |
| 196 | 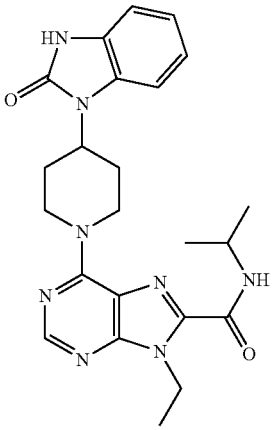 [SMILES: CCn1c(C(=O)NC(C)C)nc2c(N3CCC(n4c(=O)[nH]c5ccccc54)CC3)ncnc21] | 9-ethyl-N-(1-methylethyl)-6-[4-(2-oxo-2,3-dihydro-1H-benzimidazol-1-yl)piperidin-1-yl]-9H-purine-8-carboxamide |

TABLE 1-continued

| Compound Number | Structure | Name |
|---|---|---|
| 197 | 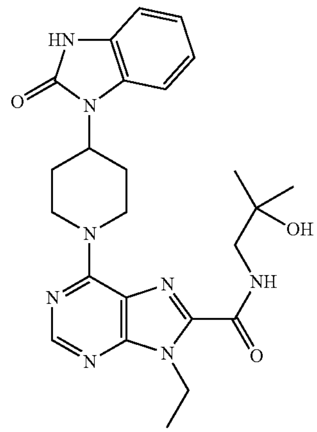 [SMILES: CCn1c(C(=O)NCC(C)(C)O)nc2c(N3CCC(n4c(=O)[nH]c5ccccc54)CC3)ncnc21] | 9-ethyl-N-(2-hydroxy-2-methylpropyl)-6-[4-(2-oxo-2,3-dihydro-1H-benzimidazol-1-yl)piperidin-1-yl]-9H-purine-8-carboxamide |
| 198 | 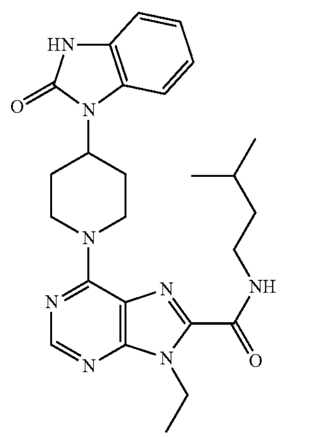 [SMILES: CCn1c(C(=O)NCCC(C)C)nc2c(N3CCC(n4c(=O)[nH]c5ccccc54)CC3)ncnc21] | 9-ethyl-N-(3-methylbutyl)-6-[4-(2-oxo-2,3-dihydro-1H-benzimidazol-1-yl)piperidin-1-yl]-9H-purine-8-carboxamide |
| 199 | 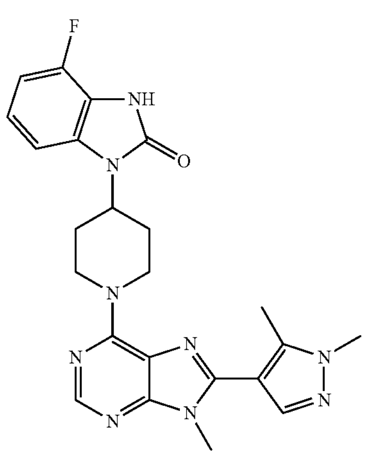 [SMILES: Cc1c(-c2nc3c(N4CCC(n5c(=O)[nH]c6c(F)cccc65)CC4)ncnc3n2C)cnn1C] | N-(cyclopropylmethyl)-9-methyl-6-[1-(2-methylphenyl)-1,4,6,7-tetrahydro-5H-pyrazolo[4,3-c]pyridin-5-yl]-9H-purine-8-carboxamide |

TABLE 1-continued

| Compound Number | Structure | Name |
|---|---|---|
| 200 | 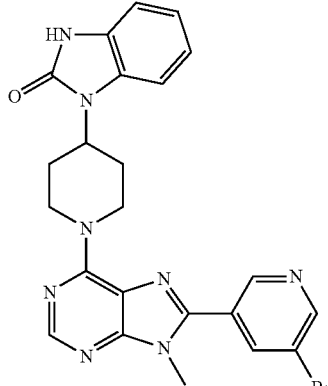 | N-(cyclopropylmethyl)-9-methyl-6-[1-(3-methylphenyl)-1,4,6,7-tetrahydro-5H-pyrazolo[4,3-c]pyridin-5-yl]-9H-purine-8-carboxamide |
| 201 | 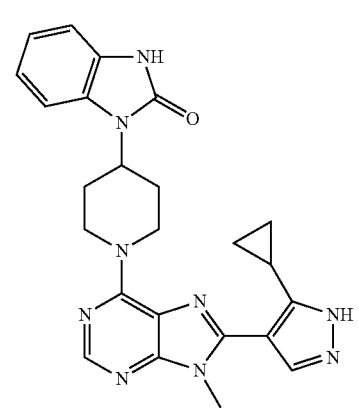 [SMILES: Cn1c(-c2cn[nH]c2C2CC2)nc2c(N3CCC(n4c(=O)[nH]c5ccccc54)CC3)ncnc21] | N-(cyclopropylmethyl)-6-[1-(2,4-dimethylphenyl)-1,4,6,7-tetrahydro-5H-pyrazolo[4,3-c]pyridin-5-yl]-9-methyl-9H-purine-8-carboxamide |
| 202 | 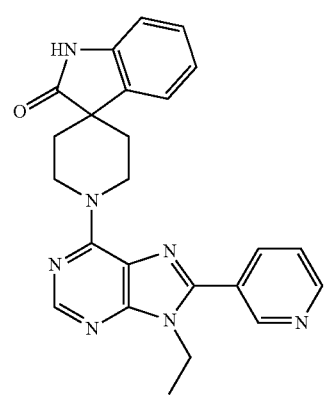 [SMILES: CCn1c(-c2cccnc2)nc2c(N3CCC4(CC3)C(=O)Nc3ccccc34)ncnc21] | N-(cyclopropylmethyl)-6-[1-(2,6-dimethylphenyl)-1,4,6,7-tetrahydro-5H-pyrazolo[4,3-c]pyridin-5-yl]-9-methyl-9H-purine-8-carboxamide |
| 203 | 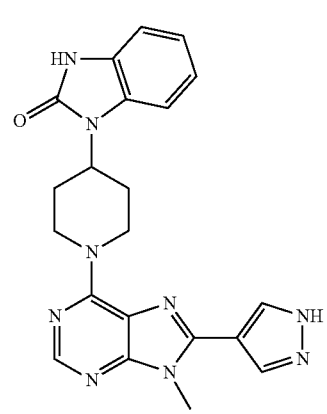 [SMILES: Cn1c(-c2cn[nH]c2)nc2c(N3CCC(n4c(=O)[nH]c5ccccc54)CC3)ncnc21] | 1-{1-[9-methyl-8-(1H-pyrazol-4-yl)-9H-purin-6-yl]piperidin-4-yl}-1,3-dihydro-2H-benzimidazol-2-one |

TABLE 1-continued
| Compound Number | Structure | Name |
|---|---|---|
| 204 | 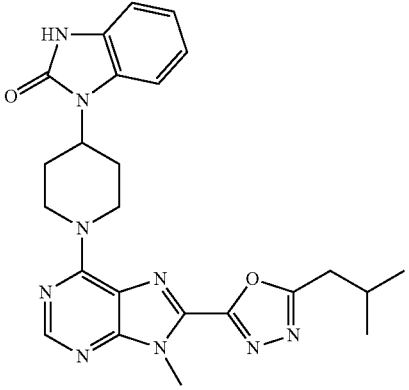 [SMILES: CC(C)Cc1nnc(-c2nc3c(N4CCC(n5c(=O)[nH]c6ccccc65)CC4)ncnc3n2C)o1] | 1-(1-{9-methyl-8-[5-(2-methylpropyl)-1,3,4-oxadiazol-2-yl]-9H-purin-6-yl}piperidin-4-yl)-1,3-dihydro-2H-benzimidazol-2-one |
| 205 | 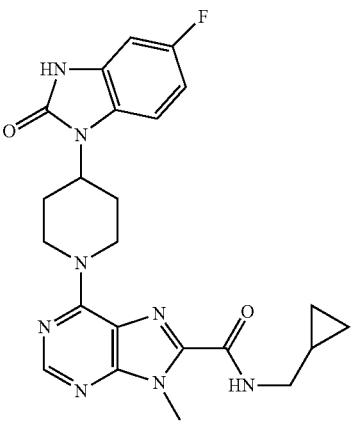 [SMILES: Cn1c(C(=O)NCC2CC2)nc2c(N3CCC(n4c(=O)[nH]c5cc(F)ccc54)CC3)ncnc21] | N-(cyclopropylmethyl)-6-[4-(5-fluoro-2-oxo-2,3-dihydro-1H-benzimidazol-1-yl)piperidin-1-yl]-9-methyl-9H-purine-8-carboxamide |
| 206 | 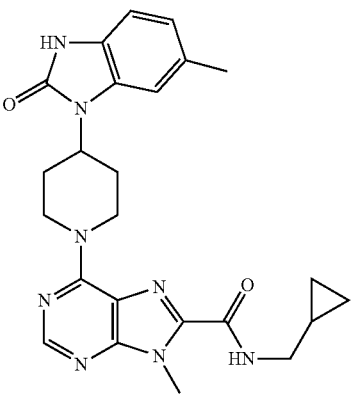 [SMILES: Cc1ccc2[nH]c(=O)n(C3CCN(c4ncnc5c4nc(C(=O)NCC4CC4)n5C)CC3)c2c1] | N-(cyclopropylmethyl)-9-methyl-6-[4-(6-methyl-2-oxo-2,3-dihydro-1H-benzimidazol-1-yl)piperidin-1-yl]-9H-purine-8-carboxamide |

TABLE 1-continued
| Compound Number | Structure | Name |
|---|---|---|
| 207 | 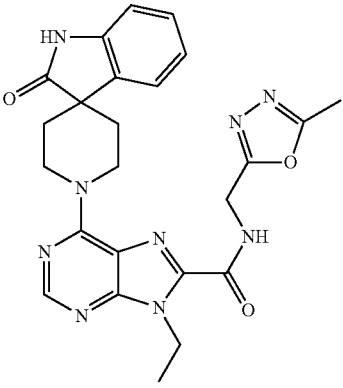 [SMILES: CCn1c(C(=O)NCc2nnc(C)o2)nc2c(N3CCC4(CC3)C(=O)Nc3ccccc34)ncnc21] | 9-ethyl-N-[(5-methyl-1,3,4-oxadiazol-2-yl)methyl]-6-(2-oxo-1,2-dihydro-1'H-spiro[indole-3,4'-piperidin]-1'-yl)-9H-purine-8-carboxamide |
| 208 | 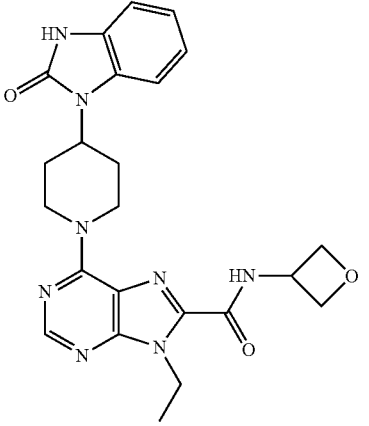 [SMILES: CCn1c(C(=O)NC2COC2)nc2c(N3CCC(n4c(=O)[nH]c5ccccc54)CC3)ncnc21] | 9-ethyl-N-oxetan-3-yl-6-[4-(2-oxo-2,3-dihydro-1H-benzimidazol-1-yl)piperidin-1-yl]-9H-purine-8-carboxamide |
| 209 | 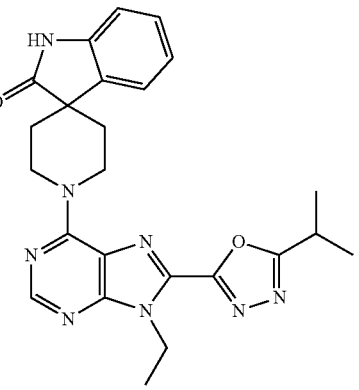 | 1'-{9-ethyl-8-[5-(1-methylethyl)-1,3,4-oxadiazol-2-yl]-9H-purin-6-yl}spiro[indole-3,4'-piperidin]-2(1H)-one |

TABLE 1-continued

| Compound Number | Structure | Name |
|---|---|---|
| 210 | 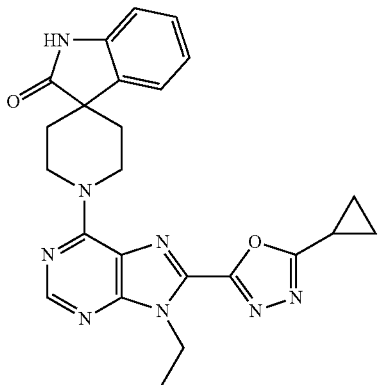 [SMILES: CCn1c(-c2nnc(C3CC3)o2)nc2c(N3CCC4(CC3)C(=O)Nc3ccccc34)ncnc21] | 1'-[8-(5-cyclopropyl-1,3,4-oxadiazol-2-yl)-9-ethyl-9H-purin-6-yl]spiro[indole-3,4'-piperidin]-2(1H)-one |
| 211 | 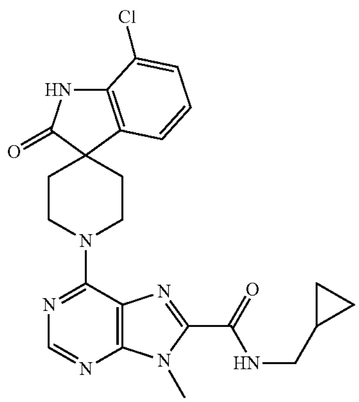 [SMILES: Cn1c(C(=O)NCC2CC2)nc2c(N3CCC4(CC3)C(=O)Nc3c(Cl)cccc34)ncnc21] | 6-(7-chloro-2-oxo-1,2-dihydro-1'H-spiro[indole-3,4'-piperidin]-1'-yl)-N-(cyclopropylmethyl)-9-methyl-9H-purine-8-carboxamide |
| 212 | 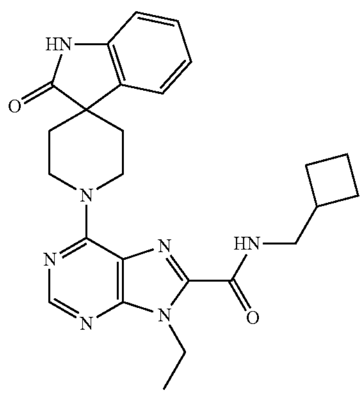 [SMILES: CCn1c(C(=O)NCC2CCC2)nc2c(N3CCC4(CC3)C(=O)Nc3ccccc34)ncnc21] | N-(cyclobutylmethyl)-9-ethyl-6-(2-oxo-1,2-dihydro-1'H-spiro[indole-3,4'-piperidin]-1'-yl)-9H-purine-8-carboxamide |
| 213 | Chiral | 1'-(9-ethyl-8-{[(3R)-3-fluoropyrrolidin-1-yl]carbonyl}-9H-purin-6-yl)spiro[indole-3,4'-piperidin]-2(1H)-one |

TABLE 1-continued

| Compound Number | Structure | Name |
|---|---|---|
| 214 | 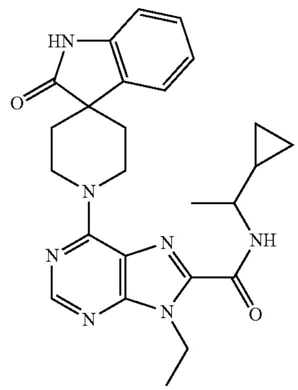 [SMILES: CCn1c(C(=O)NC(C)C2CC2)nc2c(N3CCC4(CC3)C(=O)Nc3ccccc34)ncnc21] | N-(1-cyclopropylethyl)-9-ethyl-6-(2-oxo-1,2-dihydro-1'H-spiro[indole-3,4'-piperidin]-1'-yl)-9H-purine-8-carboxamide |
| 215 | 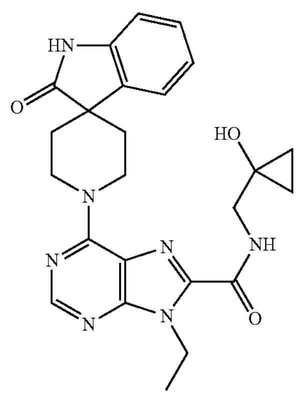 [SMILES: CCn1c(C(=O)NCC2(O)CC2)nc2c(N3CCC4(CC3)C(=O)Nc3ccccc34)ncnc21] | 9-ethyl-N-[(1-hydroxycyclopropyl)methyl]-6-(2-oxo-1,2-dihydro-1'H-spiro[indole-3,4'-piperidin]-1'-yl)-9H-purine-8-carboxamide |
| 216 | 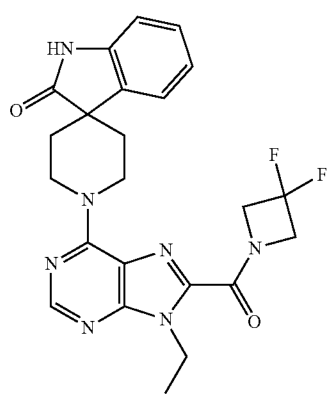 [SMILES: CCn1c(C(=O)N2CC(F)(F)C2)nc2c(N3CCC4(CC3)C(=O)Nc3ccccc34)ncnc21] | 1'-{8-[(3,3-difluoroazetidin-1-yl)carbonyl]-9-ethyl-9H-purin-6-yl}spiro[indole-3,4'-piperidin]-2(1H)-one |
| 217 | 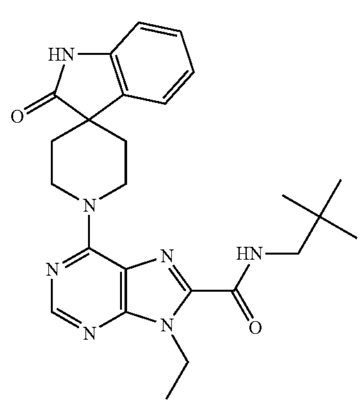 [SMILES: CCn1c(C(=O)NCC(C)(C)C)nc2c(N3CCC4(CC3)C(=O)Nc3ccccc34)ncnc21] | N-(2,2-dimethylpropyl)-9-ethyl-6-(2-oxo-1,2-dihydro-1'H-spiro[indole-3,4'-piperidin]-1'-yl)-9H-purine-8-carboxamide |

TABLE 1-continued

| Compound Number | Structure | Name |
|---|---|---|
| 218 | 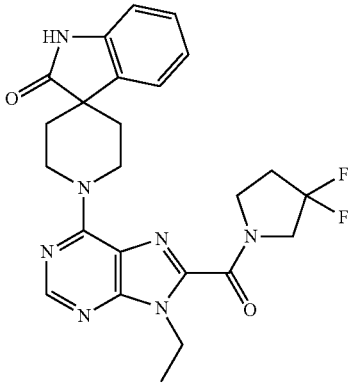 [SMILES: CCn1c(C(=O)N2CCC(F)(F)C2)nc2c(N3CCC4(CC3)C(=O)Nc3ccccc34)ncnc21] | 1'-{8-[(3,3-difluoropyrrolidin-1-yl)carbonyl]-9-ethyl-9H-purin-6-yl}spiro[indole-3,4'-piperidin]-2(1H)-one |
| 219 | 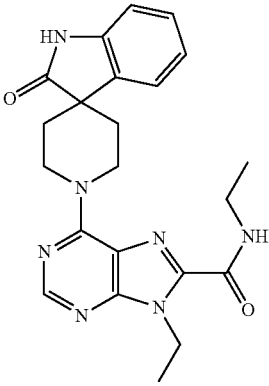 [SMILES: CCNC(=O)c1nc2c(N3CCC4(CC3)C(=O)Nc3ccccc34)ncnc2n1CC] | N,9-diethyl-6-(2-oxo-1,2-dihydro-1'H-spiro[indole-3,4'-piperidin]-1'-yl)-9H-purine-8-carboxamide |
| 220 | 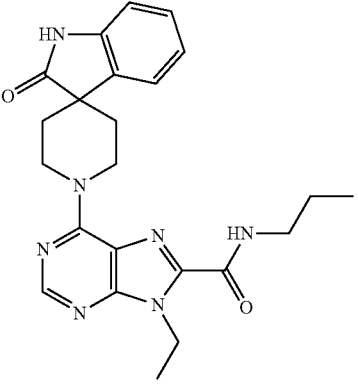 [SMILES: CCCNC(=O)c1nc2c(N3CCC4(CC3)C(=O)Nc3ccccc34)ncnc2n1CC] | 9-ethyl-6-(2-oxo-1,2-dihydro-1'H-spiro[indole-3,4'-piperidin]-1'-yl)-N-propyl-9H-purine-8-carboxamide |
| 221 | 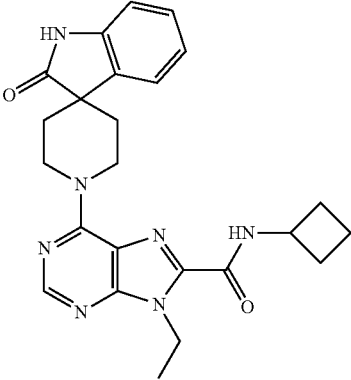 [SMILES: CCn1c(C(=O)NC2CCC2)nc2c(N3CCC4(CC3)C(=O)Nc3ccccc34)ncnc21] | N-cyclobutyl-9-ethyl-6-(2-oxo-1,2-dihydro-1'H-spiro[indole-3,4'-piperidin]-1'-yl)-9H-purine-8-carboxamide |

TABLE 1-continued

| Compound Number | Structure | Name |
|---|---|---|
| 222 | 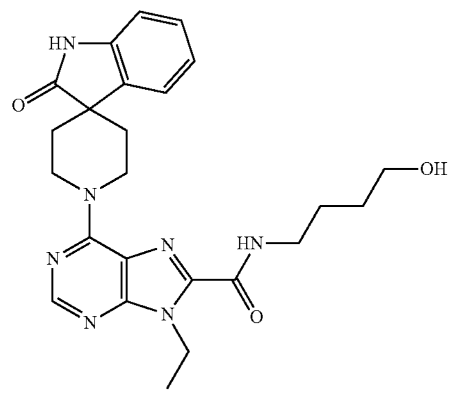 [SMILES: CCn1c(C(=O)NCCCCO)nc2c(N3CCC4(CC3)C(=O)Nc3ccccc34)ncnc21] | 9-ethyl-N-(4-hydroxybutyl)-6-(2-oxo-1,2-dihydro-1'H-spiro[indole-3,4'-piperidin]-1'-yl)-9H-purine-8-carboxamide |
| 223 | 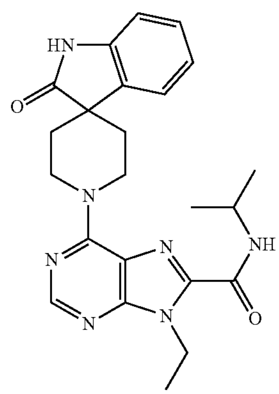 [SMILES: CCn1c(C(=O)NC(C)C)nc2c(N3CCC4(CC3)C(=O)Nc3ccccc34)ncnc21] | 9-ethyl-N-(1-methylethyl)-6-(2-oxo-1,2-dihydro-1'H-spiro[indole-3,4'-piperidin]-1'-yl)-9H-purine-8-carboxamide |
| 224 | 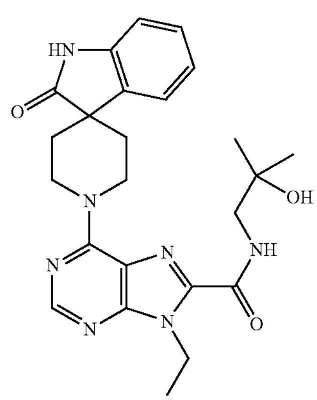 [SMILES: CCn1c(C(=O)NCC(C)(C)O)nc2c(N3CCC4(CC3)C(=O)Nc3ccccc34)ncnc21] | 9-ethyl-N-(2-hydroxy-2-methylpropyl)-6-(2-oxo-1,2-dihydro-1'H-spiro[indole-3,4'-piperidin]-1'-yl)-9H-purine-8-carboxamide |
| 225 | 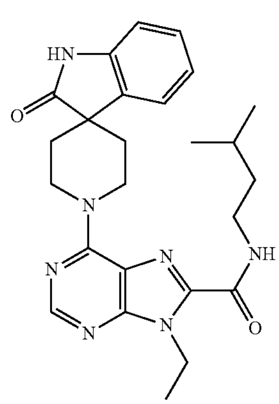 [SMILES: CCn1c(C(=O)NCCC(C)C)nc2c(N3CCC4(CC3)C(=O)Nc3ccccc34)ncnc21] | 9-ethyl-N-(3-methylbutyl)-6-(2-oxo-1,2-dihydro-1'H-spiro[indole-3,4'-piperidin]-1'-yl)-9H-purine-8-carboxamide |

TABLE 1-continued
| Compound Number | Structure | Name |
|---|---|---|
| 226 | 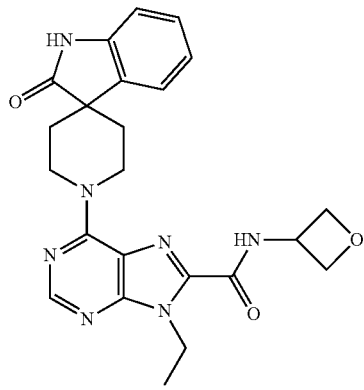 [SMILES: CCn1c(C(=O)NC2COC2)nc2c(N3CCC4(CC3)C(=O)Nc3ccccc34)ncnc21] | 9-ethyl-N-oxetan-3-yl-6-(2-oxo-1,2-dihydro-1'H-spiro[indole-3,4'-piperidin]-1'-yl)-9H-purine-8-carboxamide |
| 227 | 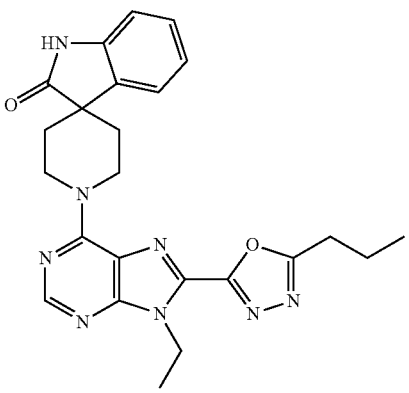 [SMILES: CCCc1nnc(-c2nc3c(N4CCC5(CC4)C(=O)Nc4ccccc45)ncnc3n2CC)o1] | 1'-[9-ethyl-8-(5-propyl-1,3,4-oxadiazol-2-yl)-9H-purin-6-yl]spiro[indole-3,4'-piperidin]-2(1H)-one |
| 228 | 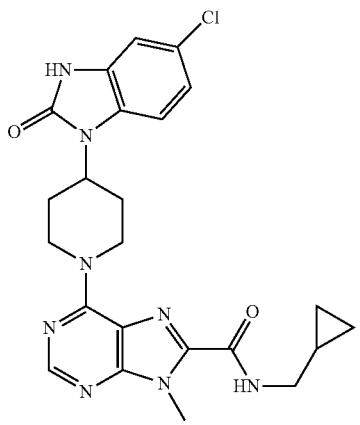 | 6-[4-(5-chloro-2-oxo-2,3-dihydro-1H-benzimidazol-1-yl)piperidin-1-yl]-N-(cyclopropylmethyl)-9-methyl-9H-purine-8-carboxamide |

TABLE 1-continued
| Compound Number | Structure | Name |
|---|---|---|
| 229 | 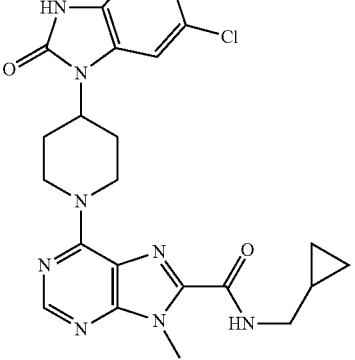 | 6-[4-(6-chloro-2-oxo-2,3-dihydro-1H-benzimidazol-1-yl)piperidin-1-yl]-N-(cyclopropylmethyl)-9-methyl-9H-purine-8-carboxamide |
| 230 | 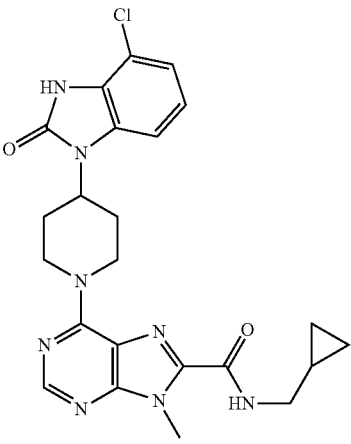 [SMILES: Cn1c(C(=O)NCC2CC2)nc2c(N3CCC(n4c(=O)[nH]c5c(Cl)cccc54)CC3)ncnc21] | 6-[4-(4-chloro-2-oxo-2,3-dihydro-1H-benzimidazol-1-yl)piperidin-1-yl]-N-(cyclopropylmethyl)-9-methyl-9H-purine-8-carboxamide |
| 231 | 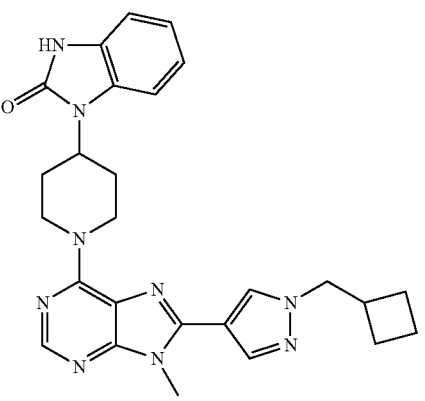 [SMILES: Cn1c(-c2cnn(CC3CCC3)c2)nc2c(N3CCC(n4c(=O)[nH]c5ccccc54)CC3)ncnc21] | 1-(1-{8-[1-(cyclobutylmethyl)-1H-pyrazol-4-yl]-9-methyl-9H-purin-6-yl}piperidin-4-yl)-1,3-dihydro-2H-benzimidazol-2-one |

TABLE 1-continued

| Compound Number | Structure | Name |
| --- | --- | --- |
| 232 | 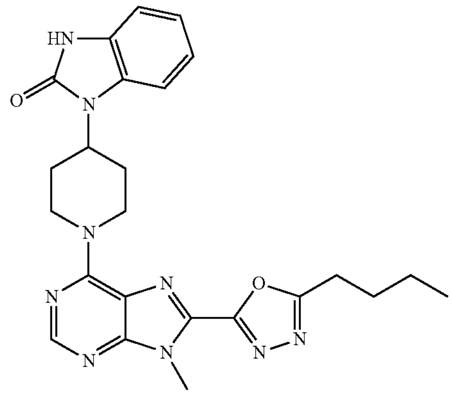 [SMILES: CCCCc1nnc(-c2nc3c(N4CCC(n5c(=O)[nH]c6ccccc65)CC4)ncnc3n2C)o1] | 1-{1-[8-(5-butyl-1,3,4-oxadiazol-2-yl)-9-methyl-9H-purin-6-yl]piperidin-4-yl}-1,3-dihydro-2H-benzimidazol-2-one |
| 233 | 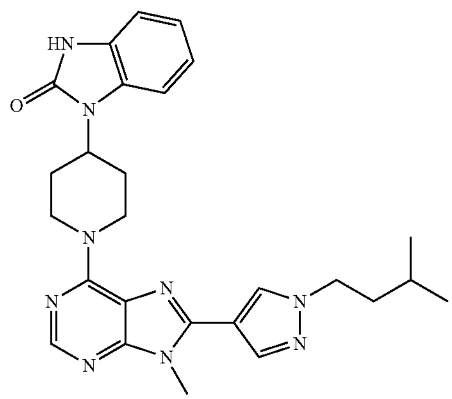 [SMILES: CC(C)CCn1cc(-c2nc3c(N4CCC(n5c(=O)[nH]c6ccccc65)CC4)ncnc3n2C)cn1] | 1-(1-{9-methyl-8-[1-(3-methylbutyl)-1H-pyrazol-4-yl]-9H-purin-6-yl}piperidin-4-yl)-1,3-dihydro-2H-benzimidazol-2-one |
| 234 | 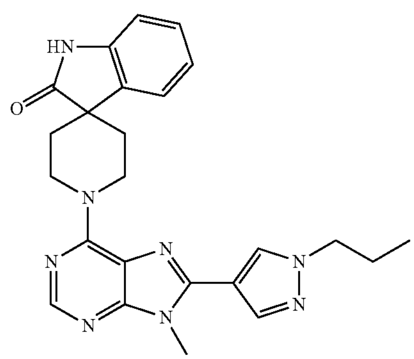 [SMILES: CCCn1cc(-c2nc3c(N4CCC5(CC4)C(=O)Nc4ccccc45)ncnc3n2C)cn1] | 1'-[9-methyl-8-(1-propyl-1H-pyrazol-4-yl)-9H-purin-6-yl]spiro[indole-3,4'-piperidin]-2(1H)-one |
| 235 | 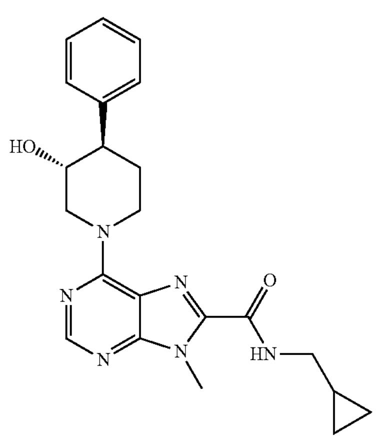 [SMILES: Cn1c(C(=O)NCC2CC2)nc2c(N3CC[C@H](c4ccccc4)[C@@H](O)C3)ncnc21] | N-(cyclopropylmethyl)-6-[(3R,4R)-3-hydroxy-4-phenylpiperidin-1-yl]-9-methyl-9H-purine-8-carboxamide |

TABLE 1-continued

| Compound Number | Structure | Name |
|---|---|---|
| 236 | 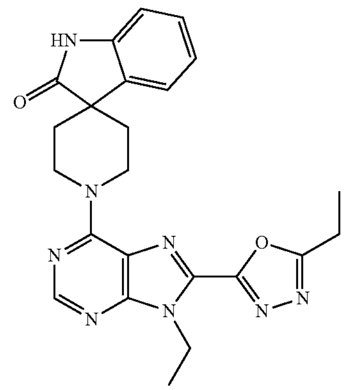 [SMILES: CCc1nnc(-c2nc3c(N4CCC5(CC4)C(=O)Nc4ccccc45)ncnc3n2CC)o1] | 1'-[9-ethyl-8-(5-ethyl-1,3,4-oxadiazol-2-yl)-9H-purin-6-yl]spiro[indole-3,4'-piperidin]-2(1H)-one |
| 237 | 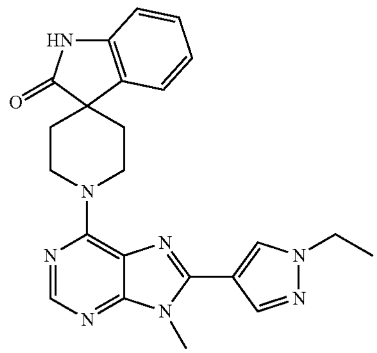 [SMILES: CCn1cc(-c2nc3c(N4CCC5(CC4)C(=O)Nc4ccccc45)ncnc3n2C)cn1] | 1'-[8-(1-ethyl-1H-pyrazol-4-yl)-9-methyl-9H-purin-6-yl]spiro[indole-3,4'-piperidin]-2(1H)-one |
| 238 | 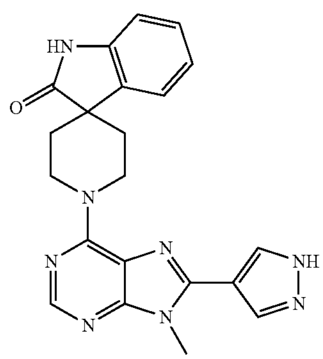 [SMILES: Cn1c(-c2cn[nH]c2)nc2c(N3CCC4(CC3)C(=O)Nc3ccccc34)ncnc21] | 1'-[9-methyl-8-(1H-pyrazol-4-yl)-9H-purin-6-yl]spiro[indole-3,4'-piperidin]-2(1H)-one |
| 239 | 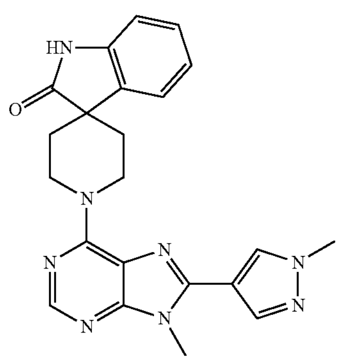 [SMILES: Cn1cc(-c2nc3c(N4CCC5(CC4)C(=O)Nc4ccccc45)ncnc3n2C)cn1] | 1'-[9-methyl-8-(1-methyl-1H-pyrazol-4-yl)-9H-purin-6-yl]spiro[indole-3,4'-piperidin]-2(1H)-one |

TABLE 1-continued
| Compound Number | Structure | Name |
|---|---|---|
| 240 | 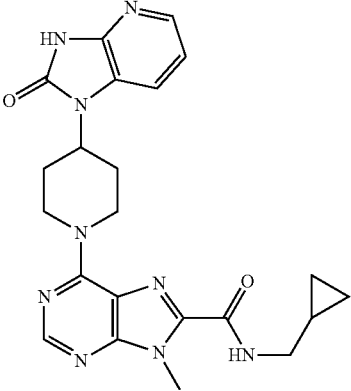 [SMILES: Cn1c(C(=O)NCC2CC2)nc2c(N3CCC(n4c(=O)[nH]c5ncccc54)CC3)ncnc21] | N-(cyclopropylmethyl)-9-methyl-6-[4-(2-oxo-2,3-dihydro-1H-imidazo[4,5-b]pyridin-1-yl)piperidin-1-yl]-9H-purine-8-carboxamide |
| 241 | 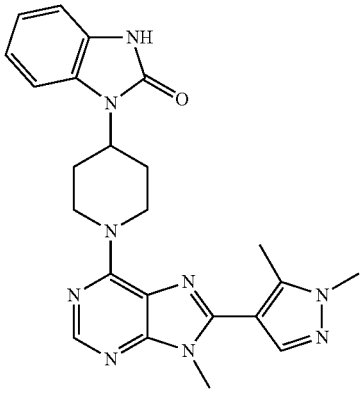 [SMILES: Cc1c(-c2nc3c(N4CCC(n5c(=O)[nH]c6ccccc65)CC4)ncnc3n2C)cnn1C] | 1-{1-[8-(1,5-dimethyl-1H-pyrazol-4-yl)-9-methyl-9H-purin-6-yl]piperidin-4-yl}-1,3-dihydro-2H-benzimidazol-2-one |
| 242 | 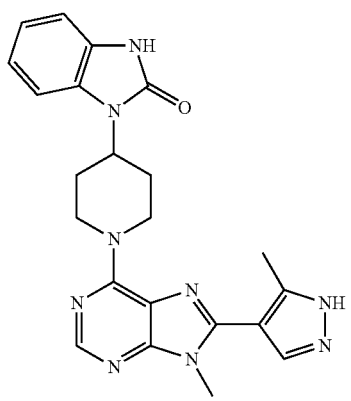 [SMILES: Cc1[nH]ncc1-c1nc2c(N3CCC(n4c(=O)[nH]c5ccccc54)CC3)ncnc2n1C] | 1-{1-[9-methyl-8-(5-methyl-1H-pyrazol-4-yl)-9H-purin-6-yl]piperidin-4-yl}-1,3-dihydro-2H-benzimidazol-2-one |

TABLE 1-continued

| Compound Number | Structure | Name |
|---|---|---|
| 243 | 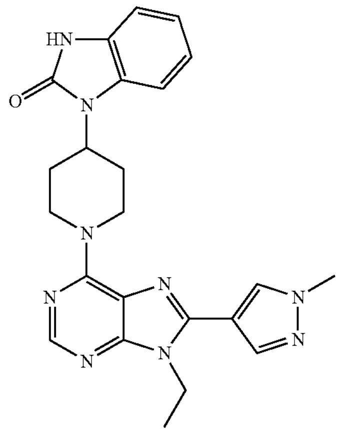 [SMILES: CCn1c(-c2cnn(C)c2)nc2c(N3CCC(n4c(=O)[nH]c5ccccc54)CC3)ncnc21] | 1-{1-[9-ethyl-8-(1-methyl-1H-pyrazol-4-yl)-9H-purin-6-yl]piperidin-4-yl}-1,3-dihydro-2H-benzimidazol-2-one |
| 244 | 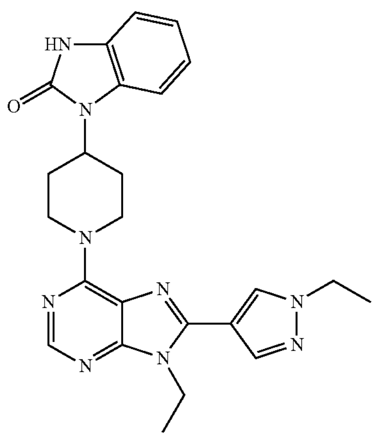 [SMILES: CCn1cc(-c2nc3c(N4CCC(n5c(=O)[nH]c6ccccc65)CC4)ncnc3n2CC)cn1] | 1-{1-[9-ethyl-8-(1-ethyl-1H-pyrazol-4-yl)-9H-purin-6-yl]piperidin-4-yl}-1,3-dihydro-2H-benzimidazol-2-one |
| 245 | 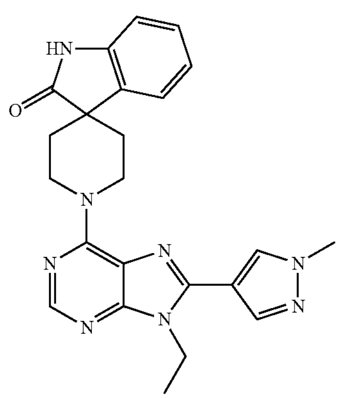 [SMILES: CCn1c(-c2cnn(C)c2)nc2c(N3CCC4(CC3)C(=O)Nc3ccccc34)ncnc21] | 1'-[9-ethyl-8-(1-methyl-1H-pyrazol-4-yl)-9H-purin-6-yl]spiro[indole-3,4'-piperidin]-2(1H)-one |

TABLE 1-continued

| Compound Number | Structure | Name |
|---|---|---|
| 246 | 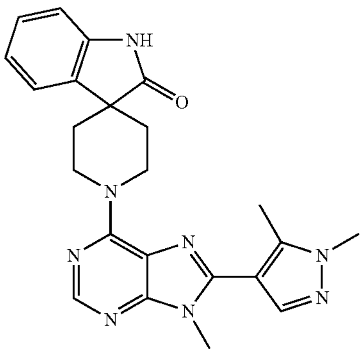 [SMILES: Cc1c(-c2nc3c(N4CCC5(CC4)C(=O)Nc4ccccc45)ncnc3n2C)cnn1C] | 1'-[8-(1,5-dimethyl-1H-pyrazol-4-yl)-9-methyl-9H-purin-6-yl]spiro[indole-3,4'-piperidin]-2(1H)-one |
| 247 | 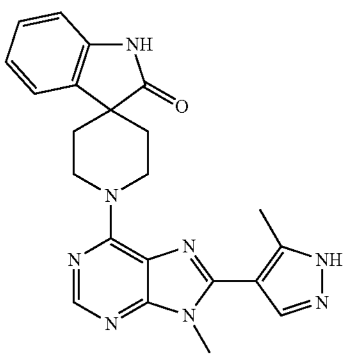 [SMILES: Cc1[nH]ncc1-c1nc2c(N3CCC4(CC3)C(=O)Nc3ccccc34)ncnc2n1C] | 1'-[9-methyl-8-(5-methyl-1H-pyrazol-4-yl)-9H-purin-6-yl]spiro[indole-3,4'-piperidin]-2(1H)-one |
| 248 | 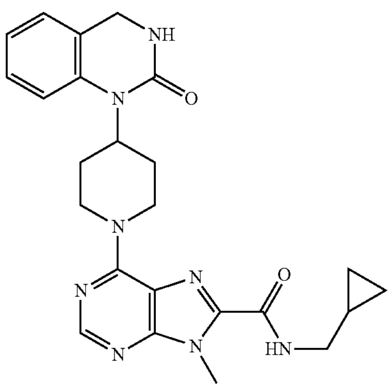 [SMILES: Cn1c(C(=O)NCC2CC2)nc2c(N3CCC(N4C(=O)NCc5ccccc54)CC3)ncnc21] | N-(cyclopropylmethyl)-9-methyl-6-[4-(2-oxo-3,4-dihydroquinazolin-1(2H)-yl)piperidin-1-yl]-9H-purine-8-carboxamide |
| 249 | 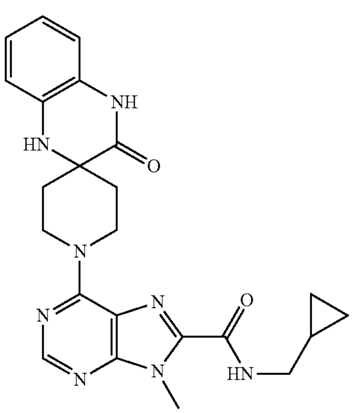 [SMILES: Cn1c(C(=O)NCC2CC2)nc2c(N3CCC4(CC3)Nc3ccccc3NC4=O)ncnc21] | N-(cyclopropylmethyl)-9-methyl-6-(3'-oxo-3',4'-dihydro-1H,1'H-spiro[piperidine-4,2'-quinoxalin]-1-yl)-9H-purine-8-carboxamide |

TABLE 1-continued

| Compound Number | Structure | Name |
|---|---|---|
| 250 | 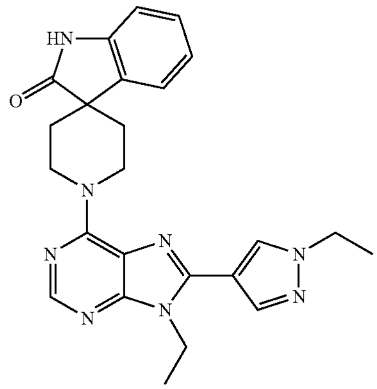 [SMILES: CCn1cc(-c2nc3c(N4CCC5(CC4)C(=O)Nc4ccccc45)ncnc3n2CC)cn1] | 1'-[9-ethyl-8-(1-ethyl-1H-pyrazol-4-yl)-9H-purin-6-yl]spiro[indole-3,4'-piperidin]-2(1H)-one |
| 251 | 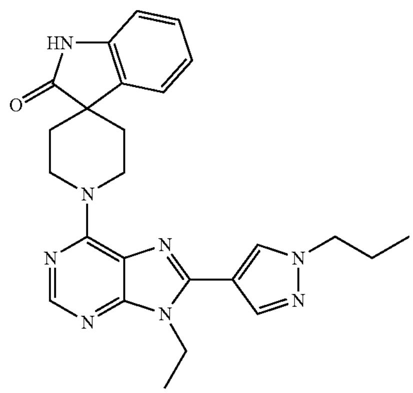 [SMILES: CCCn1cc(-c2nc3c(N4CCC5(CC4)C(=O)Nc4ccccc45)ncnc3n2CC)cn1] | 1'-[9-ethyl-8-(1-propyl-1H-pyrazol-4-yl)-9H-purin-6-yl]spiro[indole-3,4'-piperidin]-2(1H)-one |
| 252 | 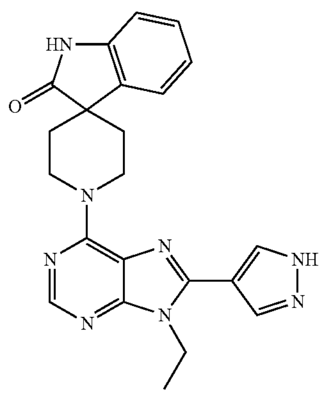 [SMILES: CCn1c(-c2cn[nH]c2)nc2c(N3CCC4(CC3)C(=O)Nc3ccccc34)ncnc21] | 1'-[9-ethyl-8-(1H-pyrazol-4-yl)-9H-purin-6-yl]spiro[indole-3,4'-piperidin]-2(1H)-one |
| 253 | 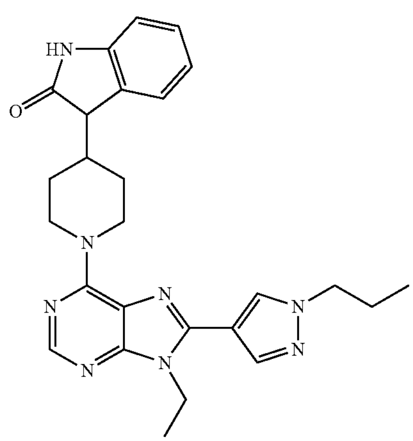 [SMILES: CCCn1cc(-c2nc3c(N4CCC(C5C(=O)Nc6ccccc65)CC4)ncnc3n2CC)cn1] | 1-{1-[9-ethyl-8-(1-propyl-1H-pyrazol-4-yl)-9H-purin-6-yl]piperidin-4-yl}-1,3-dihydro-2H-benzimidazol-2-one |

TABLE 1-continued

| Compound Number | Structure | Name |
|---|---|---|
| 254 | 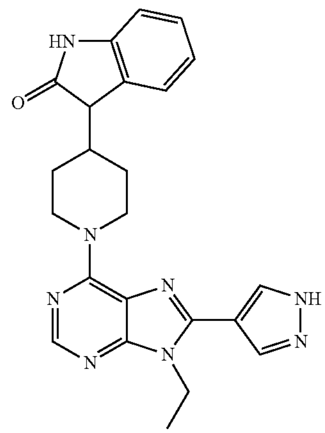 [SMILES: CCn1c(-c2cn[nH]c2)nc2c(N3CCC(C4C(=O)Nc5ccccc54)CC3)ncnc21] | 1-{1-[9-ethyl-8-(1H-pyrazol-4-yl)-9H-purin-6-yl]piperidin-4-yl}-1,3-dihydro-2H-benzimidazol-2-one |
| 255 | 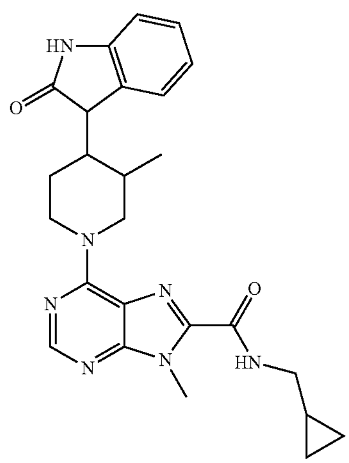 [SMILES: CC1CN(c2ncnc3c2nc(C(=O)NCC2CC2)n3C)CCC1C1C(=O)Nc2ccccc21] | N-(cyclopropylmethyl)-9-methyl-6-[3-methyl-4-(2-oxo-2,3-dihydro-1H-benzimidazol-1-yl)piperidin-1-yl]-9H-purine-8-carboxamide |
| 256 | 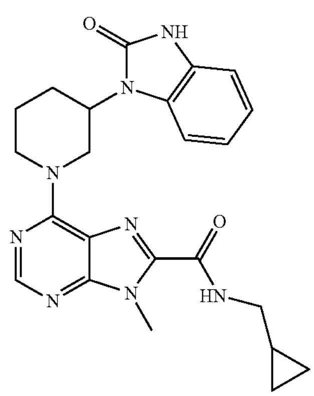 [SMILES: Cn1c(C(=O)NCC2CC2)nc2c(N3CCCC(n4c(=O)[nH]c5ccccc54)C3)ncnc21] | N-(cyclopropylmethyl)-9-methyl-6-[3-(2-oxo-2,3-dihydro-1H-benzimidazol-1-yl)piperidin-1-yl]-9H-purine-8-carboxamide |

TABLE 1-continued

| Compound Number | Structure | Name |
|---|---|---|
| 257 | 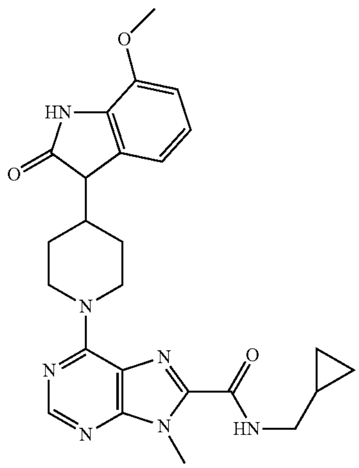 [SMILES: COc1cccc2c1NC(=O)C2C1CCN(c2ncnc3c2nc(C(=O)NCC2CC2)n3C)CC1] | N-(cyclopropylmethyl)-9-methyl-6-{4-[4-(methyloxy)-2-oxo-2,3-dihydro-1H-benzimidazol-1-yl]piperidin-1-yl}-9H-purine-8-carboxamide |
| 258 | 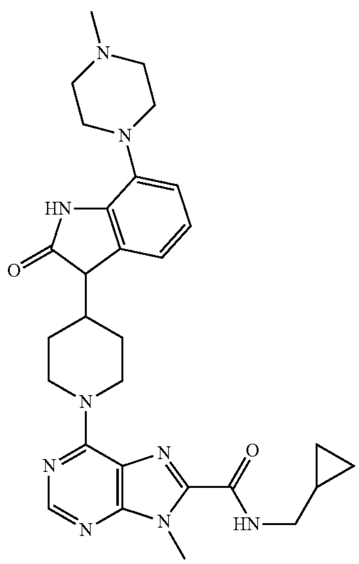 [SMILES: CN1CCN(c2cccc3c2NC(=O)C3C2CCN(c3ncnc4c3nc(C(=O)NCC3CC3)n4C)CC2)CC1] | N-(cyclopropylmethyl)-9-methyl-6-{4-[4-(4-methylpiperazin-1-yl)-2-oxo-2,3-dihydro-1H-benzimidazol-1-yl]piperidin-1-yl}-9H-purine-8-carboxamide |
| 259 | 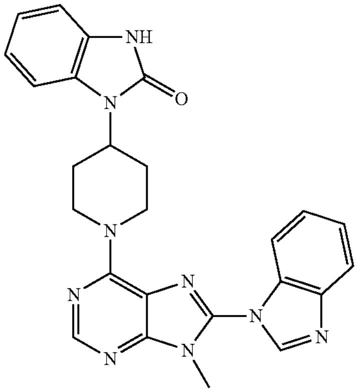 [SMILES: Cn1c(-n2cnc3ccccc32)nc2c(N3CCC(n4c(=O)[nH]c5ccccc54)CC3)ncnc21] | 1-{1-[8-(1H-benzimidazol-1-yl)-9-methyl-9H-purin-6-yl]piperidin-4-yl}-1,3-dihydro-2H-benzimidazol-2-one |

TABLE 1-continued

| Compound Number | Structure | Name |
|---|---|---|
| 260 | 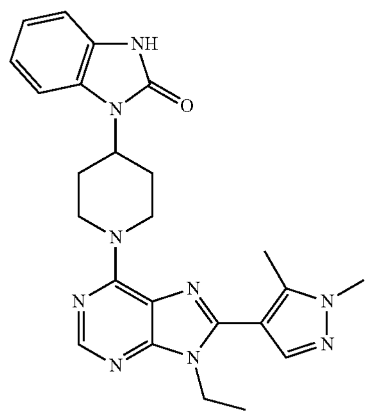 [SMILES: CCn1c(-c2cnn(C)c2C)nc2c(N3CCC(n4c(=O)[nH]c5ccccc54)CC3)ncnc21] | 1-{1-[8-(1,5-dimethyl-1H-pyrazol-4-yl)-9-ethyl-9H-purin-6-yl]piperidin-4-yl}-1,3-dihydro-2H-benzimidazol-2-one |
| 261 | 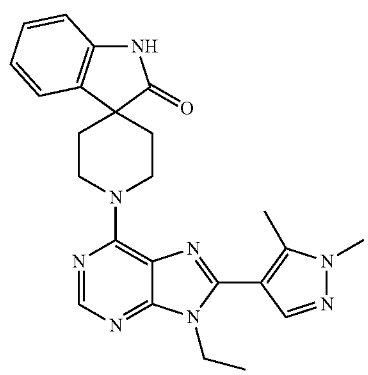 [SMILES: CCn1c(-c2cnn(C)c2C)nc2c(N3CCC4(CC3)C(=O)Nc3ccccc34)ncnc21] | 1'-[8-(1,5-dimethyl-1H-pyrazol-4-yl)-9-ethyl-9H-purin-6-yl]spiro[indole-3,4'-piperidin]-2(1H)-one |
| 262 | 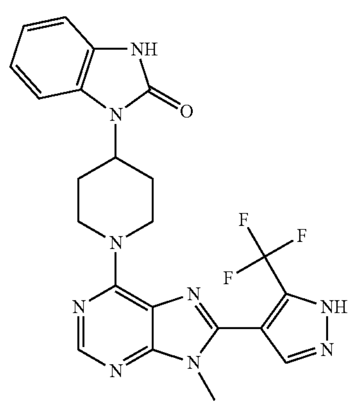 [SMILES: Cn1c(-c2cn[nH]c2C(F)(F)F)nc2c(N3CCC(n4c(=O)[nH]c5ccccc54)CC3)ncnc21] | 1-(1-{9-methyl-8-[5-(trifluoromethyl)-1H-pyrazol-4-yl]-9H-purin-6-yl}piperidin-4-yl)-1,3-dihydro-2H-benzimidazol-2-one |
| 263 | 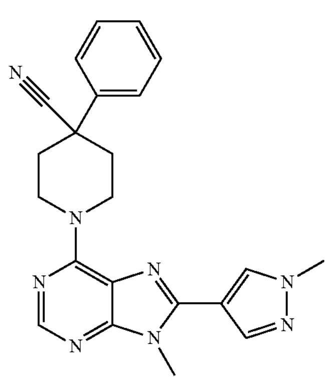 [SMILES: Cn1cc(-c2nc3c(N4CCC(C#N)(c5ccccc5)CC4)ncnc3n2C)cn1] | 1-[9-methyl-8-(1-methyl-1H-pyrazol-4-yl)-9H-purin-6-yl]-4-phenylpiperidine-4-carbonitrile |

TABLE 1-continued

| Compound Number | Structure | Name |
|---|---|---|
| 264 | 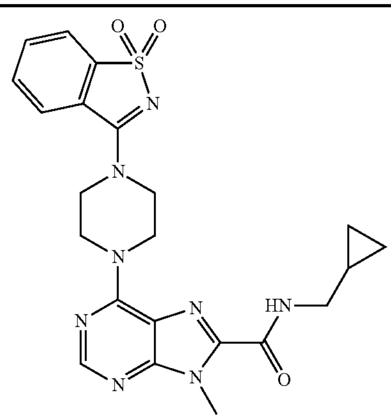 | N-(cyclopropylmethyl)-6-[4-(1,1-dioxido-1,2-benzisothiazol-3-yl)piperazin-1-yl]-9-methyl-9H-purine-8-carboxamide |
| 265 | 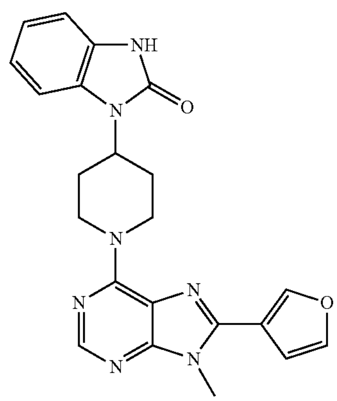 [SMILES: Cn1c(-c2ccoc2)nc2c(N3CCC(n4c(=O)[nH]c5ccccc54)CC3)ncnc21] | 1-[1-(8-furan-3-yl-9-methyl-9H-purin-6-yl)piperidin-4-yl]-1,3-dihydro-2H-benzimidazol-2-one |
| 266 | 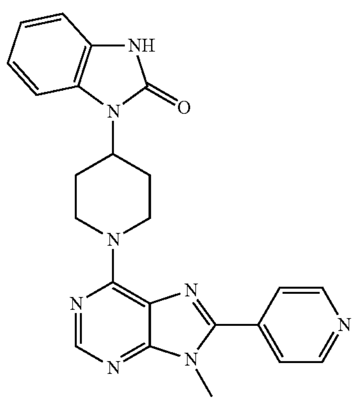 [SMILES: Cn1c(-c2ccncc2)nc2c(N3CCC(n4c(=O)[nH]c5ccccc54)CC3)ncnc21] | 1-[1-(9-methyl-8-pyridin-4-yl-9H-purin-6-yl)piperidin-4-yl]-1,3-dihydro-2H-benzimidazol-2-one |
| 267 | 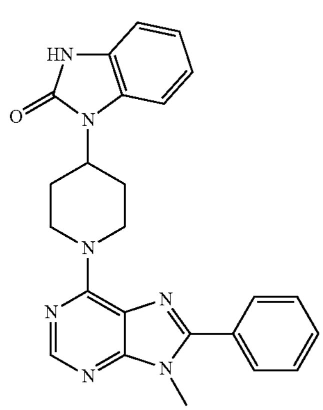 [SMILES: Cn1c(-c2ccccc2)nc2c(N3CCC(n4c(=O)[nH]c5ccccc54)CC3)ncnc21] | 1-[1-(9-methyl-8-phenyl-9H-purin-6-yl)piperidin-4-yl]-1,3-dihydro-2H-benzimidazol-2-one |

TABLE 1-continued

| Compound Number | Structure | Name |
|---|---|---|
| 268 | 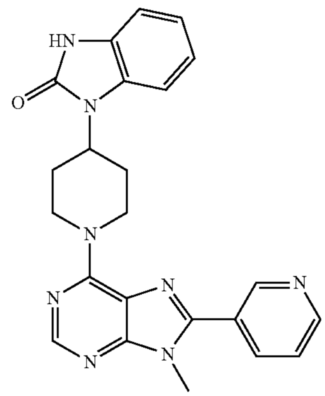 [SMILES: Cn1c(-c2cccnc2)nc2c(N3CCC(n4c(=O)[nH]c5ccccc54)CC3)ncnc21] | 1-[1-(9-methyl-8-pyridin-3-yl-9H-purin-6-yl)piperidin-4-yl]-1,3-dihydro-2H-benzimidazol-2-one |
| 269 | 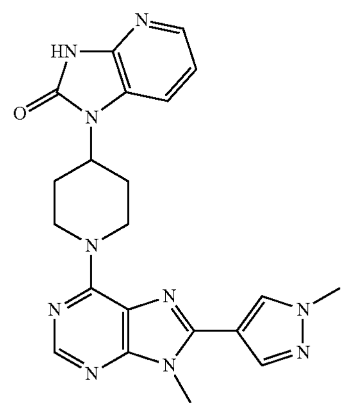 [SMILES: Cn1cc(-c2nc3c(N4CCC(n5c(=O)[nH]c6ncccc65)CC4)ncnc3n2C)cn1] | 1-{1-[9-methyl-8-(1-methyl-1H-pyrazol-4-yl)-9H-purin-6-yl]piperidin-4-yl}-1,3-dihydro-2H-imidazo[4,5-b]pyridin-2-one |
| 270 | 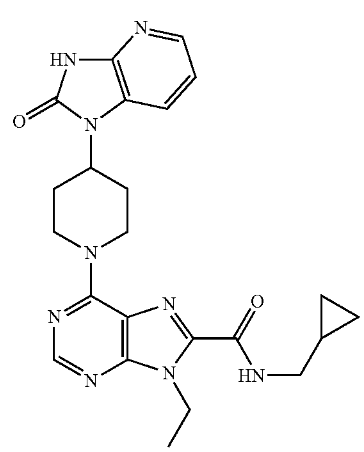 [SMILES: CCn1c(C(=O)NCC2CC2)nc2c(N3CCC(n4c(=O)[nH]c5ncccc54)CC3)ncnc21] | N-(cyclopropylmethyl)-9-ethyl-6-[4-(2-oxo-2,3-dihydro-1H-imidazo[4,5-b]pyridin-1-yl)piperidin-1-yl]-9H-purine-8-carboxamide |

TABLE 1-continued

| Compound Number | Structure | Name |
|---|---|---|
| 271 | 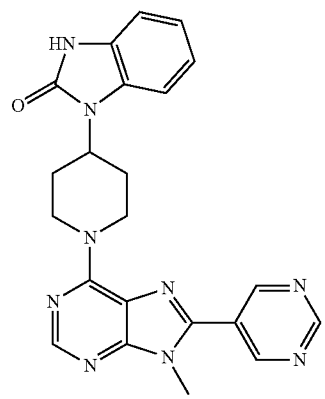 [SMILES: Cn1c(-c2cncnc2)nc2c(N3CCC(n4c(=O)[nH]c5ccccc54)CC3)ncnc21] | 1-[1-(9-methyl-8-pyrimidin-5-yl-9H-purin-6-yl)piperidin-4-yl]-1,3-dihydro-2H-benzimidazol-2-one |
| 272 | 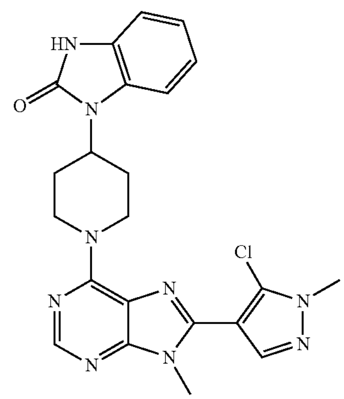 [SMILES: Cn1ncc(-c2nc3c(N4CCC(n5c(=O)[nH]c6ccccc65)CC4)ncnc3n2C)c1Cl] | 1-{1-[8-(5-chloro-1-methyl-1H-pyrazol-4-yl)-9-methyl-9H-purin-6-yl]piperidin-4-yl}-1,3-dihydro-2H-benzimidazol-2-one |
| 273 | 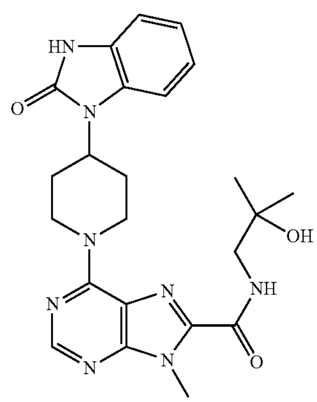 [SMILES: Cn1c(C(=O)NCC(C)(C)O)nc2c(N3CCC(n4c(=O)[nH]c5ccccc54)CC3)ncnc21] | N-(2-hydroxy-2-methylpropyl)-9-methyl-6-[4-(2-oxo-2,3-dihydro-1H-benzimidazol-1-yl)piperidin-1-yl]-9H-purine-8-carboxamide |
| 274 | 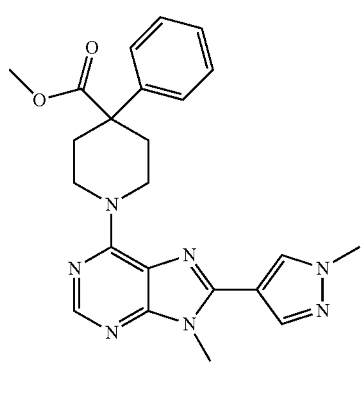 | methyl 1-[9-methyl-8-(1-methyl-1H-pyrazol-4-yl)-9H-purin-6-yl]-4-phenylpiperidine-4-carboxylate |

TABLE 1-continued

| Compound Number | Structure | Name |
|---|---|---|
| 275 | 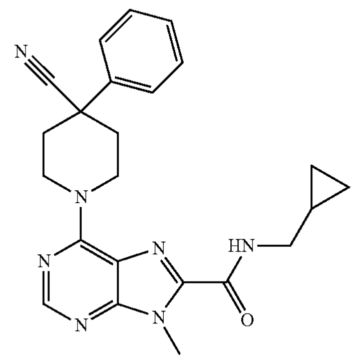 [SMILES: Cn1c(C(=O)NCC2CC2)nc2c(N3CCC(C#N)(c4ccccc4)CC3)ncnc21] | 6-(4-cyano-4-phenylpiperidin-1-yl)-N-(cyclopropylmethyl)-9-methyl-9H-purine-8-carboxamide |
| 276 | 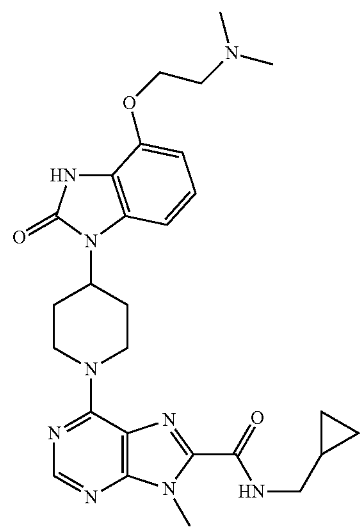 [SMILES: CN(C)CCOc1cccc2c1[nH]c(=O)n2C1CCN(c2ncnc3c2nc(C(=O)NCC2CC2)n3C)CC1] | N-(cyclopropylmethyl)-6-[4-(4-{[2-(dimethylamino)ethyl]oxy}-2-oxo-2,3-dihydro-1H-benzimidazol-1-yl)piperidin-1-yl]-9-methyl-9H-purine-8-carboxamide |
| 277 | 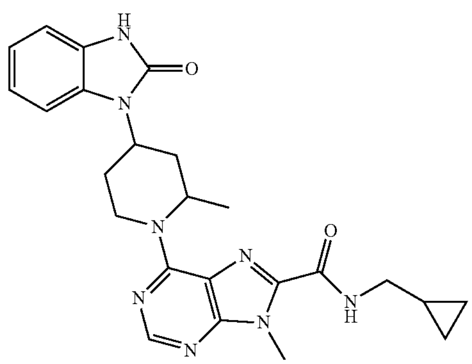 [SMILES: CC1CC(n2c(=O)[nH]c3ccccc32)CCN1c1ncnc2c1nc(C(=O)NCC1CC1)n2C] | N-(cyclopropylmethyl)-9-methyl-6-[2-methyl-4-(2-oxo-2,3-dihydro-1H-benzimidazol-1-yl)piperidin-1-yl]-9H-purine-8-carboxamide |

TABLE 1-continued

| Compound Number | Structure | Name |
|---|---|---|
| 278 | 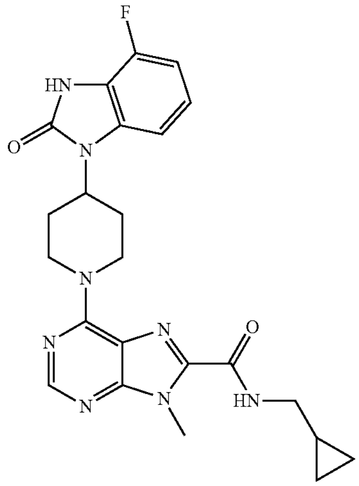 [SMILES: Cn1c(C(=O)NCC2CC2)nc2c(N3CCC(n4c(=O)[nH]c5c(F)cccc54)CC3)ncnc21] | N-(cyclopropylmethyl)-6-[4-(4-fluoro-2-oxo-2,3-dihydro-1H-benzimidazol-1-yl)piperidin-1-yl]-9-methyl-9H-purine-8-carboxamide |
| 279 | 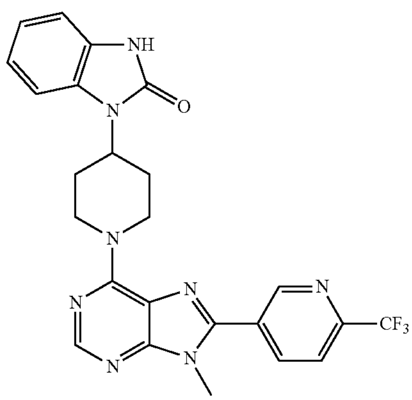 [SMILES: Cn1c(-c2ccc(C(F)(F)F)nc2)nc2c(N3CCC(n4c(=O)[nH]c5ccccc54)CC3)ncnc21] | 1-(1-{9-methyl-8-[6-(trifluoromethyl)pyridin-3-yl]-9H-purin-6-yl}piperidin-4-yl)-1,3-dihydro-2H-benzimidazol-2-one |
| 280 | 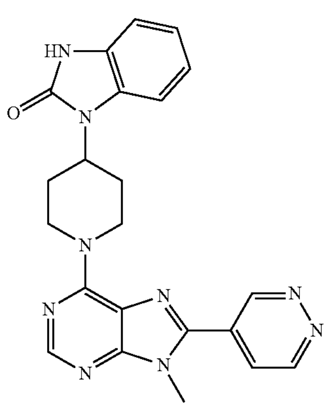 [SMILES: Cn1c(-c2ccnnc2)nc2c(N3CCC(n4c(=O)[nH]c5ccccc54)CC3)ncnc21] | 1-[1-(9-methyl-8-pyridazin-4-yl-9H-purin-6-yl)piperidin-4-yl]-1,3-dihydro-2H-benzimidazol-2-one |

TABLE 1-continued

| Compound Number | Structure | Name |
|---|---|---|
| 281 | 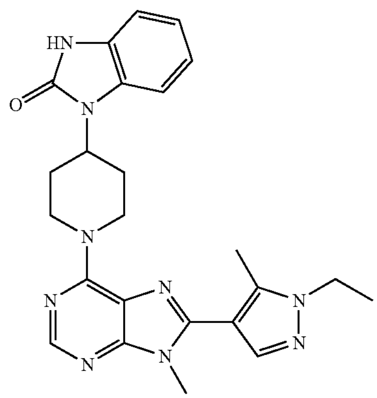 [SMILES: CCn1ncc(-c2nc3c(N4CCC(n5c(=O)[nH]c6ccccc65)CC4)ncnc3n2C)c1C] | 1-{1-[8-(1-ethyl-5-methyl-1H-pyrazol-4-yl)-9-methyl-9H-purin-6-yl]piperidin-4-yl}-1,3-dihydro-2H-benzimidazol-2-one |
| 282 | 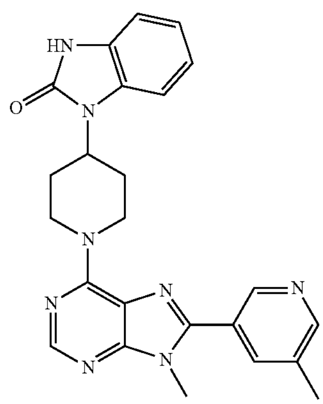 [SMILES: Cc1cncc(-c2nc3c(N4CCC(n5c(=O)[nH]c6ccccc65)CC4)ncnc3n2C)c1] | 1-{1-[9-methyl-8-(5-methylpyridin-3-yl)-9H-purin-6-yl]piperidin-4-yl}-1,3-dihydro-2H-benzimidazol-2-one |
| 283 | 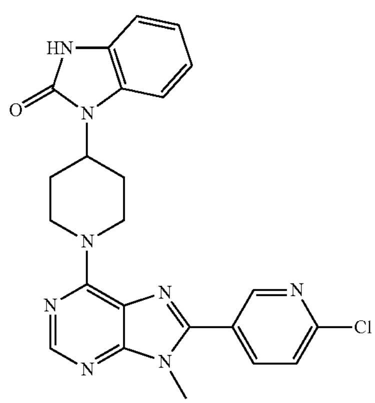 [SMILES: Cn1c(-c2ccc(Cl)nc2)nc2c(N3CCC(n4c(=O)[nH]c5ccccc54)CC3)ncnc21] | 1-{1-[8-(6-chloropyridin-3-yl)-9-methyl-9H-purin-6-yl]piperidin-4-yl}-1,3-dihydro-2H-benzimidazol-2-one |
| 284 | 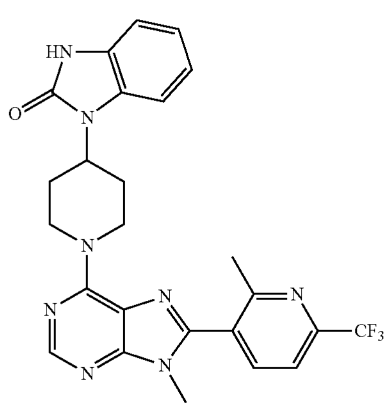 [SMILES: Cc1nc(C(F)(F)F)ccc1-c1nc2c(N3CCC(n4c(=O)[nH]c5ccccc54)CC3)ncnc2n1C] | 1-(1-{9-methyl-8-[2-methyl-6-(trifluoromethyl)pyridin-3-yl]-9H-purin-6-yl}piperidin-4-yl)-1,3-dihydro-2H-benzimidazol-2-one |

TABLE 1-continued

| Compound Number | Structure | Name |
|---|---|---|
| 285 | 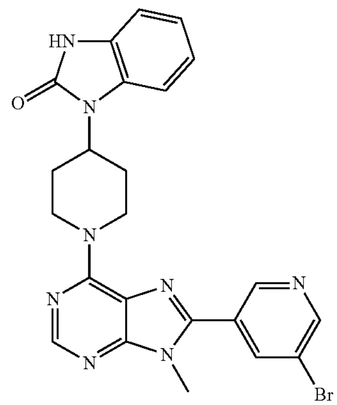 [SMILES: Cn1c(-c2cncc(Br)c2)nc2c(N3CCC(n4c(=O)[nH]c5ccccc54)CC3)ncnc21] | 1-{1-[8-(5-bromopyridin-3-yl)-9-methyl-9H-purin-6-yl]piperidin-4-yl)-1,3-dihydro-2H-benzimidazol-2-one |
| 286 | 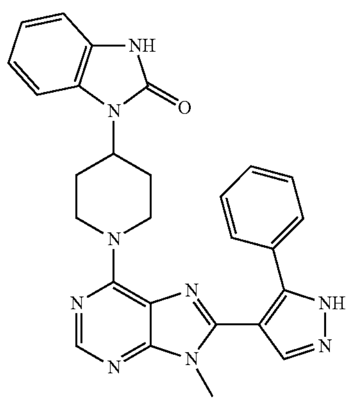 [SMILES: Cn1c(-c2cn[nH]c2-c2ccccc2)nc2c(N3CCC(n4c(=O)[nH]c5ccccc54)CC3)ncnc21] | 1-{1-[9-methyl-8-(5-phenyl-1H-pyrazol-4-yl)-9H-purin-6-yl]piperidin-4-yl}-1,3-dihydro-2H-benzimidazol-2-one |
| 287 | 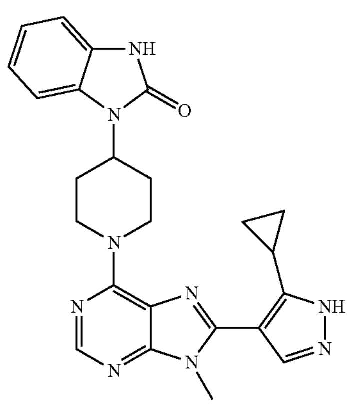 [SMILES: Cn1c(-c2cn[nH]c2C2CC2)nc2c(N3CCC(n4c(=O)[nH]c5ccccc54)CC3)ncnc21] | 1-{1-[8-(5-cyclopropyl-1H-pyrazol-4-yl)-9-methyl-9H-purin-6-yl]piperidin-4-yl}-1,3-dihydro-2H-benzimidazol-2-one |

TABLE 1-continued
| Compound Number | Structure | Name |
|---|---|---|
| 288 | 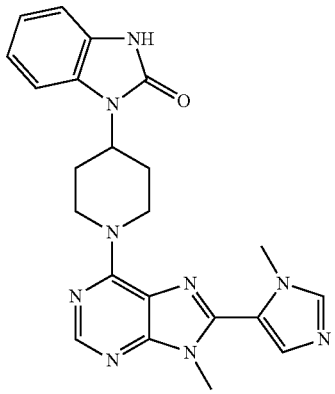 [SMILES: Cn1cncc1-c1nc2c(N3CCC(n4c(=O)[nH]c5ccccc54)CC3)ncnc2n1C] | 1-{1-[9-methyl-8-(1-methyl-1H-imidazol-5-yl)-9H-purin-6-yl]piperidin-4-yl}-1,3-dihydro-2H-benzimidazol-2-one |
| 289 | 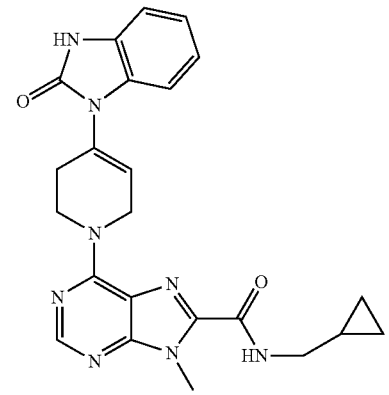 [SMILES: Cn1c(C(=O)NCC2CC2)nc2c(N3CC=C(n4c(=O)[nH]c5ccccc54)CC3)ncnc21] | N-(cyclopropylmethyl)-9-methyl-6-[4-(2-oxo-2,3-dihydro-1H-benzimidazol-1-yl)-3,6-dihydropyridin-1(2H)-yl]-9H-purine-8-carboxamide |
| 290 | 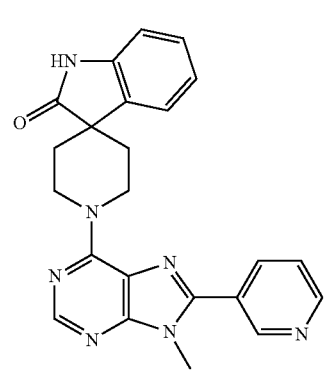 [SMILES: Cn1c(-c2cccnc2)nc2c(N3CCC4(CC3)C(=O)Nc3ccccc34)ncnc21] | 1'-(9-methyl-8-pyridin-3-yl-9H-purin-6-yl)spiro[indole-3,4'-piperidin]-2(1H)-one |
| 291 | | 1'-(9-ethyl-8-pyridin-3-yl-9H-purin-6-yl)spiro[indole-3,4'-piperidin]-2(1H)-one |

TABLE 1-continued
| Compound Number | Structure | Name |
|---|---|---|
| 292 | 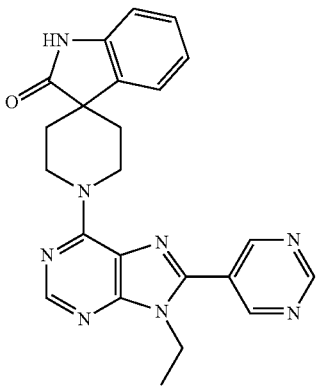 [SMILES: CCn1c(-c2cncnc2)nc2c(N3CCC4(CC3)C(=O)Nc3ccccc34)ncnc21] | 1'-(9-ethyl-8-pyrimidin-5-yl-9H-purin-6-yl)spiro[indole-3,4'-piperidin]-2(1H)-one |
| 293 | 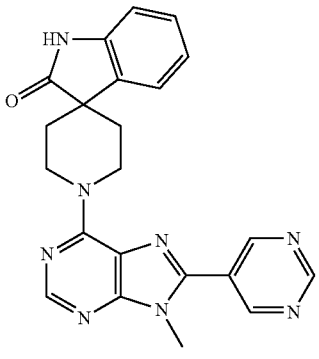 [SMILES: Cn1c(-c2cncnc2)nc2c(N3CCC4(CC3)C(=O)Nc3ccccc34)ncnc21] | 1'-(9-methyl-8-pyrimidin-5-yl-9H-purin-6-yl)spiro[indole-3,4'-piperidin]-2(1H)-one |
| 294 | 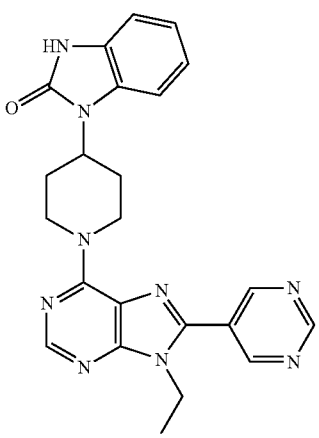 [SMILES: CCn1c(-c2cncnc2)nc2c(N3CCC(n4c(=O)[nH]c5ccccc54)CC3)ncnc21] | 1-[1-(9-ethyl-8-pyrimidin-5-yl-9H-purin-6-yl)piperidin-4-yl]-1,3-dihydro-2H-benzimidazol-2-one |

TABLE 1-continued

| Compound Number | Structure | Name |
|---|---|---|
| 295 | 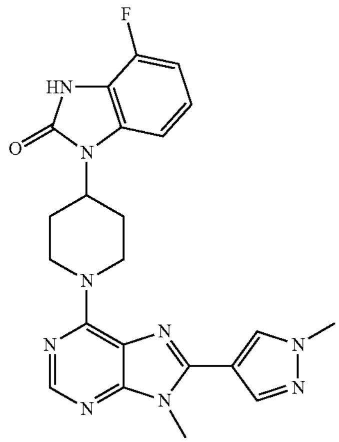 [SMILES: Cn1cc(-c2nc3c(N4CCC(n5c(=O)[nH]c6c(F)cccc65)CC4)ncnc3n2C)cn1] | 4-fluoro-1-{1-[9-methyl-8-(1-methyl-1H-pyrazol-4-yl)-9H-purin-6-yl]piperidin-4-yl}-1,3-dihydro-2H-benzimidazol-2-one |
| 296 | 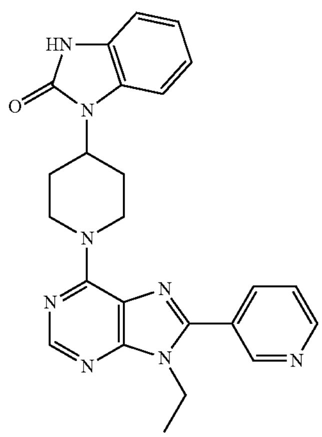 [SMILES: CCn1c(-c2cccnc2)nc2c(N3CCC(n4c(=O)[nH]c5ccccc54)CC3)ncnc21] | 1-[1-(9-ethyl-8-pyridin-3-yl-9H-purin-6-yl)piperidin-4-yl]-1,3-dihydro-2H-benzimidazol-2-one |
| 297 | 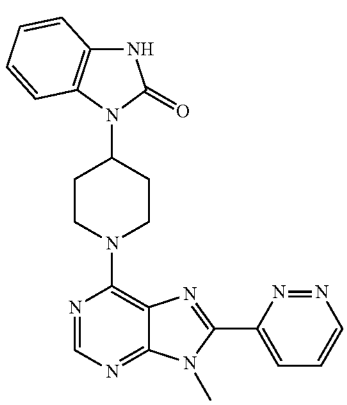 [SMILES: Cn1c(-c2cccnn2)nc2c(N3CCC(n4c(=O)[nH]c5ccccc54)CC3)ncnc21] | 1-[1-(9-methyl-8-pyridazin-3-yl-9H-purin-6-yl)piperidin-4-yl]-1,3-dihydro-2H-benzimidazol-2-one |

TABLE 1-continued

| Compound Number | Structure | Name |
|---|---|---|
| 298 | 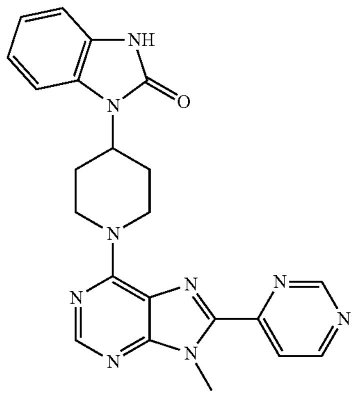 [SMILES: Cn1c(-c2ccncn2)nc2c(N3CCC(n4c(=O)[nH]c5ccccc54)CC3)ncnc21] | 1-[1-(9-methyl-8-pyrimidin-4-yl-9H-purin-6-yl)piperidin-4-yl]-1,3-dihydro-2H-benzimidazol-2-one |
| 299 | 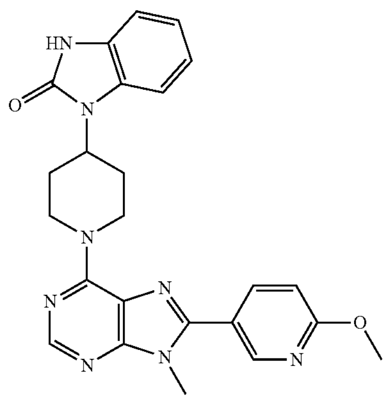 [SMILES: COc1ccc(-c2nc3c(N4CCC(n5c(=O)[nH]c6ccccc65)CC4)ncnc3n2C)cn1] | 1-(1-{9-methyl-8-[6-(methyloxy)pyridin-3-yl]-9H-purin-6-yl}piperidin-4-yl)-1,3-dihydro-2H-benzimidazol-2-one |
| 300 | 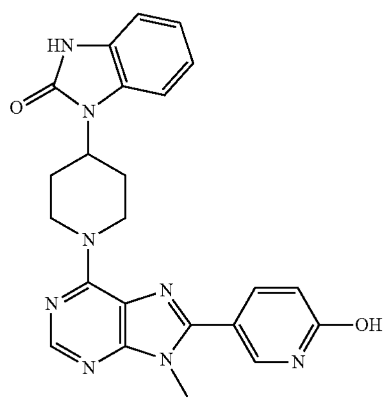 [SMILES: Cn1c(-c2ccc(O)nc2)nc2c(N3CCC(n4c(=O)[nH]c5ccccc54)CC3)ncnc21] | 1-{1-[8-(6-hydroxypyridin-3-yl)-9-methyl-9H-purin-6-yl]piperidin-4-yl}-1,3-dihydro-2H-benzimidazol-2-one |
| 301 | 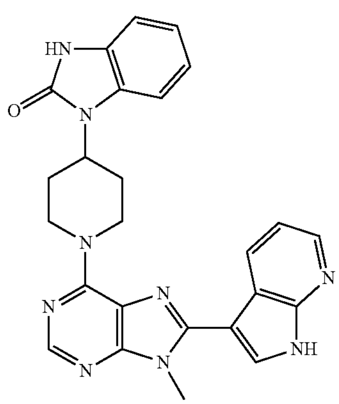 [SMILES: Cn1c(-c2c[nH]c3ncccc23)nc2c(N3CCC(n4c(=O)[nH]c5ccccc54)CC3)ncnc21] | 1-{1-[9-methyl-8-(1H-pyrrolo[2,3-b]pyridin-3-yl)-9H-purin-6-yl]piperidin-4-yl}-1,3-dihydro-2H-benzimidazol-2-one |

TABLE 1-continued

| Compound Number | Structure | Name |
|---|---|---|
| 302 | 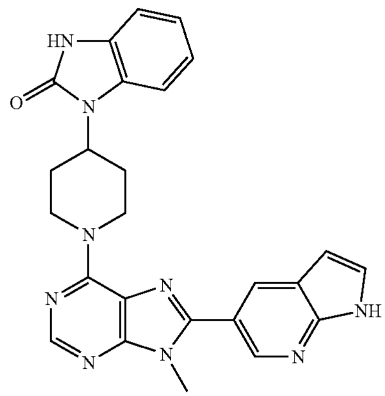 [SMILES: Cn1c(-c2cnc3[nH]ccc3c2)nc2c(N3CCC(n4c(=O)[nH]c5ccccc54)CC3)ncnc21] | 1-{1-[9-methyl-8-(1H-pyrrolo[2,3-b]pyridin-5-yl)-9H-purin-6-yl]piperidin-4-yl}-1,3-dihydro-2H-benzimidazol-2-one |
| 303 | 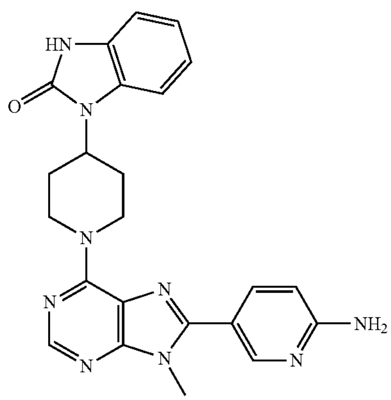 [SMILES: Cn1c(-c2ccc(N)nc2)nc2c(N3CCC(n4c(=O)[nH]c5ccccc54)CC3)ncnc21] | 1-{1-[8-(6-aminopyridin-3-yl)-9-methyl-9H-purin-6-yl]piperidin-4-yl}-1,3-dihydro-2H-benzimidazol-2-one |
| 304 | 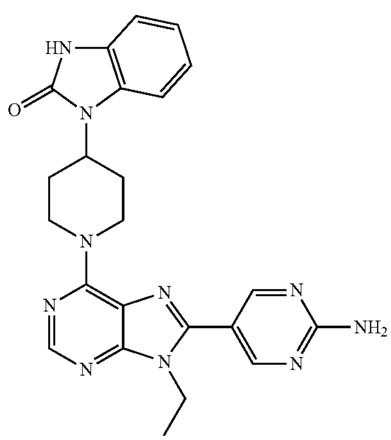 [SMILES: CCn1c(-c2cnc(N)nc2)nc2c(N3CCC(n4c(=O)[nH]c5ccccc54)CC3)ncnc21] | 1-{1-[8-(2-aminopyrimidin-5-yl)-9-ethyl-9H-purin-6-yl]piperidin-4-yl)-1,3-dihydro-2H-benzimidazol-2-one |

TABLE 1-continued

| Compound Number | Structure | Name |
|---|---|---|
| 305 | 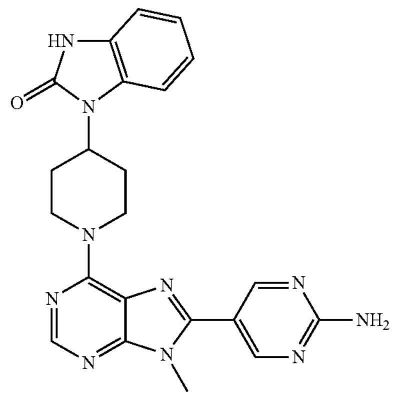 [SMILES: Cn1c(-c2cnc(N)nc2)nc2c(N3CCC(n4c(=O)[nH]c5ccccc54)CC3)ncnc21] | 1-{1-[8-(2-aminopyrimidin-5-yl)-9-methyl-9H-purin-6-yl]piperidin-4-yl}-1,3-dihydro-2H-benzimidazol-2-one |
| 306 | 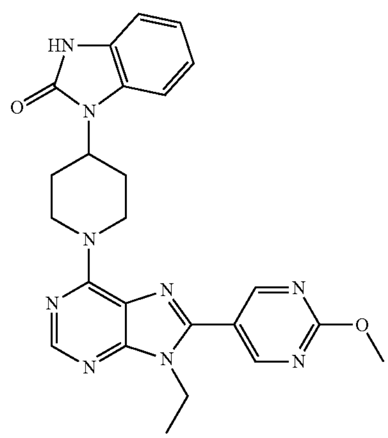 [SMILES: CCn1c(-c2cnc(OC)nc2)nc2c(N3CCC(n4c(=O)[nH]c5ccccc54)CC3)ncnc21] | 1-(1-{9-ethyl-8-[2-(methyloxy)pyrimidin-5-yl]-9H-purin-6-yl}piperidin-4-yl)-1,3-dihydro-2H-benzimidazol-2-one |
| 307 | 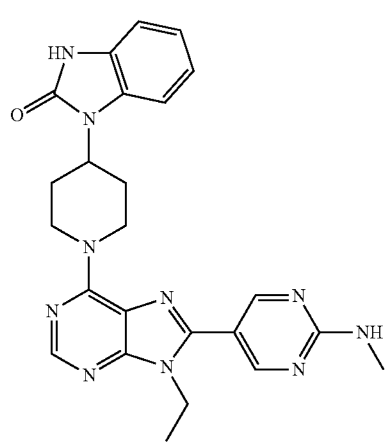 [SMILES: CCn1c(-c2cnc(NC)nc2)nc2c(N3CCC(n4c(=O)[nH]c5ccccc54)CC3)ncnc21] | 1-(1-{9-ethyl-8-[2-(methylamino)pyrimidin-5-yl]-9H-purin-6-yl)piperidin-4-yl)-1,3-dihydro-2H-benzimidazol-2-one |

TABLE 1-continued

| Compound Number | Structure | Name |
|---|---|---|
| 308 | 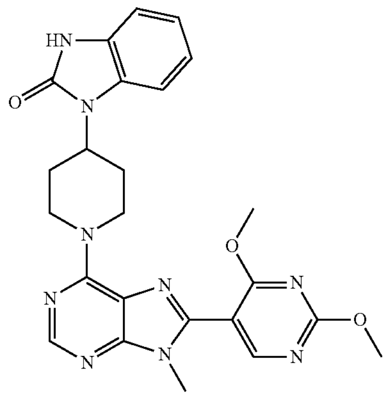 [SMILES: COc1ncc(-c2nc3c(N4CCC(n5c(=O)[nH]c6ccccc65)CC4)ncnc3n2C)c(OC)n1] | 1-(1-{8-[2,4-bis(methyloxy)pyrimidin-5-yl]-9-methyl-9H-purin-6-yl}piperidin-4-yl)-1,3-dihydro-2H-benzimidazol-2-one |
| 309 | 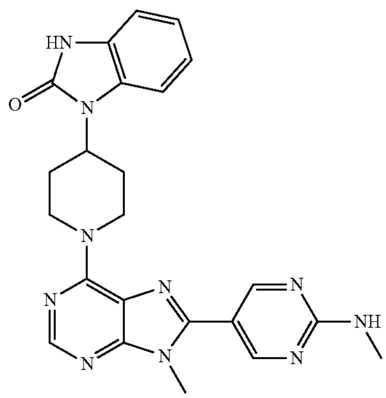 [SMILES: CNc1ncc(-c2nc3c(N4CCC(n5c(=O)[nH]c6ccccc65)CC4)ncnc3n2C)cn1] | 1-(1-{9-methyl-8-[2-(methylamino)pyrimidin-5-yl]-9H-purin-6-yl}piperidin-4-yl)-1,3-dihydro-2H-benzimidazol-2-one |
| 310 | 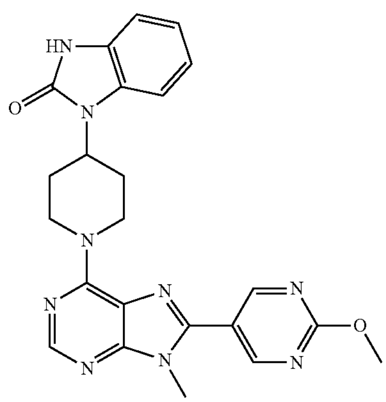 [SMILES: COc1ncc(-c2nc3c(N4CCC(n5c(=O)[nH]c6ccccc65)CC4)ncnc3n2C)cn1] | 1-(1-{9-methyl-8-[2-(methyloxy)pyrimidin-5-yl]-9H-purin-6-yl}piperidin-4-yl)-1,3-dihydro-2H-benzimidazol-2-one |
| 311 | 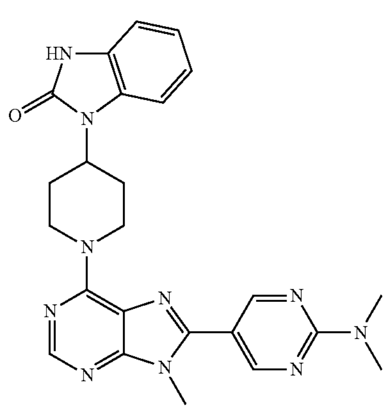 | 1-(1-{8-[2-(dimethylamino)pyrimidin-5-yl]-9-methyl-9H-purin-6-yl}piperidin-4-yl)-1,3-dihydro-2H-benzimidazol-2-one |

| Compound Number | Structure | Name |
|---|---|---|
| 312 | 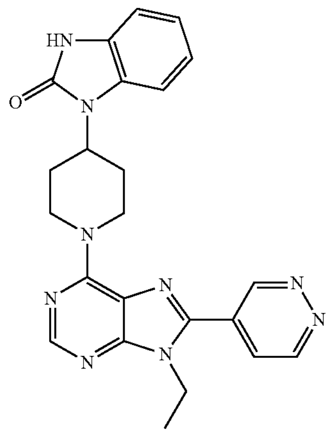 [SMILES: CCn1c(-c2ccnnc2)nc2c(N3CCC(n4c(=O)[nH]c5ccccc54)CC3)ncnc21] | 1-[1-(9-ethyl-8-pyridazin-4-yl-9H-purin-6-yl)piperidin-4-yl]-1,3-dihydro-2H-benzimidazol-2-one |
| 313 | 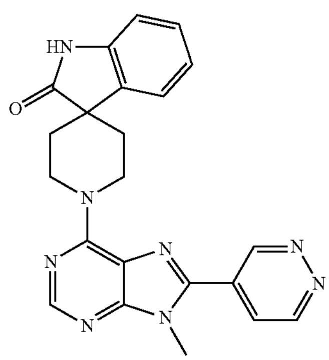 [SMILES: Cn1c(-c2ccnnc2)nc2c(N3CCC4(CC3)C(=O)Nc3ccccc34)ncnc21] | 1'-(9-methyl-8-pyridazin-4-yl-9H-purin-6-yl)spiro[indole-3,4'-piperidin]-2(1H)-one |
| 314 | 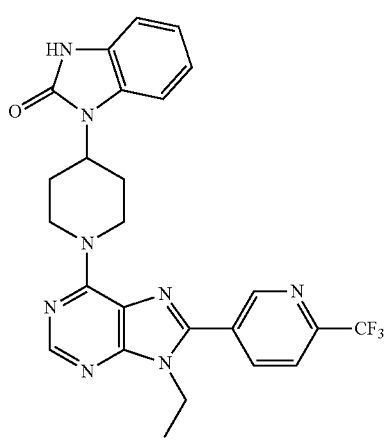 [SMILES: CCn1c(-c2ccc(C(F)(F)F)nc2)nc2c(N3CCC(n4c(=O)[nH]c5ccccc54)CC3)ncnc21] | 1-(1-{9-ethyl-8-[6-(trifluoromethyl)pyridin-3-yl]-9H-purin-6-yl}piperidin-4-yl)-1,3-dihydro-2H-benzimidazol-2-one |

TABLE 1-continued

| Compound Number | Structure | Name |
| --- | --- | --- |
| 315 | 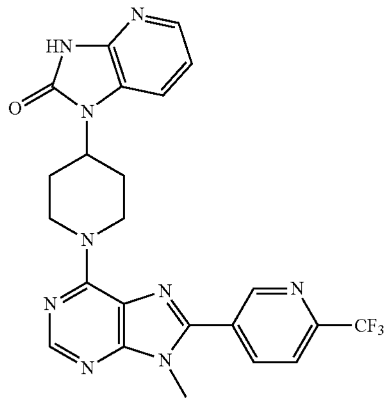 [SMILES: Cn1c(-c2ccc(C(F)(F)F)nc2)nc2c(N3CCC(n4c(=O)[nH]c5ncccc54)CC3)ncnc21] | 1-(1-{9-methyl-8-[6-(trifluoromethyl)pyridin-3-yl]-9H-purin-6-yl}piperidin-4-yl)-1,3-dihydro-2H-imidazo[4,5-b]pyridin-2-one |
| 316 | 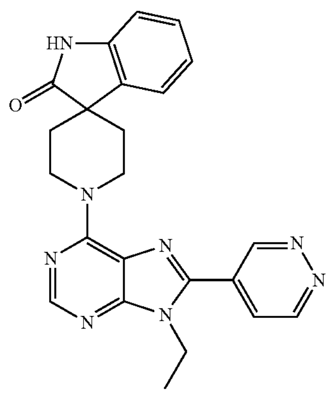 [SMILES: CCn1c(-c2ccnnc2)nc2c(N3CCC4(CC3)C(=O)Nc3ccccc34)ncnc21] | 1'-(9-ethyl-8-pyridazin-4-yl-9H-purin-6-yl)spiro[indole-3,4'-piperidin]-2(1H)-one |
| 317 | Chiral | methyl (3S,4R)-1-[9-methyl-8-(1-methyl-1H-pyrazol-4-yl)-9H-purin-6-yl]-4-(2-oxo-2,3-dihydro-1H-benzimidazol-1-yl)piperidine-3-carboxylate |

TABLE 1-continued

| Compound Number | Structure | Name |
|---|---|---|
| 318 | 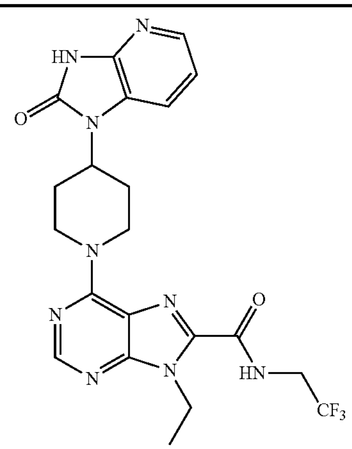 | 9-ethyl-6-[4-(2-oxo-2,3-dihydro-1H-imidazo[4,5-b]pyridin-1-yl)piperidin-1-yl]-N-(2,2,2-trifluoroethyl)-9H-purine-8-carboxamide |
| 319 | 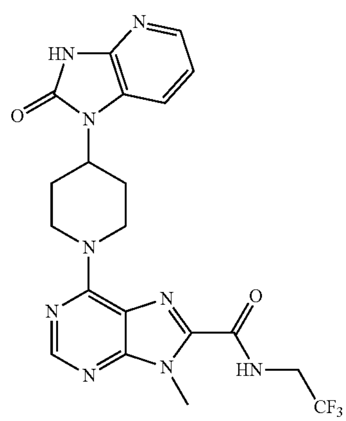 [SMILES: Cn1c(C(=O)NCC(F)(F)F)nc2c(N3CCC(n4c(=O)[nH]c5ncccc54)CC3)ncnc21] | 9-methyl-6-[4-(2-oxo-2,3-dihydro-1H-imidazo[4,5-b]pyridin-1-yl)piperidin-1-yl]-N-(2,2,2-trifluoroethyl)-9H-purine-8-carboxamide |
| 320 | 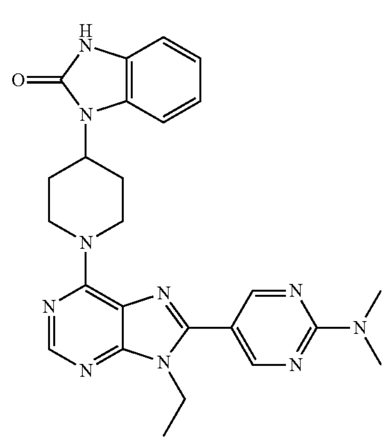 [SMILES: CCn1c(-c2cnc(N(C)C)nc2)nc2c(N3CCC(n4c(=O)[nH]c5ccccc54)CC3)ncnc21] | 1-[1-{8-[2-(dimethylamino)pyrimidin-5-yl]-9-ethyl-9H-purin-6-yl}piperidin-4-yl]-1,3-dihydro-2H-benzimidazol-2-one |

TABLE 1-continued

| Compound Number | Structure | Name |
|---|---|---|
| 321 | 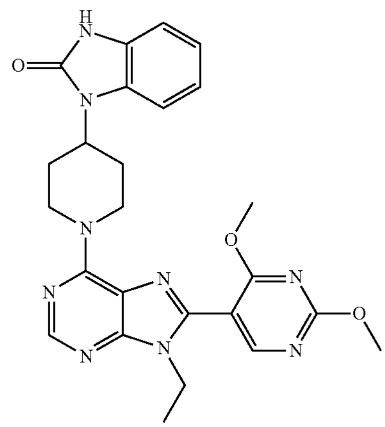 [SMILES: CCn1c(-c2cnc(OC)nc2OC)nc2c(N3CCC(n4c(=O)[nH]c5ccccc54)CC3)ncnc21] | 1-(1-{8-[2,4-bis(methyloxy)pyrimidin-5-yl]-9-ethyl-9H-purin-6-yl}piperidin-4-yl)-1,3-dihydro-2H-benzimidazol-2-one |
| 322 | 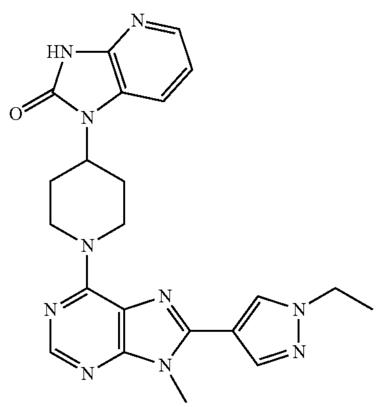 [SMILES: CCn1cc(-c2nc3c(N4CCC(n5c(=O)[nH]c6ncccc65)CC4)ncnc3n2C)cn1] | 1-{1-[8-(1-ethyl-1H-pyrazol-4-yl)-9-methyl-9H-purin-6-yl]piperidin-4-yl}-1,3-dihydro-2H-imidazo[4,5-b]pyridin-2-one |
| 323 | 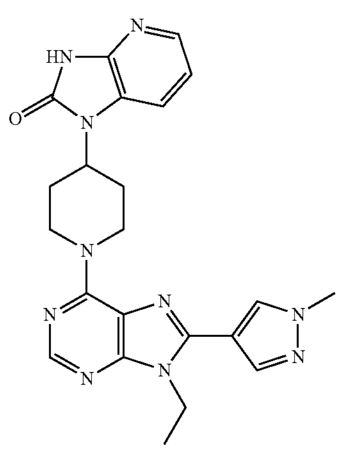 [SMILES: CCn1c(-c2cnn(C)c2)nc2c(N3CCC(n4c(=O)[nH]c5ncccc54)CC3)ncnc21] | 1-{1-[9-ethyl-8-(1-methyl-1H-pyrazol-4-yl)-9H-purin-6-yl]piperidin-4-yl}-1,3-dihydro-2H-imidazo[4,5-b]pyridin-2-one |
| 324 | | 1'-{9-ethyl-8-[6-(trifluoromethyl)pyridin-3-yl]-9H-purin-6-yl}spiro[indole-3,4'-piperidin]-2(1H)-one |

TABLE 1-continued

| Compound Number | Structure | Name |
|---|---|---|
| 325 | 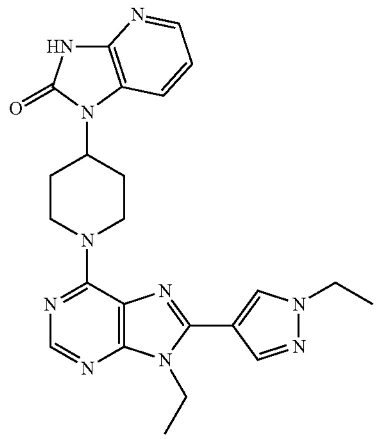 [SMILES: CCn1cc(-c2nc3c(N4CCC(n5c(=O)[nH]c6ncccc65)CC4)ncnc3n2CC)cn1] | 1-{1-[9-ethyl-8-(1-ethyl-1H-pyrazol-4-yl)-9H-purin-6-yl]piperidin-4-yl}-1,3-dihydro-2H-imidazo[4,5-b]pyridin-2-one |
| 326 | 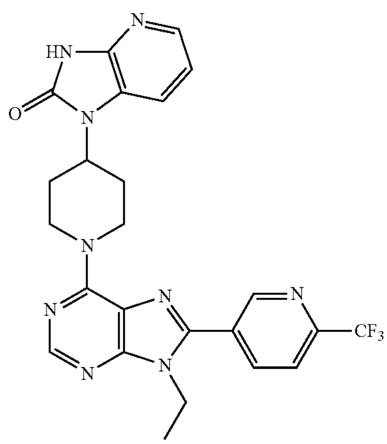 [SMILES: CCn1c(-c2ccc(C(F)(F)F)nc2)nc2c(N3CCC(n4c(=O)[nH]c5ncccc54)CC3)ncnc21] | 1-(1-{9-ethyl-8-[6-(trifluoromethyl)pyridin-3-yl]-9H-purin-6-yl}piperidin-4-yl)-1,3-dihydro-2H-imidazo[4,5-b]pyridin-2-one |
| 327 | 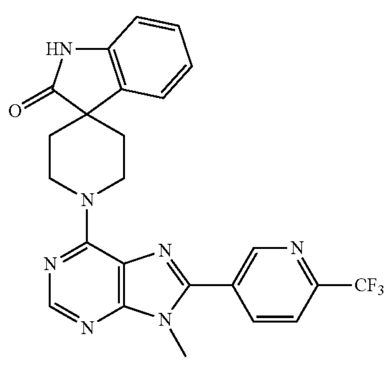 [SMILES: Cn1c(-c2ccc(C(F)(F)F)nc2)nc2c(N3CCC4(CC3)C(=O)Nc3ccccc34)ncnc21] | 1'-{9-methyl-8-[6-(trifluoromethyl)pyridin-3-yl]-9H-purin-6-yl}spiro[indole-3,4'-piperidin]-2(1H)-one |

TABLE 1-continued

| Compound Number | Structure | Name |
|---|---|---|
| 328 | 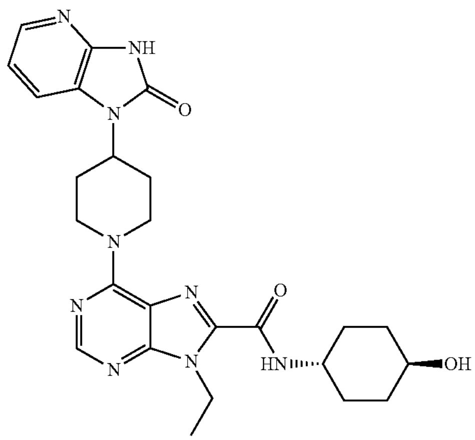 [SMILES: CCn1c(C(=O)N[C@H]2CC[C@H](O)CC2)nc2c(N3CCC(n4c(=O)[nH]c5ncccc54)CC3)ncnc21] | 9-ethyl-N-(trans-4-hydroxycyclohexyl)-6-[4-(2-oxo-2,3-dihydro-1H-imidazo[4,5-b]pyridin-1-yl)piperidin-1-yl]-9H-purine-8-carboxamide |
| 329 | 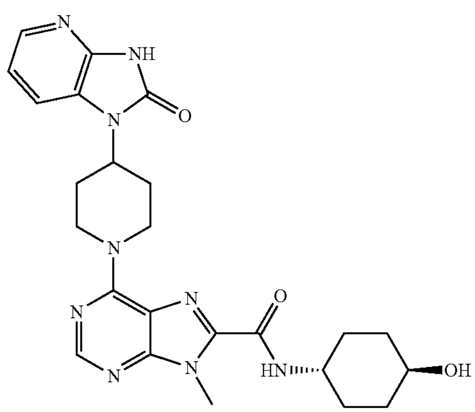 [SMILES: Cn1c(C(=O)N[C@H]2CC[C@H](O)CC2)nc2c(N3CCC(n4c(=O)[nH]c5ncccc54)CC3)ncnc21] | N-(trans-4-hydroxycyclohexyl)-9-methyl-6-[4-(2-oxo-2,3-dihydro-1H-imidazo[4,5-b]pyridin-1-yl)piperidin-1-yl]-9H-purine-8-carboxamide |
| 330 | 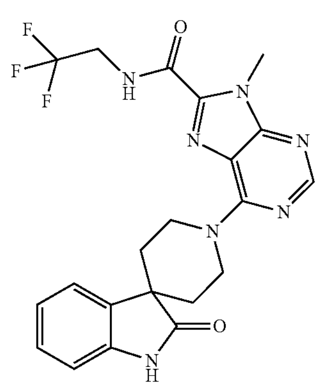 [SMILES: Cn1c(C(=O)NCC(F)(F)F)nc2c(N3CCC4(CC3)C(=O)Nc3ccccc34)ncnc21] | 1-{1-[8-(1,5-dimethyl-1H-pyrazol-4-yl)-9-methyl-9H-purin-6-yl]piperidin-4-yl}-4-fluoro-1,3-dihydro-2H-benzimidazol-2-one |

TABLE 1-continued

| Compound Number | Structure | Name |
|---|---|---|
| 331 | 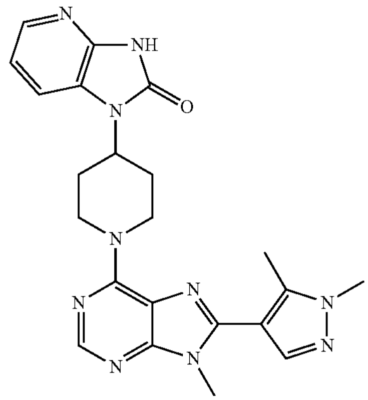 [SMILES: Cc1c(-c2nc3c(N4CCC(n5c(=O)[nH]c6ncccc65)CC4)ncnc3n2C)cnn1C] | 1-{1-[8-(1,5-dimethyl-1H-pyrazol-4-yl)-9-methyl-9H-purin-6-yl]piperidin-4-yl}-1,3-dihydro-2H-imidazo[4,5-b]pyridin-2-one |
| 332 | 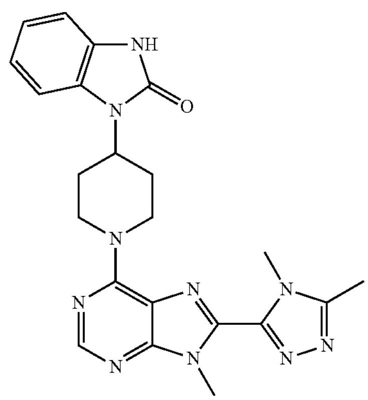 [SMILES: Cc1nnc(-c2nc3c(N4CCC(n5c(=O)[nH]c6ccccc65)CC4)ncnc3n2C)n1C] | 1-{1-[8-(4,5-dimethyl-4H-1,2,4-triazol-3-yl)-9-methyl-9H-purin-6-yl]piperidin-4-yl}-1,3-dihydro-2H-benzimidazol-2-one |
| 333 | 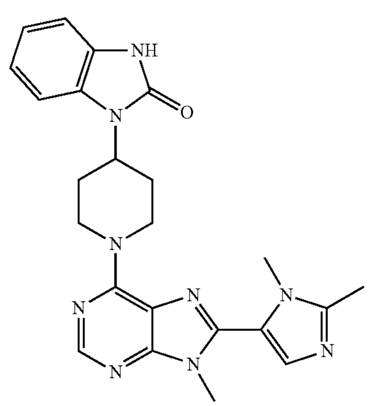 [SMILES: Cc1ncc(-c2nc3c(N4CCC(n5c(=O)[nH]c6ccccc65)CC4)ncnc3n2C)n1C] | 1-{1-[8-(1,2-dimethyl-1H-imidazol-5-yl)-9-methyl-9H-purin-6-yl]piperidin-4-yl)-1,3-dihydro-2H-benzimidazol-2-one |
| 334 | Chiral | methyl (3R,4R)-1-[9-methyl-8-(1-methyl-1H-pyrazol-4-yl)-9H-purin-6-yl]-4-(2-oxo-2,3-dihydro-1H-benzimidazol-1-yl)piperidine-3-carboxylate |

TABLE 1-continued

| Compound Number | Structure | Name |
|---|---|---|
| 335 | 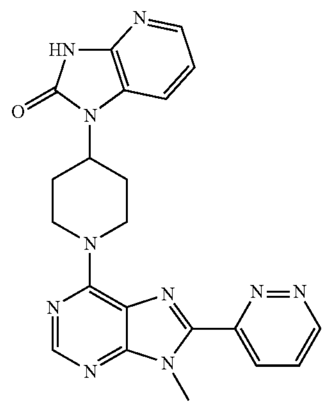 [SMILES: Cn1c(-c2cccnn2)nc2c(N3CCC(n4c(=O)[nH]c5ncccc54)CC3)ncnc21] | 1-[1-(9-methyl-8-pyridazin-3-yl-9H-purin-6-yl)piperidin-4-yl]-1,3-dihydro-2H-imidazo[4,5-b]pyridin-2-one |
| 336 | 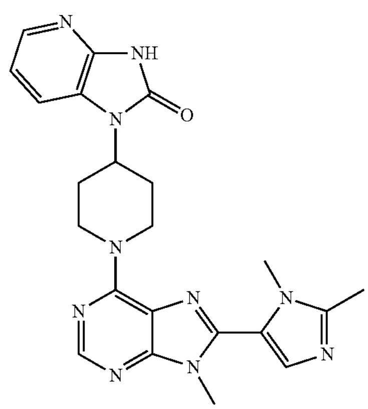 [SMILES: Cc1ncc(-c2nc3c(N4CCC(n5c(=O)[nH]c6ncccc65)CC4)ncnc3n2C)n1C] | 1-{1-[8-(1,2-dimethyl-1H-imidazol-5-yl)-9-methyl-9H-purin-6-yl]piperidin-4-yl}-1,3-dihydro-2H-imidazo[4,5-b]pyridin-2-one |
| 337 | 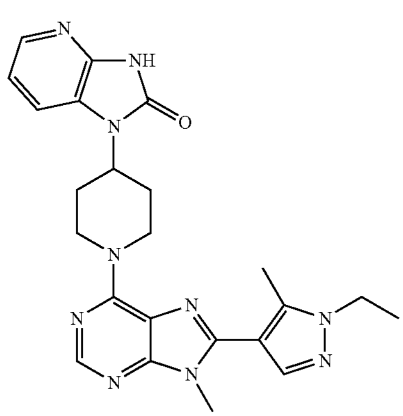 [SMILES: CCn1ncc(-c2nc3c(N4CCC(n5c(=O)[nH]c6ncccc65)CC4)ncnc3n2C)c1C] | 1-{1-[8-(1-ethyl-5-methyl-1H-pyrazol-4-yl)-9-methyl-9H-purin-6-yl]piperidin-4-yl}-1,3-dihydro-2H-imidazo[4,5-b]pyridin-2-one |

TABLE 1-continued

| Compound Number | Structure | Name |
|---|---|---|
| 338 | Chiral | 1-{(3R,4R)-3-(hydroxymethyl)-1-[9-methyl-8-(1-methyl-1H-pyrazol-4-yl)-9H-purin-6-yl]piperidin-4-yl}-1,3-dihydro-2H-benzimidazol-2-one |
| 339 | 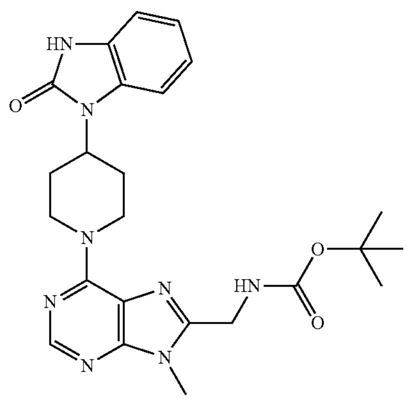 [SMILES: Cn1c(CNC(=O)OC(C)(C)C)nc2c(N3CCC(n4c(=O)[nH]c5ccccc54)CC3)ncnc21] | 1,1-dimethylethyl ({9-methyl-6-[4-(2-oxo-2,3-dihydro-1H-benzimidazol-1-yl)piperidin-1-yl]-9H-purin-8-yl}methyl)carbamate |
| 340 | 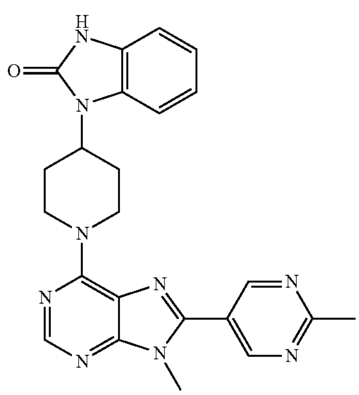 [SMILES: Cc1ncc(-c2nc3c(N4CCC(n5c(=O)[nH]c6ccccc65)CC4)ncnc3n2C)cn1] | 1-{1-[9-methyl-8-(2-methylpyrimidin-5-yl)-9H-purin-6-yl]piperidin-4-yl}-1,3-dihydro-2H-benzimidazol-2-one |
| 341 | 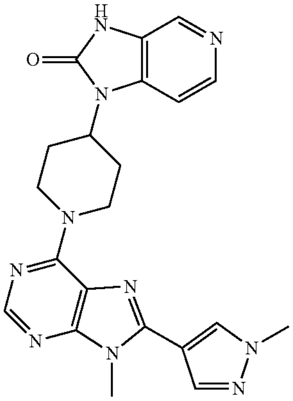 [SMILES: Cn1cc(-c2nc3c(N4CCC(n5c(=O)[nH]c6cnccc65)CC4)ncnc3n2C)cn1] | 1-{1-[9-methyl-8-(1-methyl-1H-pyrazol-4-yl)-9H-purin-6-yl]piperidin-4-yl}-1,3-dihydro-2H-imidazo[4,5-c]pyridin-2-one |

TABLE 1-continued

| Compound Number | Structure | Name |
|---|---|---|
| 342 | 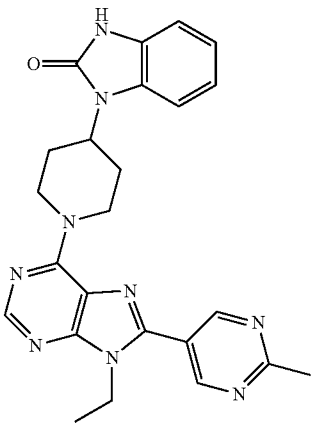 [SMILES: CCn1c(-c2cnc(C)nc2)nc2c(N3CCC(n4c(=O)[nH]c5ccccc54)CC3)ncnc21] | 1-{1-[9-ethyl-8-(2-methylpyrimidin-5-yl)-9H-purin-6-yl]piperidin-4-yl}-1,3-dihydro-2H-benzimidazol-2-one |
| 343 | 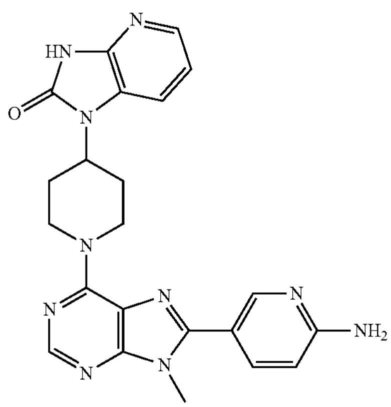 [SMILES: Cn1c(-c2ccc(N)nc2)nc2c(N3CCC(n4c(=O)[nH]c5ncccc54)CC3)ncnc21] | 1-{1-[8-(6-aminopyridin-3-yl)-9-methyl-9H-purin-6-yl]piperidin-4-yl}-1,3-dihydro-2H-imidazo[4,5-b]pyridin-2-one |
| 344 | 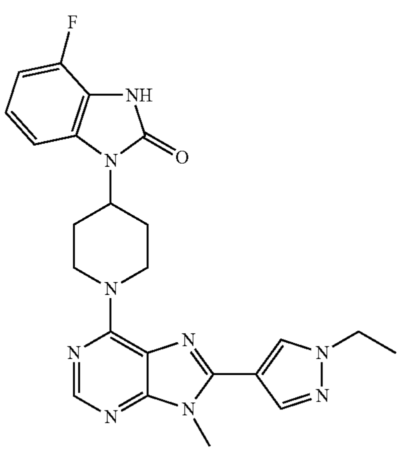 [SMILES: CCn1cc(-c2nc3c(N4CCC(n5c(=O)[nH]c6c(F)cccc65)CC4)ncnc3n2C)cn1] | 1-{1-[8-(1-ethyl-1H-pyrazol-4-yl)-9-methyl-9H-purin-6-yl]piperidin-4-yl}-4-fluoro-1,3-dihydro-2H-benzimidazol-2-one |

TABLE 1-continued

| Compound Number | Structure | | Name |
|---|---|---|---|
| 345 | 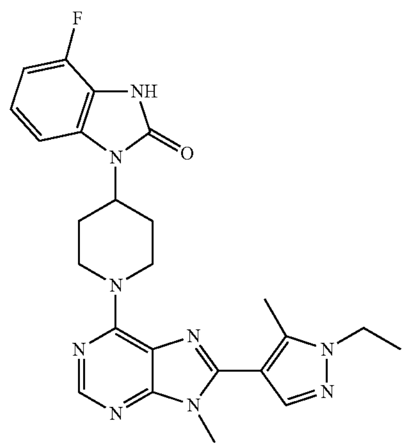 [SMILES: CCn1ncc(-c2nc3c(N4CCC(n5c(=O)[nH]c6c(F)cccc65)CC4)ncnc3n2C)c1C] | | 1-{1-[8-(1-ethyl-5-methyl-1H-pyrazol-4-yl)-9-methyl-9H-purin-6-yl]piperidin-4-yl}-4-fluoro-1,3-dihydro-2H-benzimidazol-2-one |
| 346 | 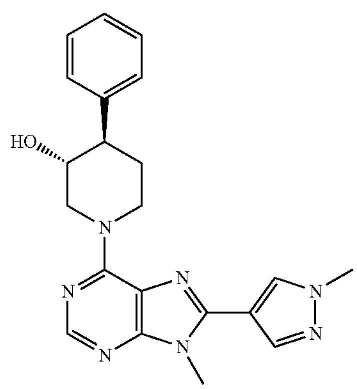 [SMILES: Cn1cc(-c2nc3c(N4CC[C@H](c5ccccc5)[C@@H](O)C4)ncnc3n2C)cn1] | | (3R,4R)-1-[9-methyl-8-(1-methyl-1H-pyrazol-4-yl)-9H-purin-6-yl]-4-phenylpiperidin-3-ol |
| 347 | 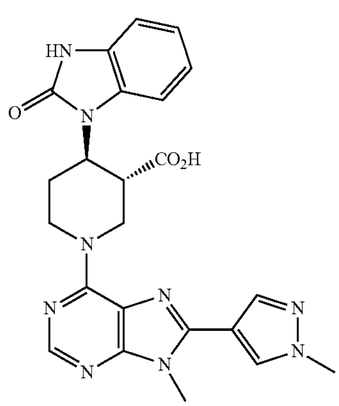 | Chiral | (3R,4R)-1-[9-methyl-8-(1-methyl-1H-pyrazol-4-yl)-9H-purin-6-yl]-4-(2-oxo-2,3-dihydro-1H-benzimidazol-1-yl)piperidine-3-carboxylic acid |

TABLE 1-continued

| Compound Number | Structure | Name |
|---|---|---|
| 348 | 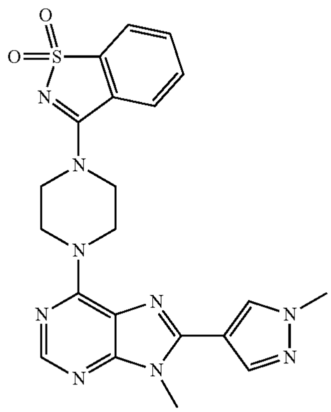 [SMILES: Cn1cc(-c2nc3c(N4CCN(C5=NS(=O)(=O)c6ccccc65)CC4)ncnc3n2C)cn1] | 6-[4-(1,1-dioxido-1,2-benzisothiazol-3-yl)piperazin-1-yl]-9-methyl-8-(1-methyl-1H-pyrazol-4-yl)-9H-purine |
| 349 | 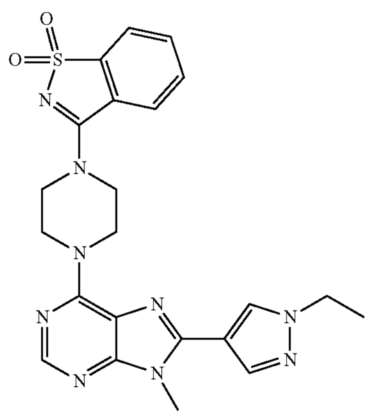 [SMILES: CCn1cc(-c2nc3c(N4CCN(C5=NS(=O)(=O)c6ccccc65)CC4)ncnc3n2C)cn1] | 6-[4-(1,1-dioxido-1,2-benzisothiazol-3-yl)piperazin-1-yl]-8-(1-ethyl-1H-pyrazol-4-yl)-9-methyl-9H-purine |
| 350 | 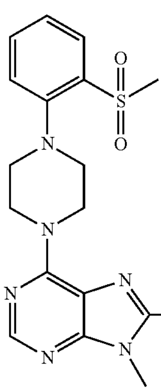 | 9-methyl-8-(1-methyl-1H-pyrazol-4-yl)-6-{4-[2-(methylsulfonyl)phenyl]piperazin-1-yl}-9H-purine |
| 351 | 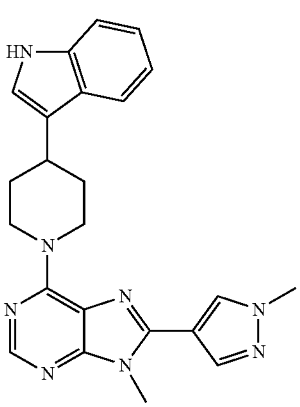 [SMILES: Cn1cc(-c2nc3c(N4CCC(c5c[nH]c6ccccc56)CC4)ncnc3n2C)cn1] | 6-[4-(1H-indol-3-yl)piperidin-1-yl]-9-methyl-8-(1-methyl-1H-pyrazol-4-yl)-9H-purine |

TABLE 1-continued

| Compound Number | Structure | Name |
|---|---|---|
| 352 | 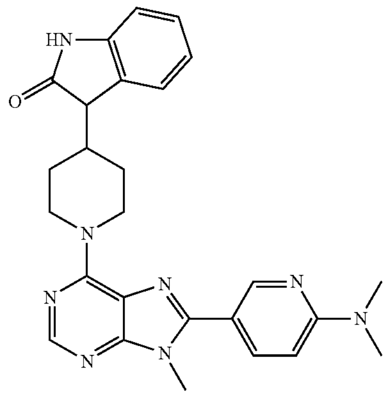 [SMILES: CN(C)c1ccc(-c2nc3c(N4CCC(C5C(=O)Nc6ccccc65)CC4)ncnc3n2C)cn1] | 1-(1-{8-[6-(dimethylamino)pyridin-3-yl]-9-methyl-9H-purin-6-yl}piperidin-4-yl)-1,3-dihydro-2H-benzimidazol-2-one |
| 353 | 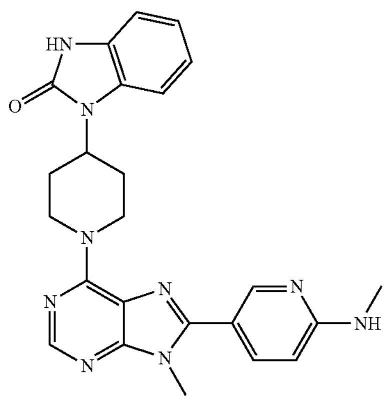 [SMILES: CNc1ccc(-c2nc3c(N4CCC(n5c(=O)[nH]c6ccccc65)CC4)ncnc3n2C)cn1] | 1-(1-{9-methyl-8-[6-(methylamino)pyridin-3-yl]-9H-purin-6-yl}piperidin-4-yl)-1,3-dihydro-2H-benzimidazol-2-one |
| 354 | 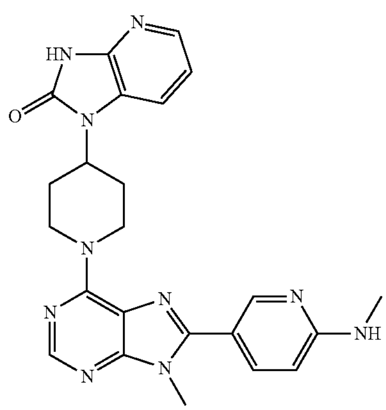 [SMILES: CNc1ccc(-c2nc3c(N4CCC(n5c(=O)[nH]c6ncccc65)CC4)ncnc3n2C)cn1] | 1-(1-{9-methyl-8-[6-(methylamino)pyridin-3-yl]-9H-purin-6-yl}piperidin-4-yl)-1,3-dihydro-2H-imidazo[4,5-b]pyridin-2-one |

TABLE 1-continued

| Compound Number | Structure | Name |
|---|---|---|
| 355 | 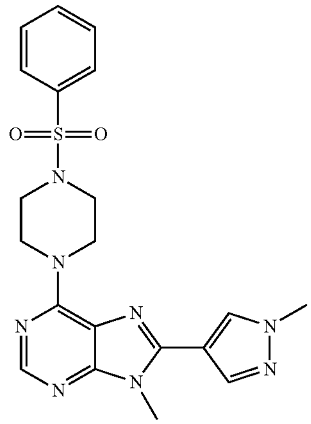 [SMILES: Cn1cc(-c2nc3c(N4CCN(S(=O)(=O)c5ccccc5)CC4)ncnc3n2C)cn1] | 9-methyl-8-(1-methyl-1H-pyrazol-4-yl)-6-[4-(phenylsulfonyl)piperazin-1-yl]-9H-purine |
| 356 | 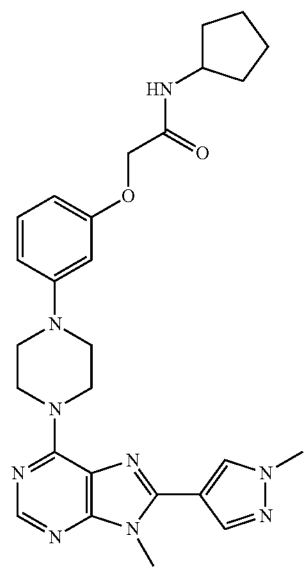 [SMILES: Cn1cc(-c2nc3c(N4CCN(c5cccc(OCC(=O)NC6CCCC6)c5)CC4)ncnc3n2C)cn1] | N-cyclopentyl-2-[(3-{4-[9-methyl-8-(1-methyl-1H-pyrazol-4-yl)-9H-purin-6-yl]piperazin-1-yl}phenyl)oxy]acetamide |
| 357 | 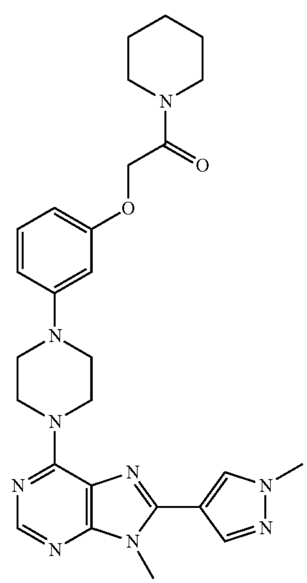 [SMILES: Cn1cc(-c2nc3c(N4CCN(c5cccc(OCC(=O)N6CCCCC6)c5)CC4)ncnc3n2C)cn1] | 9-methyl-8-(1-methyl-1H-pyrazol-4-yl)-6-(4-{3-[(2-oxo-2-piperidin-1-ylethyl)oxy]phenyl}piperazin-1-yl)-9H-purine |

TABLE 1-continued
| Compound Number | Structure | Name |
|---|---|---|
| 358 | 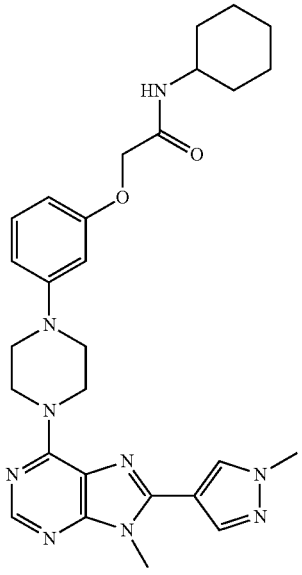 [SMILES: Cn1cc(-c2nc3c(N4CCN(c5cccc(OCC(=O)NC6CCCCC6)c5)CC4)ncnc3n2C)cn1] | N-cyclohexyl-2-[(3-{4-[9-methyl-8-(1-methyl-1H-pyrazol-4-yl)-9H-purin-6-yl]piperazin-1-yl}phenyl)oxy]acetamide |
| 359 | 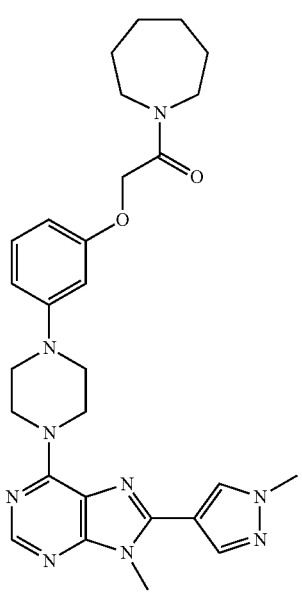 [SMILES: Cn1cc(-c2nc3c(N4CCN(c5cccc(OCC(=O)N6CCCCCC6)c5)CC4)ncnc3n2C)cn1] | 6-(4-{3-[(2-azepan-1-yl-2-oxoethyl)oxy]phenyl}piperazin-1-yl)-9-methyl-8-(1-methyl-1H-pyrazol-4-yl)-9H-purine |

TABLE 1-continued

| Compound Number | Structure | Name |
|---|---|---|
| 360 | 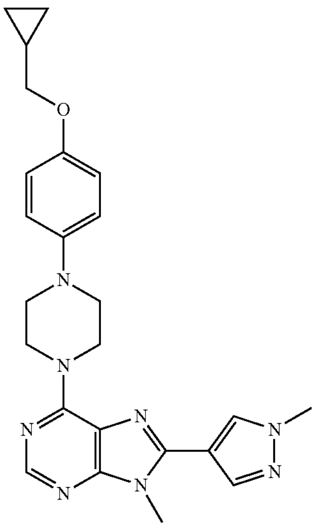 [SMILES: Cn1cc(-c2nc3c(N4CCN(c5ccc(OCC6CC6)cc5)CC4)ncnc3n2C)cn1] | 6-(4-{4-[(cyclopropylmethyl)oxy]-phenyl}piperazin-1-yl)-9-methyl-8-(1-methyl-1H-pyrazol-4-yl)-9H-purine |
| 361 | 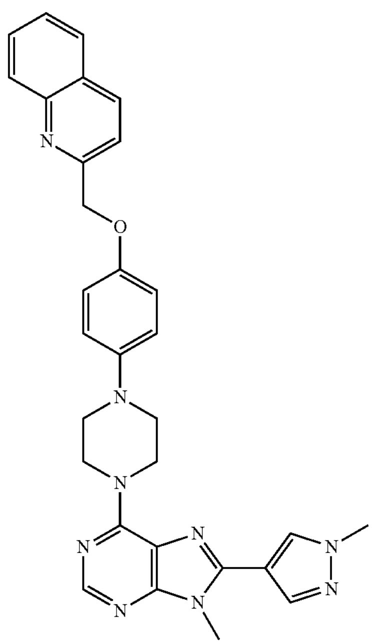 [SMILES: Cn1cc(-c2nc3c(N4CCN(c5ccc(OCc6ccc7ccccc7n6)cc5)CC4)ncnc3n2C)cn1] | 2-{[(4-(4-[9-methyl-8-(1-methyl-1H-pyrazol-4-yl)-9H-purin-6-yl]piperazin-1-yl}phenyl)oxy]methyl)-quinoline |
| 362 | 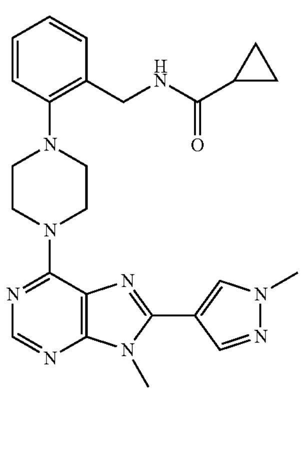 [SMILES: Cn1cc(-c2nc3c(N4CCN(c5ccccc5CNC(=O)C5CC5)CC4)ncnc3n2C)cn1] | N-[(2-{4-[9-methyl-8-(1-methyl-1H-pyrazol-4-yl)-9H-purin-6-yl]piperazin-1-yl}phenyl)methyl]cyclopropane-carboxamide |

TABLE 1-continued

| Compound Number | Structure | Name |
|---|---|---|
| 363 | 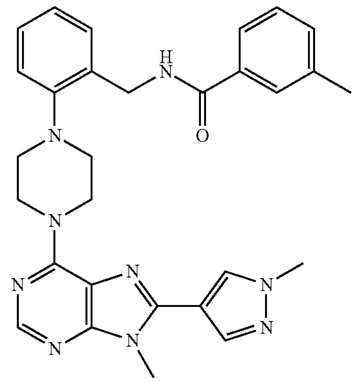 [SMILES: Cc1cccc(C(=O)NCc2ccccc2N2CCN(c3ncnc4c3nc(-c3cnn(C)c3)n4C)CC2)c1] | 3-methyl-N-[(2-{4-[9-methyl-8-(1-methyl-1H-pyrazol-4-yl)-9H-purin-6-yl]piperazin-1-yl}phenyl)methyl]benzamide |
| 364 | 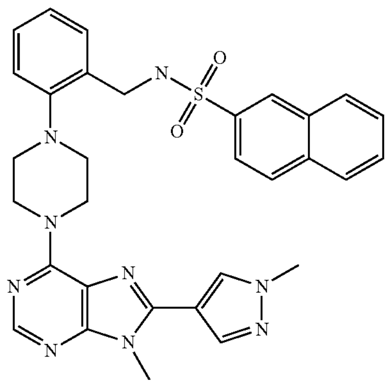 [SMILES: Cn1cc(-c2nc3c(N4CCN(c5ccccc5CNS(=O)(=O)c5ccc6ccccc6c5)CC4)ncnc3n2C)cn1] | N-[(2-{4-[9-methyl-8-(1-methyl-1H-pyrazol-4-yl)-9H-purin-6-yl]piperazin-1-yl}phenyl)methyl]naphthalene-2-sulfonamide |
| 365 | 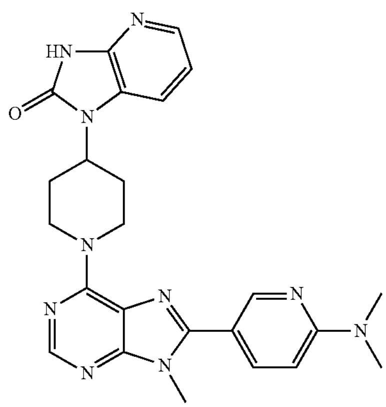 [SMILES: CN(C)c1ccc(-c2nc3c(N4CCC(n5c(=O)[nH]c6ncccc65)CC4)ncnc3n2C)cn1] | 1-(1-{8-[6-(dimethylamino)pyridin-3-yl]-9-methyl-9H-purin-6-yl}piperidin-4-yl)-1,3-dihydro-2H-imidazo[4,5-b]pyridin-2-one |
| 366 | 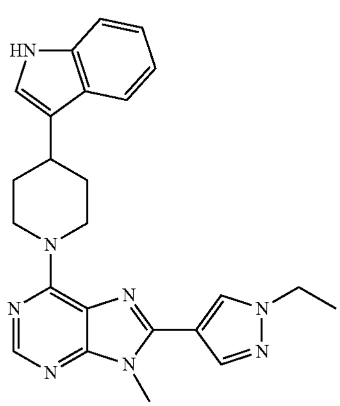 [SMILES: CCn1cc(-c2nc3c(N4CCC(c5c[nH]c6ccccc56)CC4)ncnc3n2C)cn1] | 8-(1-ethyl-1H-pyrazol-4-yl)-6-[4-(1H-indol-3-yl)piperidin-1-yl]-9-methyl-9H-purine |

TABLE 1-continued
| Compound Number | Structure | Name |
|---|---|---|
| 367 | 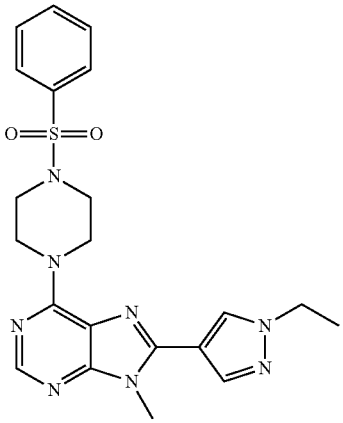 [SMILES: CCn1cc(-c2nc3c(N4CCN(S(=O)(=O)c5ccccc5)CC4)ncnc3n2C)cn1] | 8-(1-ethyl-1H-pyrazol-4-yl)-9-methyl-6-[4-(phenylsulfonyl)piperazin-1-yl]-9H-purine |
| 368 | 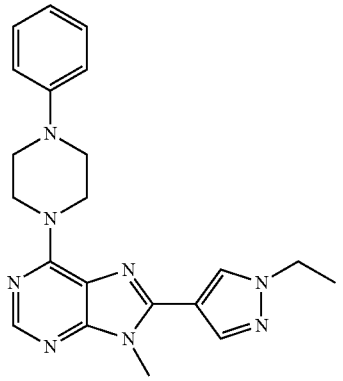 [SMILES: CCn1cc(-c2nc3c(N4CCN(c5ccccc5)CC4)ncnc3n2C)cn1] | 8-(1-ethyl-1H-pyrazol-4-yl)-9-methyl-6-(4-phenylpiperazin-1-yl)-9H-purine |
| 369 | 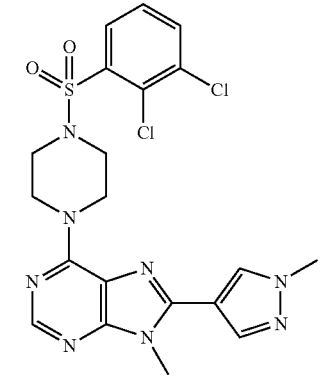 [SMILES: Cn1cc(-c2nc3c(N4CCN(S(=O)(=O)c5cccc(Cl)c5Cl)CC4)ncnc3n2C)cn1] | 6-(4-((2,3-dichlorophenyl)sulfonyl)-piperazin-1-yl)-9-methyl-8-(1-methyl-1H-pyrazol-4-yl)-9H-purine |
| 370 | 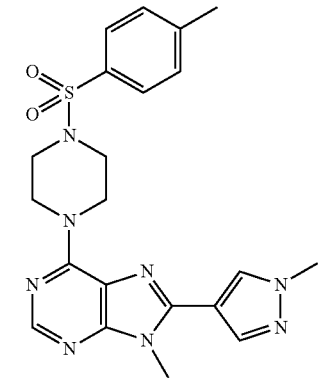 [SMILES: Cc1ccc(S(=O)(=O)N2CCN(c3ncnc4c3nc(-c3cnn(C)c3)n4C)CC2)cc1] | 9-methyl-6-{4-[(4-methylphenyl)sulfonyl]-piperazin-1-yl}-8-(1-methyl-1H-pyrazol-4-yl)-9H-purine |

TABLE 1-continued

| Compound Number | Structure | Name |
|---|---|---|
| 371 | 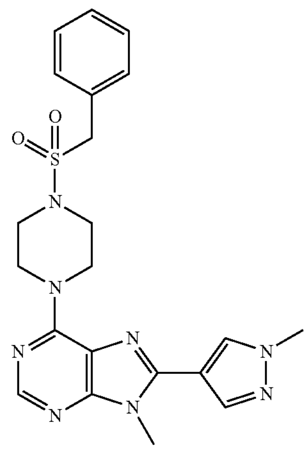 [SMILES: Cn1cc(-c2nc3c(N4CCN(S(=O)(=O)Cc5ccccc5)CC4)ncnc3n2C)cn1] | 9-methyl-8-(1-methyl-1H-pyrazol-4-yl)-6-{4-[(phenylmethyl)sulfonyl]piperazin-1-yl)-9H-purine |
| 372 | 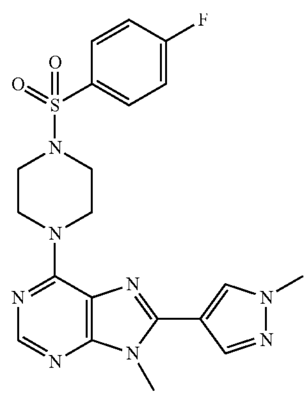 [SMILES: Cn1cc(-c2nc3c(N4CCN(S(=O)(=O)c5ccc(F)cc5)CC4)ncnc3n2C)cn1] | 6-{4-[(4-fluorophenyl)sulfonyl]piperazin-1-yl}-9-methyl-8-(1-methyl-1H-pyrazol-4-yl)-9H-purine |
| 373 | 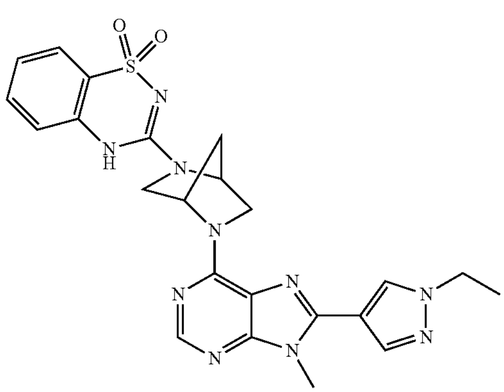 [SMILES: CCn1cc(-c2nc3c(N4CC5CC4CN5C4=NS(=O)(=O)c5ccccc5N4)ncnc3n2C)cn1] | 9-methyl-6-(4-{[4-(methyloxy)phenyl]sulfonyl}-piperazin-1-yl)-8-(1-methyl-1H-pyrazol-4-yl)-9H-purine |

TABLE 1-continued

| Compound Number | Structure | Name |
|---|---|---|
| 374 | 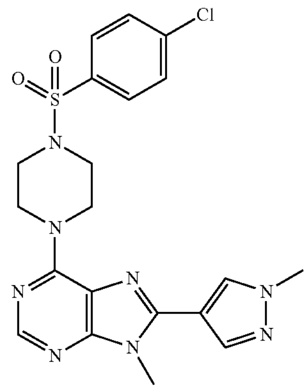 [SMILES: Cn1cc(-c2nc3c(N4CCN(S(=O)(=O)c5ccc(Cl)cc5)CC4)ncnc3n2C)cn1] | 6-{4-[(4-chlorophenyl)sulfonyl]piperazin-1-yl)-9-methyl-8-(1-methyl-1H-pyrazol-4-yl)-9H-purine |
| 375 | 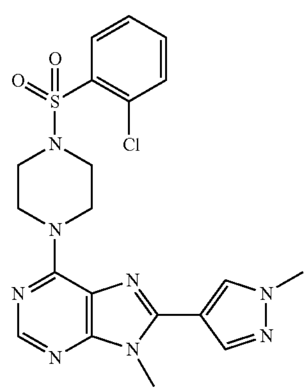 [SMILES: Cn1cc(-c2nc3c(N4CCN(S(=O)(=O)c5ccccc5Cl)CC4)ncnc3n2C)cn1] | 6-{4-[(2-chlorophenyl)sulfonyl]piperazin-1-yl}-9-methyl-8-(1-methyl-1H-pyrazol-4-yl)-9H-purine |
| 376 | 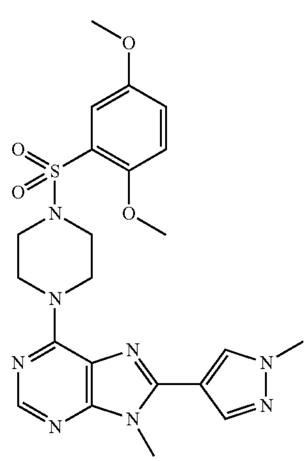 [SMILES: COc1ccc(OC)c(S(=O)(=O)N2CCN(c3ncnc4c3nc(-c3cnn(C)c3)n4C)CC2)c1] | 6-(4-([2,5-bis(methyloxy)phenyl]sulfonyl}-piperazin-1-yl)-9-methyl-8-(1-methyl-1H-pyrazol-4-yl)-9H-purine |

TABLE 1-continued

| Compound Number | Structure | Name |
|---|---|---|
| 377 | 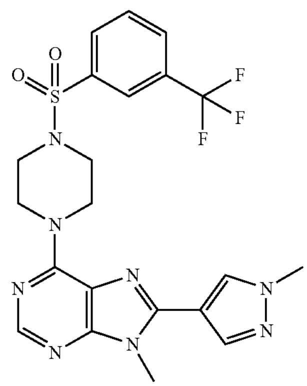 [SMILES: Cn1cc(-c2nc3c(N4CCN(S(=O)(=O)c5cccc(C(F)(F)F)c5)CC4)ncnc3n2C)cn1] | 9-methyl-8-(1-methyl-1H-pyrazol-4-yl)-6-(4-{[3-(trifluoromethyl)phenyl]sulfonyl}-piperazin-1-yl)-9H-purine |
| 378 | 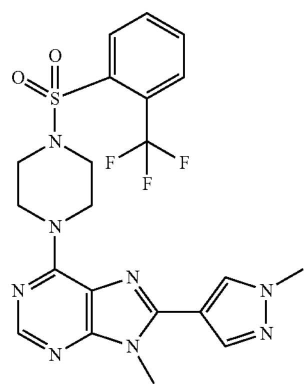 [SMILES: Cn1cc(-c2nc3c(N4CCN(S(=O)(=O)c5ccccc5C(F)(F)F)CC4)ncnc3n2C)cn1] | 9-methyl-8-(1-methyl-1H-pyrazol-4-yl)-6-(4-{[2-(trifluoromethyl)phenyl[sulfonyl}-piperazin-1-yl)-9H-purine |
| 379 | 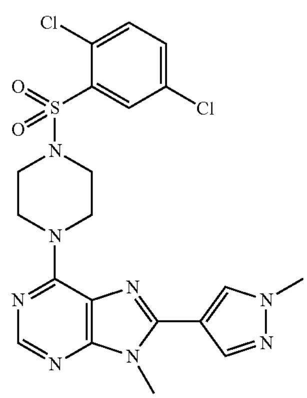 [SMILES: Cn1cc(-c2nc3c(N4CCN(S(=O)(=O)c5cc(Cl)ccc5Cl)CC4)ncnc3n2C)cn1] | 6-{4-[(2,5-dichlorophenyl)sulfonyl]piperazin-1-yl}-9-methyl-8-(1-methyl-1H-pyrazol-4-yl)-9H-purine |
| 380 | 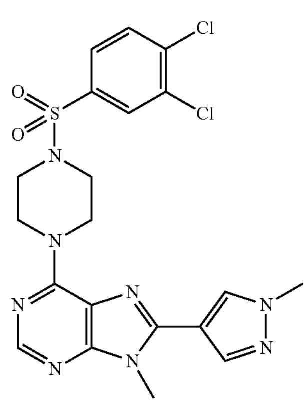 [SMILES: Cn1cc(-c2nc3c(N4CCN(S(=O)(=O)c5ccc(Cl)c(Cl)c5)CC4)ncnc3n2C)cn1] | 6-{4-[(3,4-dichlorophenyl)sulfonyl]piperazin-1-yl}-9-methyl-8-(1-methyl-1H-pyrazol-4-yl)-9H-purine |

TABLE 1-continued

| Compound Number | Structure | Name |
|---|---|---|
| 381 | 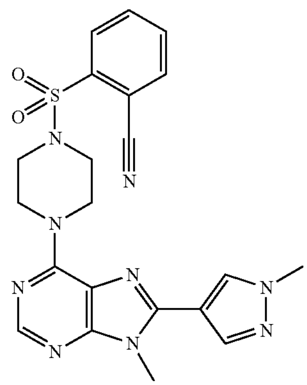 [SMILES: Cn1cc(-c2nc3c(N4CCN(S(=O)(=O)c5ccccc5C#N)CC4)ncnc3n2C)cn1] | 2-({4-[9-methyl-8-(1-methyl-1H-pyrazol-4-yl)-9H-purin-6-yl]piperazin-1-yl}sulfonyl)benzonitrile |
| 382 | 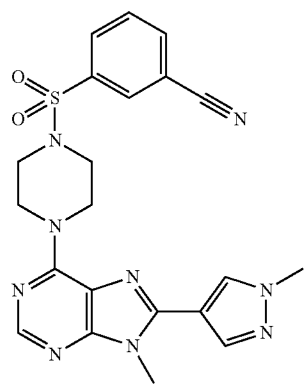 [SMILES: Cn1cc(-c2nc3c(N4CCN(S(=O)(=O)c5cccc(C#N)c5)CC4)ncnc3n2C)cn1] | 3-({4-[9-methyl-8-(1-methyl-1H-pyrazol-4-yl)-9H-purin-6-yl]piperazin-1-yl)sulfonyl)benzonitrile |
| 383 | 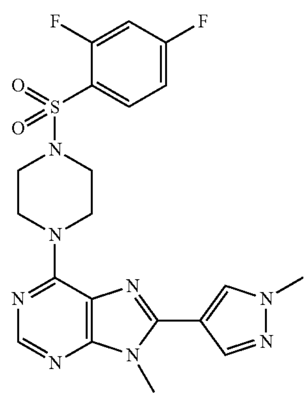 [SMILES: Cn1cc(-c2nc3c(N4CCN(S(=O)(=O)c5ccc(F)cc5F)CC4)ncnc3n2C)cn1] | 6-{4-[(2,4-difluorophenyl)sulfonyl]piperazin-1-yl}-9-methyl-8-(1-methyl-1H-pyrazol-4-yl)-9H-purine |
| 384 | 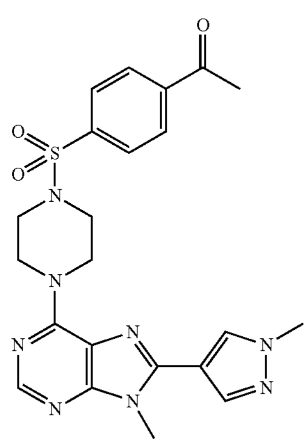 [SMILES: CC(=O)c1ccc(S(=O)(=O)N2CCN(c3ncnc4c3nc(-c3cnn(C)c3)n4C)CC2)cc1] | 1-[4-({4-[9-methyl-8-(1-methyl-1H-pyrazol-4-yl)-9H-purin-6-yl]piperazin-1-yl)sulfonyl)phenyl]ethanone |

TABLE 1-continued

| Compound Number | Structure | Name |
|---|---|---|
| 385 | 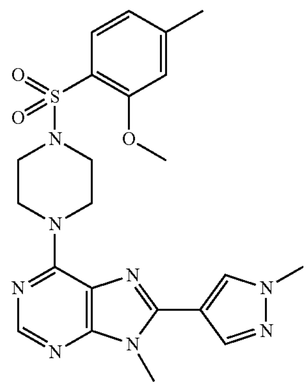 [SMILES: COc1cc(C)ccc1S(=O)(=O)N1CCN(c2ncnc3c2nc(-c2cnn(C)c2)n3C)CC1] | 9-methyl-6-(4-{[4-methyl-2-(methyloxy)phenyl]sulfonyl}-piperazin-1-yl)-8-(1-methyl-1H-pyrazol-4-yl)-9H-purine |
| 386 | 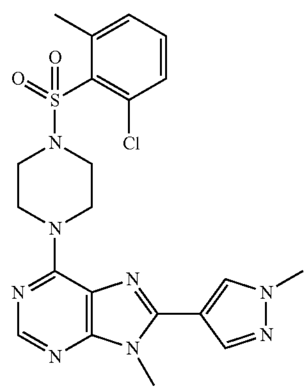 [SMILES: Cc1cccc(Cl)c1S(=O)(=O)N1CCN(c2ncnc3c2nc(-c2cnn(C)c2)n3C)CC1] | 6-{4-[(2-chloro-6-methylphenyl)sulfonyl]piperazin-1-yl)-9-methyl-8-(1-methyl-1H-pyrazol-4-yl)-9H-purine |
| 387 | 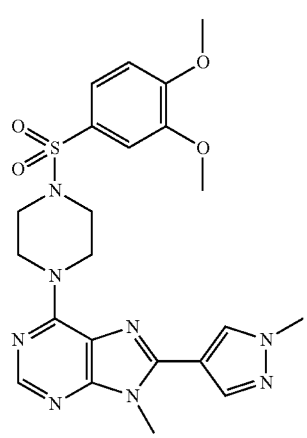 [SMILES: COc1ccc(S(=O)(=O)N2CCN(c3ncnc4c3nc(-c3cnn(C)c3)n4C)CC2)cc1OC] | 6-(4-{[3,4-bis(methyloxy)phenyl]sulfonyl}-piperazin-1-yl)-9-methyl-8-(1-methyl-1H-pyrazol-4-yl)-9H-purine |

TABLE 1-continued

| Compound Number | Structure | Name |
|---|---|---|
| 388 | 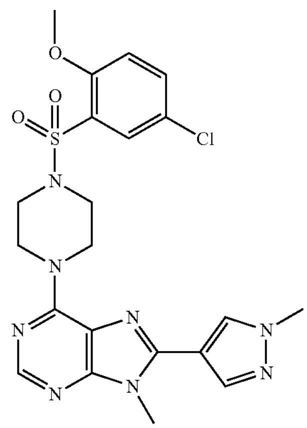 [SMILES: COc1ccc(Cl)cc1S(=O)(=O)N1CCN(c2ncnc3c2nc(-c2cnn(C)c2)n3C)CC1] | 6-(4-{[5-chloro-2-(methyloxy)phenyl]sulfonyl}-piperazin-1-yl)-9-methyl-8-(1-methyl-1H-pyrazol-4-yl)-9H-purine |
| 389 | 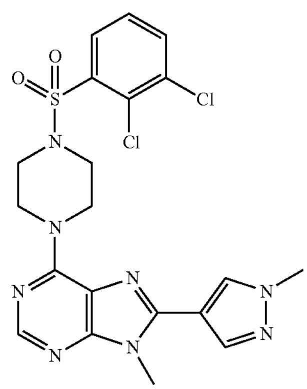 [SMILES: Cn1cc(-c2nc3c(N4CCN(S(=O)(=O)c5cccc(Cl)c5Cl)CC4)ncnc3n2C)cn1] | 6-{4-[(2,3-dichlorophenyl)sulfonyl]piperazin-1-yl}-9-methyl-8-(1-methyl-1H-pyrazol-4-yl)-9H-purine |
| 390 | 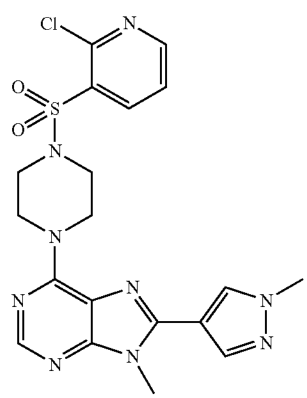 [SMILES: Cn1cc(-c2nc3c(N4CCN(S(=O)(=O)c5cccnc5Cl)CC4)ncnc3n2C)cn1] | 6-{4-[(2-chloropyridin-3-yl)sulfonyl]piperazin-1-yl}-9-methyl-8-(1-methyl-1H-pyrazol-4-yl)-9H-purine |
| 391 | 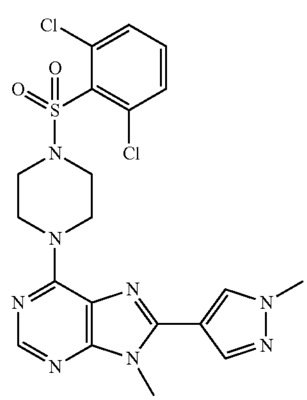 [SMILES: Cn1cc(-c2nc3c(N4CCN(S(=O)(=O)c5c(Cl)cccc5Cl)CC4)ncnc3n2C)cn1] | 6-{4-[(2,6-dichlorophenyl)sulfonyl]piperazin-1-yl}-9-methyl-8-(1-methyl-1H-pyrazol-4-yl)-9H-purine |

TABLE 1-continued

| Compound Number | Structure | Name |
|---|---|---|
| 392 | 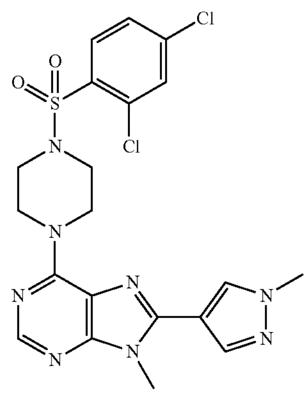 [SMILES: Cn1cc(-c2nc3c(N4CCN(S(=O)(=O)c5ccc(Cl)cc5Cl)CC4)ncnc3n2C)cn1] | 6-{4-[(2,4-dichlorophenyl)sulfonyl]piperazin-1-yl}-9-methyl-8-(1-methyl-1H-pyrazol-4-yl)-9H-purine |
| 393 | 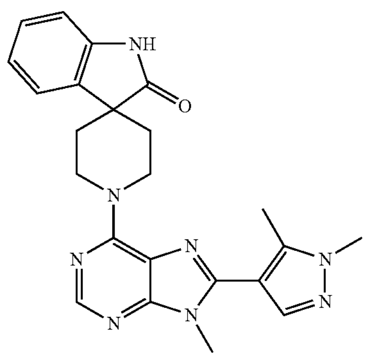 [SMILES: Cc1c(-c2nc3c(N4CCC5(CC4)C(=O)Nc4ccccc45)ncnc3n2C)cnn1C] | 1'-(8-(1,5-dimethyl-1H-pyrazol-4-yl)-9-methyl-9H-purin-6-yl)spiro[indoline-3,4'-piperidin]-2-one |
| 394 | 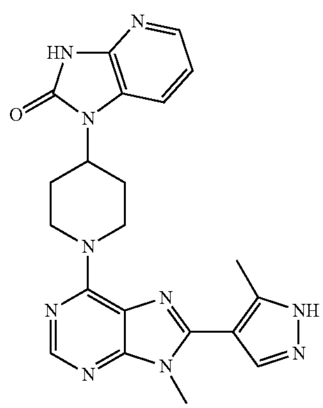 [SMILES: Cc1[nH]ncc1-c1nc2c(N3CCC(n4c(=O)[nH]c5ncccc54)CC3)ncnc2n1C] | 1-{1-[9-methyl-8-(5-methyl-1H-pyrazol-4-yl)-9H-purin-6-yl]piperidin-4-yl}-1,3-dihydro-2H-imidazo[4,5-b]pyridin-2-one |
| 395 | 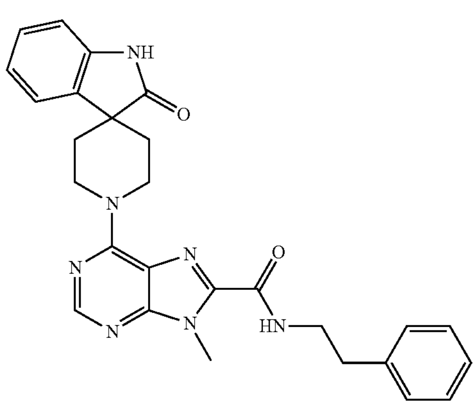 [SMILES: Cn1c(C(=O)NCCc2ccccc2)nc2c(N3CCC4(CC3)C(=O)Nc3ccccc34)ncnc21] | 9-methyl-6-(2-oxo-1,2-dihydro-1'H-spiro[indole-3,4'-piperidin]-1'-yl)-N-(2-phenylethyl)-9H-purine-8-carboxamide |

TABLE 1-continued

| Compound Number | Structure | Name |
|---|---|---|
| 396 | 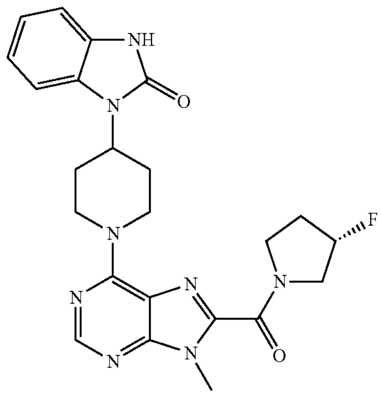 [SMILES: Cn1c(C(=O)N2CC[C@H](F)C2)nc2c(N3CCC(n4c(=O)[nH]c5ccccc54)CC3)ncnc21] | 1-[1-(8-{[(3S)-3-fluoropyrrolidin-1-yl]carbonyl)-9-methyl-9H-purin-6-yl)piperidin-4-yl]-1,3-dihydro-2H-benzimidazol-2-one |
| 397 | 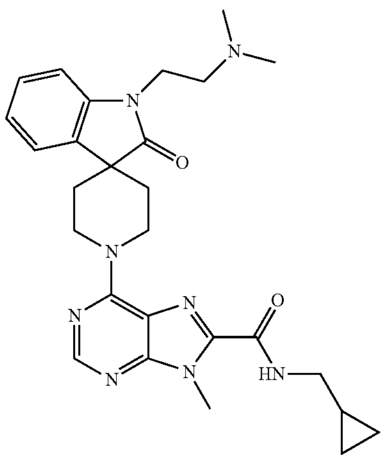 [SMILES: CN(C)CCN1C(=O)C2(CCN(c3ncnc4c3nc(C(=O)NCC3CC3)n4C)CC2)c2ccccc21] | N-(cyclopropylmethyl)-6-{1-[2-(dimethylamino)ethyl]-2-oxo-1,2-dihydro-1'H-spiro[indole-3,4'-piperidin]-1'-yl}-9-methyl-9H-purine-8-carboxamide |

In another aspect, the invention provides a pharmaceutical composition which comprises 1) a compound, as a single stereoisomer or mixture of isomers thereof, according to any one of Formula compounds of Formula I, Ia, Ib, Ic, Id, and II or IIa, or according to any one of the above embodiments or a compound in Table 1, optionally as a pharmaceutically acceptable salt thereof, and 2) a pharmaceutically acceptable carrier, excipient, and/or diluent thereof.

In another aspect, the invention provides a method of treating disease, disorder, or syndrome where the disease is associated with uncontrolled, abnormal, and/or unwanted cellular activities effected directly or indirectly by PI3K delta which method comprises administering to a human in need thereof a therapeutically effective amount of a compound of any of Formula to any one of Formula compounds of Formula I, Ia, Ib, Ic, Id, and II or IIa, a compound of any one of the above embodiments, or a compound from Table 1, optionally as a pharmaceutically acceptable salt or pharmaceutical composition thereof. In another embodiment of embodiment (V), the disease is cancer. In another embodiment of embodiment (V), the disease is cancer and the Compound is of Formula I or a Compound from Table 1.

In another aspect, the invention provides a method of treating a disease, disorder, or syndrome which method comprises administering to a patient a therapeutically effective amount of a compound of any of Formula I, Ia, Ib, Ic, Id, II, or IIa, a compound of any one of the above embodiments, or a compound from Table 1, optionally as a pharmaceutically acceptable salt thereof, or a pharmaceutical composition comprising a therapeutically effective amount of a compound of Formula I, Ia, Ib, Ic, Id, II, or IIa, a compound of any one of the above embodiments, or a compound from Table 1, and a pharmaceutically acceptable carrier, excipient, or diluent.

In another embodiment, the disease is cancer and the Compound is the compound of Formula I or a compound from Table 1.

General Administration

In one aspect, the invention provides pharmaceutical compositions comprising an inhibitor of PI3K delta according to the invention and a pharmaceutically acceptable carrier, excipient, or diluent. In certain other specific embodiments, administration is by the oral route. Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracistemally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, specifically in unit dosage forms suitable for simple administration of precise dosages.

The compositions will include a conventional pharmaceutical carrier or excipient and a compound of the invention as the/an active agent, and, in addition, may include carriers and adjuvants, etc.

Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylalted hydroxytoluene, etc.

The choice of formulation depends on various factors such as the mode of drug administration (e.g., for oral administration, formulations in the form of tablets, pills or capsules) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One specific route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Compressed gases may be used to disperse a compound of this invention in aerosol form. Inert gases suitable for this purpose are nitrogen, carbon dioxide, etc.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts or solvates, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

If formulated as a fixed dose, such combination products employ the compounds of this invention within the dosage range described above and the other pharmaceutically active agent(s) within its approved dosage range. Compounds of the instant invention may alternatively be used sequentially with known pharmaceutically acceptable agent(s) when a combination formulation is inappropriate.

Utility

Compounds of the Invention have activity for PI3K-delta. Compounds of this invention have been tested using the assays described in the Biological Examples and have been determined to be inhibitors of PI3K-delta. Suitable in vitro assays for measuring PI3K delta activity and the inhibition thereof by compounds are known in the art. For further details of an in vitro assay for measuring PI3K delta see the Biological Examples herein. Cell-based assays for measurement of in vitro efficacy in treatment of cancer are known in the art. In addition, assays are described in the Biological Examples provided herein. Suitable in vivo models for cancer are known to those of ordinary skill in the art. For further details of in vivo models for prostate adenocarcinoma, glioblastoma, lung carcinoma, and melanoma, see the Biological Examples described herein. Following the examples disclosed herein, as well as that disclosed in the art, a person of ordinary skill in the art can determine the activity of a compound of this invention.

Compounds of Formula I are useful for treating diseases, including autoimmune disorders, inflammatory diseases, and cancers, which are listed below.

Cancers: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [neplrroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastorna multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma.

Autoimmune diseases: Hashimoto's thyroiditis, systemic lupus erythematosus (SLE), Goodpasture's syndrome, pemphigus, receptor autoimmune diseases, Basedow's disease (Graves' disease), myasthemia gravis, insulin resistant diseases, autoimmune hemolytic anemia, autoimmune thrombocytopenic purpura, autoimmune encephalomyelitis, rheumatism, rheumatoid arthritis, scleroderma, mixed connective tissue disease, polymyositis, pernicious anemia, idiopathic Addison's disease, some types of infertility, glomerulonephritis, bullous pemphigus, Sjogren's syndrome, some types of diabetes, adrenergic agent resistance, chronic active hepatitis, primary biliary cirrhosis, endocrine failure, vitiligo, angiitis, post-cardiac surgery syndrome, urticaria, atopic dermatiti and multiple sclerosis, autoimmune polyglandular disease (also known as autoimmune polyglandular syndrome), autoimmune alopecia; pernicious anemia; vitiligo; autoimmune hypopituatarism, and Guillain-Barre syndrome.

Inflammatory Diseases: asthma, allergic rhinitis, psoriasis, inflammatory arthritis, rheumatoid arthritis, psoriatic arthritis or osteoarthritis, irritable bowel syndrome, ulcerative colitis, Crohn's disease, respiratory allergies (asthma, hay fever, allergic rhinitis) or skin allergies, scleracierma, mycosis fungoides, acute inflammatory responses (such as acute respiratory distress syndrome and ishchemia/reperfusion injury), dermatomyositis, alopecia greata, chronic actinic dermatitis, eczema, Behcet's disease, Pustulosis palmoplanteris, Pyoderma gangrenum, Sezary's syndrome, atopic dermatitis, systemic sclerosis, and morphea.

Thus, in one embodiment, the invention provides a method of inhibiting PI3K delta comprising contacting the PI3K delta with an effective amount of a compound as disclosed herein.

In another embodiment, the invention provides a method of treating a PI3K delta modulated disease comprising administering to a mammal in need of such treatment a therapeutically effective amount of a compound as disclosed herein.

In another embodiment, the invention provides a method of treating cancer disease mediated by PI3K delta comprising administering to a mammal in need of such treatment a therapeutically effective amount of a compound as disclosed herein.

Compounds of the invention are also useful as inhibitors of PI3Kdelta in vivo for studying the in vivo role of PI3Kdelta in biological processes, including the diseases described herein. Accordingly, the invention also comprises a method of inhibiting PI3Kdelta in vivo comprising administering a compound or composition of the invention to a mammal.

General Synthesis

Compounds of this invention can be made by the synthetic procedures described below. The starting materials and reagents used in preparing these compounds are either available from commercial suppliers such as Aldrich Chemical Co. (Milwaukee, Wis.), or Bachem (Torrance, Calif.), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, $4^{th}$ Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure. The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure and over a temperature range from about −78° C. to about 150° C., more specifically from about 0° C. to about 125° C. and more specifically at about room (or ambient) temperature, e.g., about 20° C. Unless otherwise stated (as in the case of hydrogenation), all reactions are performed under an atmosphere of nitrogen.

Prodrugs can be prepared by techniques known to one skilled in the art. These techniques generally modify appropriate functional groups in a given compound. These modified functional groups regenerate original functional groups by routine manipulation or in vivo. Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

The compounds of the invention, or their pharmaceutically acceptable salts, may have asymmetric carbon atoms or quaternized nitrogen atoms in their structure. Compounds of the Invention that may be prepared through the syntheses described herein may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this invention.

Some of the compounds of the invention contain an active ketone —C(O)CF$_3$ and may exist in part or in whole as the —C(OH$_2$)CF$_3$ form. Regardless of whether the compound is drawn as the —C(O)CF$_3$ or —C(OH$_2$)CF$_3$ form, both are included within the scope of the Invention. Although an individual compound may be drawn as the —C(O)CF$_3$ form, one of ordinary skill in the art would understand that the compound may exist in part or in whole as the —C(OH$_2$)CF$_3$ form and that the ratio of the two forms may vary depending on the compound and the conditions in which it exists.

Some of the compounds of the invention may exist as tautomers. For example, where a ketone or aldehyde is present, the molecule may exist in the enol form; where an amide is present, the molecule may exist as the imidic acid; and where an enamine is present, the molecule may exist as an imine. All such tautomers are within the scope of the invention. Regardless of which structure or which terminology is used, each tautomer is included within the scope of the Invention. The present invention also includes N-oxide derivatives and protected derivatives of compounds of the Invention. For example, when compounds of the Invention contain an oxidizable nitrogen atom, the nitrogen atom can be converted to an N-oxide by methods well known in the art. When compounds of the Invention contain groups such as hydroxy, carboxy, thiol or any group containing a nitrogen atom(s), these groups can be protected with a suitable "protecting group" or "protective group". A comprehensive list of suitable protective groups can be found in T. W. Greene, *Protective Groups in Organic Synthesis*, John Wiley & Sons, Inc. 1991, the disclosure of which is incorporated herein by reference in its entirety. The protected derivatives of compounds of the Invention can be prepared by methods well known in the art.

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereoisomeric salts or complexes which may be separated, for example, by crystallization; via formation of diastereoisomeric derivatives which may be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents or by converting on enantiomer to the other by asymmetric transformation. For a mixture of enantiomers, enriched in a particular enantiomer, the major component enantiomer may be further enriched (with concomitant loss in yield) by recrystallization.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The chemistry for the preparation of the compounds of this invention is known to those skilled in the art. In fact, there may be more than one process to prepare the compounds of the invention. The following examples illustrate but do not limit the invention. All references cited herein are incorporated by reference in their entirety.

SYNTHETIC EXAMPLES

Example 1

N-(Cyclopropylmethyl)-9-methyl-6-[4-(2-oxo-2,3-dihydro-1H-benzimidazol-1-yl)piperidin-1-yl]-9H-purine-8-carboxamide (Compound 4)

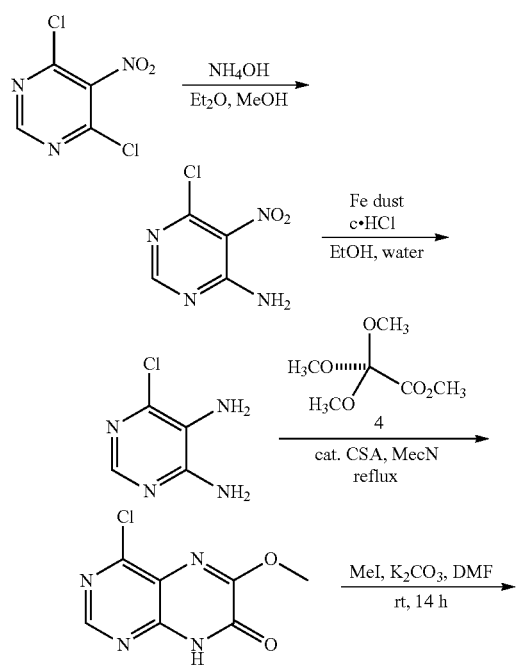

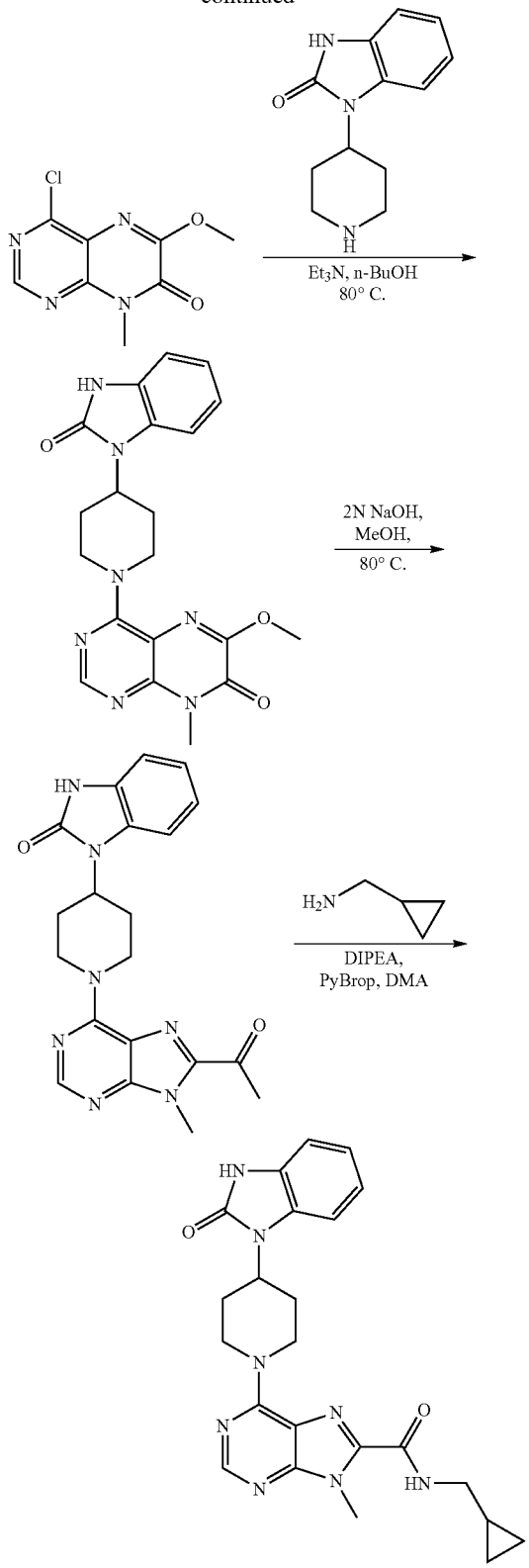

6-Chloro-5-nitropyrimidin-4-amine

A solution of 28% aqueous ammonium hydroxide (670 mL, 5.35 mol, 1.04 equiv) was added in a drop-wise fashion to a rapidly stirred solution of the 4,6-dichloro-5-nitropyrimidine solid (1000 g, 5.16 mol, 1.00 equiv) in diethyl ether (4000 mL) and methanol (670 mL). The addition was carried out over a period of 2 hours. Upon completion of addition, the resulting yellow solid was filtered off, washed with water and hexane, and dried under reduced pressure to give the title compound as a yellow solid (yield: 675 g). This crude solid was used in the next step without any further purification. $^1$H NMR (400 MHz, DMSO-$d_6$): δ 8.97 (s, 1H), 7.91 (broad s, 2H). MS (EI) for $C_4H_3ClN_4O_2$: 175 (MH$^+$).

6-Chloropyrimidine-4,5-diamine

Iron dust (1000 g, 17.9 mol) was added to a solution of the crude 6-chloro-5-nitropyrimidin-4-amine (500 g, 2.87 mol) in ethanol (5000 mL) and water (1000 mL). A catalytic amount of concentrated hydrochloric acid (10 mL) was slowly added to the reaction mixture over a period of 20 minutes. During the course of the addition the reaction temperature was observed to increase to 85° C. without external heating and the reaction mixture's color changed from yellow-brown to dark red. After the reaction mixture had cooled down to a temperature of 50° C., the slurry was filtered through a Celite pad, which was then washed with ethanol (3×250 mL). The resulting filtrate was concentrated under reduced pressure to give a yellow solid. This solid was then washed with hexane and dried under reduced pressure to give the title compound as a brown solid. (253 g, overall yield over two steps: 37.1% yield). $^1$H NMR (400 MHz, DMSO-$d_6$): δ 7.61 (s, 1H), 6.71 (broad s, 2H), 4.94 (broad s, 2H). MS (EI) for $C_4H_5ClN_4$: 145 (MH$^+$).

Methyl trimethoxyacetate

To a one-neck 1 L round bottom flask containing a Teflon stirrer bar was added dimethyl oxalate (100 g, 847 mmol) followed by phosphorus pentachloride (182 g, 872 mmol). A reflux condenser was attached to the flask and the mixture was then heated, with stirring, at 115° C. for approximately 18 hours. The mixture was initially difficult to stir as both compounds were solids. However, as the reaction mixture was heated up, the dimethyl oxalate gradually melted and the phosphorus pentachloride dissolved, resulting in a bright yellow homogeneous reaction mixture, which faded to a dull yellow color as the reaction progressed. After 18 hours, the reaction mixture was allowed to cool to 70° C. (external heating mantle) and was distilled through a short path distillation apparatus at reduced pressure (approximately 5-10 Torr). Two separate fractions were collected. The first fraction distilled over around 40° C. and was identified as phosphorus oxychloride. The second fraction was collected over ice (the receiving flask was resting in an ice bath) between 45-52° C. and was identified as the desired compound, methyl 2,2-dichloro-2-methoxyacetate, 95.4 g, 65%, as a clear, colorless liquid. (Note: It was not uncommon to have unreacted phosphorus pentachloride codistill with one or both fractions as a light yellow solid. This was best removed by cooling the distillate to 0° C. with an ice bath and then filtering the mixture through a medium porosity glass fitted funnel.) $^1$H NMR (400 MHz, DMSO-$d_6$): δ 3.95 (s, 3H), 3.83 (s, 3H). MS (EI) for $C_4H_6Cl_2O_3$: 174 (MH$^+$).

A 500 mL round bottom flask was charged with methyl 2,2-dichloro-2-methoxyacetate (50 g, 248.5 mmol, 1 equiv). This was cooled to 0° C. with an ice bath at which point anhydrous methanol (34.33 g, 745.7 mmol, 44 mL, 3 equiv) was added with stirring over the course of 5 minutes. The mixture was then immediately diluted with anhydrous diethyl ether (150 mL). While maintaining the reaction at 0° C. with an external ice bath, anhydrous pyridine (49.10 g, 621.4 mmol, 50.20 mL, 2.5 equiv) was added via a pressure equalizing addition funnel over 1 hour. The reaction mixture was then rapidly stirred for an additional 30 minutes at 0° C. The stirring was then stopped and the mixture allowed to stand at room temperature for 72 hours where upon long white needles were formed in solution. The resulting mixture was filtered through a medium porosity glass frit, and the recovered solids were washed with diethyl ether. The filtrate was then concentrated by rotary evaporation under reduced pressure to yield a pale yellow oil. This oil was subsequently cooled to 0° C. with an ice bath. The oil was then rapidly stirred, and pyrrolidine (25 mL) was added in a drop wise fashion, by means of a pressure equalizing addition funnel, over a period of 20 minutes. The solution rapidly turned yellowish-orange in color. Upon completion of addition of the pyrrolidine, the mixture was stirred for an additional 30 minutes at 0° C., and then subjected to a reduced pressure distillation collecting unreacted pyrrolidine and ethanol at 40 Torr and 28° C. followed by the desired material, methyl 2,2,2-trimethoxyacetate (44 g, 80% yield) at 2 Torr and 58° C., as a colorless liquid.
$^1$H NMR (400 MHz, DMSO-$d_6$): δ 3.80 (s, 3H), 3.30 (s, 9H). MS (EI) for $C_6H_{12}O_5$: 145 (MH$^+$).

4-Chloro-6-methoxypteridin-7(8H)-one

To a 50 mL round bottom flask at room temperature with a Teflon stir bar was added 6-chloropyrimidine-4,5-diamine (25 g, 172.9 mmol, 1 equiv), and anhydrous acetonitrile (300 mL). Ethyl 2,2,2-triethoxyacetate (36.87 g, 224.8 mmol, 36.9 mL, 1.3 equiv) followed by a catalytic quantity of 10-camphorsulfonic acid (3 g, 12.97 mmol, 0.075 equiv) were then added. The stirred reaction mixture was then heated to reflux for 16 hours. The reaction mixture was then cooled to room temperature and concentrated under reduced pressure to approximately 100 mL on a rotary evaporator and poured into 500 mL of vigorously stirring ice water. The resulting slurry was rapidly stirred for 20 minutes, and the resulting tan solid was then filtered through a medium porosity glass fritted funnel and was dried on the vacuum line to give the title compound as a brown solid (25.7 g, 76% yield). $^1$H NMR (400 MHz, DMSO-$d_6$): δ 13.32 (broad s, 1H), 8.62 (s, 1H), 3.99 (s, 3H). MS (EI) for $C_7H_5ClN_4O_2$: 213 (MH$^+$).

4-Chloro-6-methoxy-8-methylpteridin-7(8H)-one

To a 100 mL round bottomed flask was added 4-chloro-6-methoxypteridin-7(8H)-one (2.09 g, 9.8 mmol, 1.0 equiv) and anhydrous N,N-dimethylformamide (10 mL). Anhydrous potassium carbonate (6.8 g, 49 mmol, 5 equiv) was added in one portion to the reaction flask followed by the drop wise addition of iodomethane (2.09 g, 15 mmol, 1.5 equiv) over the course of 1 minute. The reaction was then vigorously stirred at room temperature. LC/MS analysis at 14 hours indicated the reaction was complete. The reaction mixture was then passed through a glass-sintered funnel and the recovered solids were washed with N,N-dimethylformamide (1×10 mL) and dichloromethane (3×15 mL) to give a dark brown filtrate. The solvent was evaporated at reduced pressure and the resulting powder was redissolved in dichloromethane (200 mL) and washed with saturated sodium chloride solution (200 mL). The organic layer was dried with anhydrous sodium sulfate, filtered, and concentrated under reduced pressure to yield 1.72 g (pale brown powder, 77% yield) of 4-chloro-6-methoxy-8-methylpteridin-7(8H)-one as the desired material. $^1$H NMR (400 MHz, DMSO-$d_6$): δ 8.76 (s, 1H), 4.04 (s, 3H), 3.56 (s, 3H). MS (EI) for $C_8H_7ClN_4O_2$: 227 (MH$^+$).

8-Methyl-6-(methyloxy)-4-[4-(2-oxo-2,3-dihydro-1H-benzimidazol-1-yl)piperidin-1-yl]pteridin-7(8H)-one 4-Chloro-6-methoxy-8-methylpteridin-7(8H)-one (4.00 g, 17.7 mmol, 1 equiv) and 1-piperidin-4-yl-1,3-dihydro-2H-benzimidazol-2-one (3.83 g, 17.7 mmol, 1 equiv) were suspended in anhydrous n-butanol (40 mL) in a 250 mL one-necked round-bottomed flask. Triethylamine (35.30 mmol, 3.57 g, 4.92 mL, 2 equiv) was added to the flask, and the stirred reaction mixture was heated to 80° C. The reaction was monitored by LC/MS and was complete after 6 hours. The resulting tan colored suspension was cooled to room temperature and filtered. The collected solid was washed with n-butanol (10 mL) and anhydrous ether (25 mL). The solid was air-dried to give the desired material, 6-methoxy-8-methyl-4-[4-(2-oxo-2,3-dihydro-1H-benzimidazol-1-yl)piperidin-1-yl]pteridin-7(8H)-one as a pale yellow colored solid (5.69 g, 79% yield.). $^1$H NMR (400 MHz, DMSO-$d_6$): δ 10.83 (broad s, 1H), 8.33 (s, 1H), 7.13 (m, 1H), 6.93 (m, 3H), 5.30 (d, 1H), 4.54 (1H), 3.88 (s, 3H), 3.55 (s, 3H), 3.20 (t, 2H), 2.42 (dq, 2H), 1.82 (d, 2H). MS (EI) for $C_{20}H_{21}N_7O_3$: 408 (MH$^+$).

9-Methyl-6-[4-(2-oxo-2,3-dihydro-1H-benzimidazol-1-yl)piperidin-1-yl]-9H-purine-8-carboxylic acid Methanol (25 mL) and aqueous 2M sodium hydroxide solution (25.4 mmol, 12.7 mL, 10 equiv) were added to 8-methyl-6-(methyloxy)-4-[4-(2-oxo-2,3-dihydro-1H-benzimidazol-1-yl)piperidin-1-yl]pteridin-7(8H)-one (1.00 g, 2.54 mmol, 1 equiv) in a 100 mL single-necked round bottomed flask fitted with a Teflon stirrer. The resulting stirred slurry was then heated to 80° C. and the reaction was monitored by LC/MS. The reaction mixture gradually became clear and homogenous. LC/MS indicated that the reaction was complete after 12 hours. The new product peak was characterized by a 394 (MH$^+$) molecular ion and a 350 (MH$^+$–44 (—CO$_2$) decarboxylation fragmentation peak. The reaction mixture was then allowed to cool to room temperature. The stirred reaction mixture was then acidified to pH 2 by the gradual addition of aqueous 3M hydrochloric acid, resulting in the precipitation of a white solid. The resulting slurry was then stirred for 30 minutes and then filtered off. The solid was washed with cold water (2×10 mL) and dried at reduced pressure to give 5.89 g (82% yield) of the title compound as a white solid. $^1$H NMR (400 MHz, DMSO-$d_6$): δ 10.89 (broad s, 1H), 8.33 (s, 1H), 7.17 (dd, 1H), 6.91 (m, 3H), 5.40 (v broad s, 2H), 4.56 (t, 1H), 3.22 (broad s, 2H), 2.33 (d, 2H), 1.85 (d, 2H). MS (EI) for $C_{18}H_{17}N_7O_3$: 394 (MH$^+$), 350 (MH$^{+-}$44 (—CO$_2$).

N-(cyclopropylmethyl)-9-methyl-6-[4-(2-oxo-2,3-dihydro-1H-benzimidazol-1-yl)piperidin-1-yl]-9H-purine-8-carboxamide: (Compound 4)

A 50 mL round bottomed flask fitted with a Teflon stirrer was charged 9-methyl-6-[4-(2-oxo-2,3-dihydro-1H-benzimidazol-1-yl)piperidin-1-yl]-9H-purine-8-carboxylic acid (0.715 g, 1.817 mmol, 1 equiv) and anhydrous N,N-dimethylacetamide (8 mL) and stirred. Diisoproplyethylamine (1.17 g, 9.08 mmol, 1.58 mL, 5 equiv) and cycicoproplymethylamine (0.258 g, 3.63 mmol, 0.31 mL, 2 equiv) were then added, and the reaction mixture quickly became homogeneous. The reaction mixture was stirred for 2 minutes at room temperature. Bromo-tris-pyrrolidino phosphonium-hexafluoro-phosphate (PyBrop, 1.27 g, 2.72 mmol, 1.5 equiv) was added in one lot and the reaction mixture was allowed to stir at room temperature. The progress of the reaction was monitored by LC/MS. After 4 hours the reaction was quenched by the addition of methanol (4 mL) and water (1 mL). The mixture was subsequently filtered through a 0.2 μm, 17 mm nylon syringe filter. The resulting solid free solution was purified by preparative HPLC (reverse-phase, acetonitrile/water with 0.01% ammonium acetate), followed by concentration in vacuo and lyophilization to afford the desired material, N-(cyclopropylmethyl)-9-methyl-6-[4-(2-oxo-2,3-dihydro-1H-benzimidazol-1-yl)piperidin-1-yl]-9H-purine-8-carboxamide as a white solid.

Alternatively, the reaction mixture was transferred to a separatory funnel using ethyl acetate (100 mL) and washed with 0.5M citric acid (100 mL. The aqueous layer was further washed with ethyl acetate (3×100 mL). The combined ethyl acetate washes were then washed with 1M potassium carbonate solution (100 mL), water (3×100 mL) and saturated sodium chloride solution (100 mL). The organic solution was then dried over anhydrous sodium sulfate, filtered and evaporated under reduced pressure to give a clear viscous oil The resulting oil was then triturated with methanol (25 mL) to give a white solid which was stirred for 30 minutes at room temperature, filtered, washed with methanol (5 mL) and dried under reduced pressure to give N-(cyclopropylmethyl)-9-methyl-6-[4-(2-oxo-2,3-dihydro-1H-benzimidazol-1-yl)piperidin-1-yl]-9H-purine-8-carboxamide as a white solid. $^1$H NMR (400 MHz, DMSO-$d_6$): δ 10.63 (broad s, 1H), 8.65 (t, 3H), 8.09 (s, 1H), 6.94 (m, 1H), 6.70 (m, 3H), 5.40 (v. broad s, 2H), 4.35 (m, 1H), 3.76 (s, 3H), 3.02 (m, 2H), 2.93 (t, 2H), 2.11 (m, 2H), 1.63 (d, 2H), 0.84 (m, 1H), 0.18 (m, 2H), 0.02 (m, 2H). MS (EI) for $C_{22}H_{24}N_8O_2$: 433 (MH$^+$).

Example 2

N-(Cyclopropylmethyl)-9-methyl-6-(2-oxo-1,2-dihydro-1'H-spiro[indole-3,4'-piperidin]-1'-yl)-9H-purine-8-carboxamide (Compound 6)

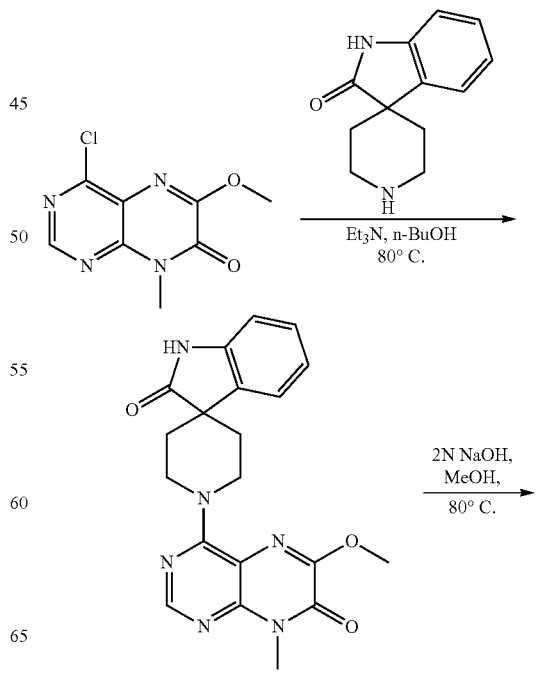

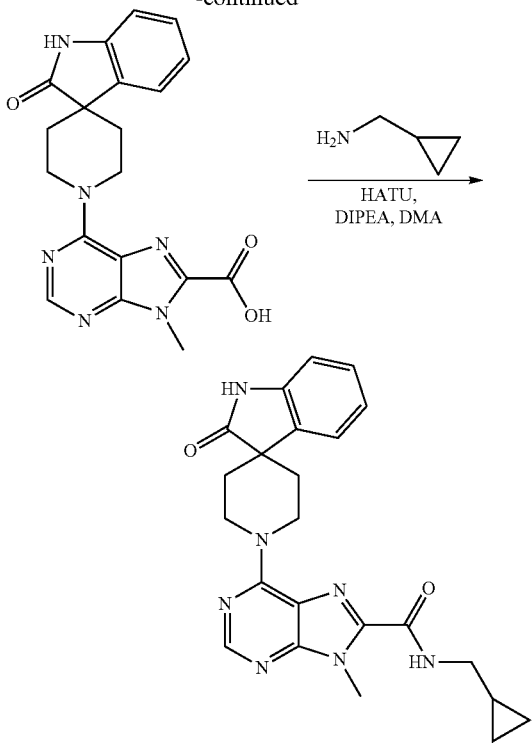

6-Methoxy-8-methyl-4-(2-oxospiro[indoline-3,4'-piperidine]-1'-yl)pteridin-7(8H)-one Into a 100 mL round bottomed flask were placed 4-Chloro-6-methoxy-8-methylpteridin-7(8H)-one (2.00 g, 8.83 mmol, 1 equiv) and spiro[indoline-3,4'-piperidin]-2-one (2.14 g, 10.6 mmol, 1.2 equiv). Anhydrous n-butanol (20 mL) and triethylamine (2.46 mL, 2 equiv) were added and reaction mixture was heated to 80° C. with stirring. The reaction was complete as monitored by LC/MS after 5 hours. The solvent was stripped by rotary evaporation, and the residue rinsed with water (5 mL) to yield a tan precipitate, which was collected by vacuum filtration and rinsed with water to afford the desired product which was used directly without any further purification. $^1$H NMR (400 MHz, DMSO-$d_6$): δ 10.49 (s, 1H), 8.39 (s, 1H), 7.49 (d, 1H), 7.20 (d, 1H), 6.97 (t, 1H), 6.87 (t, 1H), 4.53-4.45 (m, 4H), 3.80 (s, 3H), 3.55 (s, 3H), 1.93-1.80 (m, 4H). MS (EI) for $C_{20}H_{20}N_6O_3$: 393 (MH$^+$).

9-Methyl-6-(2-oxo-1,2-dihydro-1'H-spiro[indole-3,4'-piperidin]-1'-yl)-9H-purine-8-carboxylic acid The 6-methoxy-8-methyl-4-(2-oxospiro[indoline-3,4'-piperidine]-1'-yl)pteridin-7(8H)-one was slurried in methanol (45 mL). An aqueous solution of sodium hydroxide (2N, 45 mL) was added and the reaction mixture heated to 80° C. with stirring. LC/MS indicated that the reaction was complete after 12 hours. The new product peak was characterized by a 379 (MH$^+$) molecular ion and a 335 (MH$^+$−44 (—CO$_2$)) decarboxylation fragmentation peak. The reaction mixture was then allowed to cool to room temperature. The methanol was removed by rotary evaporation and the remaining solution acidified with 4N aqueous hydrochloric acid to pH 3. The resulting precipitate was filtered, washed with cold water and dried under vacuum to afford the desired product (1.4 g, 41% yield after 2 steps). $^1$H NMR (400 MHz, DMSO-$d_6$): δ 10.50 (s, 1H), 8.37 (s, 1H), 7.36 (d, 1H), 7.15 (t, 1H), 6.92 (t, 1H), 6.87 (d, 1H), 5.07-4.97 (m, 1H), 4.75-4.65 (m, 1H), 4.40-4.17 (m, 2H), 3.96 (s, 3H), 1.83-1.73 (m, 4H). MS (EI) for $C_{19}H_{18}N_6O_3$: 379 (MH$^+$), 335 (MH$^+$−44 (—CO$_2$)).

N-(cyclopropylmethyl)-9-methyl-6-(2-oxo-1,2-dihydro-1'H-spiro[indole-3,4'-piperidin]-1'-yl)-9H-purine-8-carboxamide: (Compound 6)

Into 5 mL of anhydrous DMA in a 25 mL round bottomed flask were dissolved 9-methyl-6-(2-oxo-1,2-dihydro-1'H-spiro[indole-3,4'-piperidin]-1'-yl)-9H-purine-8-carboxylic acid (800 mg, 2.11 mmol, 1.0 equiv), cyclopropylmethanamine (217 µL, 2.54 mmol, 1.2 equiv), diisopropylethylamine (1846 µL, 10.57 mmol, 5 equiv), and 2-(7-aza-1H-benzotriazole-1-yl)-1,1,3,3-tetramethyluronium hexafluorophosphate (HATU, 965 mg, 2.54 mmol, 1.2 equiv). The reaction was stirred for four hours then purified directly by preparative reverse-phase HPLC (acetonitrile/water with 1% formic acid), followed by concentration in vacuo and lyophilization to afford the desired material (501 mg, 55% yield) as a white powder. $^1$H NMR (400 MHz, DMSO-$d_6$): δ 10.26 (s, 1H), 8.63 (t, 1H), 8.18 (s, 1H), 7.27 (d, 1H), 6.97 (t, 1H), 6.73 (t, 1H), 6.65 (d, 1H), 5.0-4.60 (br, 1H), 4.55-4.35 (br, 1H), 4.30-4.00 (br 2H), 3.75 (s, 3H), 2.95 (t, 2H), 1.70-1.55 (m, 4H), 0.90-0.80 (m, 1H), 0.18-0.13 (M, 2h), 0.08-0.00 (m, 2H). MS (EI) for $C_{23}H_{25}N_7O_2$: 432 (MH$^+$).

Example 3

N,N,9-Trimethyl-6-(4-oxo-1-phenyl-1,3,8-triazaspiro[4.5]dec-8-yl)-9H-purine-8-carboxamide (Compound 7)

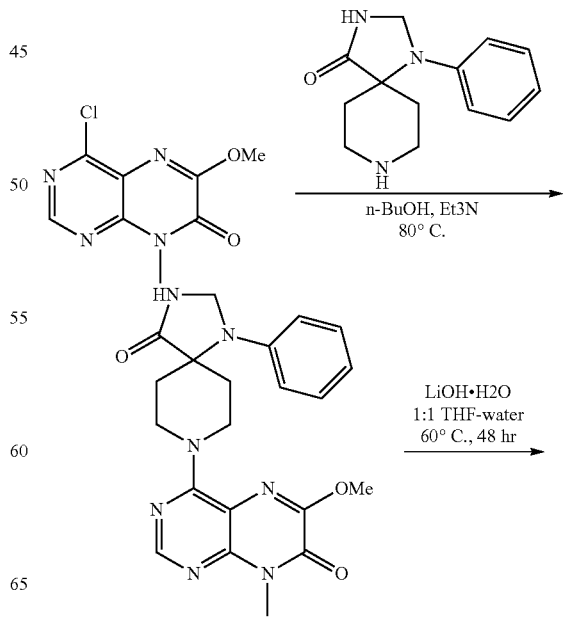

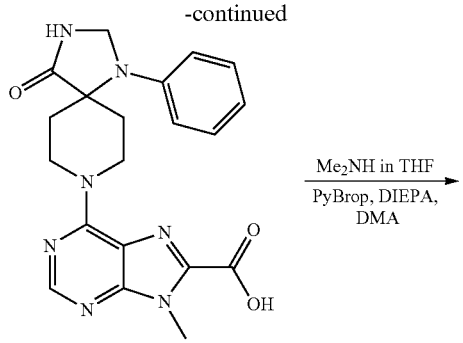

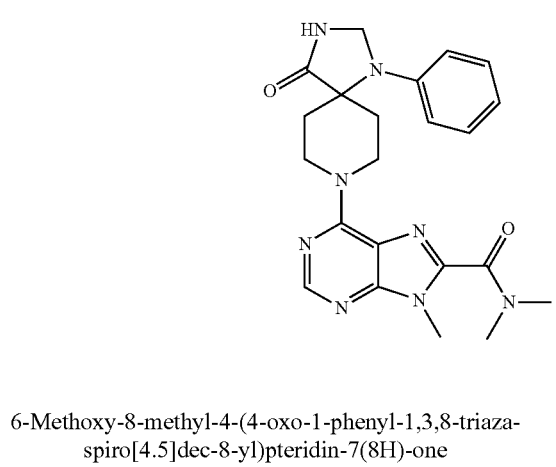

6-Methoxy-8-methyl-4-(4-oxo-1-phenyl-1,3,8-triaza-spiro[4.5]dec-8-yl)pteridin-7(8H)-one 6-methoxy-8-methyl-4-(4-oxo-1-phenyl-1,3,8-triazaspiro[4.5]dec-8-yl)pteridin-7(8H)-one was prepared in an analogous fashion to 8-methyl-6-(methyloxy)-4-[4-(2-oxo-2,3-dihydro-1H-benzimidazol-1-yl)piperidin-1-yl]pteridin-7(8H)-one, in which the 1-piperidin-4-yl-1,3-dihydro-2H-benzimidazol-2-one was replaced with commercially available 1-phenyl-1,3,8-triazaspiro[4.5]decan-4-one. $^1$H NMR (400 MHz, DMSO-d$_6$): δ 8.82 (s, 1H), 8.37 (s, 1H), 7.08 (t, 2H), 6.66 (t, 1H), 6.61 (d, 1H), 4.99 (d, 2H), 4.60 (s, 2H), 3.81 (s, 3H), 3.57 (s, 3H), 2.63 (m, 2H), 1.76 (d, 2H); MS (EI) for C$_{21}$H$_{23}$N$_7$O$_3$; 422 (MH$^+$).

9-Methyl-6-(4-oxo-1-phenyl-1,3,8-triazaspiro[4.5]dec-8-yl)-9H-purine-8-carboxylic acid 6-Methoxy-8-methyl-4-(4-oxo-1-phenyl-1,3,8-triazaspiro[4.5]dec-8-yl)pteridin-7(8H)-one (1 g, 2.37 mmol) was treated with lithium hydroxide monohydrate (0.281 g, 4.74 mmol) tetrahydrofuran (2.5 mL) and water (2.5 mL). This mixture was stirred at 60° C. for 48 hours. The reaction mixture was cool to room temperature acidified to pH 4 with 1 M hydrochloric acid (8 mL) and evaporated under reduced pressure. The resulting crude material was then used in the next step without any further purification. MS (EI) for C$_{20}$H$_{21}$N$_7$O$_3$: 408 (MH$^+$), 364 (MH$^+$−44 (—CO$_2$)).

N,N,9-trimethyl-6-(4-oxo-1-phenyl-1,3,8-triazaspiro[4.5]dec-8-yl)-9H-purine-8-carboxamide N,N,9-Trimethyl-6-(4-oxo-1-phenyl-1,3,8-triazaspiro[4.5]dec-8-yl)-9H-purine-8-carboxamide was synthesized in an analogous fashion to N-(cyclopropylmethyl)-9-methyl-6-[4-(2-oxo-2,3-dihydro-1H-benzimidazol-1-yl)piperidin-1-yl]-9H-purine-8-carboxamide by coupling 9-methyl-6-[4-(2-oxo-2,3-dihydro-1H-benzimidazol-1-yl]piperidin-1-yl]-9H-purine-8-carboxylic acid (0.09 g, 0.21 mmol) and dimethyl amine (2 M in tetrahydrofuran) to give 0.046 g of N,N,9-trimethyl-6-(4-oxo-1-phenyl-1,3,8-triazaspiro[4.5]dec-8-yl)-9H-purine-8-carboxamide as a white solid. $^1$H NMR (400 MHz, DMSO-d$_6$): δ 8.81 (s, 1H), 8.23 (s, 1H), 7.07 (dd, 2H), 6.63 (m, 3H), 5.06 (d, 2H), 4.59 (s, 2H), 3.73 (dd, 2H), 3.55 (s, 3H), 3.33 (m, 2H), 3.17 (s, 6H), 2.61 (td, 2H), 1.71 (d, 2H). MS (EI) for C$_{26}$H$_{28}$N$_8$O$_2$: 435 (MH$^+$).

Example 4

9-Cyclopropyl-N-(cyclopropylmethyl)-6-[4-(2-oxo-2,3-dihydro-1H-benzimidazol-1-yl)piperidin-1-yl]-9H-purine-8-carboxamide (Compound 171)

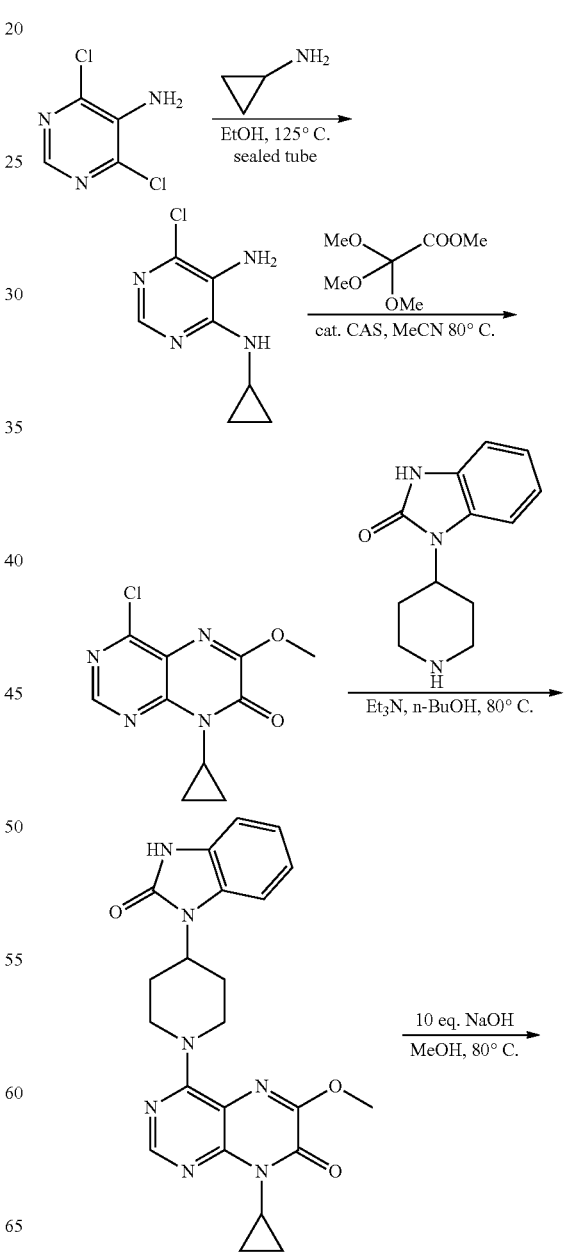

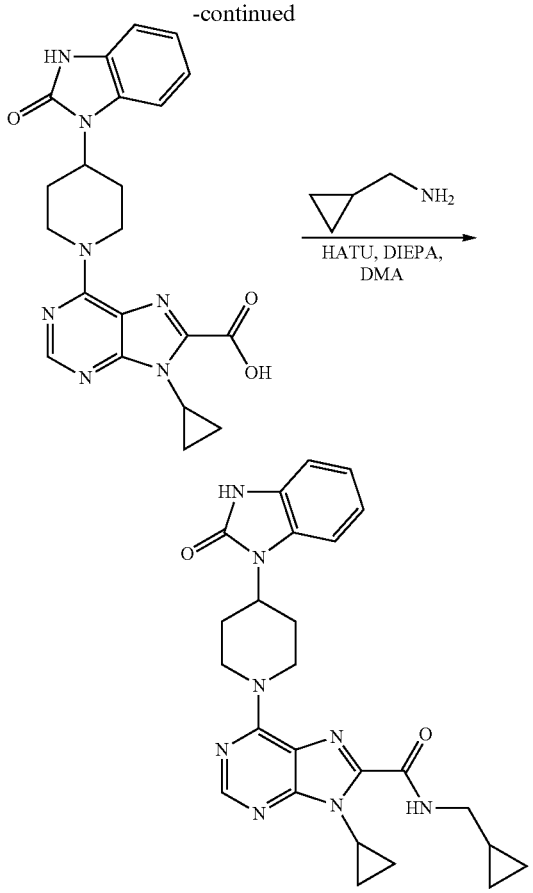

6-Chloro-N⁴-cyclopropylpyrimidine-4,5-diamine

A stirred solution of 4,6-dichloropyrimidin-5-amine (10 g, 60.9 mmol) and cyclopropylamine (10.44 g, 182.93 mmol, 12.7 mL) in absolute ethanol (100 mL) wee heated at 125° C. in a sealed tube for 4 days. The reaction mixture was then concentrated under reduced pressure to give a yellow solid which was triturated with cold water (200 mL). The resulting slurry was stirred for one hour at room temperature and then filtered. The isolated solid was washed with water (2×25 mL) and dried under reduced pressure to give 11.32 g of the title compound as a pale yellow solid, which was used without any further purification.

$^1$H NMR (400 MHz, DMSO-$d_6$): δ 7.76 (d, 1H), 6.94 (d, 1H), 4.97 (s, 2H), 3.34 (s, 3H), 2.81 (m, 1H), 0.70 (m, 2H), 0.46 (m, 2H). MS (EI) for $C_7H_9ClN_4$: 185 (MH⁺).

4-Chloro-8-cyclopropyl-6-methoxypteridin-7(8H)-one 4-chloro-8-cyclopropyl-6-methoxypteridin-7(8H)-one was prepared in the same manner as 4-chloro-8-methyl-6-methoxypteridin-7(8H)-one. The reaction of 6-Chloro-N⁴-cyclopropyl-pyrimidine-4,5-diamine (3.00 g, 16.2 mmol), methyl 2,2,2-trimethocyacetate (3.73 g, 22.7 mmol), 1-camphorsulfonic acid (0.754 g, 3.25 mmol) in acetonitrile (30 mL) at 80° C. for 16 hours gave 3.045 g of 4-chloro-8-cyclopropyl-6-methoxypteridin-7(8H)-one as a tan colored solid. $^1$H NMR (400 MHz, DMSO-$d_6$): δ 8.75 (s, 1H), 4.01 (s, 3H), 2.95 (m, 1H), 1.16 (m, 2H), 0.86 (m, 2H). MS (EI) $C_{10}H_9ClN_4O_2$: 253 (MH⁺).

8-Cyclopropyl-6-methoxy-4-[4-(2-oxo-2,3-dihydro-1H-benzimidazol-1-yl)piperidin-1-yl]pteridin-7(8H)-one 8-Cyclopropyl-6-methoxy-4-[4-(2-oxo-2,3-dihydro-1H-benzimidazol-1-yl)piperidin-1-yl]pteridin-7(8H)-one was prepared in the same manner as 8-methyl-6-methoxy-4-[4-(2-oxo-2,3-dihydro-1H-benzimidazol-1-yl)piperidin-1-yl]pteridin-7(8H)-one. The reaction of 4-chloro-8-cyclopropyl-6-methoxypteridin-7(8H)-one (0.59 g, 2.33 mmol), 1-piperidin-4-yl-1,3-dihydro-2H-benzimidazol-2-one (0.507 g, 2.33 mmol, triethylamine (0.708 g, 7.99 mmol, 0.98 mL). anhydrous n-butanol (8 mL) at 80° C. for 16 hours gave rise to 0.856 g of 8-cyclopropyl-6-methoxy-4-[4-(2-oxo-2,3-dihydro-1H-benzimidazol-1-yl)piperidin-1-yl]pteridin-7 (8H)-one as a light brown solid, which was used without any further purification.

$^1$H NMR (400 MHz, DMSO-$d_6$): δ 10.85 (s, 1H), 8.36 (s, 1H), 7.15 (m, 1H), 6.95 (m, 3H), 5.27 (d, 2H), 4.53 (m, 1H), 3.86 (s, 3H), 3.38 (m, 1H), 3.19 (t, 2H), 2.43 (m, 2H), 1.82 (d, 2H), 1.15 (m, 2H), 0.84 (m, 2H). MS (EI) for $C_{22}H_{23}N_7O_3$: 434 (MH⁺).

9-Cydopropyl-6-[4-(2-oxo-2,3-dihydro-1H-benzimidazol-1-yl)piperidin-1-yl]-9H-purine-8-carboxylic acid 9-Cyclopropyl-6-[4-(2-oxo-2,3-dihydro-1H-benzimidazol-1-yl)piperidin-1-yl]-9H-purine-8-carboxylic acid was prepared in the same manner as 9-methyl-6-[4-(2-oxo-2,3-dihydro-1H-benzimidazol-1-yl)piperidin-1-yl]-9H-purine-8-carboxylic acid. The 8-cyclopropyl-6-methoxy-4-[4-(2-oxo-2,3-dihydro-1H-benzimidazol-1-yl)piperidin-1-yl]pteridin-7(8H)-one (0.836 g, 1.93 mmol) was treated with 2M sodium hydroxide (10 mL, 20 mmol) in methanol at 80° C. for 18 hours gave 0.789 of 9-cyclopropyl-6-[4-(2-oxo-2,3-dihydro-1H-benzimidazol-1-yl)piperidin-1-yl]-9H-purine-8-carboxylic acid as an off-white solid. $^1$H NMR (400 MHz, DMSO-$d_6$): δ 11.20 (br s, 1H), 8.07 (s, 1H), 6.93 (m, 1H), 6.71 (m, 3H), 5.19 (broad s, 2H), 4.27 (m, 1H), 3.40 (m, 2H), 3.19 (t, 2H), 2.43 (m, 2H), 1.82 (d, 2H), 1.15 (m, 2H), 0.84 (m, 2H). MS (EI) for $C_{21}H_{21}N_7O_4$: 420 (MH⁺).

9-Cyclopropyl-N-(cyclopropylmethyl)-6-[4-(2-oxo-2,3-dihydro-1H-benzimidazol-1-yl)piperidin-1-yl]-9H-purine-8-carboxamide (Compound 231)

9-Cyclopropyl-N-(cyclopropylmethyl)-6-[4-(2-oxo-2,3-dihydro-1H-benzimidazol-1-yl)piperidin-1-yl]-9H-purine-8-carboxamide was prepared in the same manner as 9-methyl-N-(cyclopropylmethyl)-6-[4-(2-oxo-2,3-dihydro-1H-benzimidazol-1-yl)piperidin-1-yl]-9H-purine-8-carboxamide. The 9-cyclopropyl-6-[4-(2-oxo-2,3-dihydro-1H-benzimidazol-1-yl)piperidin-1-yl]-9H-purine-8-carboxylic acid (0.09 g, 0.21 mmol) was treated with cyclopropylamine (0.305 g, 0.429 g mmol, 0.037 mL), HATU (0.163 g, 0.429 mmol), diisopropylethylamine (0.110 g, 0.858 mmol, 0.149 mL) and DMA (8 mL) at room temperature for 18 hours. Purification by preparative reverse phase HPLC (eluting with 0.01% aqueous ammonium acetate and acetonitrile) yielded 0.057 g of 9-cyclopropyl-N-(cyclopropylmethyl)-6-[4-(2-oxo-2,3-dihydro-1H-benzimidazol-1-yl)piperidin-1-yl]-9H-purine-8-carboxamide as a white solid. $^1$H NMR (400 MHz, DMSO-$d_6$): δ 10.50 (broad s, 1H), 8.63 (t, 1H), 8.07 (s, 1H), 6.98 (m, 1H), 6.6.716 (m, 3H), 5.11 (broad s, 2H), 4.30 (m, 1H), 3.38 (m, 1H), 3.13 (dd, 1H), 2.93 (t,4H), 2.07 (t, 2H), 1.63 (m, 2H), 0.83 (m, 4H), 0.18 (m, 2H), 0.02 (m, 2H). MS (EI) for $C_{25}H_{28}N_8O_2$: 473 (MH⁺).

Example 5

9-Methyl-6-[4-(2-oxo-2,3-dihydro-1H-imidazo[4,5-b]pyridin-1-yl)piperidin-1-yl]-N-(2,2,2-trifluoroethyl)-9H-purine-8-carboxamide (Compound 319)

i)

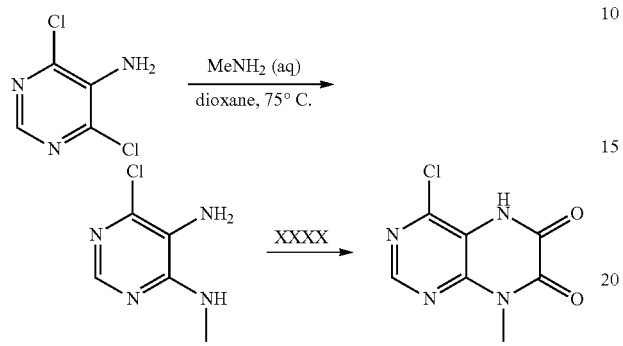

ii)

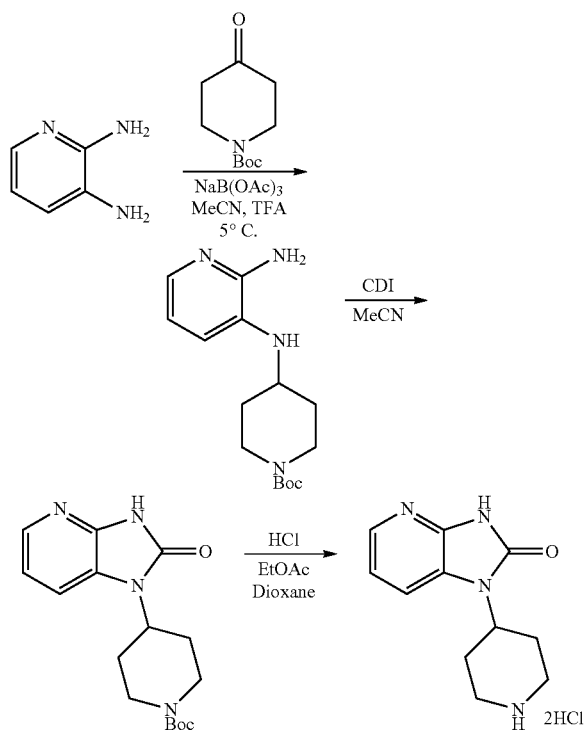

iii)

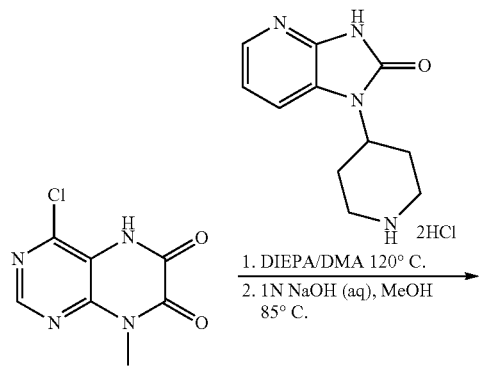

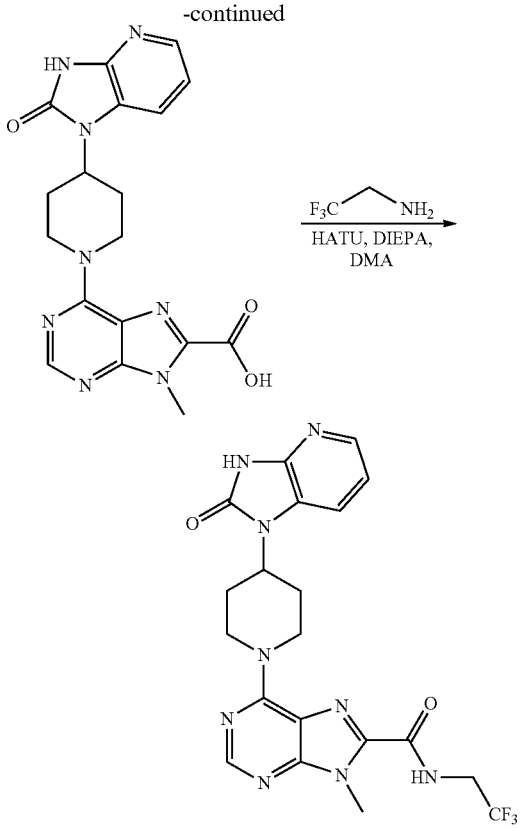

6-Chloro-$N^4$-methylpyrimidine-4,5-diamine

A 50 mL 3-necked flask fitted with a thermometer was charged with 1,4-dioxane (20 mL) and 4,5-dichloropyrimidine-5-amine (5.00 g, 30.5 mmol). The reaction mixture was then stirred for 30 minutes at room temperature to ensure complete dissolution of the 4,5-dichloropyrimidine-5-amine, after which a solution of methylamine in water (40% by weight, 120 mmol, 9.3 mL) was added over a period of 30 minutes by means of a pressure-equalized dropping funnel. Upon completion of addition, the dropping funnel was replaced with a reflux condenser. The stirred reaction mixture was then heated to 75° C. over a period of 40 minutes, and the progress was monitored by LCMS. The reaction was complete after 16 hours. The resulting mixture was then cooled to 50° C. and poured into 120 mL of ice and water (approximately 1:1 by volume), which resulted in the rapid precipitation of a solid. The resulting suspension was then for a period of 2 hours. The precipitated solids were collected by vacuum filtration, washed with ice-cold water (20 mL) and dried on the filter to give 4.76 g (98.4% yield) of 6-chloro-$N^4$-methylpyrimidine-4,5-diamine as a light yellow solid. This material was submitted to the next step without further purification. $^1$H-NMR (400 MHz, DMSO-$d_6$): δ 7.73 (s, 1H), 6.87 (d, 1H), 4.94 (broad s, 2H), 2.86 (d, 3H). MS (EI) for $C_5H_7ClN_4$: 159 (MH$^+$).

4-Chloro-6-hydroxy-8-methylpteridin-7(8H)-one

A solution of 6-Chloro-$N^4$-methylpyrimidine-4,5-diamine (4.00 g, 25.2 mmol) in anhydrous pyridine (40 mL) was cooled with stirring to 0° C. in an ice-water bath. A solution of ethyl 2-chloro-2-oxoacetate (4.13 g, 30.3 mmol, 1.2 equiv, 3.4 mL) in anhydrous dichloromethane (40 mL) was subsequently added to the reaction mixture over a period of 2 hours, and the temperature was maintained below 10° C. Upon completion of addition, the reaction mixture was allowed to warm to room temperature and stirred for an additional 1 hour, at which time analysis of the reaction mixture by LCMS indicated product in addition to unconsumed 6-chloro-N4-methylpyrimidine-4,5-diamine. Additional ethyl 2-chloro-2-oxoacetate (1.21 g, 8.83 mmol, 987 μL, 0.35 equiv) was added neat over 15 minutes, at room temperature. Upon completion of this addition and a further hour of stirring, analysis by LCMS indicated the complete consumption of 6-chloro-N4-methylpyrimidine-4,5-diamine, formation of the acylated product (m/e 259 (MH+), and partial ring closure of this product to the desired 4-chloro-6-hydroxy-8-methylpteridin-7(8H)-one (m/e 212 (MH+)). The reaction mixture was then stirred at room temperature for 16 hours and resulted in 4-chloro-6-hydroxy-8-methylpteridin-7(8H)-one as the sole product. The reaction mixture was diluted with dichloromethane (20 mL) and transferred into a separatory funnel. The resulting slurry was acidified with cold 3M hydrochloric acid to pH 1 and extracted with dichloromethane (5×20 mL). The combined dichloromethane solutions were then concentrated under reduced pressure to give a white solid (product and pyridine hydrochloride), which was triturated with cold water (25 mL). The resulting slurry was stirred at room temperature for 2 hours and filtered to give a white solid which was dried under reduced pressure to give 4.63 g of 4-chloro-6-hydroxy-8-methylpteridin-7(8H)-one as the desired product, which was used in the next step without any further purification. $^1$H NMR (400 MHz, DMSO-d$_6$): δ 12.06 (s, 1H), 8.57 (s, 1H), 3.49 (s, 3H). MS (EI) for $C_7H_5ClN_4O_2$: 213 (MH$^+$).

tert-Butyl 4-[(2-aminopyridin-3-yl)amino]piperidine-1-carboxylate

A 50 mL 3-necked round bottom flask fitted with a thermometer and an overhead stirrer was charged with tert-butyl 4-oxopiperidine-1-carboxylate (3.00 g, 15.1 mmol) and acetonitrile (25 mL, HPLC grade). The reaction mixture was stirred at room temperature for 10 minutes to ensure complete dissolution of all solid material. Pyridine-2,3-diamine (1.50 g, 13.7 mmol) was added, the slurry was stirred for an additional 30 minutes, and resulted in the formation of a dark brown solution. The reaction mixture was cooled to 5° C. and trifluoroacetic acid (2 mL) was added over a period of 20 minutes. During the course of the addition, fuming was observed, accompanied by a slight temperature rise to 10-15° C. The reaction mixture was stirred for an additional 30 minutes at 5-10° C., and sodium triacetoxyborohydride (4.37 g, 20.6 mmol) was added over a period of 20 minutes. The ice bath was removed and the reaction mixture was stirred for an additional 30 minutes. The flask was placed back in an ice bath and aqueous 4M sodium hydroxide was added to the reaction in small portions to adjust the reaction mixture to pH 8. The solution was stirred for an additional 30 minutes, cooled to 5° C., and diluted with ice cold water (80 mL), and resulted in the formation of a brown precipitate. The resulting slurry was stirred overnight at room temperature. The solids were collected by vacuum filtration, washed with cold water (3×5 mL) and dried to constant weight to give 35.4 g (88% yield) of tert-butyl 4-(2-aminopyridin-3-ylamino)piperidine-1-carboxylate. This material was submitted to the next step without further purification. $^1$H NMR (400 MHz, DMSO-d$_6$): δ 7.25 (dd, 1H), 6.64 (d, 1H), 6.17 (dd, 1H), 5.43 (broad s, 2H), 4.48 (d, 1H), 3.88 (d, 2H), 3.38 (broad s, 1H), 2.87 (broad s, 2.87), 1.87 (d, 2H), 1.38 (s, 9H), 1.19 (m, 2H). MS (EI) for $C_{15}H_{24}N_4O_2$: 293 (MH$^+$)

tert-Butyl 4-(2-oxo-2,3-dihydro-1H-imidazo[4,5-b]pyridin-1-yl)piperidine-1-carboxylate A 100 mL round bottom flask was charged with acetonitrile (20 mL, HPLC grade) and tert-butyl 4[(2-aminopyridin-3-yl)amino]piperidine-1-carboxylate (11, 1.89 g, 6.47 mmol) was added. Upon completion of addition, acetonitrile (5 mL) was added and the resulting suspension was stirred at room temperature for 30 minutes. Carbonyl diimidazole (1.57 g, 97.1 mmol) was then added over period of 10 minutes. The reaction mixture was heated to 50° C. and stirred overnight. The resulting solution was cooled to room temperature and concentrated under reduced pressure to give a brown solid. This solid was then mixed with 20 mL of isopropyl acetate and 20 mL of ice cold water. The resulting thick slurry was stirred overnight at room temperature. The brown solids were collected by vacuum filtration, washed with cold water (3×25 mL) and isopropyl acetate (3×25 mL) to give a light gray solid, which was dried to constant weight to give 1.73 g (84% yield) of tert-butyl 4-(2-oxo-2,3-dihydro-1H-imidazo[4,5-b]pyridin-1-yl)piperidine-1-carboxylate. This material was submitted to the next step without further purification. $^1$H NMR (400 MHz, DMSO-d$_6$): δ 11.56 (broad s, 1H), 7.89 (d, 1H), 7.54 (d, 1H), 6.98 (dd, 1H), 4.34 (m, 1H), 4.08 (broad m, 2H), 2.85 (broad m, 2H), 2.13 (m, 2H), 1.72 9 (d, 2H), 1.43 (s, 9H). MS (EI) for $C_{16}H_{22}N_4O_3$: 319 (MH$^+$)

1-Piperidin-4-yl-1,3-dihydro-2H-imidazo[4,5-b]pyridin-2-one dihydrochloride

A 50 mL 3-necked round bottom flask fitted with a thermometer, was charged with 30 mL of methanol (HPLC grade), and tert-butyl 4-(2-oxo-2,3-dihydro-1H-imidazo[4,5-b]pyridin-1-yl)piperidine-1-carboxylate (1.71 g, 5.37 mmol) was then added over a period of 5 minutes. The resulting brown suspension was stirred at room temperature for 30 minutes. Hydrogen chloride gas (Reagent Plus, steel cylinder, Aldrich) was carefully bubbled into the reaction mixture, resulting in a dark brown solution (Note: the temperatures of the reaction mixture rises to 38° C.). The flow of gas was stopped when the reaction mixture was saturated with hydrogen chloride. After 20 minutes a solid precipitated out of solution, and the resulting slurry was cooled to room temperature. The progress of the reaction was monitored by LCMS. The reaction was complete in 6 hours. The reaction mixture was diluted with isopropyl acetate (25 mL) and stirred for an additional 30 minutes; the solids were then collected by vacuum filtration. The resulting brown solid was washed with isopropyl acetate (5 mL), and dried to constant weight to give 1.32 g (84% yield) of 1-piperidin-4-yl-1,3-dihydro-2H-imidazo[4,5-b]pyridin-2-one dihydrochloride. This material was submitted to the next step without further purification. $^1$H NMR (400 MHz, DMSO-d$_6$): δ 11.77 (broad s, 1H), 8.32 (broad s, 3H), 7.95 (d, 1H), 7.93 (s, 1H), 7.06 (dd, 1H), 4.60 (m, 1H), 3.39 (d, 2H), 3.07 (q, 2H), 3.65 (dq, 2H), 1.86 (d, 2H). MS (EI) for $C_{11}H_{14}N_4$: 219 (MH$^+$)

9-Methyl-6-[4-(2-oxo-2,3-dihydro-1H-imidazo[4,5-b]pyridin-1-yl)piperidin-1-yl]-9H-purine-8-carboxylic acid A 100 mL round bottom flask was charged with 4-chloro-6-hydroxy-8-methylpteridin-7(8H)-one (250 mg, 1.26 mmol) and 1-piperidin-4-yl-1,3-dihydro-2H-imidazo[4,5-b]

pyridin-2-one dihydrochloride (407 mg, 1.40 mmol). Anhydrous dimethylacetamide (5 mL) and diisopropylethylamine (1 mL) were added, and the flask was capped with a reflux condenser. The reaction was then heated to 120° C. with stirring. After 4 hrs, the starting pteridinedione was completely consumed as indicated by LCMS. The reaction was cooled to room temperature, and the solvent removed by rotary evaporation.

The residue was then dissolved in methanol (20 mL) and 1 N aqueous sodium hydroxide solution (40 mL). The solution was then heated overnight at 85° C. LCMS indicated a complete conversion to the purine carboxylic acid. The reaction was cooled to room temperature and acidified with 4N hydrochloric acid in dioxane to precipitate the desired product. This precipitate was collected by vacuum filtration and washed with cold water and dried under vacuum to yield 320 mg (0.81 mmol, 64% overall yield) of 9-methyl-6-[4-(2-oxo-2,3-dihydro-1H-imidazo[4,5-b]pyridin-1-yl)piperidin-1-yl]-9H-purine-8-carboxylic acid. $^1$H NMR (400 MHz, DMSO-$d_6$) δ 11.58 (s, 1H), 8.33 (s, 1H), 7.88 (dd, 1H), 7.54 (dd, 1H), 6.94 (dd, 1H), 4.64-4.53 (m, 1H), 3.96 (s, 3H), 2.28 (td, 2H), 1.90 (d, 2H). MS (EI) for $C_{18}H_{18}N_8O_3$: 395 (MH$^+$).

9-Methyl-6-[4-(2-oxo-2,3-dihydro-1H-imidazo[4,5-b]pyridin-1-yl)piperidin-1-yl]-N-(2,2,2-trifluoroethyl)-9H-purine-8-carboxamide A 10 mL round bottom flask was charged with 9-methyl-6-[4-(2-oxo-2,3-dihydro-1H-imidazo[4,5-b]pyridin-1-yl)piperidin-1-yl]-9H-purine-8-carboxylic acid (100 mg, 0.25 mmol, 1 equiv). The material was dissolved in dimethylacetamide (1.5 mL), and diisopropylethylamine (84 μL, 0.51 mmol, 2 equiv) and 2,2,2-trifluoroethanaamine (30 μL, 0.38 mmol, 1.5 equiv) were added. 2-(7-aza-1H-benzotriazole-1-yl)-1,1,3,3-tetramethyluronium hexafluorophosphate (HATU, 116 mg, 0.30 mmol, 1.2 equiv) was then added and the reaction stirred at room temperature for two hours. The crude reaction mixture was diluted with methanol and purified by preparative reverse-phase HPLC (acetonitrile/water with 1% formic acid, 45-60 gradient). The purified fractions were combined, frozen and lyophilized to yield 29 mg of 9-methyl-6-[4-(2-oxo-2,3-dihydro-1H-imidazo[4,5-b]pyridin-1-yl)piperidin-1-yl]-N-(2,2,2-trifluoroethyl)-9H-purine-8-carboxamide. $^1$H NMR DMSO-$d_6$): δ 11.55 (s, 1H), 9.35 (t, 1H), 8.34 (s, 1H), 7.86 (dd, 1H), 7.52 (m, 1H), 6.93 (dd, 1H), 4.60 (s, 1H), 4.15 (m, 2H), 4.05 (s, 3H), 3.32 (m, 4H), 2.31 (m, 2H), 1.89 (m, 2H); MS (EI) for $C_{20}H_{20}F_3N_9O_2$: 476 (MH$^+$).

The following compounds were synthesized in an analogous fashion to the compounds described in examples 1-5.

N-(cyclopropylmethyl)-6-(4-hydroxy-4-phenylpiperidin-1-yl)-9-methyl-9H-purine-8-carboxamide (CMPD 3);

9-methyl-6-[4-(2-oxo-2,3-dihydro-1H-benzimidazol-1-yl)piperidin-1-yl]-N-(tetrahydro-2H-pyran-4-ylmethyl)-9H-purine-8-carboxamide (CMPD 5);

8-[9-methyl-8-(pyrrolidin-1-ylcarbonyl)-9H-purin-6-yl]-1-phenyl-1,3,8-triazaspiro[4.5]decan-4-one (CMPD 8);

8-[9-methyl-8-(piperidin-1-ylcarbonyl)-9H-purin-6-yl]-1-phenyl-1,3,8-triazaspiro[4.5]decan-4-one (CMPD 9);

8-{8-[3-(dimethylamino)azetidin-1-yl]carbonyl}-9-methyl-9H-purin-6-yl}-1-phenyl-1,3,8-triazaspiro[4.5]decan-4-one (CMPD 10);

9-methyl-6-[4-(2-oxo-2,3-dihydro-1H-benzimidazol-1-yl)piperidin-1-yl]-N-(tetrahydro-2H-pyran-3-ylmethyl)-9H-purine-8-carboxamide (CMPD 11);

N-[(1-hydroxycyclopropyl)methyl]-9-methyl-6-[4-(2-oxo-2,3-dihydro-1H-benzimidazol-1-yl)piperidin-1-yl]-9H-purine-8-carboxamide (CMPD 12);

N-(4-hydroxybutyl)-9-methyl-6-(2-oxo-1,2-dihydro-1'H-spiro[indole-3,4'-piperidin]-1'-yl)-9H-purine-8-carboxamide (CMPD 13);

N-cyclopropyl-9-methyl-6-(2-oxo-1,2-dihydro-1'H-spiro[indole-3,4'-piperidin]-1'-yl)-9H-purine-8-carboxamide (CMPD 14);

N-cyclobutyl-9-methyl-6-(2-oxo-1,2-dihydro-1'H-spiro[indole-3,4'-piperidin]-1'-yl)-9H-purine-8-carboxamide (CMPD 15);

N-butyl-9-methyl-6-(2-oxo-1,2-dihydro-1'H-spiro[indole-3,4'-piperidin]-1'-yl)-9H-purine-8-carboxamide (CMPD 16);

N-(furan-2-ylmethyl)-9-methyl-6-(2-oxo-1,2-dihydro-1'H-spiro[indole-3,4'-piperidin]-1'-yl)-9H-purine-8-carboxamide (CMPD 17);

N-(2,3-dihydro-1H-inden-1-yl)-9-methyl-6-(2-oxo-1,2-dihydro-1'H-spiro[indole-3,4'-piperidin]-1'-yl)-9H-purine-8-carboxamide (CMPD 18);

N-(3-hydroxypropyl)-9-methyl-6-(2-oxo-1,2-dihydro-1'H-spiro[indole-3,4'-piperidin]-1'-yl)-9H-purine-8-carboxamide (CMPD 19);

9-methyl-6-(2-oxo-1,2-dihydro-1'H-spiro[indole-3,4'-piperidin]-1'-yl)-N-(2-thienylmethyl)-9H-purine-8-carboxamide (CMPD 20);

9-methyl-6-(2-oxo-1,2-dihydro-1'H-spiro[indole-3,4'-piperidin]-1'-yl)-N-(2-pyridin-2-ylethyl)-9H-purine-8-carboxamide (CMPD 21);

9-methyl-6-(2-oxo-1,2-dihydro-1'H-spiro[indole-3,4'-piperidin]-1'-yl)-N-(pyridin-4-ylmethyl)-9H-purine-8-carboxamide (CMPD 22);

9-methyl-6-(2-oxo-1,2-dihydro-1'H-spiro[indole-3,4'-piperidin]-1'-yl)-N-(1-phenylethyl)-9H-purine-8-carboxamide (CMPD 23);

9-methyl-N-(1-methylethyl)-6-(2-oxo-1,2-dihydro-1'H-spiro[indole-3,4'-piperidin]-1'-yl)-9H-purine-8-carboxamide (CMPD 24);

N-(2-hydroxyethyl)-9-methyl-6-(2-oxo-1,2-dihydro-1'H-spiro[indole-3,4'-piperidin]-1'-yl)-9H-purine-8-carboxamide (CMPD 25);

9-methyl-N-([2-(methyloxy)phenyl]methyl)-6-(2-oxo-1,2-dihydro-1'H-spiro[indole-3,4'-piperidin]-1'-yl)-9H-purine-8-carboxamide (CMPD 26);

9-methyl-N-[(2-methylphenyl)methyl]-6-(2-oxo-1,2-dihydro-1'H-spiro[indole-3,4'-piperidin]-1'-yl)-9H-purine-8-carboxamide (CMPD 27);

N-[(3-fluorophenyl)methyl]-9-methyl-6-(2-oxo-1,2-dihydro-1'H-spiro[indole-3,4'-piperidin]-1'-yl)-9H-purine-8-carboxamide (CMPD 28);

9-methyl-N-([4-(methyloxy)phenyl]methyl)-6-(2-oxo-1,2-dihydro-1'H-spiro[indole-3,4'-piperidin]-1'-yl)-9H-purine-8-carboxamide (CMPD 29);

9-methyl-6-(2-oxo-1,2-dihydro-1'H-spiro[indole-3,4'-piperidin]-1'-yl)-N-(2,2,2-trifluoroethyl)-9H-purine-8-carboxamide (CMPD 30);

9-methyl-6-(2-oxo-1,2-dihydro-1'H-spiro[indole-3,4'-piperidin]-1'-yl)-N-(2-phenylpropyl)-9H-purine-8-carboxamide (CMPD 31);

N-ethyl-9-methyl-6-(2-oxo-1,2-dihydro-1H-spiro[indole-3,4'-piperidin]-1'-yl)-9H-purine-8-carboxamide (CMPD 32);

9-methyl-6-(2-oxo-1,2-dihydrol-1'H-spiro[indole-3,4'-piperidin]-1'-yl)-N-(2-phenylethyl)-9H-purine-8-carboxamide (CMPD 395)

N-[(2,4-difluorophenyl)methyl]-9-methyl-6-(2-oxo-1,2-dihydro-1'H-spiro[indole-3,4'-piperidin]-1'-yl)-9H-purine-8-carboxamide (CMPD 33);

9-methyl-N-(2-methylpropyl)-6-(2-oxo-1,2-dihydro-1'H-spiro[indole-3,4'-piperidin]-1'-yl)-9H-purine-8-carboxamide (CMPD 34);

1'-[9-methyl-8-(pyrrolidin-1-ylcarbonyl)-9H-purin-6-yl]spiro[indole-3,4'-piperidin]-2(1H)-one (CMPD 35);

9-methyl-6-(2-oxo-1,2-dihydro-1'H-spiro[indole-3,4'-piperidin]-1'-yl)-N-propyl-9H-purine-8-carboxamide (CMPD 36);

N-hexyl-9-methyl-6-(2-oxo-1,2-dihydro-1'H-spiro[indole-3,4'-piperidin]-1'-yl)-9H-purine-8-carboxamide (CMPD 37);

N,9-dimethyl-N-(1-methylethyl)-6-(2-oxo-1,2-dihydro-1'H-spiro[indole-3,4'-piperidin]-1'-yl)-9H-purine-8-carboxamide (CMPD 38):

N-(2-cyanoethyl)-N,9-dimethyl-6-(2-oxo-1,2-dihydro-1'H-spiro[indole-3,4'-piperidin]-1'-yl)-9H-purine-8-carboxamide (CMPD 39);

9-methyl-N-(3-methylbutyl)-6-(2-oxo-1,2-dihydro-1'H-spiro[indole-3,4'-piperidin]-1'-yl)-9H-purine-8-carboxamide (CMPD 40);

1'-{8-[(3-hydroxyazetidin-1-yl)carbonyl]-9-methyl-9H-purin-6-yl}spiro[indole-3,4'-piperidin]-2(1H)-one (CMPD 41);

N-(4-hydroxybutyl)-9-methyl-6-[4-(2-oxo-2,3-dihydro-1H-benzimidazol-1-yl)piperidin-1-yl]-9H-purine-8-carboxamide (CMPD 42);

N-cyclopropyl-9-methyl-6-[4-(2-oxo-2,3-dihydro-1H-benzimidazol-1-yl)piperidin-1-yl]-9H-purine-8-carboxamide (CMPD 43);

N-cyclobutyl-9-methyl-6-[4-(2-oxo-2,3-dihydro-1H-benzimidazol-1-yl)piperidin-1-yl]-9H-purine-8-carboxamide (CMPD 44);

N-butyl-9-methyl-6-[4-(2-oxo-2,3-dihydro-1H-benzimidazol-1-yl)piperidin-1-yl]-9H-purine-8-carboxamide (CMPD 45);

N-(furan-2-ylmethyl)-9-methyl-6-[4-(2-oxo-2,3-dihydro-1H-benzimidazol-1-yl)piperidin-1-yl]-9H-purine-8-carboxamide (CMPD 46);

N-(2,3-dihydro-1H-inden-1-yl)-9-methyl-6-[4-(2-oxo-2,3-dihydro-1H-benzimidazol-1-yl)piperidin-1-yl]-9H-purine-8-carboxamide (CMPD 47);

N-(3-hydroxypropyl)-9-methyl-6-[4-(2-oxo-2,3-dihydro-1H-benzimidazol-1-yl)piperidin-1-yl]-9H-purine-8-carboxamide (CMPD 48);

9-methyl-6-[4-(2-oxo-2,3-dihydro-1H-benzimidazol-1-yl)piperidin-1-yl]-N-(2-thienylmethyl)-9H-purine-8-carboxamide (CMPD 49);

N-(1,3-benzodioxol-5-ylmethyl)-9-methyl-6-[4-(2-oxo-2,3-dihydro-1H-benzimidazol-1-yl)piperidin-1-yl]-9H-purine-8-carboxamide (CMPD 50);

9-methyl-6-[4-(2-oxo-2,3-dihydro-1H-benzimidazol-1-yl)piperidin-1-yl]-N-(2-pyridin-2-ylethyl)-9H-purine-8-carboxamide (CMPD 51);

9-methyl-6-[4-(2-oxo-2,3-dihydro-1H-benzimidazol-1-yl)piperidin-1-yl]-N-(pyridin-4-ylmethyl)-9H-purine-8-carboxamide (CMPD 52);

9-methyl-6-[4-(2-oxo-2,3-dihydro-1H-benzimidazol-1-yl)piperidin-1-yl]-N-(1-phenylethyl)-9H-purine-8-carboxamide (CMPD 53);

9-methyl-N-(1-methylethyl)-6-[4-(2-oxo-2,3-dihydro-1H-benzimidazol-1-yl)piperidin-1-yl]-9H-purine-8-carboxamide (CMPD 54);

N-(2-hydroxyethyl)-9-methyl-6-[4-(2-oxo-2,3-dihydro-1H-benzimidazol-1-yl)piperidin-1-yl]-9H-purine-8-carboxamide (CMPD 55);

9-methyl-N-{[2-(methyloxy)phenyl]methyl}-6-[4-(2-oxo-2,3-dihydro-1H-benzimidazol-1-yl)piperidin-1-yl]-9H-purine-8-carboxamide (CMPD 56);

9-methyl-N-[(2-methylphenyl)methyl]-6-[4-(2-oxo-2,3-dihydro-1H-benzimidazol-1-yl)piperidin-1-yl]-9H-purine-8-carboxamide (CMPD 57);

N-[(3-fluorophenyl)methyl]-9-methyl-6-[4-(2-oxo-2,3-dihydro-1H-benzimidazol-1-yl)piperidin-1-yl]-9H-purine-8-carboxamide (CMPD 58);

9-methyl-N-{[4-(methyloxy)phenyl]methyl}-6-[4-(2-oxo-2,3-dihydro-1H-benzimidazol-1-yl)piperidin-1-yl]-9H-purine-8-carboxamide (CMPD 59);

9-methyl-6-[4-(2-oxo-2,3-dihydro-1H-benzimidazol-1-yl)piperidin-1-yl]-N-(2,2,2-trifluoromethyl)-9H-purine-8-carboxamide (CMPD 60);

9-methyl-6-[4-(2-oxo-2,3-dihydro-1H-benzimidazol-1-yl)piperidin-1-yl]-N-(2-phenylpropyl)-9H-purine-8-carboxamide (CMPD 61);

N-ethyl-9-methyl-6-[4-(2-oxo-2,3-dihydro-1H-benzimidazol-1-yl)piperidin-1-yl]-9H-purine-8-carboxamide (CMPD 62);

N-[2-(4-chlorophenyl)ethyl]-9-methyl-6-[4-(2-oxo-2,3-dihydro-1H-benzimidazol-1-yl)piperidin-1-yl]-9H-purine-8-carboxamide (CMPD 63);

9-methyl-N-[2-(4-methylphenyl)ethyl]-6-[4-(2-oxo-2,3-dihydro-1H-benzimidazol-1-yl)piperidin-1-yl]-9H-purine-8-carboxamide (CMPD 64);

9-methyl-6-[4-(2-oxo-2,3-dihydro-1H-benzimidazol-1-yl)piperidin-1-yl]-N-(3-phenylpropyl)-9H-purine-8-carboxamide (CMPD 65);

N-[(2,4-difluorophenyl)methyl]-9-methyl-6-[4-(2-oxo-2,3-dihydro-1H-benzimidazol-1-yl)piperidin-1-yl]-9H-purine-8-carboxamide (CMPD 66);

9-methyl-N-(2-methylpropyl)-6-[4-(2-oxo-2,3-dihydro-1H-benzimidazol-1-yl)piperidin-1-yl]-9H-purine-8-carboxamide (CMPD 67);

1-{1-[9-methyl-8-(pyrrolidin-1-ylcarbonyl)-9H-purin-6-yl]piperidin-4-yl}-1,3-dihydro-2H-benzimidazol-2-one (CMPD 68);

9-methyl-6-[4-(2-oxo-2,3-dihydro-1H-benzimidazol-1-yl)piperidin-1-yl]-N-propyl-9H-purine-8-carboxamide (CMPD 69);

9-methyl-6-[4-(2-oxo-2,3-dihydro-1H-benzimidazol-1-yl)piperidin-1-yl]-N-pentyl-9H-purine-8-carboxamide (CMPD 70);

N-hexyl-9-methyl-6-[4-(2-oxo-2,3-dihydro-1H-benzimidazol-1-yl)piperidin-1-yl]-9H-purine-8-carboxamide (CMPD 71);

9-methyl-N-(3-methylbutyl)-6-[4-(2-oxo-2,3-dihydro-1H-benzimidazol-1-yl)piperidin-1-yl]-9H-purine-8-carboxamide (CMPD 72);

1-(1-[8-[(3-hydroxypyrrolidin-1-yl)carbonyl]-9-methyl-9H-purin-6-yl]piperidin-4-yl)-1,3-dihydro-2H-benzimidazol-2-one (CMPD 73);

1-(1-{8-[(3-hydroxyazetidin-1-yl)carbonyl]-9-methyl-9H-purin-6-yl}piperidin-4-yl)-1,3-dihydro-2H-benzimidazol-2-one (CMPD 74);

N-(1,1-dimethylethyl)-9-methyl-6-(2-oxo-1,2-dihydro-1'H-spiro[indole-3,4'-piperidin]-1'-yl)-9H-purine-8-carboxamide (CMPD 75);

9-methyl-6-(2-oxo-1,2-dihydro-1'H-spiro[indole-3,4'-piperidin]-1'-yl)-N-(tetrahydro-2H-pyran-4-ylmethyl)-9H-purine-8-carboxamide (CMPD 77);

9-methyl-6-(2-oxo-1,2-dihydro-1'H-spiro[indole-3,4'-piperidin]-1'-yl)-N-(tetrahydro-2H-pyran-2-ylmethyl)-9H-purine-8-carboxamide (CMPD 82);

N-(2-hydroxy-2-methylpropyl)-9-methyl-6-(2-oxo-1,2-dihydro-1'H-spiro[indole-3,4'-piperidin]-1'-yl)-9H-purine-8-carboxamide (CMPD 83);

N-(1-cyclopropylethyl)-9-methyl-6-(2-oxo-1,2-dihydro-1'H-spiro[indole-3,4'-piperidin]-1'-yl)-9H-purine-8-carboxamide (CMPD 84);

9-methyl-6-(2-oxo-1,2-dihydro-1'H-spiro[indole-3,4'-piperidin]-1'-yl)-N-(tetrahydrofuran-2-ylmethyl)-9H-purine-8-carboxamide (CMPD 85);

9-methyl-6-(2-oxo-1,2-dihydro-1'H-spiro[indole-3,4'-piperidin]-1'-yl)-N-(tetrahydro-2H-pyran-4-yl)-9H-purine-8-carboxamide (CMPD 86);

N-(trans-4-hydroxycyclohexyl)-9-methyl-6-(2-oxo-1,2-dihydro-1'H-spiro[indole-3,4'-piperidin]-1'-yl)-9H-purine-8-carboxamide (CMPD 87);

N-(cyclohexylmethyl)-9-methyl-6-(2-oxo-1,2-dihydro-1'H-spiro[indole-3,4'-piperidin]-1'-yl)-9H-purine-8-carboxamide (CMPD 88);

N-(cyclobutylmethyl)-9-methyl-6-(2-oxo-1,2-dihydro-1'H-spiro[indole-3,4'-piperidin]-1'-yl)-9H-purine-8-carboxamide (CMPD 89);

1'-[8-(azetidin-1-ylcarbonyl)-9-methyl-9H-purin-6-yl]spiro[indole-3,4'-piperidin]-2(1H)-one (CMPD 90);

N,9-dimethyl-6-[4-(2-oxo-2,3-dihydro-1H-benzimidazol-1-yl)piperidin-1-yl]-9H-purine-8-carboxamide (CMPD 91);

N,9-dimethyl-N-(methyloxy)-6-[4-(2-oxo-2,3-dihydro-1H-benzimidazol-1-yl)piperidin-1-yl]-9H-purine-8-carboxamide (CMPD 94);

N-(2,2-dimethylpropyl)-9-methyl-6-(2-oxo-1,2-dihydro-1'H-spiro[indole-3,4'-piperidin]-1'-yl)-9H-purine-8-carboxamide (CMPD 96);

N-(cyclopropylmethyl)-9-ethyl-6-[4-(2-oxo-2,3-dihydro-1H-benzimidazol-1-yl)piperidin-1-yl]-9H-purine-8-carboxamide (CMPD 97);

N-(cyclopropylmethyl)-9-methyl-6-(2-oxo-1,2-dihydro-1'H-spiro[indole-3,3'-pyrrolidin]-1'-yl)-9H-purine-8-carboxamide (CMPD 98);

N-(cyclopropylmethyl)-9-methyl-6-(1-oxo-4-phenyl-2,8-diazaspiro[4.5]dec-8-yl)-9H-purine-8-carboxamide (CMPD 99);

N-(cyclopropylmethyl)-6-[4-(1H-indol-3-yl)piperidin-1-yl]-9-methyl-9H-purine-8-carboxamide (CMPD 100);

N-(cyclopropylmethyl)-9-methyl-6-{4-[2-(trifluoromethyl)-1H-benzimidazol-1-yl]piperidin-1-yl}-9H-purine-8-carboxamide (CMPD 101);

1'-{8-[(3,3-difluoroazetidin-1-yl)carbonyl]-9-methyl-9H-purin-6-yl}spiro[indole-3,4'-piperidin]-2(1H)-one (CMPD 103);

1-(1-{8-[(3,3-difluoroazetidin-1-yl)carbonyl]-9-methyl-9H-purin-6-yl}piperidin-4-yl)-1,3-dihydro-2H-benzimidazol-2-one (CMPD 104);

N-(4,4-difluorocyclohexyl)-9-methyl-6-(2-oxo-1,2-dihydro-1'H-spiro[indole-3,4'-piperidin]-1'-yl)-9H-purine-8-carboxamide (CMPD 105);

1'-{8-[(3,3-difluoropyrrolidin-1-yl)carbonyl]-9-methyl-9H-purin-6-yl}spiro[indole-3,4'-piperidin]-2(1H)-one (CMPD 106);

N-(4,4-difluorocyclohexyl)-9-methyl-6-[4-(2-oxo-2,3-dihydro-1H-benzimidazol-1-yl)piperidin-1-yl]-9H-purine-8-carboxamide (CMPD 207);

1-(1-{8-[(3,3-difluoropyrrolidin-1-yl)carbonyl]-9-methyl-9H-purin-6-yl}piperidin-4-yl)-1,3-dihydro-2H-benzimidazol-2-one (CMPD 108);

1'-(8-{[(3S)-3-fluoropyrrolidin-1-yl]carbonyl}-9-methyl-9H-purin-6-yl)spiro[indole-3,4'-piperidin]-2(1H)-one (CMPD 109);

1'-(8-{[(3R)-3-fluoropyrrolidin-1-yl]carbonyl}-9-methyl-9H-purin-6-yl)spiro[indole-3,4'-piperidin]-2(1H)-one (CMPD 110);

N-(trans-4-hydroxycyclohexyl)-9-methyl-6-[4-(2-oxo-2,3-dihydro-1H-benzimidazol-1-yl)piperidin-1-yl]-9H-purine-8-carboxamide (CMPD 111);

1-[1-(8-{[(3S)-3-fluoropyrrolidin-1-yl]-carbonyl}-9-methyl-9H-purin-6-yl)piperidin-4-yl]-1,3-dihydro-2H-benzimidazol-2-one (CMPD 396);

1-[1-(8-{[(3R)-3-fluoropyrrolidin-1-yl]carbonyl}-9-methyl-9H-purin-6-yl)piperidin-4-yl]-1,3-dihydro-2H-benzimidazol-2-one (CMPD 112);

N-(cyclopropylmethyl)-9-methyl-6-[4-(2-oxo-2,3-dihydro-1H-indol-1-yl)piperidin-1-yl]-9H-purine-8-carboxamide (CMPD 117);

N-(cyclopropylmethyl)-9-methyl-6-[4-(2-oxo-1,3-benzoxazol-3(2H)-yl)piperidin-1-yl]-9H-purine-8-carboxamide (CMPD 118);

N-(cyclopropylmethyl)-9-methyl-6-(3-oxo-2,3-dihydro-1'H-spiro[indene-1,4'-piperidin]-1'-yl)-9H-purine-8-carboxamide (CMPD 119);

N-(cyclopropylmethyl)-9-methyl-6-(2-oxo-2,3-dihydro-1'H-spiro[indene-1,4'-piperidin]-1'-yl)-9H-purine-8-carboxamide (CMPD 120);

N-(cyclopropylmethyl)-6-[4-(1H-indol-1-yl)piperidin-1-yl]-9-methyl-9H-purine-8-carboxamide (CMPD 121);

N-(cyclopropylmethyl)-9-methyl-6-(2-oxo-1'H-spiro[1-benzofuran-3,4'-piperidin]-1'-yl)-9H-purine-8-carboxamide (CMPD 129);

N-(cyclopropylmethyl)-6-(2-hydroxy-2,3-dihydro-1'H-spiro[indene-1,4'-piperidin]-1'-yl)-9-methyl-9H-purine-8-carboxamide (CMPD 130);

N-(cyclopropylmethyl)-9-methyl-6-[4-(2-oxo-2,3-dihydro-1H-indol-3-yl)piperidin-1-yl]-9H-purine-8-carboxamide (CMPD 131);

N-(cyclopropylmethyl)-9-methyl-6-(1'H,3H-spiro[2-benzofuran-1,4'-piperidin]-1'-yl)-9H-purine-8-carboxamide (CMPD 132);

N-(cyclopropylmethyl)-6-[4-(2,2-dioxido-2,1,3-benzothiadiazol-1(3H)-yl)piperidin-1-yl]-9-methyl-9H-purine-8-carboxamide (CMPD 133);

N-(cyclopropylmethyl)-9-methyl-6-[5-(1-methylethyl)-2-oxo-1,2-dihydro-1'H-spiro[indole-3,4'-piperidin]-1'-yl]-9H-purine-8-carboxamide (CMPD 136);

N-(cyclopropylmethyl)-9-methyl-6-[3-(2-oxo-2,3-dihydro-1H-benzimidazol-1-yl)azetidin-1-yl]-9H-purine-8-carboxamide (CMPD 137);

N-(cyclopropylmethyl)-9-methyl-6-(3-oxo-1'H,3H-spiro[2-benzofuran-1,4'-piperidin]-1'-yl)-9H-purine-8-carboxamide (CMPD 138);

9-methyl-6-[4-(2-oxo-2,3-dihydro-1H-benzimidazol-1-yl)piperidin-1-yl]-N-prop-2-yn-1-yl-9H-purine-8-carboxamide (CMPD 139);

9-methyl-6-(2-oxo-1,2-dihydro-1'H-spiro[indole-3,4'-piperidin]-1'-yl)-N-prop-2-yn-1-yl-9H-purine-8-carboxamide (CMPD 140);

N-(cyclopropylmethyl)-9-methyl-6-(1-methyl-2-oxo-1,2-dihydro-1'H-spiro[indole-3,4'-piperidin]-1'-yl)-9H-purine-8-carboxamide (CMPD 141);

N-(cyclopropylmethyl)-9-methyl-6-(3-oxo-2,3-dihydro-1'H-spiro[isoindole-1,4'-piperidir]-1'-yl)-9H-purine-8-carboxamide (CMPD 142);

6-[4-(1H-1,2,3-benzotriazol-1-yl)piperidin-1-yl]-N-(cyclopropylmethyl)-9-methyl-9H-purine-8-carboxamide (CMPD 143);

N-(cyclopropylmethyl)-9-methyl-6-{3-[2-oxo-5-(trifluoromethyl)-2,3-dihydro-1H-benzimidazol-1-yl]azetidin-1-yl}-9H-purine-8-carboxamide (CMPD 145);

6-[4-(2-amino-1H-benzimidazol-1-yl)piperidin-1-yl]-N-(cyclopropylmethyl)-9-methyl-9H-purine-8-carboxamide (CMPD 150);

N-(cyclopropylmethyl)-9-methyl-6-(1-phenyl-1,4,6,7-tetrahydro-5H-pyrazolo[4,3-c]pyridin-5-yl)-9H-purine-8-carboxamide (CMPD 151);

9-ethyl-N-(trans-4-hydroxycyclohexyl)-6-[4-(2-oxo-2,3-dihydro-1H-benzimidazol-1-yl)piperidin-1-yl]-9H-purine-8-carboxamide (CMPD 154);

9-ethyl-6-[4-(2-oxo-2,3-dihydro-1H-benzimidazol-1-yl)piperidin-1-yl]-N-(2,2,2-trifluoroethyl)-9H-purine-8-carboxamide (CMPD 155);

9-ethyl-6-[4-(2-oxo-2,3-dihydro-1H-benzimidazol-1-yl)piperidin-1-yl]-N-(tetrahydro-2H-pyran-4-ylmethyl)-9H-purine-8-carboxamide (CMPD 156);

N-butyl-9-ethyl-6-[4-(2-oxo-2,3-dihydro-1H-benzimidazol-1-yl)piperidin-1-yl]-9H-purine-8-carboxamide (CMPD 157);

9-ethyl-N-(2-methylpropyl)-6-[4-(2-oxo-2,3-dihydro-1H-benzimidazol-1-yl)piperidin-1-yl]-9H-purine-8-carboxamide (CMPD 158);

9-ethyl-N-(trans-4-hydroxycyclohexyl)-6-(2-oxo-1,2-dihydro-1'H-spiro[indole-3,4'-piperidin]-1'-yl)-9H-purine-8-carboxamide (CMPD 159);

9-ethyl-6-(2-oxo-1,2-dihydro-1'H-spiro[indole-3,4'-piperidin]-1'-yl)-N-(2,2,2-trifluoroethyl)-9H-purine-8-carboxamide (CMPD 160);

9-ethyl-6-(2-oxo-1,2-dihydro-1'H-spiro[indole-3,4'-piperidin]-1'-yl)-N-(tetrahydro-2H-pyran-4-ylmethyl)-9H-purine-8-carboxamide (CMPD 161);

N-butyl-9-ethyl-6-(2-oxo-1,2-dihydro-1'H-spiro[indole-3,4'-piperidin]-1'-yl)-9H-purine-8-carboxamide (CMPD 162);

N-(cyclopropylmethyl)-9-ethyl-6-(2-oxo-1,2-dihydro-1'H-spiro[indole-3,4'-piperidin]-1'-yl)-9H-purine-8-carboxamide (CMPD 163);

9-ethyl-N-(2-methylpropyl)-6-(2-oxo-1,2-dihydro-1'H-spiro[indole-3,4'-piperidin]-1'-yl)-9H-purine-8-carboxamide (CMPD 164);

6-(7-bromo-2-oxo-1,2-dihydro-1'H-spiro[indole-3,4'-piperidin]-1'-yl)-N-(cyclopropylmethyl)-9-methyl-9H-purine-8-carboxamide (CMPD 168);

N-(cyclopropylmethyl)-9-methyl-6-[4-(2-thioxo-2,3-dihydro-1H-benzimidazol-1-yl)piperidin-1-yl]-9H-purine-8-carboxamide (CMPD 169);

N-(cyclopropylmethyl)-9-methyl-6-(4-oxo-4,5-dihydro-1'H,3H-spiro[1,5-benzoxazepine-2,4'-piperidin]-1'-yl)-9H-purine-8-carboxamide (CMPD 170);

N-(cyclopropylmethyl)-9-methyl-6-[3-(2-oxo-2,3-dihydro-1H-benzimidazol-1-yl)pyrrolidin-1-yl]-9H-purine-8-carboxamide (CMPD 172);

9-cyclopropyl-N-(2-methylpropyl)-6-[4-(2-oxo-2,3-dihydro-1H-benzimidazol-1-yl)piperidin-1-yl]-9H-purine-8-carboxamide (CMPD 173);

9-cyclopropyl-N-(cyclopropylmethyl)-6-(2-oxo-1,2-dihydro-1'H-spiro[indole-3,4'-piperidin]-1'-yl)-9H-purine-8-carboxamide (CMPD 175);

9-cyclopropyl-N-(2-methylpropyl)-6-(2-oxo-1,2-dihydro-1'H-spiro[indole-3,4'-piperidin]-1'-yl)-9H-purine-8-carboxamide (CMPD 176);

N-(2-methylpropyl)-6-[4-(2-oxo-2,3-dihydro-1H-benzimidazol-1-yl)piperidin-1-yl]-9-(2,2,2-trifluoroethyl)-9H-purine-8-carboxamide (CMPD 183);

N-(cyclobutylmethyl)-9-ethyl-6-[4-(2-oxo-2,3-dihydro-1H-benzimidazol-1-yl)piperidin-1-yl]-9H-purine-8-carboxamide (CMPD 185);

1-[1-(9-ethyl-8-{[(3R)-3-fluoropyrrolidin-1-yl]carbonyl}-9H-purin-6-yl)piperidin-4-yl]-1,3-dihydro-2H-benzimidazol-2-one (CMPD 186);

N-(1-cyclopropylethyl)-9-ethyl-6-[4-(2-oxo-2,3-dihydro-1H-benzimidazol-1-yl)piperidin-1-yl]-9H-purine-8-carboxamide (CMPD 187);

9-ethyl-N-[(1-hydroxycyclopropyl)methyl]-6-[4-(2-oxo-2,3-dihydro-1H-benzimidazol-1-yl)piperidin-1-yl]-9H-purine-8-carboxamide (CMPD 188);

1-(1-{8[(3,3-difluoroazetidin-1-yl)carbonyl]-9-ethyl-9H-purin-6-yl}piperidin-4-yl)-1,3-dihydro-2H-benzimidazol-2-one (CMPD 189);

N-(2,2-dimethylpropyl)-9-ethyl-6-[4-(2-oxo-2,3-dihydro-1H-benzimidazol-1-yl)piperidin-1-yl]-9H-purine-8-carboxamide (CMPD 190);

1-(1-{8-[(3,3-difluoropyrrolidin-1-yl)carbonyl]-9-ethyl-9H-purin-6-yl}piperidin-4-yl)-1,3-dihydro-2H-benzimidazol-2-one (CMPD 191);

N,9-diethyl-6-[4-(2-oxo-2,3-dihydro-1H-benzimidazol-1-yl)piperidin-1-yl]-9H-purine-8-carboxamide (CMPD 192);

9-ethyl-6-[4-(2-oxo-2,3-dihydro-1H-benzimidazol-1-yl)piperidin-1-yl]-N-propyl-9H-purine-8-carboxamide (CMPD 193);

N-cyclobutyl-9-ethyl-6-[4-(2-oxo-2,3-dihydro-1H-benzimidazol-1-yl)piperidin-1-yl]-9H-purine-8-carboxamide (CMPD 194);

9-ethyl-N-(4-hydroxybutyl)-6-[4-(2-oxo-2,3-dihydro-1H-benzimidazol-1-yl)piperidin-1-yl]-9H-purine-8-carboxamide (CMPD 195);

9-ethyl-N-(1-methylethyl)-6-[4-(2-oxo-2,3-dihydro-1H-benzimidazol-1-yl)piperidin-1-yl]-9H-purine-8-carboxamide (CMPD 196);

9-ethyl-N-(2-hydroxy-2-methylpropyl)-6-[4-(2-oxo-2,3-dihydro-1H-benzimidazol-1-yl)piperidin-1-yl]-9H-purine-8-carboxamide (CMPD 197);

9-ethyl-N-(3-methylbutyl)-6-[4-(2-oxo-2,3-dihydro-1H-benzimidazol-1-yl)piperidin-1-yl]-9H-purine-8-carboxamide (CMPD 198);

N-(cyclopropylmethyl)-9-methyl-6-[1-(2-methylphenyl)-1,4,6,7-tetrahydro-5H-pyrazolo[4,3-c]pyridin-5-yl]-9H-purine-8-carboxamide (CMPD 199);

N-(cyclopropylmethyl)-9-methyl-6-[1-(3-methylphenyl)-1,4,6,7-tetrahydro-5H-pyrazolo[4,3-c]pyridin-5-yl]-9H-purine-8-carboxamide (CMPD 200);

N-(cyclopropylmethyl)-6-[1-(2,4-dimethyl phenyl)-1,4,6,7-tetrahydro-5H-pyrazolo[4,3-c]pyridin-5-yl]-9-methyl-9H-purine-8-carboxamide (CMPD 201);

N-(cyclopropylmethyl)-6-[1-(2,6-dimethylphenyl)-1,4,6,7-tetrahydro-5H-pyrazolo[4,3-c]pyridin-5-yl]-9-methyl-9H-purine-8-carboxamide (CMPD 202);

N-(cyclopropylmethyl)-6-[4-(5-fluoro-2-oxo-2,3-dihydro-1H-benzimidazol-1-yl)piperidin-1-yl]-9-methyl-9H-purine-8-carboxamide (CMPD 205);

N-(cyclopropylmethyl)-9-methyl-6-[4-(6-methyl-2-oxo-2,3-dihydro-1H-benzimidazol-1-yl)piperidin-1-yl]-9H-purine-8-carboxamide (CMPD 206);

9-ethyl-N-[(5-methyl-1,3,4-oxadiazol-2-yl)methyl]-6-(2-oxo-1,2-dihydro-1'H-spiro[indole-3,4'-piperidin]-1'-yl)-9H-purine-8-carboxamide (CMPD 207);

9-ethyl-N-oxetan-3-yl-6-[4-(2-oxo-2,3-dihydro-1H-benzimidazol-1-yl)piperidin-1-yl]-9H-purine-8-carboxamide (CMPD 208);

6-(7-chloro-2-oxo-1,2-dihydro-1'H-spiro[indole-3,4'-piperidin]-1'-yl)-N-(cyclopropylmethyl)-9-methyl-9H-purine-8-carboxamide (CMPD 211);

N-(cyclobutylmethyl)-9-ethyl-6-(2-oxo-1,2-dihydro-1'H-spiro[indole-3,4'-piperidin]-1'-yl)-9H-purine-8-carboxamide (CMPD 212);

1'-(9-ethyl-81 [(3R)-3-fluoropyrrolidin-1-yl]carbonyl)-9H-purin-6-yl)spiro[indole-3,4'-piperidin]-2(1H)-one (CMPD 213);

N-(1-cyclopropylethyl)-9-ethyl-6-(2-oxo-1,2-dihydro-1'H-spiro[indole-3,4'-piperidin]-1'-yl)-9H-purine-8-carboxamide (CMPD 214);

9-ethyl-N-[(1-hydroxycyclopropyl)methyl]-6-(2-oxo-1,2-dihydro-1'H-spiro[indole-3,4'-piperidin]-1'-yl)-9H-purine-8-carboxamide (CMPD 215);

1'-{8-[(3,3-difluoroazetidin-1-yl)carbonyl]-9-ethyl-9H-purin-6-yl}spiro[indole-3,4'-piperidin]-2(1H)-one (CMPD 216);

N-(2,2-dimethylpropyl)-9-ethyl-6-(2-oxo-1,2-dihydro-1'H-spiro[indole-3,4'-piperidin]-1'-yl)-9H-purine-8-carboxamide (CMPD 217);

1'-{8-[(3,3-difluoropyrrolidin-1-yl)carbonyl]-9-ethyl-9H-purin-6-yl}spiro[indole-3,4'-piperidin]-2(1H)-one (CMPD 218);

N,9-diethyl-6-(2-oxo-1,2-dihydro-1'H-spiro[indole-3,4'-piperidin]-1'-yl)-9H-purine-8-carboxamide (CMPD 219);

9-ethyl-6-(2-oxo-1,2-dihydro-1'H-spiro[indole-3,4'-piperidin]-1'-yl)-N-propyl-9H-purine-8-carboxamide (CMPD 220);

N-cyclobutyl-9-ethyl-6-(2-oxo-1,2-dihydro-1'H-spiro[indole-3,4'-piperidin]-1'-yl)-9H-purine-8-carboxamide (CMPD 221);

9-ethyl-N-(4-hydroxybutyl)-6-(2-oxo-1,2-dihydro-1'H-spiro[indole-3,4'-piperidin]-1'-yl)-9H-purine-8-carboxamide (CMPD 222);

9-ethyl-N-(1-methylethyl)-6-(2-oxo-1,2-dihydro-1'H-spiro[indole-3,4'-piperidin]-1'-yl)-9H-purine-8-carboxamide (CMPD 223);

9-ethyl-N-(2-hydroxy-2-methylpropyl)-6-(2-oxo-1,2-dihydro-1'H-spiro[indole-3,4'-piperidin]-1'-yl)-9H-purine-8-carboxamide (CMPD 224);

9-ethyl-N-(3-methylbutyl)-6-(2-oxo-1,2-dihydro-1'H-spiro[indole-3,4'-piperidin]-1'-yl)-9H-purine-8-carboxamide (CMPD 225);

9-ethyl-N-oxetan-3-yl-6-(2-oxo-1,2-dihydro-1'H-spiro[indole-3,4'-piperidin]-1'-yl)-9H-purine-8-carboxamide (CMPD 226);

6-[4-(5-chloro-2-oxo-2,3-dihydro-1H-benzimidazol-1-yl)piperidin-1-yl]-N-(cyclopropylmethyl)-9-methyl-9H-purine-8-carboxamide (CMPD 228);

6-[4-(6-chloro-2-oxo-2,3-dihydro-1H-benzimidazol-1-yl)piperidin-1-yl]-N-(cyclopropylmethyl)-9-methyl-9H-purine-8-carboxamide (CMPD 229);

6-[4-(4-chloro-2-oxo-2,3-dihydro-1H-benzimidazol-1-yl)piperidin-1-yl]-N-(cyclopropylmethyl)-9-methyl-9H-purine-8-carboxamide (CMPD 230);

N-(cyclopropylmethyl)-6-[(3R,4R)-3-hydroxy-4-phenylpiperidin-1-yl]-9-methyl-9H-purine-8-carboxamide (CMPD 235);

N-(cyclopropylmethyl)-6-{1-[2-(dimethylamino)ethyl]-2-oxo-1,2-dihydro-1'H-spiro[indole-3,4'-piperidin]-1'-yl}-9-methyl-9H-purine-8-carboxamide (CMPD 397);

N-(cyclopropylmethyl)-9-methyl-6-[4-(2-oxo-2,3-dihydro-1H-imidazo[4,5-b]pyridin-1-yl)piperidin-1-yl]-9H-purine-8-carboxamide (CMPD 240);

N-(cyclopropylmethyl)-9-methyl-6-[4-(2-oxo-3,4-dihydroquinazolin-1(2H)-yl)piperidin-1-yl]-9H-purine-8-carboxamide (CMPD 248);

N-(cyclopropylmethyl)-9-methyl-6-(3'-oxo-3',4'-dihydro-1H,1'H-spiro[piperidine-4,2'-quinoxalin]-1-yl)-9H-purine-8-carboxamide (CMPD 249);

N-(cyclopropylmethyl)-9-methyl-6-[3-methyl-4-(2-oxo-2,3-dihydro-1H-benzimidazol-1-yl)piperidin-1-yl]-9H-purine-8-carboxamide (CMPD 255);

N-(cyclopropylmethyl)-9-methyl-6-[3-(2-oxo-2,3-dihydro-1H-benzimidazol-1-yl)piperidin-1-yl]-9H-purine-8-carboxamide (CMPD 256);

N-(cyclopropylmethyl)-9-methyl-6-{4-[4-(methyloxy)-2-oxo-2,3-dihydro-1H-benzimidazol-1-yl]piperidin-1-yl}-9H-purine-8-carboxamide (CMPD 257);N-(cyclopropylmethyl)-9-methyl-6-{4-[4-(4-methylpiperazin-1-yl)-2-oxo-2,3-dihydro-1H-benzimidazol-1-yl]piperidin-1-yl}-9H-purine-8-carboxamide (CMPD 258);

N-(cyclopropylmethyl)-6-[4-(1,1-dioxido-1,2-benzisothiazol-3-yl)piperazin-1-yl]-9-methyl-9H-purine-8-carboxamide (CMPD 264);

N-(cyclopropylmethyl)-9-ethyl-6-[4-(2-oxo-2,3-dihydro-1H-imidazo[4,5-b]pyridin-1-yl)piperidin-1-yl]-9H-purine-8-carboxamide (CMPD 270);

N-(2-hydroxy-2-methylpropyl)-9-methyl-6-[4-(2-oxo-2,3-dihydro-1H-benzimidazol-1-yl)piperidin-1-yl]-9H-purine-8-carboxamide (CMPD 273);

6-(4-cyano-4-phenylpiperidin-1-yl)-N-(cyclopropylmethyl)-9-methyl-9H-purine-8-carboxamide (CMPD 275);

N-(cyclopropylmethyl)-6-[4-(4-{[2-(dimethylamino)ethyl]oxy}-2-oxo-2,3-dihydro-1H-benzimidazol-1-yl)piperidin-1-yl]-9-methyl-9H-purine-8-carboxamide (CMPD 276);

N-(cyclopropylmethyl)-9-methyl-6-[2-methyl-4-(2-oxo-2,3-dihydro-1H-benzimidazol-1-yl)piperidin-1-yl]-9H-purine-8-carboxamide (CMPD 277);

N-(cyclopropylmethyl)-6-[4-(4-fluoro-2-oxo-2,3-dihydro-1H-benzimidazol-1-yl)piperidin-1-yl]-9-methyl-9H-purine-8-carboxamide (CMPD 278);

N-(cyclopropylmethyl)-9-methyl-6-[4-(2-oxo-2,3-dihydro-1H-benzimidazol-1-yl)-3,6-dihydropyridin-1(2H)-yl]-9H-purine-8-carboxamide (CMPD 289);

9-ethyl-6-[4-(2-oxo-2,3-dihydro-1H-imidazo[4,5-b]pyridin-1-yl)piperidin-1-yl]-N-(2,2,2-trifluoroethyl)-9H-purine-8-carboxamide (CMPD 318);

9-ethyl-N-(trans-4-hydroxycyclohexyl)-6-[4-(2-oxo-2,3-dihydro-1H-imidazo[4,5-b]pyridin-1-yl)piperidin-1-yl]-9H-purine-8-carboxamide (CMPD 328); and N-(trans-4-hydroxycyclohexyl)-9-methyl-6-[4-(2-oxo-2,3-dihydro-1H-imidazo[4,5-b]pyridin-1-yl)piperidin-1-yl]-9H-purine-8-carboxamide (CMPD 329).

Example 6

Methyl 9-methyl-6-(2-oxo-1,2-dihydro-1'H-spiro[indole-3,4'-piperidin]-1'-yl)-9H-purine-8-carboxylate (Compound 76)

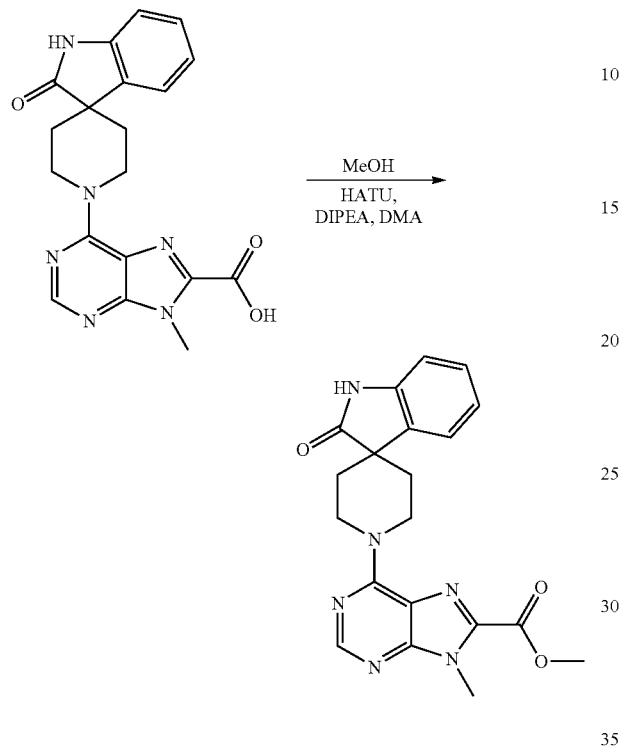

Methyl 9-methyl-6-(2-oxo-1,2-dihydro-1'H-spiro[indole-3,4'-piperidin]-1'-yl)-9H-purine-8-carboxylate Into 10 mL of anhydrous DMA in a 25 mL round bottomed flask were dissolved 9-methyl-6-(2-oxo-1,2-dihydro-1'H-spiro[indole-3,4'-piperidin]-1'-yl)-9H-purine-8-carboxylic acid (378 mg, 1.0 mmol, 1 equiv), methanol (203 μL, 5.0 mmol, 5 equiv), diisopropylethylamine (210 μL, 1.2 mmol, 1.2 equiv), and 2-(7-aza-1H-benzotriazol-1-yl)-1,1,3,3-tetramethyluronium hexafluorophosphate (HATU, 500 mg, 1.3 mmol, 1.3 equiv). The reaction was stirred for four hours then purified directly by preparative reverse-phase HPLC (acetonitrile/water with 1% formic acid), followed by concentration in vacuo and lyophilization to afford the desired material (65 mg) as a white powder. $^1$H NMR (400 MHz, DMSO-$d_6$): δ 10.46 (s, 1H), 8.36 (s, 1H), 7.45 (d, 1H), 7.18 (td, 1H), 6.93 (td, 1H), 6.84 (t, 1H), 3.96 (s, 3H), 3.90 (s, 3H), 1.83 (s, 4H). MS (EI) for $C_{20}H_{20}N_6O_3$: 393 (MH$^+$).

The following compounds were synthesized in an analogous fashion to the compounds described in example 6.

Methyl 9-methyl-6-[4-(2-oxo-2,3-dihydro-1H-benzimidazol-1-yl)piperidin-1-yl]-9H-purine-8-carboxylate (CMPD 78);

Cyclopropylmethyl 9-methyl-6-[4-(2-oxo-2,3-dihydro-1H-benzimidazol-1-yl)piperidin-1-yl]-9H-purine-8-carboxylate (CMPD 79); and Ethyl 9-methyl-6-[4-(2-oxo-2,3-dihydro-1H-benzimidazol-1-yl)piperidin-1-yl]-9H-purine-8-carboxylate (CMPD 80).

Example 7

1-[1-(8,9-Dimethyl-9H-purin-6-yl)piperidin-4-yl]-1,3-dihydro-2H-benzimidazol-2-one (Compound 81)

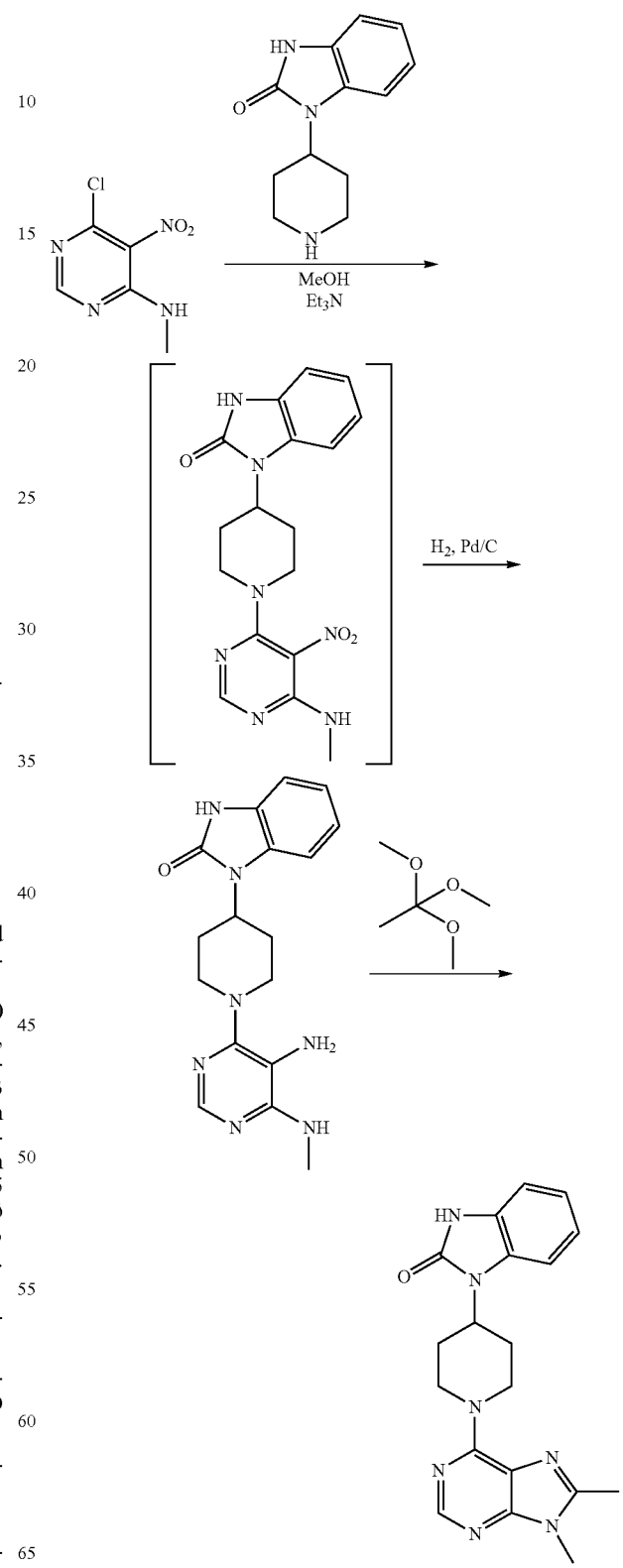

1-{1-[5-Amino-6-(methylamino)pyrimidin-4-yl] piperidin-4-yl}-1,3-dihydro-2H-benzimidazol-2-one To a suspension of 6-chloro-N-methyl-5-nitropyrimidin-4-amine (550 mg, 2.92 mmol) in methanol (11 mL) was added triethylamine (0.55 mL, 3.94 mmol) and 4-(2-keto-1-benzimidazolinyl)piperidine (638 mg, 2.94 mmol). The mixture was stirred at ambient temperature for 1 h and then 10 wt % Pd on C (wet) was added and the mixture was stirred under hydrogen for 1 h. The mixture was diluted with methanol and was filtered through Celite. The filtrate was concentrated and the resulting solid was triturated with a solution of 50% aqueous methanol. The methanol was removed in vacuo and the aqueous slurry was filtered and dried to afford 1-{1-[5-amino-6-(methylamino)pyrimidin-4-yl]piperidin-4-yl}-1,3-dihydro-2H-benzimidazol-2-one (842 mg, 2.48 mmol, 85% yield) as a peach colored solid. $^1$H NMR (400 MHz, DMSO-$d_6$): δ 10.86 (s, 1H), 7.82 (s, 1H), 7.43-7.36 (m, 1H), 7.01-6.94 (m, 3H), 6.29 (q, 1H), 4.31 (tt, 1H), 4.20 (s, 2H), 3.50 (br d, 2H), 2.85 (d, 3H), 2.74 (t, 2H), 2.54 (qd, 2H), 1.68 (dd, 2H). MS (EI) for $C_{17}H_{21}N_7O$: 340 (MH$^+$).

1-[1-(8,9-Dimethyl-9H-purin-6-yl)piperidin-4-yl]-1,3-dihydro-2H-benzimidazol-2-one To 1-{1-[5-amino-6-(methylamino)pyrimidin-4-yl]piperidin-4-yl}-1,3-dihydro-2H-benzimidazol-2-one (150 mg, 0.442 mmol) in acetonitrile (2 mL) was added camphorsulfonic acid (4.9 mg, 0.02 mmol) and trimethylorthoacetate (2 mL, 16.6 mmol). The mixture was heated at reflux for 15 h, then was cooled to ambient and was purified by preparative-HPLC to afford 1-[1-(8,9-dimethyl-9H-purin-6-yl)piperidin-4-yl]-1,3-dihydro-2H-benzimidazol-2-one as a beige solid (28 mg, 0.077 mmol, 17% yield).

$^1$H NMR (400 MHz, DMSO-$d_6$): δ10.83 (s, 1H), 8.21 (s, 1H), 7.15-7.08 (m, 1H), 6.96-6.89 (m, 3H), 5.55 (br s, 2H), 4.57-4.46 (m, 1H), 3.64 (s, 3H), 3.13 (t, 2H), 2.48 (s, 3H), 2.35-2.21 (m, 2H), 1.85-1.76 (m, 2H). MS (EI) for $C_{19}H_{21}N_7O$: 364 (MH$^+$).

The following compounds were synthesized in an analogous fashion to the compounds described in example 7.

1-[1-(8-ethyl-9-methyl-9H-purin-6-yl)piperidin-4-yl]-1,3-dihydro-2H-benzimidazol-2-one (CMPD 92);
1-[1-(8-butyl-9-methyl-9H-purin-6-yl)piperidin-4-yl]-1,3-dihydro-2H-benzimidazol-2-one (CMPD 335);
1-(1-{9-methyl-8-[(1E)-prop-1-en-1-yl]-9H-purin-6-yl}piperidin-4-yl)-1,3-dihydro-2H-benzimidazol-2-one (CMPD 144); and
1,1-dimethylethyl({9-methyl-6-[4-(2-oxo-2,3-dihydro-1H-benzimidazol-1-yl)piperidin-1-yl]-9H-purin-8-yl}methyl)carbamate (CMPD 339).

Example 8

1-{1-[9-Methyl-8-(trifluoromethyl)-9H-purin-6-yl] piperidin-4-yl}-1,3-dihydro-2H-benzimidazol-2-one (Compound 134)

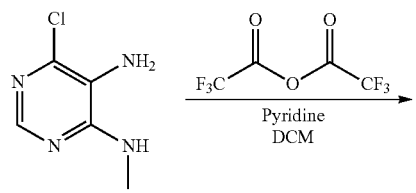

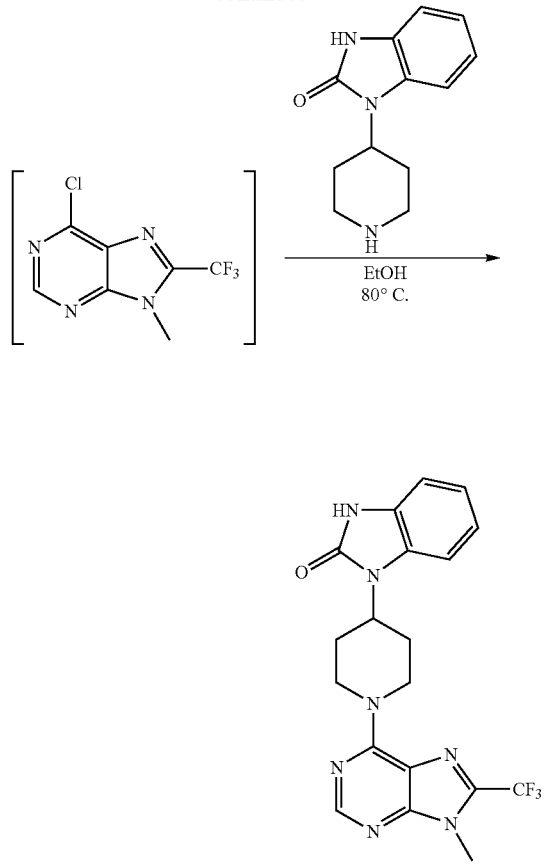

1-{1-[9-Methyl-8-(trifluoromethyl)-9H-purin-6-yl] piperidin-4-yl}-1,3-dihydro-2H-benzimidazol-2-one 6-Chloro-$N^4$-methylpyrimidine-4,5-diamine (100 mg, 0.63 mmol) was dissolved in dichloromethane (3 mL) along with pyridine (1.02 mL, 12.6 mmol) followed by the addition of trifluoroacetic anhydride (0.175 mL, 1.26 mmol). The reaction was stirred at room temperature overnight. Another 175 uL of anhydride was added and the reaction was stirred for 4 hours. The crude reaction mixture was diluted with dichloromethane and was washed with water. The organic layer was collected, was dried over magnesium sulfate, was filtered and was concentrated under reduced pressure to give 6-chloro-9-methyl-8-(trifluoromethyl)-9H-purine as an oil. This oil was dissolved in ethanol (3 mL) along with DIPEA (0.2 mL, 1.26 mmol) followed by the addition of 4-(2-keto-1-benzimidazolinyl)piperidine (205 mg, 0.95 mmol). The reaction was heated to 80° C. overnight. The product was purified by preparative HPLC to afford 1-{1-[9-methyl-8-(trifluoromethyl)-9H-purin-6-yl]piperidin-4-yl}-1,3-dihydro-2H-benzimidazol-2-one (46.5 mg, 0.112 mmol, 17% yield). $^1$H NMR (400 MHz, DMSO-$d_6$): δ10.85 (s, 1H), 8.40 (s, 1H), 7.20-7.14 (m, 1H), 6.98-6.89 (m, 3H), 5.55 (br, 2H), 4.56 (tt, 1H), 3.85 (d, 3H), 3.38-3.29 (m, 2H), 2.43-2.24 (m, 2H), 1.86 (br d, 2H). MS (EI) for $C_{19}H_{18}F_3N_7O$: 418 (MH$^+$).

Example 9

1-[1-(8-Acetyl-9-methyl-9H-purin-6-yl)piperidin-4-yl]-1,3-dihydro-2H-benzimidazol-2-one (Compound 95)

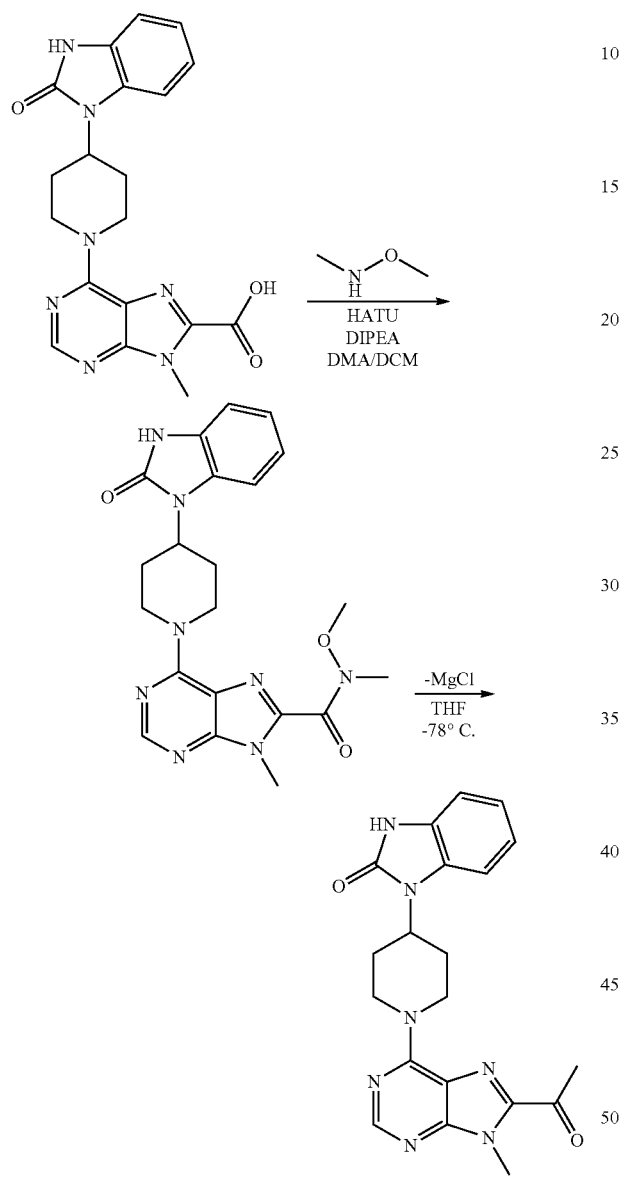

N-Methoxy-N,9-dimethyl-6-[4-(2-oxo-2,3-dihydro-1H-benzimidazol-1-yl)piperidin-1-yl]-9H-purine-8-carboxamide 9-Methyl-6-[4-(2-oxo-2,3-dihydro-1H-benzimidazol-1-yl)piperidin-1-yl]-9H-purine-8-carboxylic acid (450 mg, 1.14 mmol) was dissolved in dimethylacetamide (3 mL) and DIPEA (0.57 mL, 3.43 mmol). N,O-Dimethylhydroxylamine hydrochloride salt (123 mg, 1.26 mmol) was added to the solution, followed by dichloromethane (3 mL) and HATU (522 mg, 1.37 mmol). The reaction was stirred at room temperature for 1 hour. The crude reaction mixture was concentrated, diluted with 80 mL of dichloromethane, was washed with 2×50 mL of water and 3×50 mL of saturated potassium carbonate. The organic layer was collected, dried over magnesium sulfate, was filtered and was concentrated to afford N-methoxy-N,9-dimethyl-6-[4-(2-oxo-2,3-dihydro-1H-benzimidazol-1-yl)piperidin-1-yl]-9H-purine-8-carboxamide (quantitative yield) as an oil. $^1$H NMR (400 MHz, DMSO-d$_6$): δ 10.84 (s, 1H), 8.32 (s, 1H), 7.18-7.12 (m, 1H), 6.96-6.88 (m, 3H), 5.38 (br s, 2H), 4.55 (tt, 1H), 3.76 (s, 3H), 3.75 (s, 3H), 3.49-3.09 (m, 5H), 2.40-2.23 (m, 2H), 1.83 (br d, 2H). MS (EI) for C$_{21}$H$_{24}$N$_8$O$_3$: 437 (MH$^+$).

1-[1-(8-Acetyl-9-methyl-9H-purin-6-yl)piperidin-4-yl]-1,3-dihydro-2H-benzimidazol-2-one N-Methoxy-N,9-dimethyl-6-[4-(2-oxo-2,3-dihydro-1H-benzimidazol-1-yl)piperidin-1-yl]-9H-purine-8-carboxamide (30 mg, 0.07 mmol) was dissolved into THF (2 mL) under nitrogen and cooled to −78° C. Methylmagnesium chloride (3 M in THF; 0.046 mL, 0.14 mmol) was added to the reaction mixture. The reaction was stirred at −78° C. for 30 minutes and slowly warmed to room temperature. After 1 hour, the crude reaction mixture was concentrated, diluted with ethyl acetate, washed with water and saturated potassium carbonate. The organic layer was collected, was concentrated, was dissolved into methanol and was purified by preparative HPLC to afford 1-[1-(8-acetyl-9-methyl-9H-purin-6-yl)piperidin-4-yl]-1,3-dihydro-2H-benzimidazol-2-one (9.3 mg, 0.023 mmol, 34% yield). $^1$H NMR (400 MHz, DMSO-d$_6$): δ 10.85 (s, 1H), 8.35 (s, 1H), 7.20-7.14 (m, 1H), 6.96-6.88 (m, 3H), 6.27-4.92 (m, 2H), 4.66-4.45 (m, 1H), 3.93 (s, 3H), 3.42-3.20 (m, 2H), 2.63 (s, 3H), 2.42-2.26 (m, 2H), 1.87 (br d, 2H). MS (EI) for C$_{20}$H$_{21}$N$_7$O$_2$: 392 (MH$^+$).

The following compound was synthesized in an analogous fashion to the compounds described in example 9.

1-[1-(8-butanoyl-9-methyl-9H-purin-6-yl)piperidin-4-yl]-1,3-dihydro-2H-benzimidazol-2-one (CMPD 113).

Example 10

1-{1-[8-(1H-Imidazol-1-yl)-9-methyl-9H-purin-6-yl]piperidin-4-yl}-1,3-dihydro-2H-benzimidazol-2-one (Compound 124)

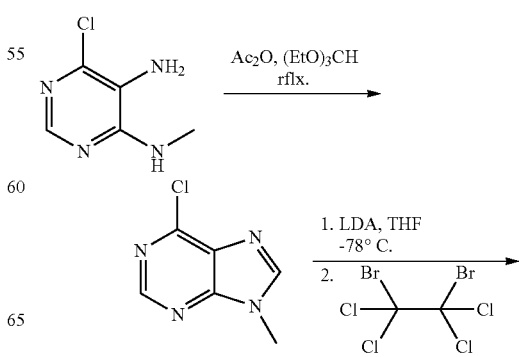

-continued

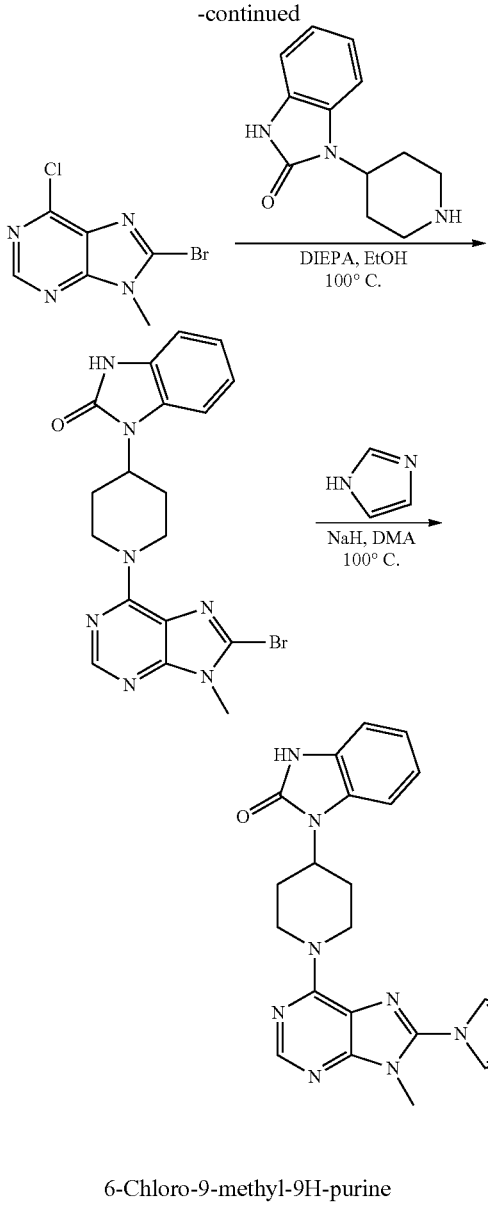

6-Chloro-9-methyl-9H-purine 6-chloro-N-4-methylpyrimidine-4,5-diamine (5 g, 31.53 mmol) was dissolved in acetic anhydride (20 mL) and triethylorthoformate (20 mL). The resulting mixture was warmed to reflux for 3 hours. Upon cooling, the reaction mixture was concentrated in vacuo and the residue was dissolved in hot benzene (200 mL), mixed with charcoal and filtered. The filtrate was concentrated to 30 mL and heated to dissolve all solids. 4 g of the title compound crystallized as yellow crystals. $^1$H NMR (400 MHz, DMSO-d$_6$): δ 8.73 (s, 1H), 8.62 (s, 1H), 3.84 (s, 3H).

8-Bromo-6-chloro-9-methyl-9H-purine

To a dry flask was added diisopropyl amine (1.6 mL, 11.42 mmol) and THF (15 mL). The solution was cooled to −78° C. and n-butyllithium (2.5M in hexanes, 4.5 mL, 11.25 mmol) was added dropwise. After stirring for 10 minutes at −78° C., the solution was warmed to 0° C. and allowed to stir for an additional 10 minutes. The solution was cooled back to −78° C. and 6-chloro-9-methyl-9H-purine (1.5 g, 8.9 mmol) was added as a suspension in THF (20 mL). After stirring for 20 minutes −78° C., 1,2-dibromotetrachloroethane was added (5.7 g, 17.5 mmol), and after an additional 20 minutes the reaction was quenched with the addition of sat. aq. NH$_4$Cl (15 mL). Upon warming to room temperature, the solution was diluted with ethyl acetate (75 mL) and the aqueous layer was discarded. The organics were washed with brine and dried using magnesium sulfate. The solvent was removed in vacuo to provide a brown solid that was purified by column chromatography (25-50% ethyl acetate in hexanes) to yield 1.493 g tan solid product. $^1$H NMR (400 MHz, DMSO-d$_6$): δ 8.84 (d, J=72.7 Hz, 1H), 3.76 (s, 3H).

1-[1-(8-Bromo-9-methyl-9H-purin-6-yl)piperidin-4-yl]-1,3-dihydro-2H-benzimidazol-2-one 8-bromo-6-chloro-9-methyl-9H-purine (175 mg, 0.71 mmol) was combined with 4-(2-keto-1-benzimidazolinyl)piperidine (185 mg, 0.85 mmol) and dissolved in ethanol (2 mL). The resulting solution was warmed to 100° C. in a sealed tube for 15 minutes. A precipitate formed which was collected and washed with ethanol. An amount of 225 mg of a tan solid was isolated, which was 80% pure an indicated by LCMS analysis. A portion of this material was purified by prep HPLC to provide 6 mg of a white solid. $^1$H NMR (400 MHz, DMSO-d$_6$): δ 10.80 (s, 1H), 8.21 (s, 1H), 7.14-7.00 (m, 1H), 6.88 (m, 3H), 5.38 (s, 2H), 4.48 (m, 1H), 3.62 (s, 3H), 3.13 (s, 2H), 2.25 (m, 2H), 1.78 (m, 2H). EI (MS) for $C_{18}H_{18}BrN_7O$, found 428.

1-{1-[8-(1H-imidazol-1-yl)-9-methyl-9H-purin-6-yl]piperidin-4-yl}-1,3-dihydro-2H-benzimidazol-2-one 1-[1-(8-Bromo-9-methyl-9H-purin-6-yl)piperidin-4-yl]-1,3-dihydro-2H-benzimidazol-2-one (50 mg, 0.12 mmol) was dissolved in ethanol (1 mL). To this solution was added imidazole (24 mg, 0.35 mmol) and diisopropylethylamine (39 µL, 0.23 mmol). This mixture was irradiated in the microwave at 180° C. for 6 hours. The ethanol was removed in vacuo and replaced by DMA (1 mL). To this solution was added 1 equiv. of sodium hydride. After heating to 100° C. for 1 hour, the mixture was filtered and purified by prep HPLC to obtain 24 mg of the desired product. $^1$H NMR (400 MHz, DMSO-d$_6$): δ 10.85 (s, 1H), 8.39-8.28 (m, 1H), 8.27-8.16 (m, 1H), 7.78 (m, 1H), 7.18 (m, 1H), 7.14 (m, 1H), 6.99-6.82 (m, 3H), 5.47 (s, 1H), 4.63-4.40 (m, 1H), 3.67 (s, 3H), 3.22 (m, 3H), 2.42-2.20 (m, 2H), 1.80 (m, 2H). EI (MS) for $C_{21}H_{21}N_9O$, found 416 (MH$^+$).

The following compounds were synthesized in an analogous fashion to the compounds described in example 10.

1-[1-(9-methyl-8-pyrrolidin-1-yl-9H-purin-6-yl)piperidin-4-yl]-1,3-dihydro-2H-benzimidazol-2-one (CMPD 126);

1-{1-[9-methyl-8-(1H-pyrrol-1-yl)-9H-purin-6-yl]piperidin-4-yl}-1,3-dihydro-2H-benzimidazol-2-one (CMPD 127);

1-{1-[8-(4-bromo-1H-imidazol-1-yl)-9-methyl-9H-purin-6-yl]piperidin-4-yl}-1,3-dihydro-2H-benzimidazol-2-one (CMPD 153);

1-(1-{9-methyl-8-[4-(trifluoromethyl)-1H-imidazol-1-yl]-9H-purin-6-yl}piperidin-4-yl)-1,3-dihydro-2H-benzimidazol-2-one (CMPD 165);

1-(1-{9-methyl-8-[4-(1-methylethenyl)-1H-imidazol-1-yl]-9H-purin-6-yl}piperidin-4-yl)-1,3-dihydro-2H-benzimidazol-2-one (CMPD 167); and 1-{1-[8-(1H-benzimidazol-1-yl)-9-methyl-9H-purin-6-yl]piperidin-4-yl}-1,3-dihydro-2H-benzimidazol-2-one (CMPD 259).

Example 11

1-{1-[8-(1-Ethyl-1H-pyrazol-4-yl)-9-methyl-9H-purin-6-yl]piperidin-4-yl}-1,3-dihydro-2H-benzimidazol-2-one (Compound 146)

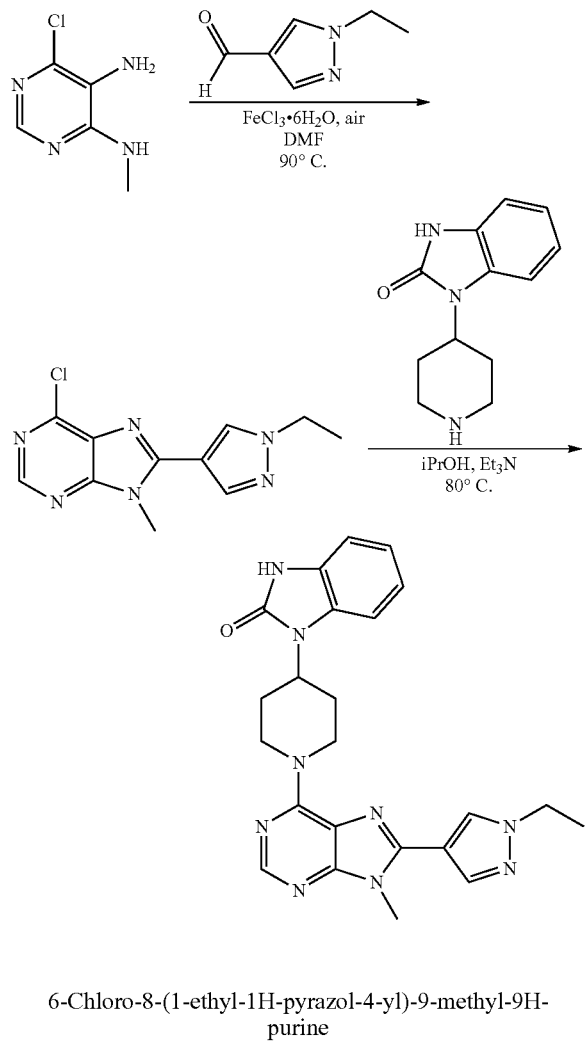

6-Chloro-8-(1-ethyl-1H-pyrazol-4-yl)-9-methyl-9H-purine

To a solution of 6-chloro-$N^4$-methylpyrimidine-4,5-diamine (300 mg, 1.9 mmol) in anhydrous DMF (8 mL) were added 1-ethyl-1H-pyrazole-4-carbaldehyde (236 mg, 1.9 mmol) and Iron (III) chloride hexahydrate (0.51 g, 1.9 mmol). The dark brown solution was heated to 90° C. for 14 hour in an open air vessel. The reaction mixture was cooled to room temperature and poured over ice (20 g). The resulting precipitate was collected by vacuum filtration, and triturated with 10 mL of ethanol at 50° C. for 30 min. The solids were collected by vacuum filtration to give 514 mg of the title compound. $^1$H NMR (400 MHz, DMSO-$d_6$): δ 8.66 (t, 2H), 8.19 (s, 1H), 4.25 (q, 2H), 3.95 (s, 3H), 1.43 (t, 3H); MS (EI) for $C_{11}H_{11}ClN_6$: 263.3 (MH$^+$).

1-{1-[8-(1-Ethyl-1H-pyrazol-4-yl)-9-methyl-9H-purin-6-yl]piperidin-4-yl}-1,3-dihydro-2H-benzimidazol-2-one To a solution of 1-piperidin-4-yl-1,3-dihydro-2H-benzimidazol-2-one (0.1 g, 0.33 mmol) in an anhydrous isopropanol (8 mL) and triethylamine (0.2 mL) was added 6-chloro-8-(1-ethyl-1H-pyrazol-4-yl)-9-methyl-9H-purine (65 mg, 0.25 mmol). The reaction mixture was heated to 80° C. for 16 hours, and cooled to room temperature. The resulting precipitates were collected by vacuum filtration, and triturated with 15 mL of ethanol at 75° C. for 30 min. The solids were collected by vacuum filtration to give 107 mg (97% yield) of the title compound. $^1$H-NMR (400 MHz, DMSO-$d_6$): δ 10.86 (s, 1H), 8.44 (s, 1H), 8.25 (s, 1H), 8.03 (d, 1H), 7.13 (dd, 1H), 6.93 (m, 3H), 5.61 (s, 2H), 4.53 (dd, 1H), 4.22 (q, 2H), 3.84 (s, 3H), 3.18 (s, 2H), 2.33 (m, 2H), 1.82 (d, 2H), 1.40 (t, 3H); MS (EI) for $C_{23}H_{25}N_9O$: 444.3 (MH$^+$).

Example 12

1-{1-[9-Methyl-8-(1-methyl-1H-pyrazol-4-yl)-9H-purin-6-yl]piperidin-4-yl}-1,3-dihydro-2H-benzimidazol-2-one (Compound 149)

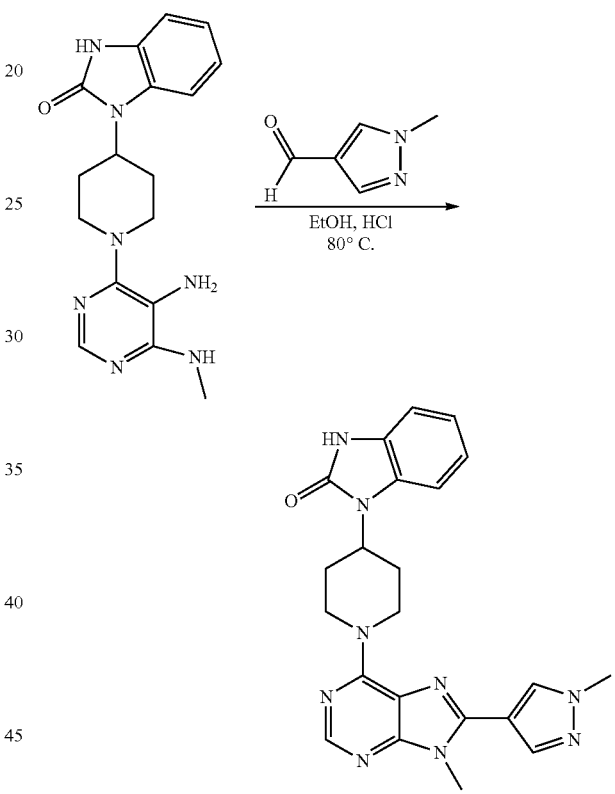

1-{1-[9-Methyl-8-(1-methyl-1H-pyrazol-4-yl)-9H-purin-6-yl]piperidin-4-yl}-1,3-dihydro-2H-benzimidazol-2-one To a solution of 1-(1-(5-amino-6-(methylamino)pyrimidin-4-yl)piperidin-4-yl)-1H-benzo[d]imidazol-2(3H)-one (70 mg, 0.2 mmol) in anhydrous ethanol (8 mL) were added 1-methyl-1H-pyrazole-4-carbaldehyde (34 mg, 0.3 mmol) and catalytic amount of hydrochloric acid (0.05 mL, 4M HCl in Dioxane, Aldrich). The reaction mixture was heated to 80° C. for 18 hours. The resulting precipitate was collected by vacuum filtration, washed with ethanol (2 mL) and dried under reduced pressure, to give 62.6 mg (70% yield) of the title compound. $^1$H NMR (400 MHz, DMSO-$d_6$): δ 10.84 (s, 1H), 8.41 (s, 1H), 8.25 (s, 1H), 8.02 (s, 1H), 7.13 (dd, 1H), 6.93 (m, 3H), 4.53 (m, 1H), 3.92 (s, 3H), 3.81 (d, 3H), 3.33 (m, 2H), 3.24 (m, 2H), 2.33 (m, 2H), 1.82 (d, 2H); MS (EI) for $C_{22}H_{23}N_9O$: 430.4 (MH$^+$).

Example 13

1-(1-{8-[1-(Cyclobutylmethyl)-1H-pyrazol-4-yl]-9-methyl-9H-purin-6-yl}piperidin-4-yl)-1,3-dihydro-2H-benzimidazol-2-one (Compound 231)

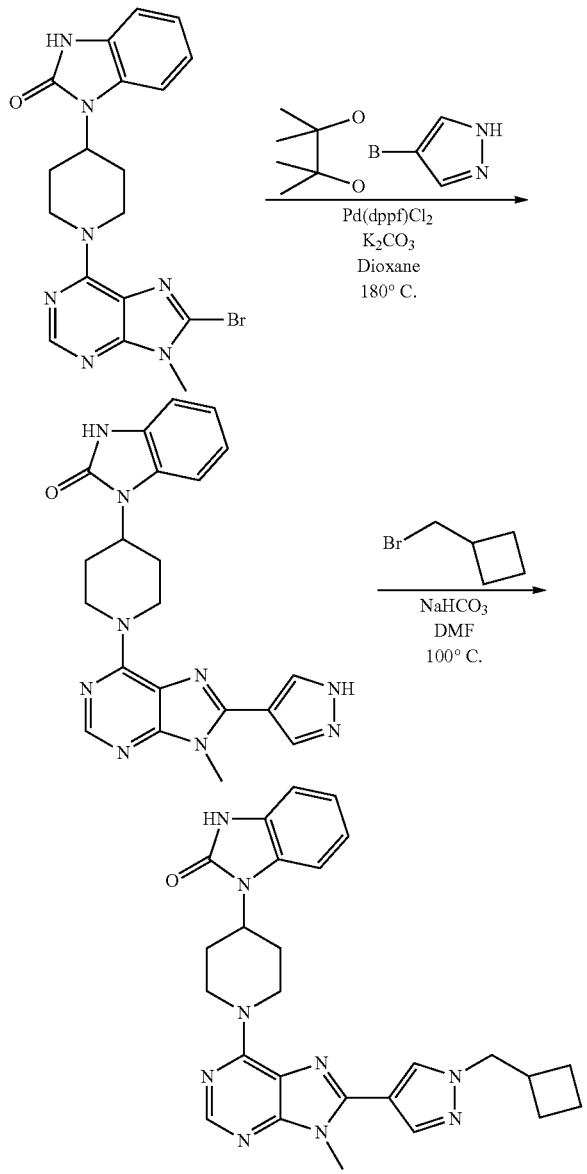

1-{1-[9-Methyl-8-(1H-pyrazol-4-yl)-9H-purin-6-yl]piperidin-4-yl}-1,3-dihydro-2H-benzimidazol-2-one To a solution of Pyrazole-4-boronic acid pinacol ester (181 mg, 0.93 mmol) in dioxane (1.5 mL) and water (0.2 mL) were added 1-(1-(8-bromo-9-methyl-9H-purin-6-yl)piperidin-4-yl)-1H-benzo[d]imidazol-2(3H)-one (100 mg, 0.23 mmol), Pd(dppf)Cl$_2$ (19 mg, 0.02 mmol), and tribasic potassium phosphate (297 mg, 1.4 mmol). The reaction mixture was heated in a microwave reactor to 180° C. for 60 min. The product was purified by preparatory HPLC (reverse-phase, acetonitrile/water with 0.1% formic acid) to give 60 mg (62.8% yield) of the title compound. $^1$H NMR (400 MHz, DMSO-d$_6$): δ 13.40 (s, 1H), 10.81 (d, 1H), 8.42 (s, 1H), 8.19-8.00 (m, 1H), 7.13 (dd, 1H), 6.99-6.88 (m, 3H), 4.60- 4.47 (m, 1H), 3.84 (s, 3H), 3.18 (t, 2H), 2.40-2.25 (m, 2H), 1.80 (t, 2H); MS (EI) for C$_{21}$H$_{21}$N$_9$O: 416.4 (MH$^+$).

1-(1-{8-[1-(Cyclobutylmethyl)-1H-pyrazol-4-yl]-9-methyl-9H-purin-6-yl}piperidin-4-yl)-1,3-dihydro-2H-benzimidazol-2-one To a solution of 1-{1-[9-methyl-8-(1H-pyrazol-4-yl)-9H-purin-6-yl]piperidin-4-yl}-1,3-dihydro-2H-benzimidazol-2-one (30 mg, 0.07 mmol) in DMF (0.5 mL) were added (bromomethyl)cyclobutane (0.02 mL, 0.18 mmol), and sodium bicarbonate (9 mg, 0.11 mmol). The reaction mixture was heated to 100° C. for 24 hours. The product was purified by preparatory HPLC (reverse-phase, acetonitrile/water with 0.1% formic acid) to give 7 mg (23% yield) of the title compound. $^1$H NMR (400 MHz, DMSO-d$_6$): δ 10.85 (s, 1H), 8.42 (s, 1H), 8.25 (s, 1H), 8.01 (t, 1H), 7.13 (dd, 1H), 6.95-6.90 (m, 3H), 4.62-4.45 (m, 1H), 4.21 (d, 2H), 3.86-3.82 (m, 3H), 2.79 (dt, 1H), 2.40-2.25 (m, 2H), 2.01-1.92 (m, 2H), 1.87-1.70 (m, 6H); MS (EI) for C$_{26}$H$_{29}$N$_9$O: 484.5 (MH$^+$).

Example 14

1'-[8-(1-Ethyl-1H-pyrazol-4-yl)-9-methyl-9H-purin-6-yl]spiro[indole-3,4'-piperidin]-2(1H)-one (Compound 237)

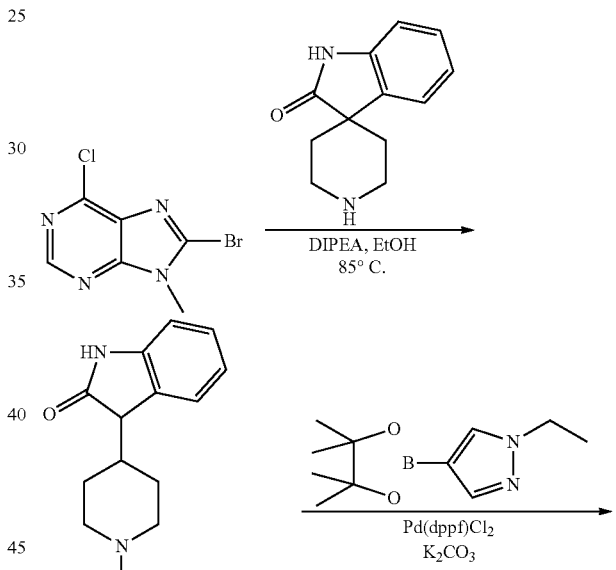

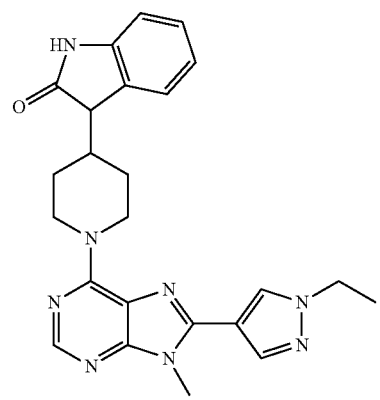

1'-(8-Bromo-9-methyl-9H-purin-6-yl)spiro[indoline-3,4-piperidin]-2-one

To a solution of spiro(indoline-3,4'-piperidin)-2-one hydrochloride (1.04 g, 4.42 mmol) in an anhydrous ethanol (15 mL) and diisopropylethyl amine (1.5 mL) was added 8-bromo-6-chloro-9-methyl-9H-purine (1.0 g, 4.04 mmol). The reaction mixture was heated to 85° C. for 30 min. The resulting solution was cooled to room temperature and the precipitate was collected by vacuum filtration, washed with ethanol (2 mL) and dried under reduced pressure. The resulting solid was triturated with 15 mL of ethanol at 80° C. for 30 min. The precipitate was collected by vacuum filtration to give 940 mg (57% yield) of the title compound. MS (EI) for $C_{18}H_{17}BrN_6O$: 413.4 (MH$^+$).

1'-[8-(1-Ethyl-1H-pyrazol-4-yl)-9-methyl-9H-purin-6-yl]spiro[indole-3,4'-piperidin]-2(1H)-one To a solution of 1-ethyl-1H-pyrazole-4-boronic acid pinacol ester (134 mg, 0.60 mmol) in dioxane (1.5 mL) and water (0.2 mL) were added 1'-(8-bromo-9-methyl-9H-purin-6-yl) spiro[indoline-3A'-piperidin]-2-one (100 nig, 0.24 mmol), Pd(dppf)Cl$_2$ (20 mg, 0.02 mmol), and tribasic potassium phosphate (153 mg, 0.72 mmol). The reaction mixture was heated in a microwave reactor to 150° C. for 10 min. The product was purified by preparatory HPLC (reverse-phase, acetonitrile/water with 0.1% formic acid) to give 48 mg (46.7% yield) of the title compound. $^1$H NMR (400 MHz, DMSO-d$_6$): δ 10.45 (s, 1H), 8.42 (s, 1H), 8.24 (s, 1H), 8.05 (s, 1H), 7.47 (d, 1H), 7.18 (t, 1H), 6.93 (t, 1H), 6.85 (d, 1H), 4.21 (q, 2H), 3.84 (s, 3H), 1.82 (m, 4H), 1.41 (t, 3H); MS (EI) for $C_{23}H_{24}N_8O$: 429.4 (MH$^+$).

Example 15

1-[9-Methyl-8-(1-methyl-1H-pyrazol-4-yl)-9H-purin-6-yl]-4-phenylpiperidine-4-carbonitrile (Compound 263)

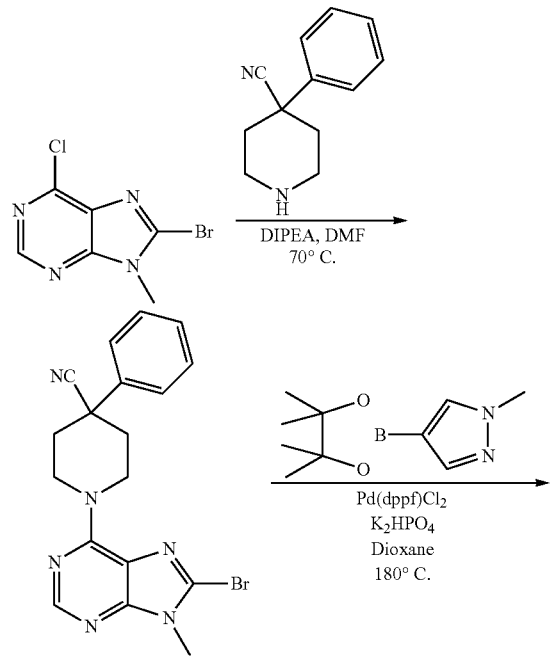

1-(8-Bromo-9-methyl-9H-purin-6-yl)-4-phenylpiperidine-4-carbonitrile

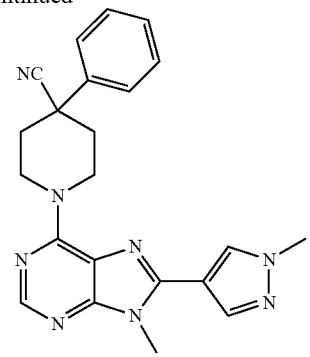

8-bromo-6-chloro-9-methyl-9H-purine (200 mg, 0.80 mmol) was dissolved in DMF (4 mL). To this solution was added diisopropylethylamine (0.21 mL, 1.21 mmol). To this stirred mixture was added 4-cyano-4-phenylpiperidine hydrochloride (165 mg, 0.88 mmol) dissolved in a small amount of DMF. The resulting mixture was heated to 70° C. and stirred for 30 minutes. The solvent was removed in vacuo and the crude material was used without purification.

1-[9-Methyl-8-(1-methyl-1H-pyrazol-4-yl)-9H-purin-6-yl]-4-phenylpiperidine-4-carbonitrile 1-(8-bromo-9-methyl-9H-purin-6-yl)-4-phenylpiperidine-4-carbonitrile (400 mg, 1.0 mmol), 1-Methylpyrazole-4-boronic acid pinacol ester (419 mg, 2.0 mmol), and potassium phosphate (427 mg, 2.0 mmol) were suspended in dioxane (5 mL). To that mixture was added Pd(dppf)Cl$_2$ (82 mg, 0.10 mmol) and water. This suspension was heated to 150° C. in the microwave for 30 minutes. Upon cooling, the resulting mixture was filtered through Celite and a PL-thiol SPE cartridge. The filtrate was then purified by prep HPLC to afford 2 mg of the desired product. $^1$H NMR (400 MHz, DMSO-d$_6$): δ 8.42 (s, 1H), 8.26 (s, 1H), 8.03 (s, 1H), 7.59-7.51 (m, 2H), 7.42 (m, 2H), 7.35 (m, 1H), 5.62 (s, 2H), 3.93 (s, 3H), 3.84 (s, 3H), 3.34 (m, 4H), 2.27 (m, 2H), 2.08 (m, 2H). EI (MS) for $C_{22}H_{22}N_8$: 399.29 (MH$^+$).

Example 16

1-{1-[8-(1-Ethyl-5-methyl-1H-pyrazol-4-yl)-9-methyl-9H-purin-6-yl]piperidin-4-yl}-1,3-dihydro-2H-imidazo[4,5-b]pyridin-2-one (Compound 337)

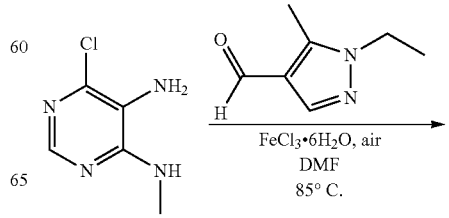

1H), 7.95 (s, 1H), 7.85 (d, 1H), 7.47 (d, 1H), 6.92 (dd, 1H), 5.60 (broad s, 2H), 4.55 (m, 1H), 4.14 (q, 2H), 3.77 (s, 3H), 3.22 (m, 2H), 2.51 (s, 3H), 2.26 (m, 2H), 1.86 (d, 2H), 1.33 (t, 3H); MS (EI) for $C_{23}H_{26}N_{10}O$: 459.3 (MH$^+$).

Example 17

9-Methyl-8-(1-methyl-1H-pyrazol-4-yl)-6-(4-{3-[(2-oxo-2-piperidin-1-ylethyl)oxy]phenyl}piperazin-1-yl)-9H-purine (Compound 357)

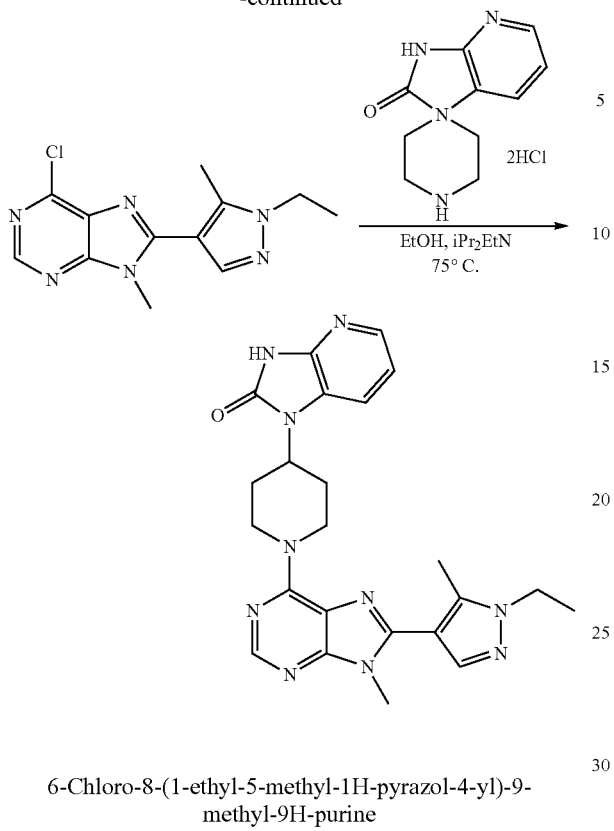

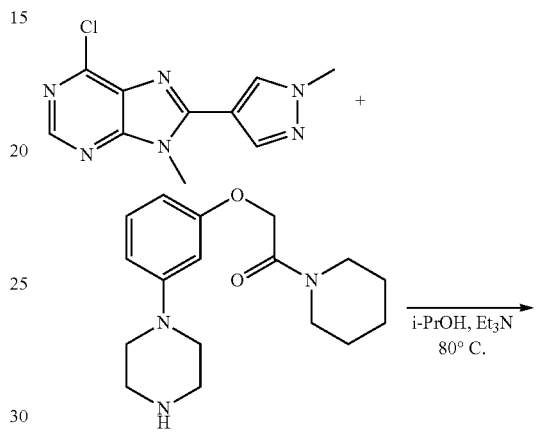

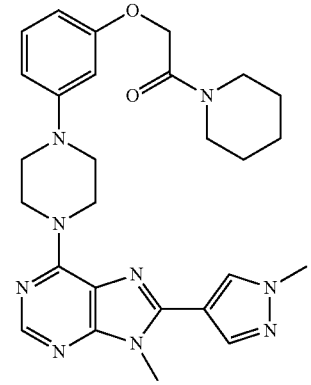

6-Chloro-8-(1-ethyl-5-methyl-1H-pyrazol-4-yl)-9-methyl-9H-purine

To a solution of 6-chloro-$N^4$-methylpyrimidine-4,5-diamine (355 mg, 2.25 mmol) in anhydrous DMF (8 mL) were added 1-ethyl-1H-5-methyl-pyrazole-4-carbaldehyde (340 mg, 2.46 mmol, Alinda Chemical) and Iron (III) chloride hexahydrate (0.61 g, 2.25 mmol). The dark brown solution was heated to 85° C. for 14 hour in an open air vessel. The reaction mixture was cooled to room temperature and poured over ice (5 g). The resulting precipitate was collected by vacuum filtration, and triturated with 5 mL of ethanol at 50° C. for 30 min. The solids were collected by vacuum filtration to give 465 mg (74.8% yield) of the title compound. $^1$H NMR (400 MHz, DMSO-d$_6$): δ 8.67 (s, 1H), 8.09 (s, 1H), 4.18 (q, 2H), 3.89 (s, 3H), 2.63 (s, 3H), 1.35 (t, 3H); MS (EI) for $C_{12}H_{13}ClN_6$: 277.3 (MH$^+$).

1-{1-[8-(1-Ethyl-5-methyl-1H-pyrazol-4-yl)-9-methyl-9H-purin-6-yl]piperidin-4-yl}-1,3-dihydro-2H-imidazo[4,5-b]pyridin-2-one To a solution of 1-piperidin-4-yl-1,3-dihydro-2H-imidazolo[4,5-b]pyridin-2-one dihydrochloride (0.22 g, 0.78 mmol) in an anhydrous ethanol (8 mL) and diisopropylethylamine (0.56 mL) was added 6-chloro-8-(1-ethyl-5-methyl-1H-pyrazol-4-yl)-9-methyl-9H-purine (0.18 g, 0.65 mmol). The reaction mixture was heated to 75° C. for 18 hours. The resulting solution was cooled to room temperature, and concentrated under reduced pressure. The solids were dissolved in dichloromethane (15 mL), and the solution was washed with water (10 mL). The organic layer was concentrated under reduced pressure. The resulting solids were collected by vacuum filtration, and triturated with 5 mL of ethanol at 75° C. for 30 min. The precipitate was collected by vacuum filtration to give 218 mg (73% yield) of the title compound. $^1$H-NMR (400 MHz, DMSO-d$_6$): δ 11.54 (s, 1H), 8.25 (s, 9-Methyl-8-(1-methyl-1H-pyrazol-4-yl)-6-(4-{3-[(2-oxo-2-piperidin-1-ylethyl)oxy]phenyl}piperazin-1-yl)-9H-purine A stirred solution of 6-chloro-9-methyl-8-(1-methyl-1H-pyrazol-4-yl)-9H-purine (30 mg, 0.12 mmol), 2-(3-(piperazin-1-yl)phenoxy)-1-(piperidin-1-yl)ethanone (45.5 mg, 0.15 mmol), and triethylamine (84.0 uL, 0.60 mmol) in isopropyl alcohol (2.0 mL) were heated to 80° C. for 16 hours. The reaction mixture was cooled to room temperature and concentrated under reduced pressure. The product was purified by preparatory HPLC (reverse-phase, acetonitrile/water with 0.1% formic acid) to give 6.1 mg (10% yield) of the title compound. $^1$H NMR (400 MHz, DMSO-d$_6$): δ 8.44 (s, 1H), 8.27-8.25 (m, 1H), 8.05 (s, 1H), 7.12 (t, 1H), 6.62 (dd, 1H), 6.55 (t, 1H), 6.39-6.35 (m, 1H), 4.73 (s, 2H), 3.96 (s, 3H), 3.85 (s, 3H), 3.46-3.37 (m, 4H), 3.30-3.24 (m, 6H), 3.17 (d, 2H), 1.63-1.48 (m, 4H), 1.43 (s, 2H). MS (EI) for $C_{27}H_{33}N_9O_2$: 516.7 (MH$^+$).

Example 18

6-(4-{4-[(Cyclopropylmethyl)oxy]phenyl}piperazin-1-yl)-9-methyl-8-(1-methyl-1H-pyrazol-4-yl)-9H-purine (Compound 360)

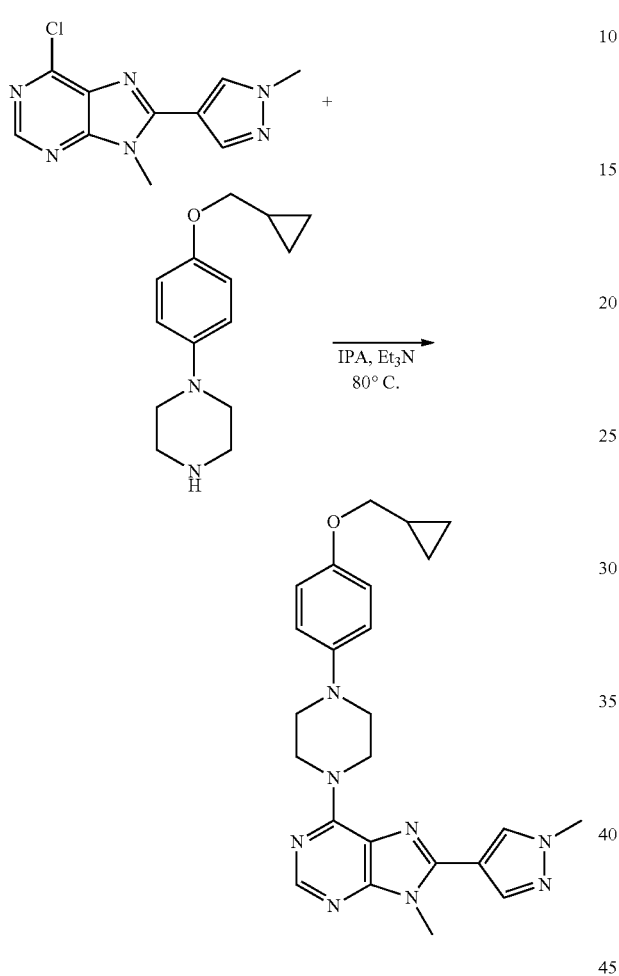

6-(4-{4-[(Cyclopropylmethyl)oxy]phenyl}piperazin-1-yl)-9-methyl-8-(1-methyl-1H-pyrazol-4-yl)-9H-purine A stirred solution of 6-chloro-9-methyl-8-(1-methyl-1H-pyrazol-4-yl)-9H-purine (30 mg, 0.12 mmol), 1-(4-(cyclopropylmethoxy)phenyl)piperazine (34.8 mg, 0.15 mmol), and triethylamine (84.0 uL, 0.60 mmol) in isopropyl alcohol (2.0 mL) were heated to 80° C. for 16 hours. The reaction mixture was cooled to room temperature and concentrated under reduced pressure. The product was purified by preparatory HPLC (reverse-phase, acetonitrile/water with 0.1% formic acid) to give 16.1 mg (30% yield) of the title compound.

$^1$H NMR (400 MHz, DMSO-$d_6$): δ 8.44 (s, 1H), 8.27-8.23 (m, 1H), 8.05 (s, 1H), 6.97-6.91 (m, 2H), 6.86-6.79 (m, 2H), 3.96 (s, 3H), 3.85 (s, 3H), 3.73 (d, 2H), 3.16-3.08 (m, 4H), 1.24-1.12 (m, 1H), 0.58-0.51 (m, 2H), 0.33-0.23 (m, 2H). MS (EI) for $C_{24}H_{28}N_8O$: 445.7 (MH$^+$).

Example 19

3-Methyl-N-[(2-{4-[9-methyl-8-(1-methyl-1H-pyrazol-4-yl)-9H-purin-6-yl]piperazin-1-yl}phenyl)methyl]benzamide (Compound 363)

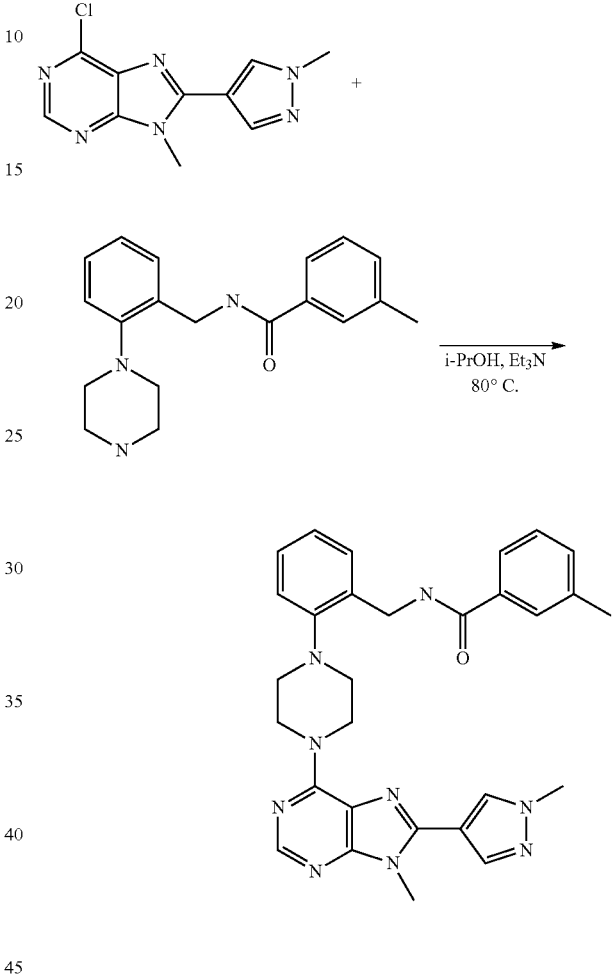

3-Methyl-N-[(2-{4-[9-Methyl-8-(1-methyl-1H-pyrazol-4-yl)-9H-purin-6-yl]piperazin-1-yl}phenyl)methyl]benzamide A stirred solution of 6-chloro-9-methyl-8-(1-methyl-1H-pyrazol-4-yl)-9H-purine (30 mg, 0.12 mmol), 3-methyl-N-(2-(piperazin-1-yl)benzyl)benzamide (46.4 mg, 0.15 mmol), and triethylamine (84.0 uL, 0.60 mmol) in isopropyl alcohol (2.0 mL) were heated to 80° C. for 16 hours. The reaction mixture was cooled to room temperature and concentrated under reduced pressure. The product was purified by preparatory HPLC (reverse-phase, acetonitrile/water with 0.1% formic acid) to give 31.5 mg (50% yield) of the title compound.

$^1$H NMR (400 MHz, DMSO-$d_6$) δ 8.92 (t, 1H), 8.42 (s, 1H), 8.25 (s, 1H), 8.03 (s, 1H), 7.74 (s, 1H), 7.71 (dd, 1H), 7.35 (dd, 1.7 Hz, 2H), 7.24 (dd, 1H), 7.22-7.18 (m, 1H), 7.14 (d, 1H), 7.09-7.03 (m, 1H), 4.66 (d, 2H), 3.93 (s, 3H), 3.84 (s, 3H), 3.00 (t, 4H), 2.35 (s, 3H). MS (EI) for $C_{29}H_{31}N_9O$: 522.8 (ar).

Example 20

6-(4-([5-Chloro-2-(methyloxy)phenyl]sulfonyl)piperazin-1-yl)-9-methyl-8-(1-methyl-1H-pyrazol-4-yl)-9H-purine (Compound 388)

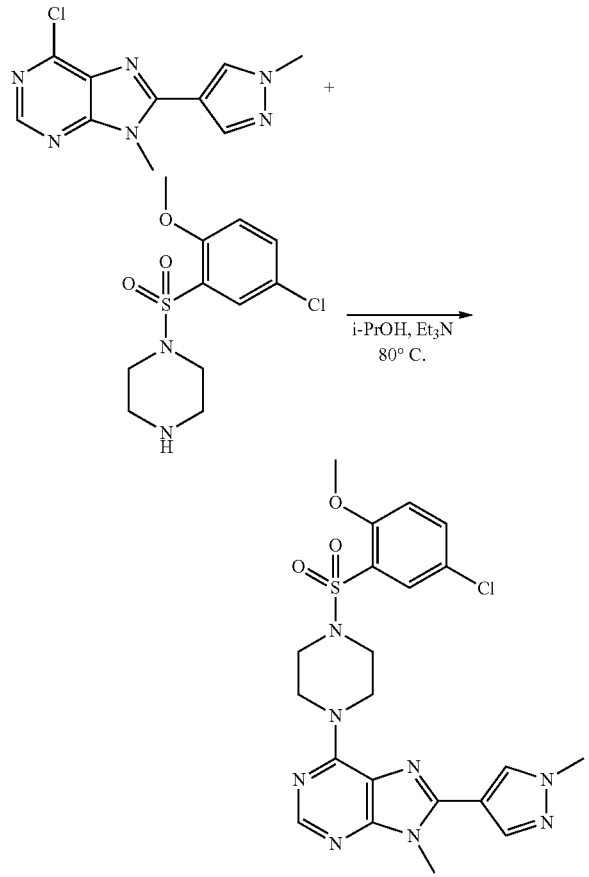

6-(4-{[5-Chloro-2-(methyloxy)phenyl]sulfonyl}piperazin-1-yl)-9-methyl-8-(1-methyl-1H-pyrazol-4-yl)-9H-purine A stirred solution of 6-chloro-9-methyl-8-(1-methyl-1H-pyrazol-4-yl)-9H-purine (30 mg, 0.12 mmol), 1-(5-chloro-2-methoxyphenylsulfonyl)piperazine (43.6 mg, 0.15 mmol, Oakwood Products, Inc.), and triethylaminem (84.0 uL, 0.60 mmol) in isopropyl alcohol (2.0 mL) were heated to 80° C. for 16 hours. The resulting precipitate was collected by vacuum filtration, washed with ethanol (2 mL), water (2 mL) and diethyl ether (2 mL) and dried under reduced pressure, to give 29.6 mg (49% yield) of the title compound. $^1$H NMR (400 MHz, DMSO-$d_6$) δ 8.43 (s, 1H), 8.23 (s, 1H), 8.05 (s, 1H), 7.70 (dt, 2H), 7.27 (d, 1H), 3.95 (s, 3H), 3.88 (s, 3H), 3.83 (s, 3H), 3.31-3.25 (m, 4H). MS (EI) for $C_{21}H_{23}ClN_8O_3S$: 503.7 (MH$^+$).

The following compounds were synthesized in an analogous fashion to the compounds described in examples 11-20:

1-{1-[9-methyl-8-(5-methylfuran-2-yl)-9H-purin-6-yl]piperidin-4-yl}-1,3-dihydro-2H-benzimidazol-2-one (CMPD 115);

1-[1-(8-furan-2-yl-9-methyl-9H-purin-6-yl)piperidin-4-yl]-1,3-dihydro-2H-benzimidazol-2-one (CMPD 116);

1-{1-[9-methyl-8-(3-methylfuran-2-yl)-9H-purin-6-yl]piperidin-4-yl}-1,3-dihydro-2H-benzimidazol-2-one (CMPD 128);

1-{1-[9-methyl-8-(1,3-oxazol-5-yl)-9H-purin-6-yl]piperidin-4-yl}-1,3-dihydro-2H-benzimidazol-2-one (CMPD 135);

1-{1-[9-methyl-8-(1-propyl-1H-pyrazol-4-yl)-9H-purin-6-yl]piperidin-4-yl}-1,3-dihydro-2H-benzimidazol-2-one (CMPD 147);

1-(1-{9-methyl-8-[1-(2-methylpropyl)-1H-pyrazol-4-yl]-9H-purin-6-yl}piperidin-4-yl)-1,3-dihydro-2H-benzimidazol-2-one (CMPD 148);

1-(1-{9-methyl-8-[1-(1-methylethyl)-1H-pyrazol-4-yl]-9H-purin-6-yl}piperidin-4-yl)-1,3-dihydro-2H-benzimidazol-2-one (CMPD 152);

1-{1-[9-methyl-8-(1H-pyrrol-3-yl)-9H-purin-6-yl]piperidin-4-yl}-1,3-dihydro-2H-benzimidazol-2-one (CMPD 166);

1-{1-(8-[1-(2-hydroxyethyl)-1H-pyrazol-4-yl]-9-methyl-9H-purin-6-yl}piperidin-4-yl)-1,3-dihydro-2H-benzimidazol-2-one (CMPD 178);

1-{1-[9-methyl-8-(1,3-oxazol-4-yl)-9H-purin-6-yl]piperidin-4-yl}-1,3-dihydro-2H-benzimidazol-2-one (CMPD 179);

ethyl (4-{9-methyl-6-[4-(2-oxo-2,3-dihydro-1H-benzimidazol-1-yl)piperidin-1-yl]-9H-purin-8-yl}-1H-pyrazol-1-yl)acetate (CMPD 181);

1-(1-{9-methyl-8-[1-(3-methylbutyl)-1H-pyrazol-4-yl]-9H-purin-6-yl}piperidin-4-yl)-1,3-dihydro-2H-benzimidazol-2-one (CMPD 233);

1'-[9-methyl-8-(1-propyl-1H-pyrazol-4-yl)-9H-purin-6-yl]spiro[indole-3,4'-piperidin]-2(1H)-one (CMPD 234);

1'-[9-methyl-8-(1H-pyrazol-4-yl)-9H-purin-6-yl]spiro[indole-3,4'-piperidin]-2(1H)-one (CMPD 238);

1'-[9-methyl-8-(1-methyl-1H-pyrazol-4-yl)-9H-purin-6-yl]spiro[indole-3,4'-piperidin]-2(1H)-one (239);

1-{1-[8-(1,5-dimethyl-1H-pyrazol-4-yl)-9-methyl-9H-purin-6-yl]piperidin-4-yl}-1,3-dihydro-2H-benzimidazol-2-one (CMPD 241);

1-{1-[9-methyl-8-(5-methyl-1H-pyrazol-4-yl)-9H-purin-6-yl]piperidin-4-yl}-1,3-dihydro-2H-benzimidazol-2-one (CMPD 242);

1-{1-[9-ethyl-8-(1-methyl-1H-pyrazol-4-yl)-9H-purin-6-yl]piperidin-4-yl}-1,3-dihydro-2H-benzimidazol-2-one (CMPD 243);

1-{1-[9-ethyl-8-(1-ethyl-1H-pyrazol-4-yl)-9H-purin-6-yl]piperidin-4-yl}-1,3-dihydro-2H-benzimidazol-2-one (CMPD 244);

1'-[9-ethyl-8-(1-methyl-1H-pyrazol-4-yl)-9H-purin-6-yl]spiro[indole-3,4'-piperidin]-2(1H)-one (CMPD 245);

1'-[8-(1,5-dimethyl-1H-pyrazol-4-yl)-9-methyl-9H-purin-6-yl]spiro[indole-3,4'-piperidin]-2(1H)-one (CMPD 246);

1'-[9-methyl-8-(5-methyl-1H-pyrazol-4-yl)-9H-purin-6-yl]spiro[indole-3,4'-piperidin]-2(1H)-one (CMPD 247);

1'-[9-ethyl-8-(1-ethyl-1H-pyrazol-4-yl)-9H-purin-6-yl]spiro[indole-3,4'-piperidin]-2(1H)-one (CMPD 250);

1'-[9-ethyl-8-(1-propyl-1H-pyrazol-4-yl)-9H-purin-6-yl]spiro[indole-3,4'-piperidin]-2(1H)-one (CMPD 251);

1'-[9-ethyl-8-(1H-pyrazol-4-yl)-9H-purin-6-yl]spiro[indole-3,4'-piperidin]-2(1H)-one; (CMPD 252)

1-{1-[9-ethyl-8-(1-propyl-1H-pyrazol-4-yl)-9H-purin-6-yl]piperidin-4-yl}-1,3-dihydro-2H-benzimidazol-2-one (CMPD 253);

1-{1-[9-ethyl-8-(1H-pyrazol-4-yl)-9H-purin-6-yl]piperidin-4-yl}-1,3-dihydro-2H-benzimidazol-2-one (CMPD 254);

1-{1-[8-(1,5-dimethyl-1H-pyrazol-4-yl)-9-ethyl-9H-purin-6-yl]piperidin-4-yl}-1,3-dihydro-2H-benzimidazol-2-one (CMPD 260);

1'-[8-(1,5-dimethyl-1H-pyrazol-4-yl)-9-ethyl-9H-purin-6-yl]spiro[indole-3,4'-piperidin]-2(1H)-one (CMPD 261);

1-(1-{9-methyl-8-[5-(trifluoromethyl)-1H-pyrazol-4-yl]-9H-purin-6-yl}piperidin-4-yl)-1,3-dihydro-2H-benzimidazol-2-one (CMPD 262);

1-[1-(8-furan-3-yl-9-methyl-9H-purin-6-yl)piperidin-4-yl]-1,3-dihydro-2H-benzimidazol-2-one (CMPD 265);

1-{1-[9-methyl-8-(1-methyl-1H-pyrazol-4-yl)-9H-purin-6-yl]piperidin-4-yl}-1,3-dihydro-2H-imidazo[4,5-b]pyridin-2-one (CMPD 269);

1-{1-[8-(5-chloro-1-methyl-1H-pyrazol-4-yl)-9-methyl-9H-purin-6-yl]piperidin-4-yl}-1,3-dihydro-2H-benzimidazol-2-one (CMPD 272);

methyl 1-[9-methyl-8-(1-methyl-1H-pyrazol-4-yl)-9H-purin-6-yl]-4-phenylpiperidine-4-carboxylate (CMPD 274);

1-{1-[8-(1-ethyl-5-methyl-1H-pyrazol-4-yl)-9-methyl-9H-purin-6-yl]piperidin-4-yl}-1,3-dihydro-2H-benzimidazol-2-one (CMPD 281);

1-{1-[9-methyl-8-(5-phenyl-1H-pyrazol-4-yl)-9H-purin-6-yl]piperidin-4-yl}-1,3-dihydro-2H-benzimidazol-2-one (CMPD 286);

1-{1-[8-(5-cyclopropyl-1H-pyrazol-4-yl)-9-methyl-9H-purin-6-yl]piperidin-4-yl}-1,3-dihydro-2H-benzimidazol-2-one (CMPD 287);

1-{1-[9-methyl-8-(1-methyl-1H-imidazol-5-yl)-9H-purin-6-yl]piperidin-4-yl}-1,3-dihydro-2H-benzimidazol-2-one (CMPD 288);

4-fluoro-1-{1-[9-methyl-8-(1-methyl-1H-pyrazol-4-yl)-9H-purin-6-yl]piperidin-4-yl}-1,3-dihydro-2H-benzimidazol-2-one (CMPD 295);

1-{1-[9-methyl-8-(1H-pyrrolo[2,3-b]pyridin-3-yl)-9H-purin-6-yl]piperidin-4-yl}-1,3-dihydro-2H-benzimidazol-2-one (CMPD 301);

1-{1-[9-methyl-8-(1H-pyrrolo[2,3-b]pyridin-5-yl)-9H-purin-6-yl]piperidin-4-yl}-1,3-dihydro-2H-benzimidazol-2-one (CMPD 302);

methyl (3S,4R)-1-[9-methyl-8-(1-methyl-1H-pyrazol-4-yl)-9H-purin-6-yl]-4-(2-oxo-2,3-dihydro-1H-benzimidazol-1-yl)piperidine-3-carboxylate (CMPD 317);

1-{1-[8-(1-ethyl-1H-pyrazol-4-yl)-9-methyl-9H-purin-6-yl]piperidin-4-yl}-1,3-dihydro-2H-imidazo[4,5-b]pyridin-2-one (CMPD 322);

1-{1-[9-ethyl-8-(1-methyl-1H-pyrazol-4-yl)-9H-purin-6-yl]piperidin-4-yl}-1,3-dihydro-2H-imidazo[4,5-b]pyridin-2-one (CMPD 323);

1-{1-[9-ethyl-8-(1-ethyl-1H-pyrazol-4-yl)-9H-purin-6-yl]piperidin-4-yl}-1,3-dihydro-2H-imidazo[4,5-b]pyridin-2-one (CMPD 325);

1-{1-[8-(1,5-dimethyl-1H-pyrazol-4-yl)-9-methyl-9H-purin-6-yl]piperidin-4-yl}-4-fluoro-1,3-dihydro-2H-benzimidazol-2-one (CMPD 330);

1-{1-[8-(1,5-dimethyl-1H-pyrazol-4-yl)-9-methyl-9H-purin-6-yl]piperidin-4-yl}-1,3-dihydro-2H-imidazo[4,5-b]pyridin-2-one (CMPD 331);

1-{1-[8-(1,2-dimethyl-1H-imidazol-5-yl)-9-methyl-9H-purin-6-yl]piperidin-4-yl}-1,3-dihydro-2H-benzimidazol-2-one (CMPD 333);

methyl (3R,4R)-1-[9-methyl-8-(1-methyl-1H-pyrazol-4-yl)-9H-purin-6-yl]-4-(2-oxo-2,3-dihydro-1H-benzimidazol-1-yl)piperidine-3-carboxylate (CMPD 334);

1-{1-[8-(1,2-dimethyl-1H-imidazol-5-yl)-9-methyl-9H-purin-6-yl]piperidin-4-yl}-1,3-dihydro-2H-imidazo[4,5-b]pyridin-2-one (CMPD 336);

1-{(3R,4R)-3-(hydroxymethyl)-1-[9-methyl-8-(1-methyl-1H-pyrazol-4-yl)-9H-purin-6-yl]piperidin-4-yl}-1,3-dihydro-2H-benzimidazol-2-one (CMPD 338);

1-{1-[9-methyl-8-(1-methyl-1H-pyrazol-4-yl)-9H-purin-6-yl]-4-phenylpiperidin-4-yl}methanamine (CMPD 1);

1-{1-[9-methyl-8-(1-methyl-1H-pyrazol-4-yl)-9H-purin-6-yl]piperidin-4-yl}-1,3-dihydro-2H-imidazo[4,5-c]pyridin-2-one (CMPD 341);

1-{1-[8-(1-ethyl-1H-pyrazol-4-yl)-9-methyl-9H-purin-6-yl]piperidin-4-yl}-4-fluoro-1,3-dihydro-2H-benzimidazol-2-one (CMPD 344);

1-{1-[8-(1-ethyl-5-methyl-1H-pyrazol-4-yl)-9-methyl-9H-purin-6-yl]piperidin-4-yl}-4-fluoro-1,3-dihydro-2H-benzimidazol-2-one (CMPD 345);

(3R,4R)-1,9-methyl-8-(1-methyl-1H-pyrazol-4-yl)-9H-purin-6-yl)-4-phenylpiperidin-3-ol (CMPD 346);

(3R,4R)-1-[9-methyl-8-(1-methyl-1H-pyrazol-4-yl)-9H-purin-6-yl]-4-(2-oxo-2,3-dihydro-1H-benzimidazol-1-yl)piperidine-3-carboxylic acid (CMPD 347);

6-[4-(1,1-dioxido-1,2-benzisothiazol-3-yl)piperazin-1-yl]-9-methyl-8-(1-methyl-1H-pyrazol-4-yl)-9H-purine (CMPD 348);

6-[4-(1,1-dioxido-1,2-benzisothiazol-3-yl)piperazin-1-yl]-8-(1-ethyl-1H-pyrazol-4-yl)-9-methyl-9H-purine (CMPD 349);

9-methyl-8-(1-methyl-1H-pyrazol-4-yl)-6-{4-[2-(methylsulfonyl)phenyl]piperazin-1-yl}-9H-purine (CMPD 350);

6-[4-(1H-indol-3-yl)piperidin-1-yl]-9-methyl-8-(1-methyl-1H-pyrazol-4-yl)-9H-purine (CMPD 351);

9-methyl-8-(1-methyl-1H-pyrazol-4-yl)-6-[4-(phenylsulfonyl)piperazin-1-yl]-9H-purine (CMPD 355);

N-cyclopentyl-2-[(3-{4-[9-methyl-8-(1-methyl-1H-pyrazol-4-yl)-9H-purin-6-yl]piperazin-1-yl}phenyl)oxy]acetamide (CMPD 356);

N-cyclohexyl-2-[(3-{4-[9-methyl-8-(1-methyl-1H-pyrazol-4-yl)-9H-purin-6-yl]piperazin-1-yl}phenyl)oxy]acetamide (CMPD 358);

6-(4-{3-[(2-azepan-1-yl-2-oxoethyl)oxy]phenyl}piperazin-1-yl)-9-methyl-8-(1-methyl-1H-pyrazol-4-yl)-9H-purine (CMPD 359);

2-{[(4-{4-[9-methyl-8-(1-methyl-1H-pyrazol-4-yl)-9H-purin-6-yl]piperazin-1-yl}phenyl)oxy]methyl}quinoline (CMPD 361);

N-[(2-{4-[9-methyl-8-(1-methyl-1H-pyrazol-4-yl)-9H-purin-6-yl]piperazin-1-yl}phenyl)methyl]cyclopropanecarboxamide (CMPD 362);

N-[(2-{4-[9-methyl-8-(1-methyl-1H-pyrazol-4-yl)-9H-purin-6-yl]piperazin-1-yl}phenyl)methyl]naphthalene-2-sulfonamide (CMPD 364);

8-(1-ethyl-1H-pyrazol-4-yl)-6-[4(1H-indol-3-yl)piperidin-1-yl]-9-methyl-9H-purine (CMPD 366);

8-(1-ethyl-1H-pyrazol-4-yl)-9-methyl-6-[4-(phenylsulfonyl)piperazin-1-yl]-9H-purine (CMPD 367);

8-(1-ethyl-1H-pyrazol-4-yl)-9-methyl-6-(4-phenylpiperazin-1-yl)-9H-purine (CMPD 368);

9-methyl-6-{4-[(4-methylphenyl)sulfonyl]piperazin-1-yl}-8-(1-methyl-1H-pyrazol-4-yl)-9H-purine (CMPD 370);

9-methyl-8-(1-methyl-1H-pyrazol-4-yl)-6-{4-[(phenylmethyl)sulfonyl]piperazin-1-yl}-9H-purine (CMPD 371);

6-{4-[(4-fluorophenyl)sulfonyl]piperazin-1-yl}-9-methyl-8-(1-methyl-1H-pyrazol-4-yl)-9H-purine (CMPD 372);

9-methyl-6-(4-{[4-methyloxy)phenyl]sulfonyl}piperazin-1-yl)-8-(1-methyl-1H-pyrazol-4-yl)-9H-purine (CMPD 373);

6-{4-[(4-chlorophenyl)sulfonyl]piperazin-1-yl}-9-methyl-8-(1-methyl-1H-pyrazol-4-yl)-9H-purine (CMPD 374);

6-{4-[(2-chlorophenyl)sulfonyl]piperazin-1-yl}-9-methyl-8-(1-methyl-1H-pyrazol-4-yl)-9H-purine (CMPD 375);

6-(4-{[2,5-bis(methyloxy)phenyl]sulfonyl}piperazin-1-yl)-9-methyl-8-(1-methyl-1H-pyrazol-4-yl)-9H-purine (CMPD 376);

9-methyl-8(1-methyl-1H-pyrazol-4-yl)-6-(4-{[3-(trifluoromethyl)phenyl]sulfonyl}piperazin-1-yl)-9H-purine (CMPD 377);

9-methyl-8-(1-methyl-1H-pyrazol-4-yl)-6-(4-{[2-(trifluoromethyl)phenyl]sulfonyl}piperazin-1-yl)-9H-purine (CMPD 378);

6-{4-[(2,5-dichlorophenyl)sulfonyl]piperazin-1-yl}-9-methyl-8-(1-methyl-1H-pyrazol-4-yl)-9H-purine (CMPD 379);

6-{4-[(3,4-dichlorophenyl)sulfonyl]piperazin-1-yl}-9-methyl-8-(1-methyl-1H-pyrazol-4-yl)-9H-purine (CMPD 380);

2-({4-[9-methyl-8(1-methyl-1H-pyrazol-4-yl)-9H-purin-6-yl]piperazin-1-yl}sulfonyl)benzonitrile (CMPD 381);

3-({4-[9-methyl-8-(1-methyl-1H-pyrazol-4-yl)-9H-purin-6-yl]piperazin-1-yl}sulfonyl)benzonitrile (CMPD 382);

6-{4-[(2,4-difluorophenyl)sulfonyl]piperazin-1-yl}-9-methyl-8-(1-methyl-1H-pyrazol-4-yl)-9H-purine (CMPD 383);

1-[4-({4-[9-methyl-8-(1-methyl-1H-pyrazol-4-yl)-9H-purin-6-yl]piperazin-1-yl}sulfonyl)phenyl]ethanone (CMPD 384);

9-methyl-6-(4-{[4-methyl-2-(methyloxy)phenyl]sulfonyl}piperazin-1-yl)-8-(1-methyl-1H-pyrazol-4-yl)-9H-purine (CMPD 385);

6-{(4-[(2-chloro-6-methylphenyl)sulfonyl]piperazin-1-yl}-9-methyl-8-(1-methyl-1H-pyrazol-4-yl)-9H-purine (CMPD 386);

6-{4-[(3,4-bis(methyloxy)phenyl]sulfonyl}piperazin-1-yl)-9-methyl-8-(1-methyl-1H-pyrazol-4-yl)-9H-purine (CMPD 387);

6-{4-[(2,3-dichlorophenyl)sulfonyl]piperazin-1-yl}-9-methyl-8-(1-methyl-1H-pyrazol-4-yl)-9H-purine (CMPD 389);

6-{4-[(2-chloropyridin-3-yl)sulfonyl]piperazin-1-yl}-9-methyl-8-(1-methyl-1H-pyrazol-4-yl)-9H-purine (CMPD 390);

6-{4-[(2,6-dichlorophenyl)sulfonyl]piperazin-1-yl}-9-methyl-8-(1-methyl-1H-pyrazol-4-yl)-9H-purine (CMPD 391);

6-{4-[(2,4-dichlorophenyl)sulfonyl]piperazin-1-yl}-9-methyl-8-(1-methyl-1H-pyrazol-4-yl)-9H-purine (CMPD 392); and 1-{1-[9-methyl-8-(5-methyl-1H-pyrazol-4-yl)-9H-purin-6-yl]piperidin-4-yl}-1,3-dihydro-2H-imidazo[4,5-b]pyridin-2-one (CMPD 394).

Example 21

1-{1-[8-(4,5-Dimethyl-4H-1,2,4-triazol-3-yl)-9-methyl-9H-purin-6-yl]piperidin-4-yl}-1,3-dihydro-2H-benzimidazol-2-one (Compound 332)

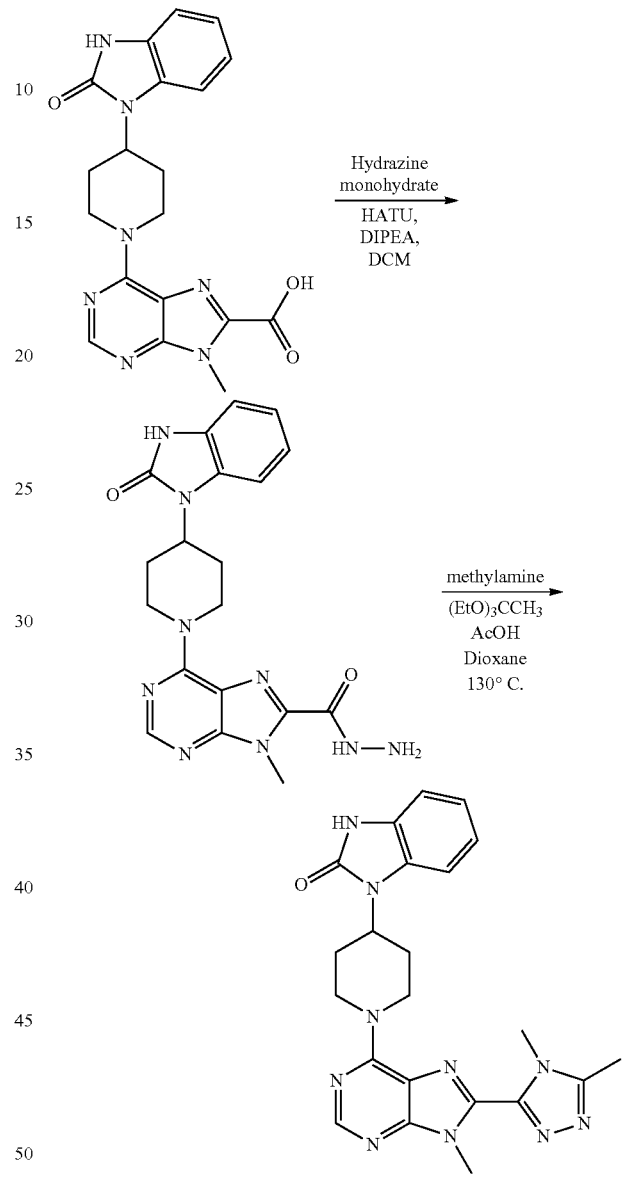

9-Methyl-6-(4-(2-oxo-2,3-dihydro-1H-benzo[d]imidazol-1-yl)piperidin-1-yl)-9H-purine-8-carbohydrazide In a 10 mL round bottomed flask, 9-Methyl-6-[4-(2-oxo-2,3-dihydro-1H-benzimidazol-1-yl)piperidin-1-yl]-9H-purine-8-carboxylic acid (250 mg, 0.68 mmol, 1 equiv) and HATU (390 mg, 1.03 mmol, 1.5 equiv) were suspended anhydrous dimethylformamide (3 mL). Diisopropylethylamine (235 μL, 1.35 mmol, 2 equiv) followed by hydrazine monohydrate (330 μL, 6.81 mmol, 10 equiv) were added and the reaction stirred for one hour. The reaction mixture was diluted with ethyl acetate (20 mL), and the extracted with water (10 mL). The combined aqueous layer was then acidified with 1N aqueous hydrochloric acid to precipitate the desired product. This precipitate was filtered off, washed with water (2 mL) and acetonitrile (1 mL) and air dried yielding 115 mg of 9-methyl-6-(4-(2-oxo-2,3-dihydro-1H-benzo[d]imidazol-1-yl)piperidin-1-yl)-9H-purine-8-carbohydrazide, which was used directly in the next step.

MS (EI) for $C_{19}H_{21}N_9O_2$: 408 (MH+).

1-{1-[8-(4,5-Dimethyl-4H-1,2,4-triazol-3-yl)-9-methyl-9H-purin-6-yl]piperidin-4-yl}-1,3-dihydro-2H-benzimidazol-2-one Into an Ace pressure tube were placed 9-methyl-6-(4-(2-oxo-2,3-dihydro-1H-benzo[d]imidazol-1-yl)piperidin-1-yl)-9H-purine-8-carbohydrazide (115 mg, 0.28 mmol, 1.0 equiv), triethyl orthoacetate (80 μL, 0.43 mmol, 1.5 equiv), methylamine (775 μL, 2M in THF, 1.55 mmol, 5.5 equiv), and acetic acid (0.5 mL), and dioxane (1.5 mL). The tube was sealed and heated at 130° C. for 12 hours. The tube was cooled to room temperature and diluted with methanol (1 mL). The title compound was isolated by preparative reverse-phase HPLC (acetonitrile/water with 1% formic acid, 25-45% gradient). Purified fractions were combined, frozen, and lyophilized to yield 28 mg material. $^1$H-NMR (400 MHz, DMSO-d$_6$): δ 10.81 (s, 1H), 8.31 (s, 1H), 7.12 (m, 1H), 6.87 (m, 3H), 5.5 (br s, 2H), 4.52 (m, 1H), 3.98 (d, 3H), 3.82 (s, 3H), 2.40 (s, 3H), 2.32 (dd, 2H), 1.82 (d, 2H); MS (EI) for $C_{22}H_{24}N_{10}O$, found 445.3 (MH+).

Example 22

1-{1-[9-Methyl-8-(5-methyl-1,3,4-oxadiazol-2-yl)-9H-purin-6-yl]piperidin-4-yl}-1,3-dihydro-2H-benzimidazol-2-one (Compound 203)

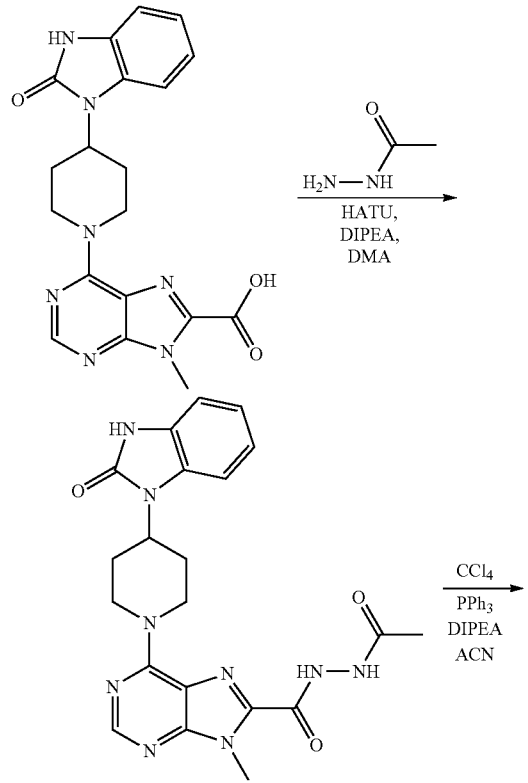

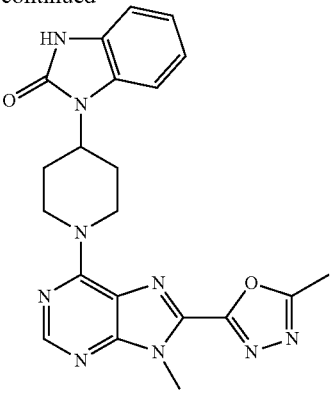

N'-acetyl-9-methyl-6-[4-(2-oxo-2,3-dihydro-1H-benzimidazol-1-yl)piperidin-1-yl]-9H-purine-8-carbohydrazide In a 10 mL round bottomed flask, 9-Methyl-6-[4-(2-oxo-2,3-dihydro-1H-benzimidazol-1-yl)piperidin-1-yl]-9H-purine-8-carboxylic acid (185 mg, 0.51 mmol, 1 equiv) and HATU (290 mg, 0.76 mmol, 1.5 equiv) were suspended anhydrous DMA (2 mL). Diisopropylethylamine (175 μL, 1.0 mmol, 2 equiv) followed by acetic hydrazide (45 mg, 0.61 mmol, 1.2 equiv) were added and the reaction stirred at room temperature overnight. The reaction mixture was diluted with ethyl acetate (20 mL), and the extracted with water (20 mL), and aqueous hydrochloric acid solution (0.1 M, 40 mL). The combined aqueous layers were then neutralized to pH=7 with saturated aqueous sodium bicarbonate. The resulting precipitate was filtered off, washed with water (2 mL) and acetonitrile (1 mL) and air dried yielding 135 mg of N'-acetyl-9-methyl-6-[4-(2-oxo-2,3-dihydro-1H-benzimidazol-1-yl)piperidin-1-yl]-9H-purine-8-carbohydrazide in 59% yield. $^1$H NMR (400 MHz, DMSO-d$_6$) δ 10.82 (s, 1H), 9.91 (s, 1H), 8.29 (s, 1H), 7.18-7.08 (m, 1H), 6.87 (dt, 3H), 4.52 (t, 1H), 3.92 (d, 3H), 2.31 (s, 2H), 1.86 (s, 3H), 1.79 (d, 2H). MS (EI) for $C_{21}H_{23}N_9O_3$: 450 (MH+).

1-{1-[9-Methyl-8-(5-methyl-1,3,4-oxadiazol-2-yl)-9H-purin-6-yl]piperidin-4-yl}-1,3-dihydro-2H-benzimidazol-2-one N'-acetyl-9-methyl-6-[4-(2-oxo-2,3-dihydro-1H-benzimidazol-1-yl)piperidin-1-yl]-9H-purine-8-carbohydrazide (85 mg, 0.19 mmol, 1 equiv) and triphenylphosphine (90 mg, 0.34 mmol, 1.8 equiv) were weighed out into a 2 dram vial and suspended in acetonitrile (1 mL). Diisopropylethylamine (165 mL, 0.95 mmol, 5 equiv) and carbontetrachloride (36 μL, 0.38 mmol, 2 equiv) were added and the reaction stirred at room temperature overnight during which time a precipitate formed. Analysis by LCMS indicated about a 40% conversion to the desired product. Neither heating to 80° C. for several hours, nor the addition of additional carbontetrachloride, DIPEA, or TPP furthered the cyclization. The precipitate was collected, dissolved in DMF (3.5 mL) and purified by preparative reverse-phase HPLC (acetonitrile/water with 1% formic acid). Fraction containing pure 1-{1-[9-methyl-8-(5-methyl-1,3,4-oxadiazol-2-yl)-9H-purin-6-yl]piperidin-4-yl}-1,3-dihydro-2H-benzimidazol-2-one were combined. The desired material precipitated upon concentration of the fractions, was collected by filtration, washed with water, and dried under vacuum, which resulted in the isolation of 16 mg of material. 1H NMR (400 MHz, DMSO-d$_6$) δ 10.80 (s, 1H), 8.33 (s, 1H), 7.16-7.10 (m, 1H), 6.93-6.82 (m, 3H), 4.53 (t, 1H), 4.03 (s, 3H), 2.59 (s, 3H), 2.30 (d, 2H), 1.83 (d, 2H). MS (EI) for $C_{21}H_{21}N_9O_2$: 432 (MH+).

The following compounds were synthesized in an analogous fashion to the compounds described in example 22:

1-{1-[8-(5-ethyl-1,3,4-oxadiazol-2-yl)-9-methyl-9H-purin-6-yl]piperidin-4-yl}-1,3-dihydro-2H-benzimidazol-2-one (CMPD 114);
1-(1-{9-methyl-8-[5-(1-methylethyl)-1,3,4-oxadiazol-2-yl]-9H-purin-6-yl}piperidin-4-yl)-1,3-dihydro-2H-benzimidazol-2-one (CMPD 112);
1-{1-[9-methyl-8-(5-propyl-1,3,4-oxadiazol-2-yl)-9H-purin-6-yl]piperidin-4-yl}-1,3-dihydro-2H-benzimidazol-2-one (CMPD 123);
1-{1-[8-(5-cyclopropyl-1,3,4-oxadiazol-2-yl)-9-methyl-9H-purin-6-yl]piperidin-4-yl}-1,3-dihydro-2H-benzimidazol-2-one (CMPD 125);
1'-{9-methyl-8-[5-(1-methylethyl)-1,3,4-oxadiazol-2-yl]-9H-purin-6-yl}spiro[indole-3,4'-piperidin]-2(1H)-one (CMPD 174);
1'-[9-methyl-8-(5-propyl-1,3,4-oxadiazol-2-yl)-9H-purin-6-yl]spiro[indole-3,4'-piperidin]-2(1H)-one (CMPD 177);
1-(1-{9-ethyl-8-[5-(1-methylethyl)-1,3,4-oxadiazol-2-yl]-9H-purin-6-yl}piperidin-4-yl)-1,3-dihydro-2H-benzimidazol-2-one (CMPD 180);
1'-[8-(5-ethyl-1,3,4-oxadiazol-2-yl)-9-methyl-9H-purin-6-yl]spiro[indole-3,4'-piperidin]-2(1H)-one (CMPD 182);
1'-[8-(5-cyclopropyl-1,3,4-oxadiazol-2-yl)-9-methyl-9H-purin-6-yl]spiro[indole-3,4'-piperidin]-2(1H)-one (CMPD 184);
1-(1-{9-methyl-8-[5-(2-methylpropyl)-1,3,4-oxadiazol-2-yl]-9H-purin-6-yl}piperidin-4-yl)-1,3-dihydro-2H-benzimidazol-2-one (CMPD 204);
1'-{9-ethyl-8-[5-(1-methylethyl)-1,3,4-oxadiazol-2-yl]-9H-purin-6-yl}spiro[indole-3,4'-piperidin]-2(1H)-one (CMPD 209);
1'-[8-(5-cyclopropyl-1,3,4-oxadiazol-2-yl)-9-ethyl-9H-purin-6-yl]spiro[indole-3,4'-piperidin]-2(1H)-one (CMPD 210);
1'-[9-ethyl-8-(5-propyl-1,3,4-oxadiazol-2-yl)-9H-purin-6-yl]spiro[indole-3,4'-piperidin]-2(1H)-one (CMPD 227);
1-(1-[8-(5-butyl-1,3,4-oxadiazol-2-yl)-9-methyl-9H-purin-6-yl]piperidin-4-yl}-1,3-dihydro-2H-benzimidazol-2-one (CMPD 232); and
1'-[9-ethyl-8-(5-ethyl-1,3,4-oxadiazol-2-yl)-9H-purin-6-yl]spiro[indole-3,4'-piperidin]-2(1H)-one (CMPD 236).

Example 23

1-[1-(9-Methyl-8-pyridin-3-yl-9H-purin-6-yl)piperidin-4-yl]-1,3-dihydro-2H-benzimidazol-2-one (Compound 268)

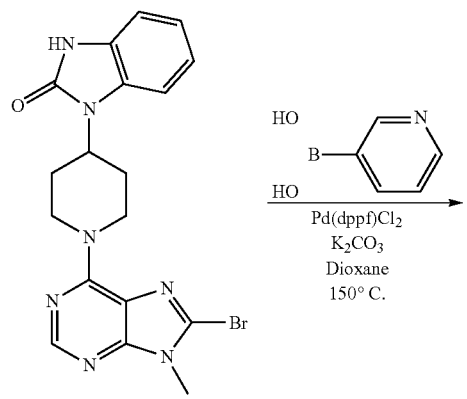

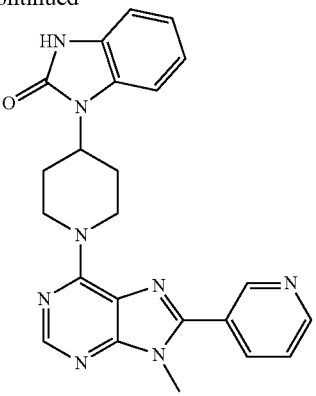

1-[1-(9-Methyl-8-pyridin-3-yl-9H-purin-6-yl)piperidin-4-yl]-1,3-dihydro-2H-benzimidazol-2-one To a solution of pyridin-3-ylboronic acid (50 mg, 0.41 mmol, Maybridge) in dioxane (0.75 mL) and water (0.1 mL) were added 1-(1-(8-bromo-9-methyl-9H-purin-6-yl)piperidin-4-yl)-1H-benzo[d]imidazol-2(3H)-one (50 mg, 0.12 mmol), Pd(dppf)Cl$_2$ (20 mg, 0.02 mmol), and tribasic potassium phosphate (75 mg, 0.36 mmol). The reaction mixture was heated in a microwave reactor to 150° C. for 20 min. The product was purified by preparatory HPLC (reverse-phase, acetonitrile/water with 0.1% formic acid) to give 15 mg (29.3% yield) of the title compound. $^1$H NMR (400 MHz, DMSO-d$_6$): δ 10.84 (s, 1H), 9.03 (m, 1H), 8.72 (dd, 1H), 8.32 (m, 1H), 8.25 (m, 1H), 7.59 (ddd, 1H), 7.15 (m, 1H), 6-91 (m, 3H), 4.55 (t, 1H), 3.85 (s, 3H), 2.35 (m, 2H), 1.84 (d, 2H); MS (EI) for C$_{23}$H$_{22}$N$_8$O: 427.4 (MH$^+$).

Example 24

1'-(9-Methyl-8-pyrimidin-5-yl-9H-purin-6-yl)spiro[indole-3,4'-piperidin]-2(1H)-one (Compound 293)

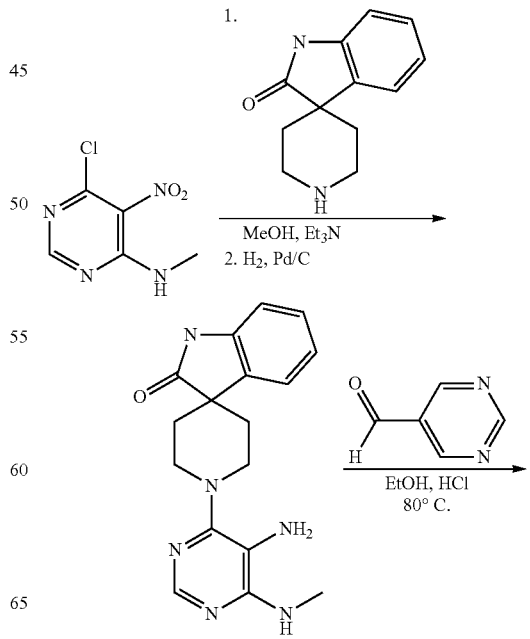

-continued

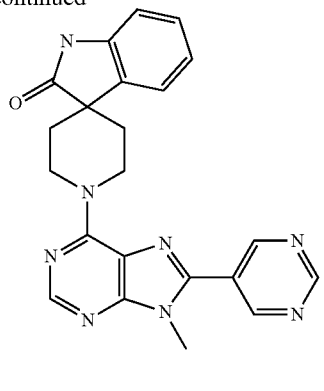

1'-(5-Amino-6-(methylamino)pyrimidin-4-yl)spiro[indoline-3,4'-piperidin]-2-one

A stirred solution of 6-chloro-N-methyl-5-nitropyrimidin-4-amine (1.0 g, 5.3 mmol) in methanol (20 mL) was added triethylamine (2.0 mL, 14.3 mmol) and spiro[indoline-3,4'-piperidin]-2-one (1072.5 mg, 5.3 mmol). The mixture was stirred at ambient temperature for 2 h and then 10 wt % Pd on C (wet) was added. The resulting mixture was stirred under hydrogen for 18 hours, diluted with methanol, and was filtered through Celite. The filtrate was concentrated, and the resulting solid was triturated with a solution of 50% aqueous methanol. The methanol was removed in vacuo and the mixture was filtered and dried under reduced pressure. The resulting compound was submitted to next step without further purification. $^1$H NMR (400 MHz, DMSO-$d_6$) δ 10.39 (s, 1H), 7.86 (s, 1H), 7.45 (d, 1H), 7.20 (td, 1H), 6.98 (t, 1H), 6.87 (d, 1H), 6.30 (q, 1H), 4.15 (s, 2H), 3.45 (dd, 2H), 3.26-3.18 (m, 2H), 2.86 (d, 3H), 1.97-1.88 (m, 2H), 1.82 (dd, 2H). MS (EI) for $C_{14}H_{20}N_6O$: 325.6 (MH$^+$).

1'-(9-Methyl-8-pyrimidin-5-yl-9H-purin-6-yl)spiro[indole-3,4'-piperidin]-2(1H)-one To a solution of 1'-[5-amino-6-(methylamino)pyrimidin-4-yl]spiro[indole-3,4'-piperidin]-2(1H)-one (100 mg, 0.30 mmol) in anhydrous ethanol (12 mL) were added pyrimidine-5-carbaldehyde (38 mg, 0.35 mmol, Apollo Scientific Ltd.) and catalytic amount of hydrochloric acid (0.05 mL, 4N, Dioxane, Aldrich). The reaction mixture was heated to 80° C. for 18 hours. The reaction mixture was cooled to room temperature and concentrated under reduced pressure. The product was purified by preparatory HPLC (reverse-phase, acetonitrile/water with 0.1% formic acid) to give 35.0 mg (28% yield) of the title compound.

$^1$H NMR (400 MHz, DMSO-$d_6$) δ10.49 (s, 1H), 9.35 (s, 1H), 9.32 (s, 2H), 8.36 (s, 1H), 7.49 (d, 1H), 7.20 (td, 1H), 6.99-6.92 (m, 1H), 6.87 (t, 1H), 3.91 (s, 3H), 1.80 (d, 4H). MS (EI) for $C_{22}H_{20}N_8O$: 413.6 (MH$^+$).

Example 25

1-[1-(9-Methyl-8-pyrimidin-4-yl-9H-purin-6-yl)piperidin-4-yl]-1,3-dihydro-2H-benzimidazol-2-one (Compound 298)

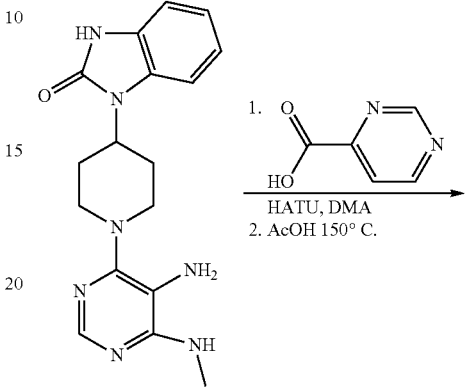

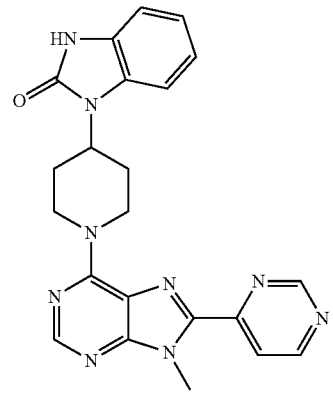

1-[1-(9-Methyl-8-pyrimidin-4-yl-9H-purin-6-yl)piperidin-4-yl]-1,3-dihydro-2H-benzimidazol-2-one To a solution of 1-(1-(5-amino-6-(methylamino)pyrimidin-4-yl)piperidin-4-yl)-1H-benzo[d]imidazol-2(3H)-one (50 mg, 0.14 mmol) in anhydrous DMA (5 mL) and diisopropylethylamine (0.5 mL) were added HATU (150 mg, 0.39 mmol), and pyrimidine-4-carboxylic acid (100 mg, 0.8 mmol). The reaction mixture was stirred for 1 h, and concentrated under reduced pressure. The resulting oil was dissolved in 10 mL of dichloromethane, and the solution was washed with 5 mL of water. The organic layer was dried over MgSO$_4$, concentrated under reduced pressure, and the residue was dissolved in Acetic acid (2 mL). The reaction mixture was heated in a microwave reactor to 150° C. for 20 min, and concentrated under reduced pressure. The product was purified by preparatory HPLC (reverse-phase, acetonitrile/water with 0.1% formic acid) to give 3 mg of the title compound. $^1$H NMR (400 MHz, DMSO-$d_6$): δ 10.85 (s, 1H), 9.34 (s, 1H), 8.96 (d, 1H), 8.36 (s, 1H), 8.27 (d, 1H), 7.21-7.14 (m, 1H), 6.93 (d, 3H), 4.64-4.52 (m, 1H), 4.18 (s, 3H), 2.37 (dd, 2H), 1.85 (t, 2H); MS (EI) for $C_{23}H_{21}N_9O$: 428.4 (MH$^+$).

Example 26

1-{1-[9-Methyl-8-(2-methylpyrimidin-5-yl)-9H-purin-6-yl]piperidin-4-yl}-1,3-dihydro-2H-benzimidazol-2-one (Compound 340)

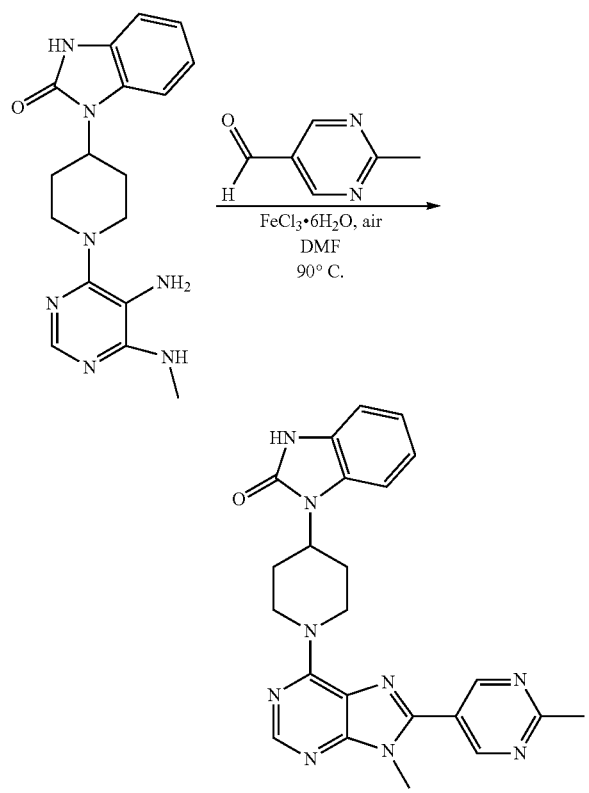

1-{1-[9-Methyl-8-(2-methylpyrimidin-5-yl)-9H-purin-6-yl]piperidin-4-yl}-1,3-dihydro-2H-benzimidazol-2-one To a solution of 1-(1-(5-amino-6-(methylamino)pyrimidin-4-yl)piperidin-4-yl)-1H-benzo[d]imidazol-2(3H)-one (300 mg, 0.88 mmol) in anhydrous DMF (5 mL) were added 2-methylpyrimidine-5-carbaldehyde (108 mg, 0.88 mmol) and Iron (III) chloride hexahydrate (0.88 g, 0.24 mmol). The dark brown solution was heated to 90° C. for 14 hour in an open air vessel. The reaction mixture was cooled to room temperature and poured over ice (5 g). The resulting mixture was extracted with ethyl acetate (50 mL), the organic layer was washed with brine (10 mL), and dried over MgSO$_4$. The solution was filtered, and concentrated under reduced pressure. The resulting solids were triturated with 15 mL of diethyl ether (15 mL) for 30 min. The precipitate was collected by vacuum filtration to give 201 mg (51% yield) of the title compound. $^1$H NMR (400 MHz, DMSO-d$_6$): δ 10.86 (s, 1H), 9.16 (s, 2H), 8.33 (s, 1H), 7.18-7.11 (m, 1H), 6.98-6.87 (m, 3H), 4.55 (t, 1H), 3.86 (s, 3H), 2.71 (s, 3H), 2.34 (dd, 2H), 1.84 (d, 2H); MS (EI) for C$_{23}$H$_{23}$N$_9$O: 442.3 (MH$^+$).

Example 27

6-(4-(((4,5-Dimethyl-2-phenyl-1H-imidazol-1-yl)oxy)methyl)piperidin-1-yl)-9-methyl-8-(1-methyl-M-pyrazol-4-yl)-9H-purine (CMPD 2)

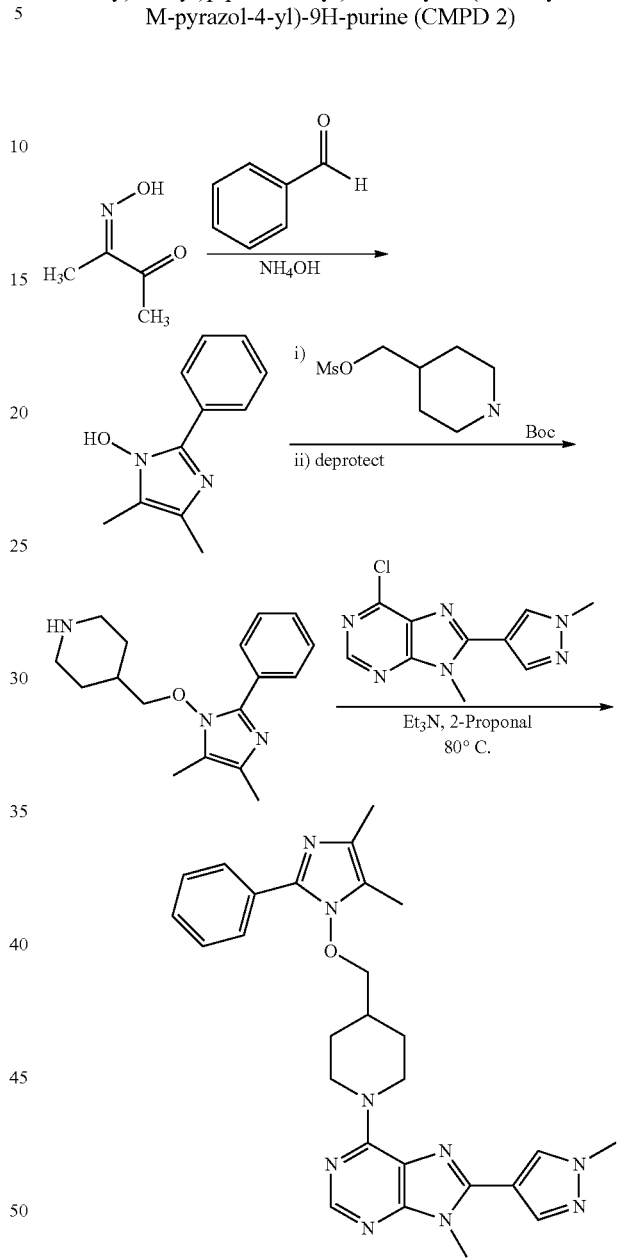

Chlorobenzaldehyde (160 mmol) was added to a suspended solution of 2,3-butanedione monoxime (240 mmol) in EtOH. After stirring for 30 minutes, 2,3-butanedione monoxime (240 mmol) and 112 mL of 28% ammonia water were added. The reaction mixture was stirred for 12 hours at room temperature. The mixture was concentrated under reduced pressure and the residue was diluted with methylene chloride. The organic layer was washed with brine, dried over MgSO$_4$ and concentrated under reduced pressure. Purification by column chromatography on silica gel with an eluent of 5% MeOH in CH$_2$Cl$_2$ gave 19.3 g (64%) of 4,5-dimethyl-2-phenyl-1H-imidazol-1-ol as a white solid.

A suspended solution of 4,5-dimethyl-2-phenyl-1H-imidazol-1-ol (49.4 mmol), tert-butyl 4-((methylsulfonyloxy)

methyl)-piperidine-1-carboxylate (46.9 mmol) and $K_2CO_3$ (74.1 mmol) in DMF was stirred at 80° C. for 12 hours. The reaction mixture was diluted with a mixture of ethyl acetate and hexane (v/v, 1/1). The solution was washed with brine, water, dried over $MgSO_4$ and concentrated under reduced pressure. Purification by column chromatography on silica gel with a 5% MeOH in MeOH with an eluent gave 17.0 g (89.3%) of the O-alkylated product as an oil.

To a stirred solution of the product (44 mmol) obtained above in 60 mL of methylene chloride, 18 mL of 26% HCl (g) in MeOH was slowly added at 0□. The reaction mixture was warmed to room temperature and stirred overnight. After complete disappearance of starting material on thin layer chromatography (TLC), the reaction mixture was concentrated under reduced pressure and dried to give 12.8 g of 4-((4,5-dimethyl-2-phenyl-1H-imidazol-1-yloxy)methyl)piperidine hydrochloride as a solid. $^1$H NMR (300 MHz, $D_2O$) δ 1.51 (m, 2H), 1.96 (d, 2H), 2.11 (m, 1H), 2.32 (d, 6H), 2.95 (t, 2H), 3.41 (d, 2H), 4.02 (d, 2H), 7.66 (m, 3H), 7.86 (m, 2H).

A stirred solution of 6-chloro-9-methyl-8-(1-methyl-1H-pyrazol-4-yl)-9H-purine (30 mg, 0.12 mmol), 44(4,5-dimethyl-2-phenyl-1H-imidazol-1-yloxy)methyl)piperidine hydrochloride (48 mg, 0.15 mmol), and triethylamine (84.0 uL, 0.60 mmol) in isopropyl alcohol (2.0 mL) were heated to 80° C. for 16 hours. The reaction mixture was cooled to room temperature and concentrated under reduced pressure. The product was purified by preparatory HPLC (reverse-phase, acetonitrile/water with 0.1% formic acid) to give 20 mg (33%) of the title compound. $^1$H NMR (400 MHz, DMSO-$d_6$) δ 8.42 (s, 1H), 8.22 (s, 1H), 8.04 (s, 1H), 7.89 (d, 2H), 7.46 (t, 2H), 7.35 (t, 1H), 3.95 (s, 3H), 3.86 (m, 2H), 3.83 (s, 3H), 3.36 (m, 2H), 3.12 (m, 2H), 2.20 (s, 3H), 2.18 (m, 1H), 2.06 (m, 3H), 1.88 (m, 2H), 1.33 (m, 2H). MS (EI) for $C_{27}H_{31}N_9O$: 498.1 (MH$^+$).

Example 28

1'-(8-(1,5-dimethyl-1H-pyrazol-4-yl)-9-methyl-9H-purin-6-yl)spiro[indoline-3,4'-piperidin]-2-one (CMPD 393

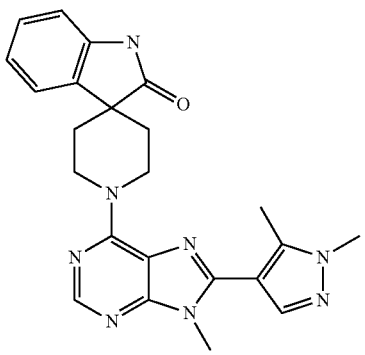 [SMILES: Cc1c(-c2nc3c(N4CCC5(CC4)C(=O)Nc4ccccc45)ncnc3n2C)cnn1C]

This compound was synthesized in an analogous fashion to the compound described in example 14. $^1$H NMR (400 MHz, DMSO-$d_6$) δ 10.40 (s, 1H), 8.21 (s, 1H), 7.88 (s, 1H), 7.43 (d, 1H), 7.13 (t, 1H), 6.88 (t, 1H), 6.81 (d, 1H), 3.76 (s, 3H), 3.73 (s, 3H), 3.35-3.25 (m, 4), 3.22 (s, 3H), 1.80-1.68 (m, 4H). MS (EI) for $C_{23}H_{24}N_8O$: 429.0 (MH$^+$).

The following compounds were synthesized in an analogous fashion to the compounds described in examples 23-26:

1-[1-(9-methyl-8-pyridin-4-yl-9H-purin-6-yl)piperidin-4-yl]-1,3-dihydro-2H-benzimidazol-2-one (CMPD 266);

1-[1-(9-methyl-8-phenyl-9H-purin-6-yl)piperidin-4-yl]-1,3-dihydro-2H-benzimidazol-2-one (CMPD 267);

1-[1-(9-methyl-8-pyrimidin-5-yl-9H-purin-6-yl)piperidin-4-yl]-1,3-dihydro-2H-benzimidazol-2-one (CMPD 271);

1-(1-{9-methyl-8-[6-(trifluoromethyl)pyridin-3-yl]-9H-purin-6-yl}piperidin-4-yl)-1,3-dihydro-2H-benzimidazol-2-one (CMPD 279);

1-[1-(9-methyl-8-pyridazin-4-yl-9H-purin-6-yl)piperidin-4-yl]-1,3-dihydro-2H-benzimidazol-2-one (CMPD 280);

1-{1-[9-methyl-8-(5-methylpyridin-3-yl)-9H-purin-6-yl]piperidin-4-yl}-1,3-dihydro-2H-benzimidazol-2-one (CMPD 282);

1-{1-[8-(6-chloropyridin-3-yl)-9-methyl-9H-purin-6-yl]piperidin-4-yl}-1,3-dihydro-2H-benzimidazol-2-one (CMPD 283);

1-(1-{9-methyl-8-[2-methyl-6-(trifluoromethyl)pyridin-3-yl]-9H-purin-6-yl}piperidin-4-yl)-1,3-dihydro-2H-benzimidazol-2-one (CMPD 284);

1-{1-[8-(5-bromopyridin-3-yl)-9-methyl-9H-purin-6-yl]piperidin-4-yl}-1,3-dihydro-2H-benzimidazol-2-one (CMPD 285);

1'-(9-methyl-8-pyridin-3-yl-9H-purin-6-yl)spiro[indole-3,4'-piperidin]-2(1H)-one (CMPD 290);

1'-(9-ethyl-8-pyridin-3-yl-9H-purin-6-yl)spiro[indole-3,4'-piperidin]-2(1H)-one (CMPD 291);

1'-(9-ethyl-8-pyrimidin-5-yl-9H-purin-6-yl)spiro[indole-3,4'-piperidin]-2(1H)-one (CMPD 292);

1-[1-(9-ethyl-8-pyrimidin-5-yl-9H-purin-6-yl)piperidin-4-yl]-1,3-dihydro-2H-benzimidazol-2-one (CMPD 294);

1-[1-(9-ethyl-8-pyridin-3-yl-9H-purin-6-yl)piperidin-4-yl]-1,3-dihydro-2H-benzimidazol-2-one (CMPD 296);

1-[1-(9-methyl-8-pyridazin-3-yl-9H-purin-6-yl)piperidin-4-yl]-1,3-dihydro-2H-benzimidazol-2-one (CMPD 297);

1-(1-{9-methyl-8-[6-(methyloxy)pyridin-3-yl]-9H-purin-6-yl}piperidin-4-yl)-1,3-dihydro-2H-benzimidazol-2-one (CMPD 299);

1-{1-[8-(6-hydroxypyridin-3-yl)-9-methyl-9H-purin-6-yl]piperidin-4-yl}-1,3-dihydro-2H-benzimidazol-2-one (CMPD 300);

1-{1-[8-(6-aminopyridin-3-yl)-9-methyl-9H-purin-6-yl]piperidin-4-yl}-1,3-dihydro-2H-benzimidazol-2-one (CMPD 303);

1-{1-[8-(2-aminopyrimidin-5-yl)-9-ethyl-9H-purin-6-yl]piperidin-4-yl}-1,3-dihydro-2H-benzimidazol-2-one (CMPD 304);

1-{1-[8-(2-aminopyrimidin-5-yl)-9-methyl-9H-purin-6-yl]piperidin-4-yl}-1,3-dihydro-2H-benzimidazol-2-one (CMPD 305);

1-(1-{9-ethyl-8-[2-(methyloxy)pyrimidin-5-yl]-9H-purin-6-yl}piperidin-4-yl)-1,3-dihydro-2H-benzimidazol-2-one (CMPD 306);

1-(1-{9-ethyl-8-[2-(methylamino)pyrimidin-5-yl]-9H-purin-6-yl}piperidin-4-yl)-1,3-dihydro-2H-benzimidazol-2-one (CMPD 307);

1-(1-{8-[2,4-bis(methyloxy)pyrimidin-5-yl]-9-methyl-9H-purin-6-yl}piperidin-4-yl)-1,3-dihydro-2H-benzimidazol-2-one (CMPD 308);

1-(1-{9-methyl-8-[2-(methylamino)pyrimidin-5-yl]-9H-purin-6-yl}piperidin-4-yl)-1,3-dihydro-2H-benzimidazol-2-one (CMPD 309);

1-(1-{9-methyl-8-[2-(methyloxy)pyrimidin-5-yl]-9H-purin-6-yl}piperidin-4-yl)-1,3-dihydro-2H-benzimidazol-2-one (CMPD 310);

1-(1-{8-[2-(dimethylamino)pyrimidin-5-yl]-9-methyl-9H-purin-6-yl}piperidin-4-yl)-1,3-dihydro-2H-benzimidazol-2-one (CMPD 311);
1-[1-(9-ethyl-8-pyridazin-4-yl-9H-purin-6-yl)piperidin-4-yl]-1,3-dihydro-2H-benzimidazol-2-one (CMPD 312);
1'-(9-methyl-8-pyridazin-4-yl-9H-purin-6-yl)spiro[indole-3,4'-piperidin]-2(1H)-one (CMPD 313);
1-(1-{9-ethyl-8-[6-(trifluoromethyl)pyridin-3-yl]-9H-purin-6-yl}piperidin-4-yl)-1,3-dihydro-2H-benzimidazol-2-one (CMPD 314);
1-(1-{9-methyl-8-[6-(trifluoromethyl)pyridin-3-yl]-9H-purin-6-yl}piperidin-4-yl)-1,3-dihydro-2H-imidazo[4,5-b]pyridin-2-one (CMPD 315);
1'-(9-ethyl-8-pyridazin-4-yl-9H-purin-6-yl)spiro[indole-3,4'-piperidin]-2(1H)-one (CMPD 316);
1-(1-{8-[2-(dimethylamino)pyrimidin-5-yl]-9-ethyl-9H-purin-6-yl}piperidin-4-yl)-1,3-dihydro-2H-benzimidazol-2-one (CMPD 320);
1-(1-{8-[2,4-bis(methyloxy)pyrimidin-5-yl]-9-ethyl-9H-purin-6-yl}piperidin-4-yl)-1,3-dihydro-2H-benzimidazol-2-one (CMPD 321);
1'-{9-ethyl-8-[6-(trifluoromethyl)pyridin-3-yl]-9H-purin-6-yl}spiro[indole-3,4'-piperidin]-2(1H)-one (CMPD 324);
1-(1-{9-ethyl-8-[6-(trifluoromethyl)pyridin-3-yl]-9H-purin-6-yl}piperidin-4-yl)-1,3-dihydro-2H-imidazo[4,5-b]pyridin-2-one (CMPD 326);
1'-{9-methyl-8-[6-(trifluoromethyl)pyridin-3-yl]-9H-purin-6-yl}spiro[indole-3,4'-piperidin]-2(1H)-one (CMPD 327);
1-[1-(9-methyl-8-pyridazin-3-yl-9H-purin-6-yl)piperidin-4-yl]-1,3-dihydro-2H-imidazo[4,5-b]pyridin-2-one (CMPD 335);
1-{1-[9-ethyl-8-(2-methylpyrimidin-5-yl)-9H-purin-6-yl]piperidin-4-yl}-1,3-dihydro-2H-benzimidazol-2-one (CMPD 342);
1-{1-[8-(6-aminopyridin-3-yl)-9-methyl-9H-purin-6-yl]piperidin-4-yl}-1,3-dihydro-2H-imidazo[4,5-b]pyridin-2-one (CMPD 343);
1-(1-{8-[6-(dimethylamino)pyridin-3-yl]-9-methyl-9H-purin-6-yl}piperidin-4-yl)-1,3-dihydro-2H-benzimidazol-2-one (CMPD 352);
1-(1-{9-methyl-8-[6-(methylamino)pyridin-3-yl]-9H-purin-6-yl}piperidin-4-yl)-1,3-dihydro-2H-benzimidazol-2-one (CMPD 353);
1-(1-{9-methyl-8-[6-(methylamino)pyridin-3-yl]-9H-purin-6-yl}piperidin-4-yl)-1,3-dihydro-2H-imidazo[4,5-b]pyridin-2-one (CMPD 354); and
1-(1-{8-[6-(dimethylamino)pyridin-3-yl]-9-methyl-9H-purin-6-yl}piperidin-4-yl)-1,3-dihydro-2H-imidazo[4,5-b]pyridin-2-one (CMPD 365).

BIOLOGICAL EXAMPLES

Example 1

Biochemical Assays

Kinase activity and compound inhibition were investigated using one or more of the assay formats described below. The ATP concentrations used in the various assays were approximately equal to or less than the $K_M$ for each of the respective kinases. Dose-response experiments were performed using an intra-plate dilution scheme with 10 different inhibitor concentrations in a 384-well microtiter plate. $IC_{50}$ values were calculated by nonlinear regression analysis using the four-parameter equation listed below:

$$Y = \min + (\max - \min)/(1 + (X/IC_{50})^N)$$  Equation 1 where Y is the observed signal, X is the inhibitor concentration, min is the background signal in the absence of enzyme (0% enzyme activity), max is the signal in the absence of inhibitor (100% enzyme activity), $IC_{50}$ is the inhibitor concentration at 50% enzyme inhibition and N represents the empirical Hill slope as a measure of cooperativity. Typically N should approximate unity. Curve fitting was performed using XLFit or ActivityBase.

Luciferase-Coupled Chemiluminescence Assay Protocol

Kinase activity is measured as the percent of ATP consumed following the kinase reaction using luciferase-luciferin-coupled chemiluminescence. Reactions were conducted in 384 or 1536-well white medium binding microtiter plates (Greiner). Kinase reactions were initiated by combining test compounds, kinase, and ATP in a 20 µL volume (6 µL volume for 1536-well plate). The reaction mixture was incubated at ambient temperature for 2 h. Following the kinase reaction, a 20 µL (or 3 L for 1536-well plate) aliquot of KinaseGlo (Promega) was added and the chemiluminescence signal measured using an EnVision plate reader (Perkin Elmer). Total ATP consumption was limited to 25-60% and the $IC_{50}$ values correlate well with those determined by radiometric assays.

PI3K delta activities of the Compounds of Formula I are provided in Table 2.

TABLE 2

PI3K Delta Activity of Compounds of Formula I
A 0 < PI3K Delta Activity < 50 nM
B 50 < PI3K Delta Activity < 250 nM
C 250 < PI3K Delta Activity < 500 nM
D 500 < PI3K Delta Activity < 1500 nM

| Compound Number | PI3K Delta Activity IC50 (nM) |
|---|---|
| 1 | D |
| 2 | D |
| 3 | B |
| 4 | B |
| 5 | A |
| 6 | B |
| 7 | D |
| 8 | C |
| 9 | B |
| 10 | D |
| 11 | C |
| 12 | B |
| 13 | B |
| 14 | B |
| 15 | B |
| 16 | B |
| 17 | B |
| 18 | C |
| 19 | B |
| 20 | B |
| 21 | D |
| 22 | B |
| 23 | D |
| 24 | B |
| 25 | C |
| 26 | D |
| 27 | D |
| 28 | C |
| 29 | D |
| 30 | A |
| 31 | D |
| 32 | B |
| 33 | D |
| 34 | A |
| 35 | D |
| 36 | B |
| 37 | D |
| 38 | D |

TABLE 2-continued

PI3K Dalta Activity of Compounds of Formula I
A 0 < PI3K Delta Activity < 50 nM
B 50 < PI3K Delta Activity < 250 nM
C 250 < PI3K Delta Activity < 500 nM
D 500 < PI3K Delta Activity < 1500 nM

| Compound Number | PI3K Delta Activity IC50 (nM) |
|---|---|
| 39 | D |
| 40 | B |
| 41 | B |
| 42 | B |
| 43 | B |
| 44 | B |
| 45 | A |
| 46 | B |
| 47 | B |
| 48 | B |
| 49 | B |
| 50 | C |
| 51 | D |
| 52 | B |
| 53 | D |
| 54 | B |
| 55 | B |
| 56 | C |
| 57 | C |
| 58 | B |
| 59 | C |
| 60 | A |
| 61 | C |
| 62 | B |
| 63 | D |
| 64 | D |
| 65 | D |
| 66 | D |
| 67 | A |
| 68 | C |
| 69 | B |
| 70 | C |
| 71 | C |
| 72 | B |
| 73 | D |
| 74 | B |
| 75 | B |
| 76 | D |
| 77 | B |
| 78 | D |
| 79 | B |
| 80 | D |
| 81 | D |
| 82 | D |
| 83 | B |
| 84 | B |
| 85 | D |
| 86 | B |
| 87 | A |
| 88 | D |
| 89 | B |
| 90 | C |
| 91 | D |
| 92 | D |
| 93 | D |
| 94 | D |
| 95 | C |
| 96 | B |
| 97 | A |
| 98 | D |
| 99 | D |
| 100 | D |
| 101 | C |
| 102 | B |
| 103 | B |
| 104 | B |
| 105 | B |
| 106 | B |
| 107 | B |
| 108 | B |
| 109 | B |
| 110 | B |
| 111 | A |
| 112 | B |
| 113 | B |
| 114 | A |
| 115 | C |
| 116 | C |
| 117 | B |
| 118 | B |
| 119 | C |
| 120 | B |
| 121 | D |
| 122 | A |
| 123 | A |
| 124 | B |
| 125 | A |
| 126 | D |
| 127 | D |
| 128 | C |
| 129 | C |
| 130 | B |
| 131 | C |
| 132 | D |
| 133 | B |
| 134 | C |
| 135 | B |
| 136 | D |
| 137 | B |
| 138 | D |
| 139 | B |
| 140 | B |
| 141 | D |
| 142 | D |
| 143 | D |
| 144 | D |
| 145 | C |
| 146 | A |
| 147 | A |
| 148 | A |
| 149 | A |
| 150 | B |
| 151 | C |
| 152 | A |
| 153 | B |
| 154 | A |
| 155 | A |
| 156 | A |
| 157 | B |
| 158 | A |
| 159 | A |
| 160 | A |
| 161 | A |
| 162 | A |
| 163 | A |
| 164 | A |
| 165 | B |
| 166 | D |
| 167 | A |
| 168 | A |
| 169 | B |
| 170 | C |
| 171 | B |
| 172 | D |
| 173 | C |
| 174 | A |
| 175 | B |
| 176 | B |
| 177 | A |
| 178 | B |
| 179 | D |
| 180 | A |

TABLE 2-continued

PI3K Dalta Activity of Compounds of Formula I
A 0 < PI3K Delta Activity < 50 nM
B 50 < PI3K Delta Activity < 250 nM
C 250 < PI3K Delta Activity < 500 nM
D 500 < PI3K Delta Activity < 1500 nM

| Compound Number | PI3K Delta Activity IC50 (nM) |
|---|---|
| 181 | C |
| 182 | A |
| 183 | C |
| 184 | A |
| 185 | A |
| 186 | A |
| 187 | A |
| 188 | A |
| 189 | A |
| 190 | A |
| 191 | A |
| 192 | B |
| 193 | A |
| 194 | A |
| 195 | A |
| 196 | A |
| 197 | A |
| 198 | B |
| 199 | D |
| 200 | D |
| 201 | D |
| 202 | D |
| 203 | A |
| 204 | A |
| 205 | B |
| 206 | C |
| 207 | C |
| 208 | A |
| 209 | A |
| 210 | A |
| 211 | A |
| 212 | A |
| 213 | A |
| 214 | A |
| 215 | A |
| 216 | A |
| 217 | A |
| 218 | A |
| 219 | A |
| 220 | A |
| 221 | A |
| 222 | B |
| 223 | A |
| 224 | A |
| 225 | B |
| 226 | A |
| 227 | A |
| 228 | D |
| 229 | D |
| 230 | B |
| 231 | A |
| 232 | A |
| 233 | B |
| 234 | A |
| 235 | D |
| 236 | A |
| 237 | A |
| 238 | A |
| 239 | A |
| 240 | B |
| 241 | A |
| 242 | A |
| 243 | A |
| 244 | A |
| 245 | A |
| 246 | A |
| 247 | A |
| 248 | C |
| 249 | D |
| 250 | A |
| 251 | A |
| 252 | A |
| 253 | A |
| 254 | A |
| 255 | B |
| 256 | C |
| 257 | B |
| 258 | B |
| 259 | A |
| 260 | A |
| 261 | A |
| 262 | B |
| 263 | B |
| 264 | D |
| 265 | B |
| 266 | C |
| 267 | D |
| 268 | A |
| 269 | A |
| 270 | A |
| 271 | A |
| 272 | A |
| 273 | A |
| 274 | D |
| 275 | B |
| 276 | C |
| 277 | B |
| 278 | B |
| 279 | A |
| 280 | B |
| 281 | A |
| 282 | A |
| 283 | A |
| 284 | D |
| 285 | A |
| 286 | A |
| 287 | A |
| 288 | A |
| 289 | B |
| 290 | A |
| 291 | A |
| 292 | A |
| 293 | A |
| 294 | A |
| 295 | A |
| 296 | A |
| 297 | B |
| 298 | C |
| 299 | A |
| 300 | D |
| 301 | A |
| 302 | A |
| 303 | A |
| 304 | A |
| 305 | A |
| 306 | A |
| 307 | A |
| 308 | B |
| 309 | A |
| 310 | A |
| 311 | A |
| 312 | A |
| 313 | B |
| 314 | A |
| 315 | A |
| 316 | A |
| 317 | D |
| 318 | A |
| 319 | A |
| 320 | A |
| 321 | D |
| 322 | A |

TABLE 2-continued

PI3K Dalta Activity of Compounds of Formula I
A 0 < PI3K Delta Activity < 50 nM
B 50 < PI3K Delta Activity < 250 nM
C 250 < PI3K Delta Activity < 500 nM
D 500 < PI3K Delta Activity < 1500 nM

| Compound Number | PI3K Delta Activity IC50 (nM) |
|---|---|
| 323 | A |
| 324 | A |
| 325 | A |
| 326 | A |
| 327 | A |
| 328 | A |
| 329 | A |
| 330 | A |
| 331 | A |
| 332 | B |
| 333 | A |
| 334 | A |
| 335 | B |
| 336 | A |
| 337 | A |
| 338 | B |
| 339 | D |
| 340 | A |
| 341 | C |
| 342 | A |
| 343 | A |
| 344 | A |
| 345 | A |
| 346 | C |
| 347 | D |
| 348 | B |
| 349 | B |
| 350 | D |
| 351 | C |
| 352 | A |
| 353 | A |
| 354 | A |
| 355 | C |
| 356 | D |
| 357 | D |
| 358 | D |
| 359 | C |
| 360 | D |
| 361 | D |
| 362 | D |
| 363 | C |
| 364 | D |
| 365 | A |
| 366 | C |
| 367 | B |
| 368 | D |
| 369 | |
| 370 | D |
| 371 | C |
| 372 | D |
| 373 | D |
| 374 | D |
| 375 | C |
| 376 | C |
| 377 | C |
| 378 | B |
| 379 | B |
| 380 | B |
| 381 | C |
| 382 | C |
| 383 | D |
| 384 | D |
| 385 | D |
| 386 | C |
| 387 | D |
| 388 | B |
| 389 | C |
| 390 | D |
| 391 | C |
| 392 | D |
| 393 | D |
| 394 | A |
| 395 | D |
| 396 | B |
| 397 | D |

Mechanism of Kinase Inhibition

Compound A which is a Compound of Formula I listed in Table 1 was characterized for reversibility of binding, inhibition type, and $K_i$ values. ATP variation studies were conducted by determining $IC_{50}$ values for Compound A against PI3Kdelta using increasing ATP concentrations. The assays were conducted by mixing 2 µL of PI3Kdelta with 0.1 µL of compound in a 384-well low volume white medium binding plate. After a 15 minute incubation, 2 µL of substrate ($PIP_2$) and ATP at varying concentrations (1500, 1000, 500, 250, 1 µM final) were added to the plate. Following incubation of the kinase reaction (15-120 minutes), 4 µL of ADP-Glo (Promega) Reagent #1 was added to the entire plate and incubated for 40 minutes. Finally, 8 µL of ADP-Glo Reagent #2 was added to the entire plate, incubated for 60 minutes, and then the plate was read using an Envision microplate reader. The resulting $IC_{50}$ values were plotted as a function of ATP concentration, and $K_i$ values were derived using the following equation.

$$IC_{50}=K_i/K_m[ATP]+K_i+[E]/2 \qquad \text{Equation 2}$$

where [E] represents the concentration of enzyme.

Reversibility of Inhibition

The reversibility of enzyme inhibition is evaluated for PI3K delta by measuring residual enzyme activity after dilution of an enzyme-inhibitor complex in saturating ATP. Inhibitor complexes were formed by incubating PI3K delta (2 µM) and a compound of Formula I (2 µM) for 30 minutes at ambient temperature. The EI complex is then serially diluted into buffer and allowed to reach equilibrium. Quantitative inhibition (approximately 75%) of the EI complex is found by measuring enzyme activity without dilution into buffer. A 5 µL sample of each dilution is then transferred to a 384-well low-volume medium binding white plate and then a 5 µL aliquot of substrate (40 µM $PIP_2$) and 1 mM ATP is added to the plate. Following an incubation of the reaction (5-60 mins) a 10 µL aliquot of ADP-Glo Reagent #1 is added and incubated for 40 minutes. Finally, 10 µL of ADP-Glo Reagent #2 is added to the plate and following a 60 minute incubation the reactions were read on the Envision Microplate Reader.

Determination of $K_M$ value for ATP

The $K_M$ value for ATP was determined using the ADP-GLO assay format described above. $K_M$ for ATP was derived by varying ATP concentrations (ranging from 15 to 1600 µM) at a fixed $PIP_2$ concentration (50 µM).

Example 2

Cellular Assays

Endogenous $AKT^{T308}$ Phosphorylation ELISA Assay in Anti-IgM Stimulated Raji Cells Raji cells (ATCC, CCL-86) were seeded at $1 \times 10^6$ cells/well onto 96-well plates (Corning, Costar 3960) in RPMI 1640 medium (ATCC, 30-2001) containing 10% FBS (Heat-Inactivated, Gibco, 10082), and 1% Penicillin/Streptomycin (Cellgro, 30-002-CI). Serial dilutions of test compounds in a final concentration of 0.3% DMSO (vehicle) were added to the cells and incubated for 90 min. Cells were stimulated with 0.25 µg/mL anti-IgM (Southern Biotech, 9023-01) for 30 min. Minimal signal wells were cells treated with 0.3% DMSO without anti-IgM stimulation; maximal signal wells were in 0.3% DMSO with anti-IgM stimulation. After stimulation, cells were spun down at 290×g for 4 min and immediately lysed with 120 µL of cold lysis buffer (50 mM Tris-HCl, pH 7.6; 150 mM NaCl; 0.1% Triton X-100; 1 mM EDTA; Protease Inhibitor Cocktail (Roche, 11697498001) and PhosSTOP (Roche, 04906837001)). To detect phospho-AKT$^{T308}$ and total AKT, commercially available ELISA kits were used (Invitrogen, KH00201 and KH00101). 100 or 10 µl, of cell lysate was transferred to phospho-AKT$^{T308}$ or total AKT plates, respectively. An additional 90 µL of lysis buffer was added to the total AKT plates. Plates were incubated overnight at 4° C. and washed four times with 200 µL of manufacturer-provided wash buffer (Invitrogen, WB01). Plates were incubated with 100 µL of detection antibody solution for 1.5 h. Plates were washed four times with 200 µL of wash buffer, then incubated for 1 h with secondary antibody using the corresponding buffer. Plates were washed as above, followed by the addition of 100 µL/well of Stabilized Chromogen solution for 20 min. The reaction was stopped by adding 100 µL of Stop Solution. Absorbance at wavelength of 450 nm was measured using a spectrophotometer (Molecular Devices, SpectraMax Plus). Intra-well normalization was accomplished by dividing the phospho-AKT$^{T308}$ OD values by the total AKT OD values. IC$_{50}$ values were then estimated by comparing the values of compound-treated samples with averages of the aforementioned minimal and maximal signal condition wells.

Western Blot Profiling Analysis of Anti-IgM-Stimulated Raji Cells

1×10$^7$ Raji cells (ATCC, CCL-86) were seeded in 14-mL round-bottom tubes in RPMI 1640 medium (ATCC, 30-2001) containing 10% FBS (Heat-Inactivated, Gibco, 10082), and 1% Penicillin/Streptomycin (Cellgro, 30-002-CI). Serial dilutions of test compound in a final concentration of 0.3% DMSO (vehicle) were added to the cells and incubated for 90 min followed by 0.25 µg/mL anti-IgM (Southern Biotech 9023-01) stimulation for 30 min. After stimulation, cells were spun down at 290×g for 4 min, washed once with cold phosphate-buffered saline (PBS; Cellgro, 21-030-CV) and immediately lysed with 120 µL of cold lysis buffer (50 mM Tris-HCl, pH 7.6; 150 mM NaCl; 0.1% Triton X-100; 1 mM EDTA; Protease Inhibitor Cocktail (Roche, 11697498001); and PhosSTOP (Roche, 04906837001)) for 30 min. Lysates were collected and cleared by centrifugation at 17,800×g for 15 min. Protein concentrations were measured by the BCA method (Pierce, 23227). Lysates were mixed with NuPage LDS sample buffer (Invitrogen, NP0007) and Reducing Agent (Invitrogen, NP0004), then heated at 70° C. for 10 min. 26 µg protein was loaded onto NuPage 4-12% Bis-Tris gels (Invitrogen, NP0323). Proteins were transferred to nitrocellulose membranes (Invitrogen, LC2001), blocked for 1 h in Odyssey Blocking Buffer (Li-Cor, 927-40000), and incubated at 4° C. overnight with the following antibodies diluted in Odyssey Blocking Buffer containing 0.1% Tween-20: Anti-phospho-AKT$^{T308}$ (1:500, Cell Signaling Technology, 2965), Anti-phospho-AKT$^{S473}$ (1:1,000, Cell Signaling Technology, 4060), Anti-AKT (1:2,000, R&D Systems, MAB 2055), Anti-phospho-PRAS40$^{T246}$ (1:500, Cell Signaling Technology, 2640), anti-phospho-GSK3β$^{S9}$ (1:500, Cell Signaling Technology, 9336), Anti-phospho-S6$^{S240/244}$ (1:500, Cell Signaling Technology, 2215), Anti-S6 (1:1,000, Cell Signaling Technology, 2217), Anti-GAPDH (1:100,000, Advanced Immunochemical Inc, MAB6C5). Membranes were washed four times for 10 min each with TBS-T buffer (50 mM Tris-HCl, pH7.2; 150 mM NaCl; 0.1% Tween-20) and blotted with Goat anti-Mouse-IRDye680 (Li-Cor, 926-32220) and Goat anti-Rabbit-IRDye800 (Li-Cor, 926-32211) secondary antibodies in Odyssey Blocking buffer containing 0.1% Tween-20 for 60 min at room temperature. Membranes were washed four times for 10 min each with TBS-T buffer and rinsed with PBS twice. The membranes were scanned using the Odyssey Scanner (Li-Cor) and the signal intensity of each band was quantified using ImageQuant (Molecular Devices). IC$_{50}$ values were calculated based on the signal with compound treatment compared to the vehicle (DMSO) control.

Western blot analysis of Anti-IgM-induced AKT Phosphorylation in Human Peripheral Blood B-lymphocytes Human primary B-lymphocytes (B cells, AllCells, PB010) were seeded at 6×10$^5$ cells/well onto 48-well cluster plates (Nunc 150687) in RPMI 1640 medium (ATCC, 30-2001) containing 10% FBS (Heat Inactivated, Gibco, 10082), 1% Penicillin/Streptomycin (Cellgro, 30-002-CI), 1% L-glutamine (Cellgro, 25-015-CI), and 50 µM β-mercaptoethanol (Gibco, 21985-023). Serial dilutions of test compound in a final concentration of 0.3% DMSO (vehicle) were added to the cells and incubated for 2 h followed by 10 µg/mL anti-IgM (Southern Biotech, 9023-01) stimulation for 5 min. After stimulation, cells were centrifuged at 290×g for 4 min, washed once with cold phosphate-buffered saline (PBS; Cellgro, 21-030-CV) and immediately lysed with 40 µL of cold lysis buffer (50 mM Tris-HCl, pH 8.0, 150 mM NaCl, 1% NP-40, 0.1% SDS, 0.5% sodium deoxycholate, 1 mM EDTA, 50 mM NaF, 1 mM sodium pyrophosphate, 1 mM sodium orthovanadate, 2 mM phenylmethylsulfonyl fluoride, 10 µg/mL aprotinin, 5 µg/mL leupeptin, and 5 µg/mL pepstatin A) for 30 min. Lysates were collected and cleared by centrifugation at 17,800×g for 15 min. Lysates were mixed with NuPage LDS sample buffer (Invitrogen NP0007) and Reducing Agent (Invitrogen, NP0004), then heated at 70° C. for 10 min. The sample was loaded onto NuPage 4-12% Bis-Tris gels (Invitrogen, NP0323). Proteins were transferred to nitrocellulose membranes (Invitrogen, LC2001), blocked for 1 h in Odyssey Blocking Buffer (Li-Cor, 927-40000), and incubated at 4° C. overnight with the following antibodies diluted in Odyssey Blocking Buffer: Anti-phospho-AKT$^{T308}$ (1:200, Cell Signaling Technology, 2965), Anti-phospho-AKT$^{s473}$ (1:200, Cell Signaling Technology, 4060), Anti-AKT (1:1, 000, R&D Systems, MAB 2055), and Anti-GAPDH (1:100, 000, Advanced Immunochemical Inc, MAB6C5). Membranes were washed four times for 10 min each with TBS-T buffer (50 mM Tris-HCl, pH7.2; 150 mM NaCl; 0.1% Tween-20) and blotted with Goat anti-Mouse-IRDye680 (Li-Cor, 926-32220) and Goat anti-Rabbit-IRDye800 (Li-Cor, 926-32211) secondary antibodies in Odyssey Blocking buffer containing 0.1% Tween-20 for 60 min at room temperature. Membranes were washed four times for 10 min each with TBS-T buffer and rinsed with PBS twice. The membranes were scanned using the Odyssey Scanner (Li-Cor) and the signal intensity of each band was quantified using ImageQuant (Molecular Devices). IC$_{50}$ values were calculated based on the signal with compound treatment compared to the vehicle (DMSO) control.

Anti-IgM-Stimulated Raji Cell TNF-Alpha Cytokine Release Assay

Raji cells (ATCC, CCL-86) were seeded at $2\times10^5$ cells/well in 96-well cell culture cluster round-bottom plates (Corning, Costar 3790) in RPMI 1640 medium (ATCC, 30-2001) containing 10% FBS (Heat-Inactivated, Gibco, 10082) with 1% Penicillin/Streptomycin (Cellgro, 30-002-CI). Cells were treated with serially diluted compounds for 2 h at 37° C. in 5% $CO_2$. Cells were stimulated with 1 µg/mL anti-IgM antibody (Southern Biotech, 9023-01) for 4 h. Minimal signal wells were treated with commercially available PI-103 (CAS 371935-74-9) and maximal signal wells were in 0.3% DMSO, both stimulated with anti-IgM. Unstimulated cells were also included as a negative control. After treatment, culture supernatants were filtered using 96-well 0.2-µm PVDF filter plates (Corning, Costar 3504).

Filtered conditioned medium was added to MSD plates (K151BHB-2) and incubated for 3 h at room temperature with agitation on a shaker (600 rpm). Plates were washed three times with phosphate-buffered saline (PBS; 137 mM NaCl, 2.7 mM KCl, 6.5 mM $Na_2HPO_4$, 1.7 mM $KH_2PO_4$) containing 0.05% Tween-20 (Bio-Rad, 161-0781). Detection Antibody Solution (Meso Scale Discovery, K151BHB-2) was added to each well and incubated for 2 h at room temperature. Plates were then washed three times with phosphate-buffered saline (PBS; 137 mM NaCl, 2.7 mM KCl, 6.5 mM $Na_2HPO_4$, 1.7 mM $KH_2PO_4$) containing 0.05% Tween-20 (Bio-Rad, 161-0781). Read Buffer T (Meso Scale Discovery, K151BHB-2) was added to each well, and then the plates were analyzed on the MSD SECTOR Imager. $IC_{50}$ values were calculated based on the signal of cells with compound treatment compared to those of the corresponding maximal and minimal signal wells.

Anti-IgM-Stimulated Human Peripheral Blood B-Lymphocytes Cytokine Release Assay

Human primary peripheral blood B cells (Negatively selected, CD19+, AllCells, PB010) were seeded at $1\times10^5$ cells/well onto 96-well microtiter cluster plates (Costar, 3790) in RPMI 1640 medium (ATCC, 30-2001) containing 10% FBS (Heat Inactivated, Gibco, 10082), 1% Penicillin/Streptomycin (Cellgro, 30-002-CI), 1% L-glutamine (Cellgro, 25-015-CI), and 50 µM β-mercaptoethanol (Gibco, 21985-0233). Serial dilutions of compound in a final concentration of 0.3% DMSO (vehicle) were added to the cells and incubated at 37° C., 5% $CO_2$ for 2 h. Duplicate wells were used for each compound concentration. Minimum signal wells received 30 µM PI-103, a pan-PI3K inhibitor. Cells in all wells were then stimulated with anti-IgM (Jackson Immunoresearch, 109-006-129) for an additional 4 h at 37° C., 5% $CO_2$. Cells were then transferred onto 96-well filter plates (Corning Costar, 3504), and supernatants collected by vacuum filtration. The supernatants were frozen at −80° C. until time of assay. According to the manufacturer's instructions, supernatants were assayed for cytokine levels using the Human Pro-inflammatory 9-Plex Tissue Culture Kit (GM-CSF, IFN-gamma, IL-1β, IL-10, IL-12 p70, IL-2, IL-6, IL-8, TNF-alpha; Meso Scale Discovery, K15007B-1). Briefly, supernatants were added onto pre-blocked assay plates and incubated at room temperature for 2 h with vigorous shaking at 600 rpm. Detection antibodies were then added onto the supernatants and incubated at room temperature for an additional 2 h with vigorous shaking at 600 rpm. Plates were washed three times with phosphate-buffered saline (PBS; 137 mM NaCl, 2.7 mM KCl, 6.5 mM $Na_2HPO_4$, 1.7 mM $KH_2PO_4$) containing 0.05% Tween-20 (Bio-Rad, 161-0781) and electrochemiluminescence detected using the MSD SI2400 plate reader. $IC_{50}$ values were calculated based on the calculated cytokine concentration with compound treatment minus the minimum signal compared to the DMSO vehicle control.

CpG ODN-Stimulated Human Peripheral Blood B-Lymphocytes Cytokine Release Assay

Human primary peripheral blood B-cells (Negatively selected, CD 19+, AllCells, PB010) were seeded at $1\times10^5$ cells/well onto 96-well microtiter cluster plates (Corning, Costar 3790) in RPMI 1640 medium (ATCC, 30-2001) containing 10% FBS (Heat Inactivated, Gibco, 10082), 1% Penicillin/Streptomycin (Cellgro, 30-002-CI), 1% L-glutamine (Cellgro, 25-015-CI), and 50 µM beta-mercaptoethanol (Gibco, 21985-023). Serial dilutions of compound in a final concentration of 0.3% DMSO (vehicle) were added to the cells and incubated at 37° C., 5% CO2 for 2 h. Duplicate wells were used for each compound concentration. Minimum signal wells received 30 µM commercially available PI-103 (CAS 371935-74-9), a pan-PI3K inhibitor. Cells in all wells were then stimulated with CpG ODN (Imgenex, IMG-2209H) for an additional 4 h at 37° C., 5% $CO_2$. Cells were then transferred onto 96-well filter plates (Corning, Costar 3504), and supernatants collected by vacuum filtration. The supernatants were frozen at −80° C. until time of assay. According to the manufacturer's instructions, supernatants were assayed for cytokine levels using the Human Pro-inflammatory 9-Plex Tissue Culture Kit (GM-CSF, IFN-gamma, IL-1 beta, IL-10, IL-12 p70, IL-2, IL-6, IL-8, TNF-alpha; Meso Scale Discovery, K15007B-1). Briefly, supernatants were added onto pre-blocked assay plates and incubated at room temperature for 2 h with vigorous shaking at 600 rpm. Detection antibodies were then added onto the supernatants and incubated at room temperature for an additional 2 h with vigorous shaking at 600 rpm. Plates were washed three times with phosphate-buffered saline (PBS; 137 mM NaCl, 2.7 mM KCl, 6.5 mM $Na_2HPO_4$, 1.7 mM $KH_2PO_4$) containing 0.05% Tween-20 (Bio-Rad, 161-0781) and electrochemiluminescence detected using the MSD SI2400 plate reader. $IC_{50}$ values were calculated based on the calculated cytokine concentration with compound treatment minus the minimum signal compared to the DMSO vehicle control.

Anti-CD3-mediated Human Peripheral Blood T-Lymphocytes Cytokine Release As

Human peripheral blood mononuclear cells (PBMCs) from healthy human donors were isolated using a sodium diatrizoate polysucrose gradient (Accuspin System Histopaque-1077, Sigma-Aldrich, A7054). Cells were then negatively selected according to manufacturer's instructions using the EasySep Human T cell Enrichment kit (Stem Cell Technologies, 19051). Cells were more than 95% pure. CD3+ T cells were seeded at $1\times10^5$ cells/well onto 96-well microtiter cluster plates (Corning, Costar 3790) in RPMI 1640 medium (ATCC, 30-2001) containing 10% FBS (Heat Inactivated, Gibco, 10082), 1% Penicillin/Streptomycin (Cellgro, 30-002-CI), 1% L-glutamine (Cellgro, 25-015-CI), and 50 µM beta-mercaptoethanol (Gibco, 21985-023). Serial dilutions of compound in a final concentration of 0.3% DMSO (vehicle) were added to the cells and incubated at 37° C., 5% $CO_2$ for 2 h. Duplicate wells were used for each compound concentration. Minimum signal wells received 30 µM commercially available PI-103 (CAS 371935-74-9), a pan-PI3K inhibitor. Cells in all wells were then seeded onto anti-human CD3-coated 96-well microtiter plates (BD Biosciences, 354725) for an additional 4 h at 37° C., 5% $CO_2$. Cells were then transferred onto 96-well filter plates (Corning, Costar 3504), and supernatants collected by vacuum filtration. The supernatants were frozen at −80° C. until time of assay.

According to the manufacturer's instructions, supernatants were assayed for cytokine levels using the Human TH1/TH2 10-Plex Tissue Culture Kit (IFN-gamma, IL-1beta, IL-10, IL-12 p70, IL-13, IL-4, IL-5, IL-8, TNF-alpha; Meso Scale Discovery, K15010B-1). Briefly, supernatants were added onto pre-blocked assay plates and incubated at room temperature for 2 h with vigorous shaking at 600 rpm. Detection antibodies were then added onto the supernatants and incubated at room temperature for an additional 2 h with vigorous shaking at 600 rpm. Plates were washed three times with phosphate-buffered saline (PBS; 137 mM NaCl, 2.7 mM KCl, 6.5 mM $Na_2HPO_4$, 1.7 mM $KH_2PO_4$) containing 0.05% Tween-20 (Bio-Rad, 161-0781) and electrochemiluminescence detected using the MSD SI2400 plate reader. $IC_{50}$ values were calculated based on the calculated cytokine concentration with compound treatment minus the minimum signal compared to the DMSO vehicle control.

LPS-stimulated Peripheral Blood Mononuclear Cell Cytokine Release Assay

Human primary peripheral blood mononuclear cells (PBMC, AliCells, PB001) were seeded at $2\times10^5$ cells/well onto 96-well microtiter cluster plates (Corning, Costar 3790) in RPMI 1640 medium (ATCC, 30-2001) containing 10% FBS (Heat Inactivated, Gibco, 10082), 1% Penicillin/Streptomycin (Cellgro, 30-002-CI), 1% L-glutamine (Cellgro, 25-015-CI), and 50 µM β-mercaptoethanol (Gibco, 21985-023). Serial dilutions of compound in a final concentration of 0.3% DMSO (vehicle) were added to the cells and incubated at 37° C., 5% $CO_2$ for 2 h. Duplicate wells were used for each compound concentration. Minimum signal wells received 30 µM commercially available PI-103 (CAS 371935-74-9), a pan-PI3K inhibitor. Cells in all wells were then stimulated with lipopolysaccharide (LPS, Sigma, L4391) for an additional 6 h at 37° C., 5% $CO_2$. Cells were then transferred onto 96-well filter plates (Corning, Costar 3504), and supernatants collected by vacuum filtration. The supernatants were frozen at −80° C. until time of assay. According to the manufacturer's instructions, supernatants were assayed for cytokine levels using the Human Pro-inflammatory 9-Plex Tissue Culture Kit (GM-CSF, IFN-gamma, IL-1beta, IL-12 p70, IL-2, IL-6, IL-8, TNF-alpha; Meso Scale Discovery, K15007B-1). Briefly, supernatants, either undiluted or diluted 1:2, were added onto pre-blocked assay plates and incubated at room temperature for 2 h with vigorous shaking at 600 rpm. Detection antibodies were then added onto the supernatants and incubated at room temperature for an additional 2 h with vigorous shaking at 600 rpm. Plates were washed three times with phosphate-buffered saline (PBS; 137 mM NaCl, 2.7 mM KCl, 6.5 mM $Na_2HPO_4$, 1.7 mM $KH_2PO_4$) containing 0.05% Tween-20 (Bio-Rad, 161-0781) and electrochemiluminescence detected using the MSD SI2400 plate reader. $IC_{50}$ values were calculated based on the calculated cytokine concentration with compound treatment minus the minimum signal compared to the DMSO vehicle control.

Primary Human B- and T-Lymphocyte BrdU Proliferation Assay

Human primary B-lymphocytes (B cells, AllCells, PB010) were seeded at $1\times10^5$ cells/well onto 96-well microtiter cluster plates (Corning, Costar 3790) and human primary T-lymphocytes (T cells, AllCells, PB009-1) were seeded at $2\times10^5$ cells/well onto anti-human CD3-coated 96-well microtiter plates (BD Biosciences, 354725) in RPMI-1640 medium (ATCC, 30-2001) containing 10% FBS (Heat Inactivated, Gibco, 10082), 1% Penicillin/Streptomycin (Cellgro, 30-002-CI), 1% L-glutamine (Cellgro, 25-015-CI), and 50 µM beta-mercaptoethanol (Gibco, 21985-023). The human primary B cells were stimulated with either anti-human IgM (Jackson Immunoresearch, 109-006-129) at a final concentration of 25 µg/mL or with CpG ODN (Imgenex, IMG-2209H) at a final concentration of 2 µg/mL. Both B and T cells were treated immediately after stimulation with a serial dilution of compound in medium (containing a final concentration of 0.3% DMSO). Triplicate wells were used for each compound concentration in B cells, and duplicate wells were used for each compound concentration in T cells. The control wells received 0.3% DMSO media. The minimum signal wells received 30 tiM of commercially available PI-103 (CAS 371935-74-9), a pan-PI3K inhibitor. The cultures were incubated at 37° C., 5% $CO_2$ for 72 h (B cells) or 96 h (T cells). To assay the cells, they were labeled with 20 µM bromodeoxyuridine (BrdU, Sigma, B5002-500MG), transferred to 96-well filter plates (Costar 3504), and then fixed with FixDenat solution (70% ethanol+0.1 M NaOH). Anti-BrdU-POD (1:2,000; Roche, 11585860001) conjugate was added to the cells, after which the plates were washed 3 times with phosphate-buffered saline (PBS; 137 mM NaCl, 2.7 mM KCl, 6.5 mM $Na_2HPO_4$, 1.7 mM $KH_2PO_4$). Substrate solution made from 1 part peroxide (Thermo Scientific, 37075A) and 1 part luminol (Thermo Scientific, 37075B) was added, and the plates were read for luminescence (0.1 s) using the Victor Wallac luminometer. $IC_{50}$ values were calculated based on the cell proliferation with compound treatment minus the minimum signal compared to the DMSO vehicle control.

MC/9 Mouse Mast Cell β-Hexosaminidase Degranulation Assay

MC/9 cells (ATCC, CRL-8306) were seeded at $1\times10^6$ cells/mL onto tissue-culture flasks (Nunc, 144903) in DMEM (Cellgro, 10-013-CV) containing 10% FBS (Heat-Inactivated, Gibco, 10082), 1.5 g/L sodium bicarbonate, 0.05 mM 2-mercaptoethanol, 10% Rat T-STIM (BD, 354115), and 1% Penicillin/Streptomycin (Cellgro, 30-002-CI). Cells were incubated with 200 ng/mL anti-DNP IgE (Sigma, D8406) overnight at 37° C. in 5% $CO_2$. Cells were washed twice with Tyrode's buffer (135 mM NaCl, 5 mM KCl, 5.6 mM glucose, 1.8 mM $CaCl_2$, 1 mM $MgCl_2$, 20 mM HEPES, and 0.5 mg/mL BSA; pH 7.3) and seeded at $2\times10^5$ cells/well in 96-well microtiter plates (Costar, 3904) in 70 µL of Tyrode's buffer. 30 µL of serially diluted test compounds in Tyrode's buffer with a final concentration of 0.3% DMSO (vehicle) were added to the cells and incubated for 75 min. Cells were stimulated with 200 ng/mL DNP-HSA (Sigma, A6661) for 45 min. Background wells were cells in 0.3% DMSO without DNP-HSA stimulation. Minimal signal wells were treated with commercially available PI-103 (CAS 371935-74-9), 10 µM) and maximal signal wells were in 0.3% DMSO, both stimulated with DNP-HSA. The final volume per well was 110 µL. After stimulation, cells were spun down at 400×g for 4 min. 50 µL of supernatant was carefully collected and transferred to a 96-well plate (Nunc, 260895) and incubated with 75 µL of 1 mM p-nitrophenyl acetyl-D-glucosamine (Sigma, N9376) in citrate buffer (pH 4.5) for 2 h at 37° C. The reaction was stopped by adding 75 µL of 2 M NaOH. Wells were measured for absorbance at wavelength of 405 nm with correction at 630 nm using a spectrophotometer (Molecular Devices, SpectraMax Plus). The average background well values were subtracted from all wells. $IC_{50}$ values were calculated based on the absorbance of cells with compound treatment compared to those of the corresponding maximal and minimal signal wells.

Example 3

Pharmacodynamic Xenograft Tumor Models

Female and male athymic nude mice (NCr) 5-8 weeks of age and weighing approximately 20-25 g are used in the following models. Prior to initiation of a study, the animals are allowed to acclimate for a minimum of 48 h. During these studies, animals are provided food and water ad libitum and housed in a room conditioned at 70-75° F. and 60% relative humidity. A 12 h light and 12 h dark cycle is maintained with automatic timers. All animals are examined daily for compound-induced or tumor-related deaths.

Tumor weight (TW) in the above models is determined by measuring perpendicular diameters with a caliper, using the following formula:

Tumor Weight (mg)=[tumor volume=length (mm)× width² (mm²)]/2

These data were recorded and plotted on a tumor weight vs. days post-implantation line graph and presented graphically as an indication of tumor growth rates. Percent inhibition of tumor growth (TGI) is determined with the following formula:

$$\left[1 - \left(\frac{(X_f - X_0)}{(Y_f - X_0)}\right)\right] * 100$$

where:
$X_0$=average TW of all tumors on group day
$X_f$=TW of treated group on Day f
$Y_f$=TW of vehicle control group on Day f If tumors regress below their starting sizes, then the percent tumor regression is determined with the following formula:

$$\left(\frac{X_0 - X_f}{X_0}\right) * 100$$

Tumor size is calculated individually for each tumor to obtain a mean±SEM value for each experimental group. Statistical significance is determined using the 2-tailed Student's t-test (significance defined as P<0.05).\\

The foregoing invention has been described in some detail by way of illustration and example, for purposes of clarity and understanding. The invention has been described with reference to various specific embodiments and techniques. However, it should be understood that many variations and modifications may be made while remaining within the spirit and scope of the invention. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled. All patents, patent applications and publications cited in this application are hereby incorporated by reference in their entirety for all purposes to the same extent as if each individual patent, patent application or publication were so individually denoted.

The invention claimed is:
1. A compound of Formula I

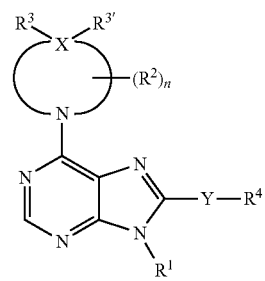

or a stereoisomer or mixture of stereoisomers thereof, optionally as a pharmaceutically acceptable salt thereof, wherein:

$R^1$ is alkyl, haloalkyl, or optionally substituted cycloalkyl;

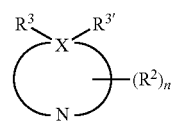

is a 4, 5, 6, or 7-membered ring, wherein:

$R^2$ at each occurrence is independently halo, hydroxy, alkyl, alkoxy, hydroxyalkyl, haloalkoxy, or —C(O)O-alkyl, or two $R^2$ groups may be joined together with the carbons to which they are attached to form a bridged or fused bicyclic ring;

n is 0, 1, 2, or 3;

X is C or N; wherein:

when X is N:
   $R^3$ is absent;
   $R^{3'}$ is aryl or heteroaryl optionally substituted with one or two groups independently selected from heteroarylalkyloxy; alkyl substituted with arylsulfonylamino; alkyl substituted with cycloalkylcarbonylamino; or
   $R^{3'}$ is —SO$_2$—R$^a$, wherein R$^a$ is optionally substituted alkyl, optionally substituted phenyl, optionally substituted phenylalkyl, or optionally substituted heteroaryl;

when X is C:
   $R^3$ is cyano, aminoalkyl, alkoxycarbonyl, or hydroxyl, and $R^{3'}$ is a optionally substituted phenyl; or
   $R^3$ is hydrogen and $R^{3'}$ is phenyl, alkyl substituted with 1-phenyl-4,5,6,7-tetrahydro-1H-pyrazolo[3,4-c]pyridinyl, optionally substituted indolyl, optionally substituted 1H-benzo[d][1,2,3]triazolyl, optionally substituted oxoindolinyl, optionally substituted benzoimidazolyl, optionally substituted pyridinyl,2-oxo-3,4-dihydroquinazolinyl, —C(O)NR$^b$R$^c$, wherein R$^b$ is hydrogen or alkyl; and R$^c$ is optionally substituted heteroarylalkyl; or
   $R^3$ is hydrogen and $R^{3'}$ is a group of formula (a), (b), (c), (d), (e), or (f):

(a) 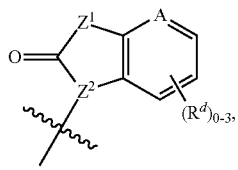

(b) 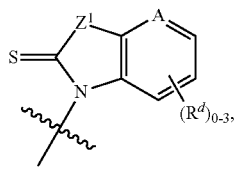

(c) 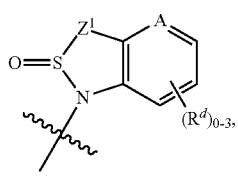

(d) 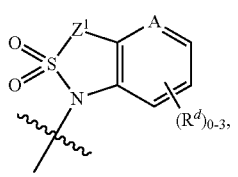

(e) 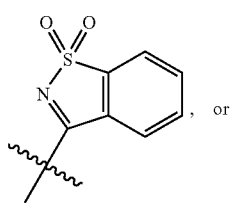

(f) 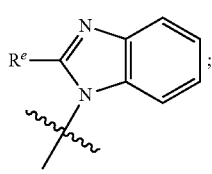

wherein:

$Z^1$ is O, NH, or N optionally substituted with aminoalkyl, alkylaminoalkyl, or dialkylaminoalkyl;

$Z^2$ is CH or N; and

A is N C—H, or C—$R^d$; or $R^3$ and $R^{3'}$ are taken together with the carbon to which they are attached to form an optionally substituted 5 or 6 membered ring (g), (h), (i), (j), (k), or (l):

(g) 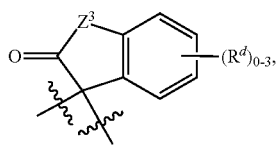

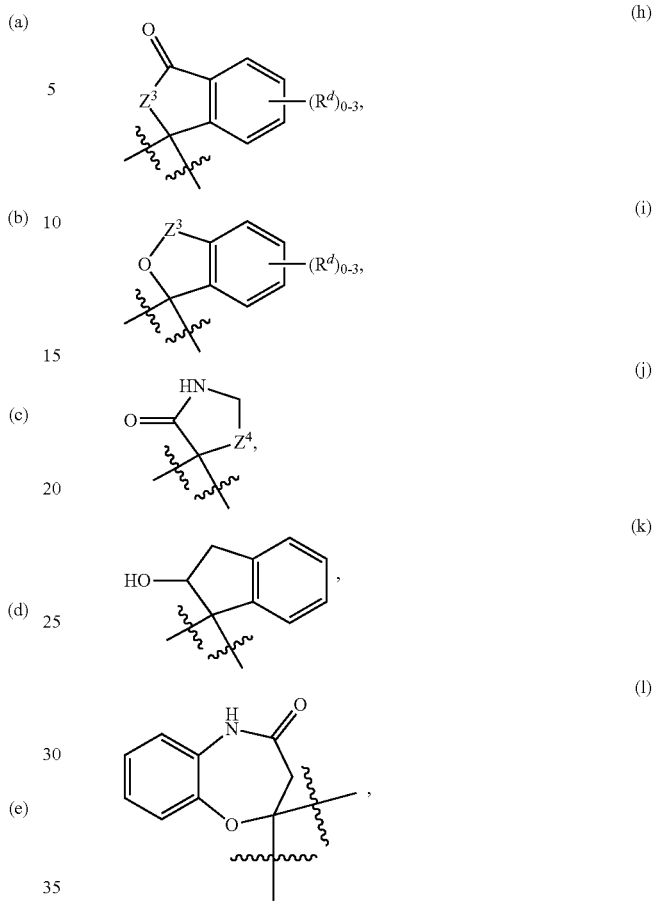

wherein: $Z^3$ is CH$_2$ or NH; $Z^4$ is NR$^f$ or CR$^f$, and R$^f$ is optionally substituted phenyl; and each $R^d$, when present, is independently halo, alkyl, optionally substituted alkoxy, or optionally substituted heterocycloalkyl, and $R^e$ is amino or haloalkyl;

Y is absent or is alkyl, —(C=O)—, —NR$^x$—(C=O)—, or —(C=O)NR$^x$—, —O—(C=O)—, —(C=O)—, —NR$^x$—(C=O)O—, or —O(C=O)NR$^x$—, wherein R$^x$ is hydrogen or optionally substituted alkyl;

$R^4$ is hydrogen, halo, optionally substituted alkyl, optionally substituted alkenyl, optionally substituted aryl, optionally substituted cycloalkyl, optionally substituted heterocycloalkyl, optionally substituted heteroaryl; and when Y is —N(R$^x$)—(C=O)—, or —(C=O)—N(R$^x$)—, R$^x$ and $R^4$ can be joined together along with the atoms to which they are attached to form a 4, 5, or 6 membered ring, optionally containing 1 or 2 additional heteroatoms selected from N, S, and O.

2. The compound of claim 1, which is a compound of Formula Ia, wherein

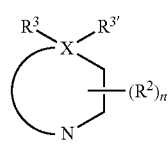

is a 5, 6, or 7-membered ring, a compound of Formula Ib, a compound of Formula Ic, or a compound of Formula Id:

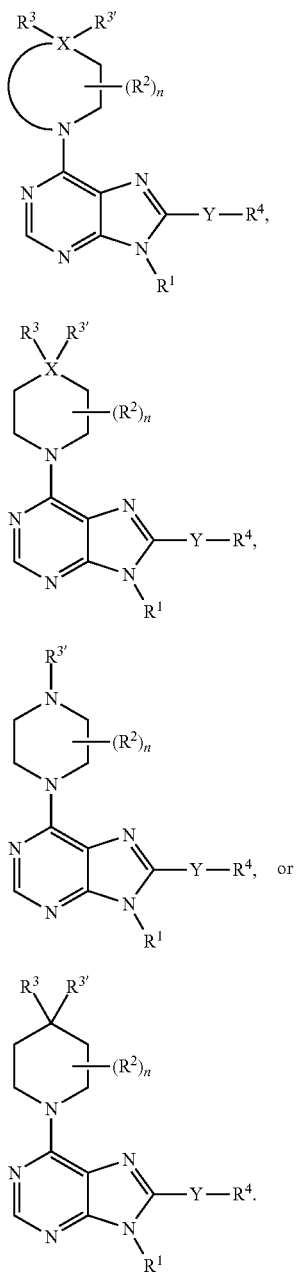

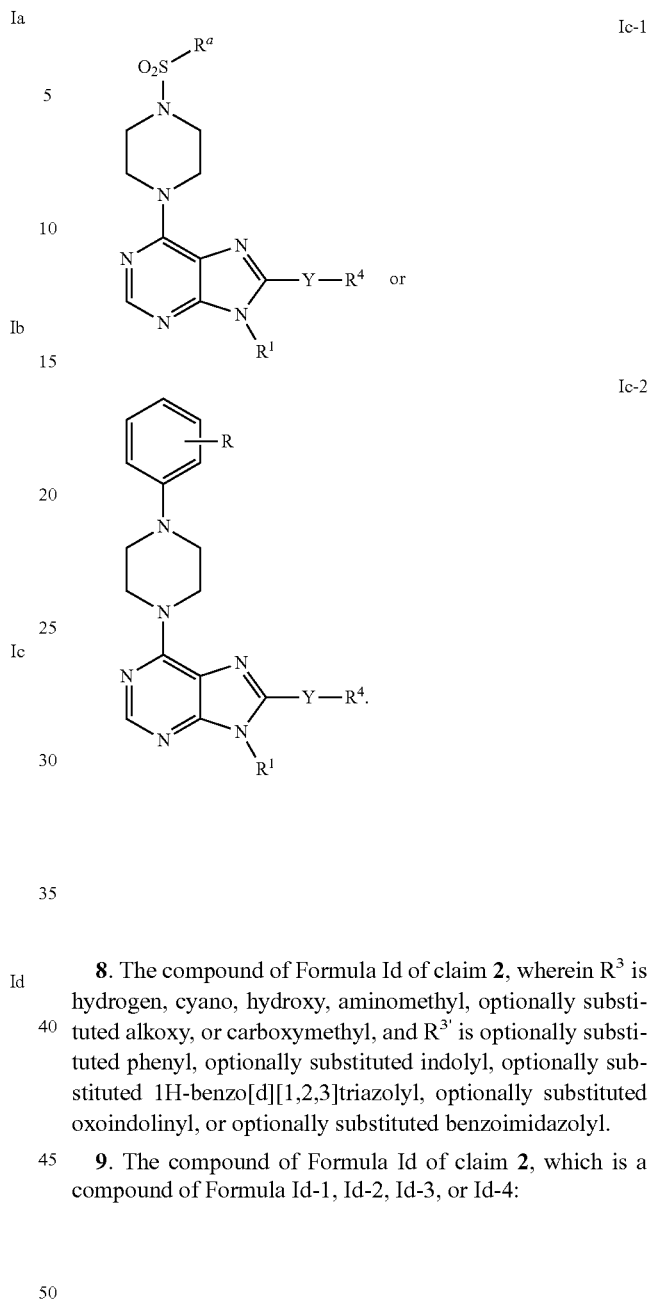

3. The compound of claim 2, wherein $R^1$ is alkyl or cycloalkyl.

4. The compound of claim 3, wherein $R^1$ is methyl, ethyl, or cyclopropyl.

5. The compound of claim 2, wherein n is 0 or 1.

6. The compound of claim 2, wherein $R^2$ is hydroxy, carboxy, methyl, or hydroxymethyl.

7. The compound of Formula Ic of claim 2, wherein the compound of Formula Ic is a compound of Formula Ic-1 or Ic-2 wherein R is heteroarylalkyloxy, alkyl substituted with arylsulfonylamino, or alkyl substituted with cycloalkylcarbonylamino:

8. The compound of Formula Id of claim 2, wherein $R^3$ is hydrogen, cyano, hydroxy, aminomethyl, optionally substituted alkoxy, or carboxymethyl, and $R^{3'}$ is optionally substituted phenyl, optionally substituted indolyl, optionally substituted 1H-benzo[d][1,2,3]triazolyl, optionally substituted oxoindolinyl, or optionally substituted benzoimidazolyl.

9. The compound of Formula Id of claim 2, which is a compound of Formula Id-1, Id-2, Id-3, or Id-4:

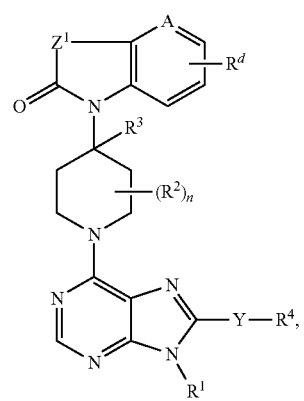

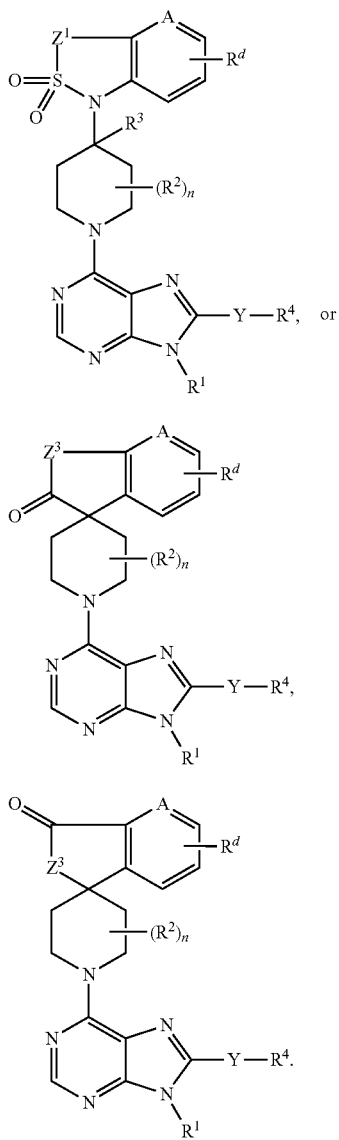
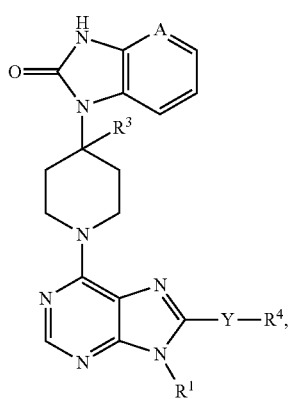
10. The compound of Formula Id-1 or Id-2 of claim 9, which is a compound of Formula Id-1(a), Id-1(b), or Id-2(a):
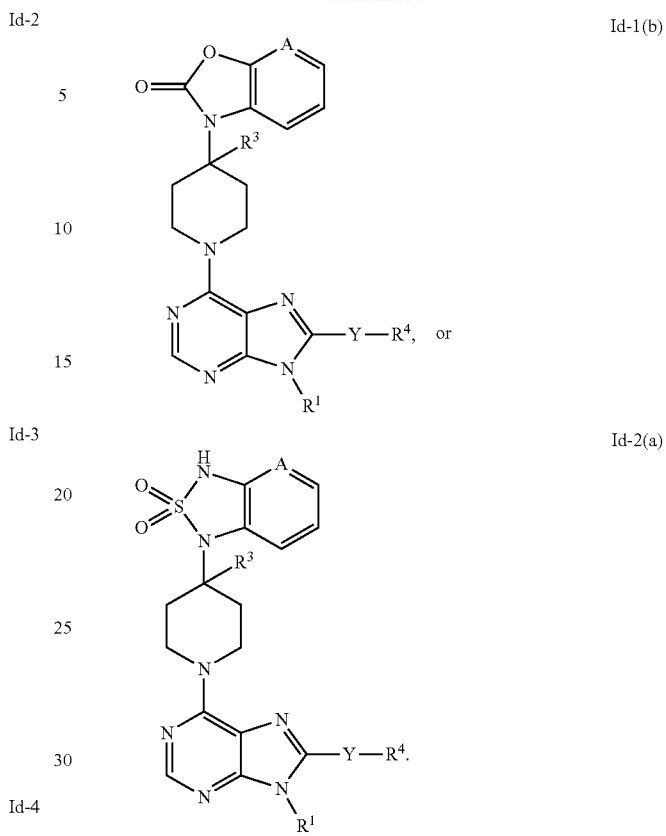
11. The compound of Formula Id-3 or Id-4 of claim 9, which is a compound of Formula Id-3(a), Id-3(b), or Id-4(a):
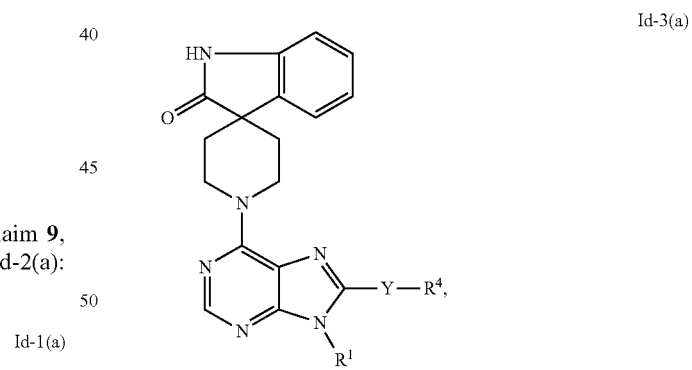
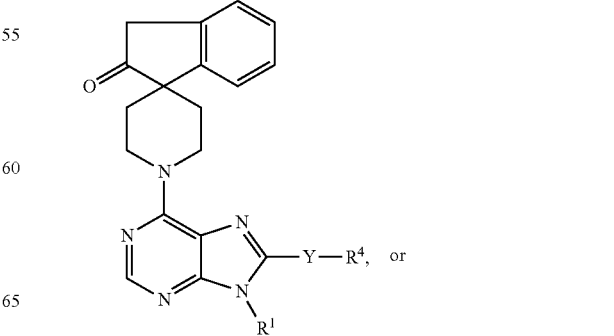

-continued

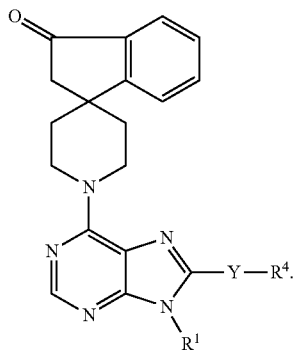

Id-4(a)

12. The compound of claim 1 wherein:

R¹ is alkyl, haloalkyl, or optionally substituted cycloalkyl;

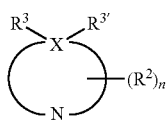

is a 4, 5, 6, or 7-membered ring, wherein:

R² at each occurrence is independently halo, hydroxy, alkyl, alkoxy, hydroxyalkyl, haloalkoxy, or —C(O)O-alkyl;

n is 0, 1, or 2;

X is C or N; wherein:

when X is N:

R³ is absent and R³' is phenyl optionally substituted with one or two groups independently selected from heteroarylalkyloxy; alkyl substituted with arylsulfonylamino; alkyl substituted with cycloalkylcarbonylamino; or R³ is —SO₂—Rᵃ, wherein Rᵃ is optionally substituted alkyl, optionally substituted phenyl, optionally substituted phenylalkyl, or optionally substituted heteroaryl;

when X is C:

R³ is cyano, aminoalkyl, alkoxycarbonyl, or hydroxy and R³' is a optionally substituted phenyl; or R³ is hydrogen and R³' is phenyl, alkyl substituted with 1-phenyl-4,5,6,7-tetrahydro-1H-pyrazolo[3,4-c]pyridinyl, 1H-indolyl, optionally substituted, 2-oxo-3,4-dihydroquinazolinyl, or —C(O)NRᵇRᶜ, wherein Rᵇ is hydrogen or alkyl; and Rᶜ is optionally substituted heteroarylalkyl; or R³ is a group of formula (a), (b), (c), (d), (e), or (f):

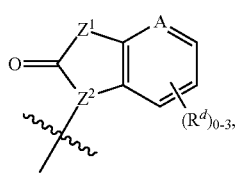

(a)

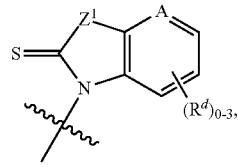

(b)

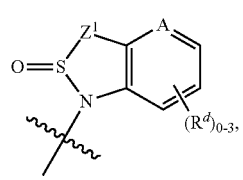

(c)

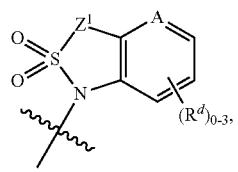

(d)

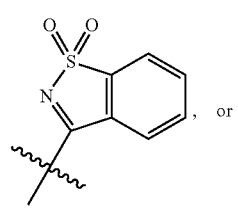

(e)

, or

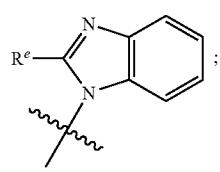

(f)

;

wherein Z¹ is O or NH or N optionally substituted with aminoalkyl, alkylaminoalkyl, or dialkylaminoalkyl;

Z² is CH or N, and A is N or C; and each Rᵈ, when present, is independently halo, alkyl, optionally substituted alkoxy, or optionally substituted heterocycloalkyl and Rᵉ is amino or haloalkyl; or R³ and R³' are taken together with the carbon to which they are attached to form an optionally substituted 5 or 6 membered ring (g), (h), (j), (k), or (l):

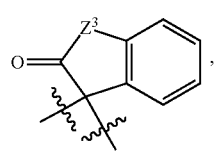

(g)

,

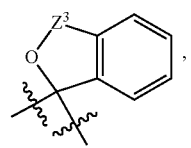

(h)

,

-continued

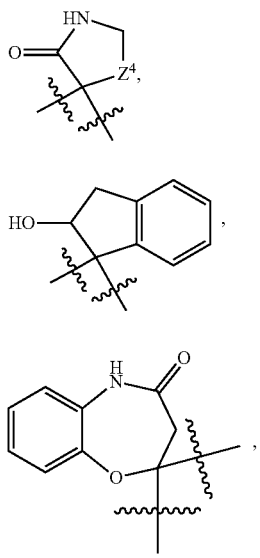

wherein: $Z^3$ is $CH_2$ or NH; $Z^4$ is $NR^f$ or $CHR^f$, wherein $R^f$ is optionally substituted phenyl;

Y is absent or is alkyl, —(C═O)—, —$NR^x$—(C═O)—, or —(C═O)$NR^x$—, —O—(C═O)—, or —(C═O)O—, —$NR^x$—(C═O)O—, or —O(C═O)$NR^x$—, wherein $R^x$ is hydrogen or optionally substituted alkyl;

$R^4$ is hydrogen, halo, optionally substituted alkyl, optionally substituted alkenyl, optionally substituted aryl, optionally substituted heterocycloalkyl, optionally substituted heteroaryl; and when Y is —$NR^x$—(C═O)—, or —(C═O)—$NR^x$—, $R^x$ and $R^4$ can be joined together along with the atoms to which they are attached to form a 4, 5, or 6 membered ring, optionally containing 1 or 2 additional heteroatoms selected from N, S, and O.

13. The compound of claim 12, wherein Y is absent and $R^4$ is ethyl, propenyl, or triflouromethyl.

14. The compound of claim 12, wherein Y—$R^4$ is:

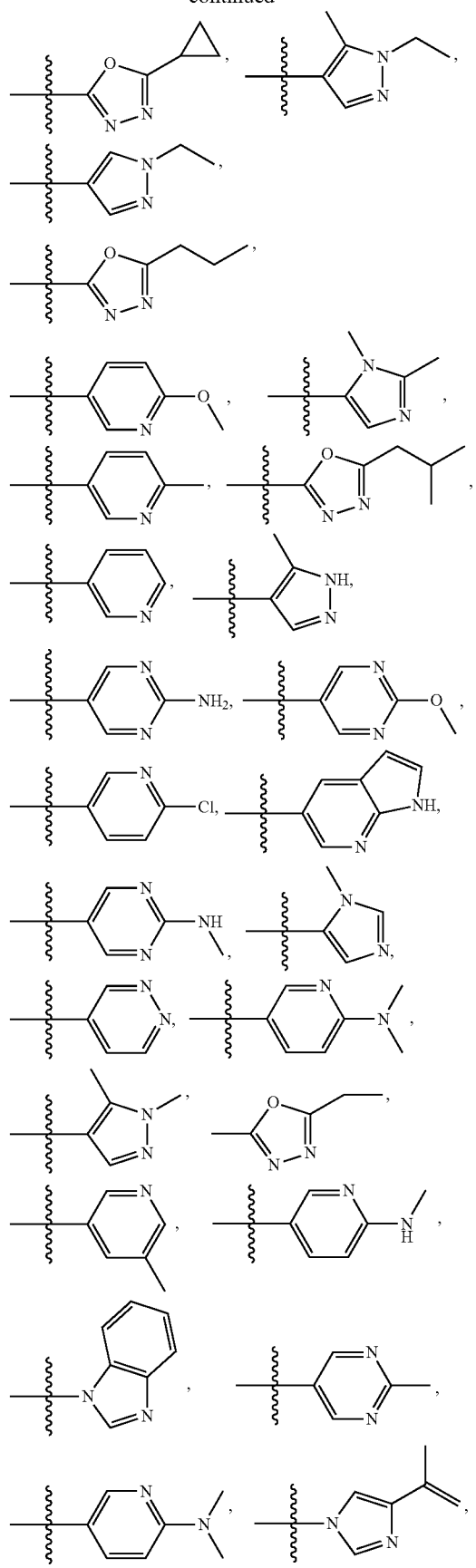

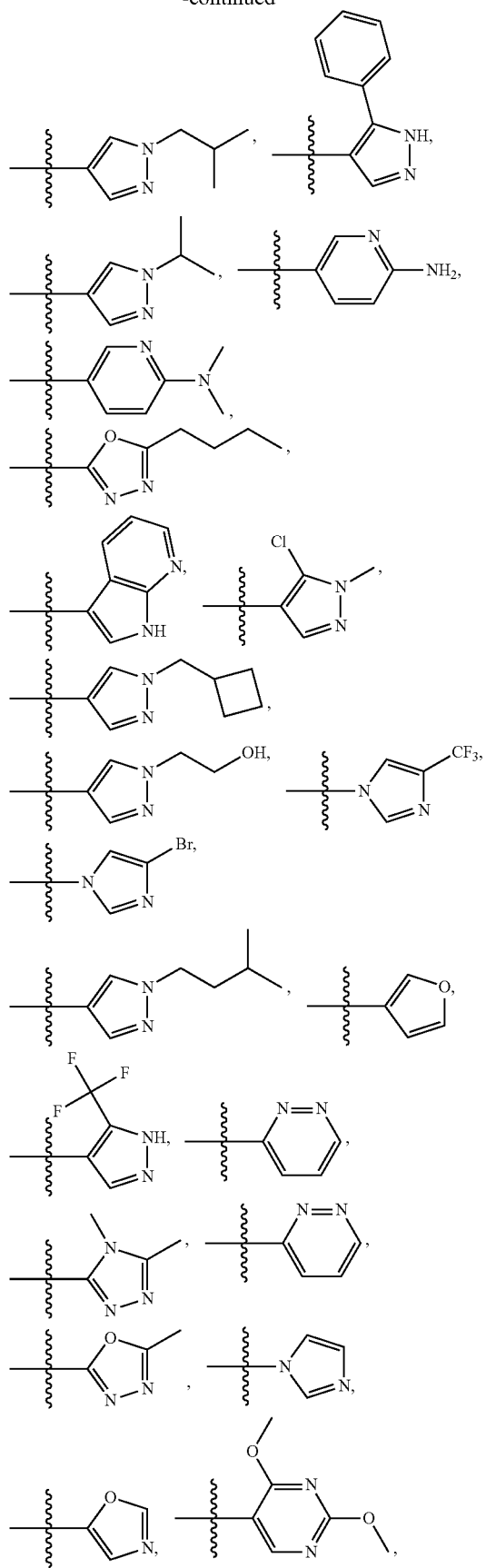
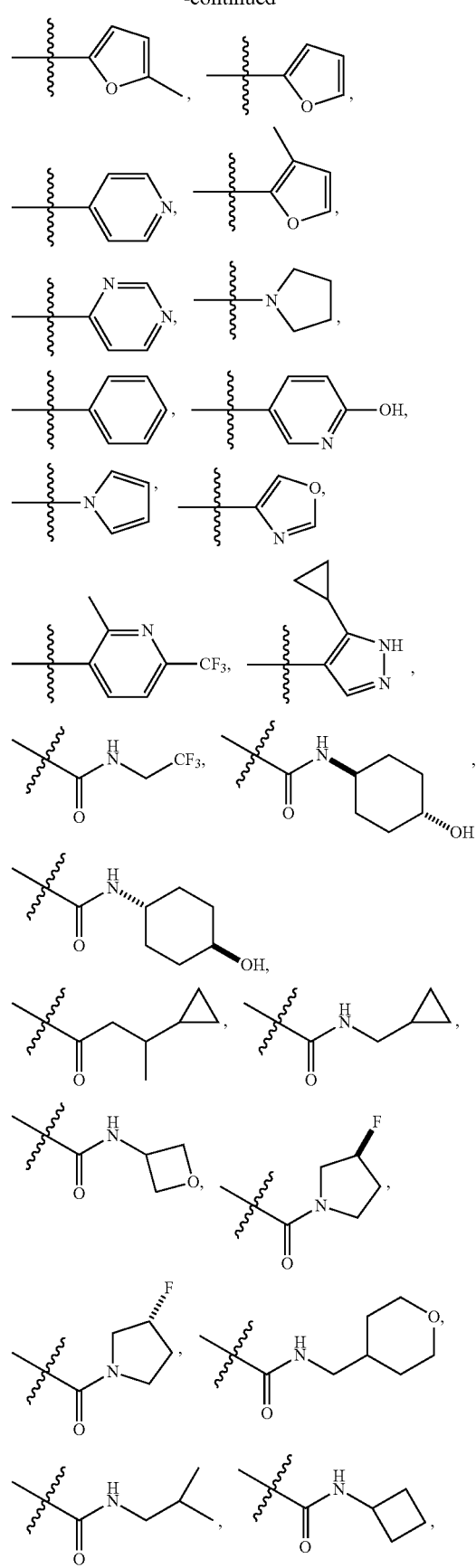

355
-continued
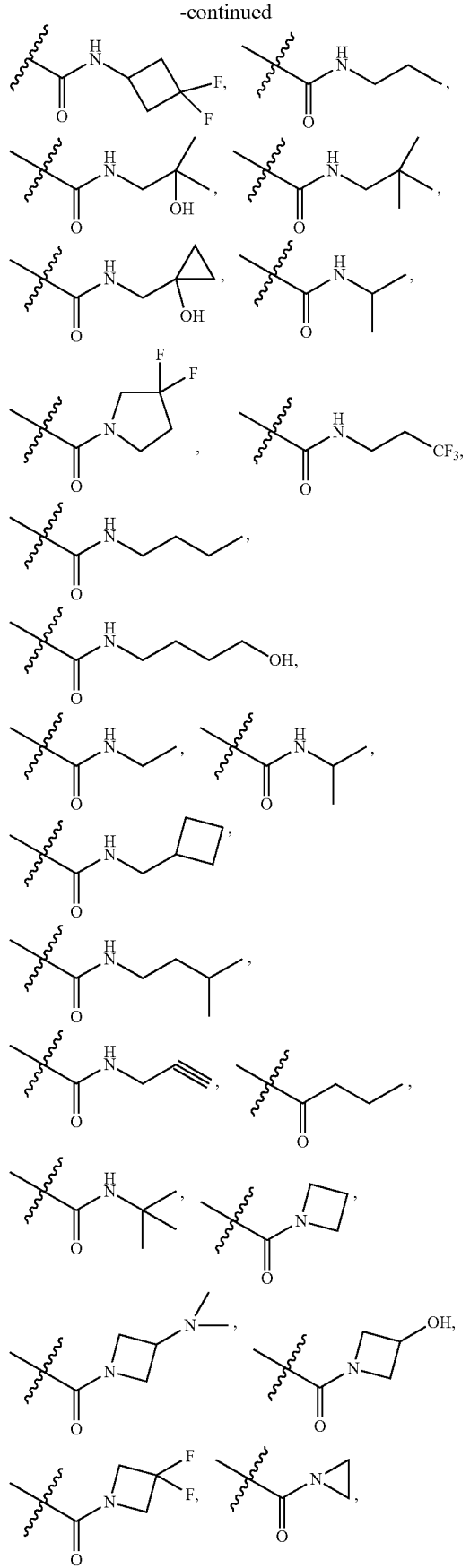
356
-continued
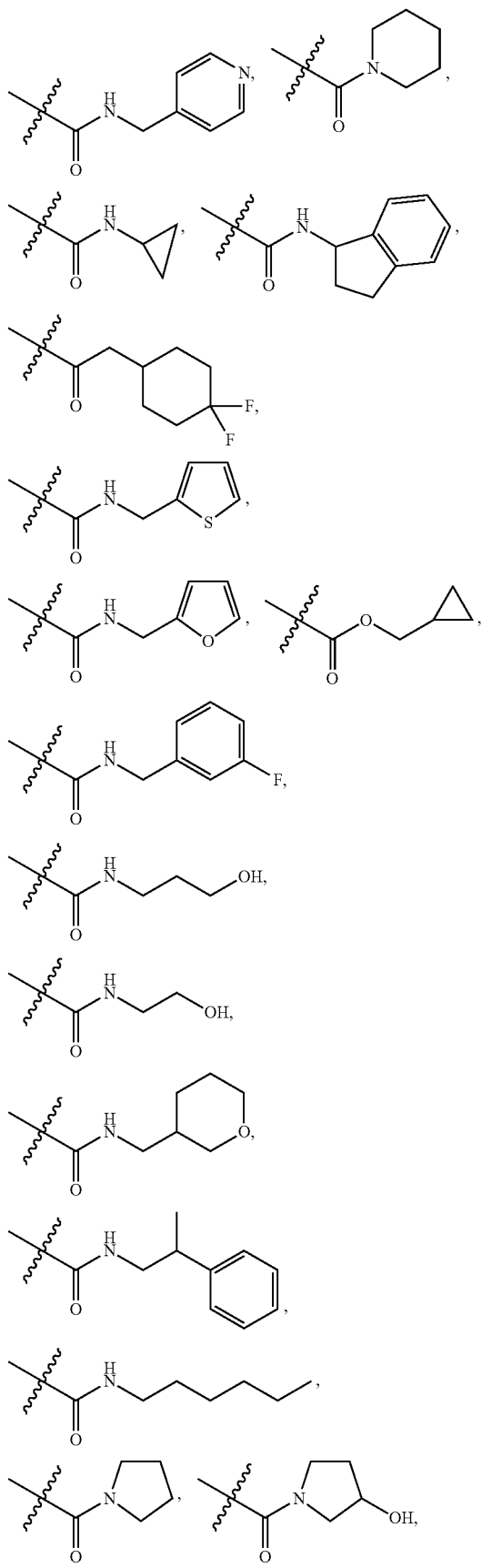

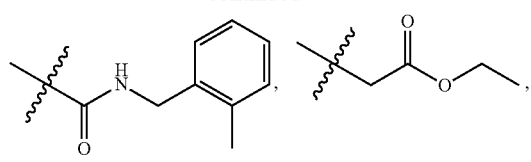
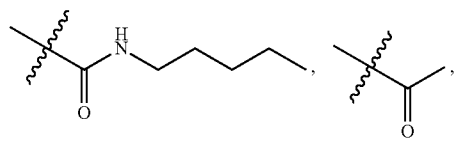
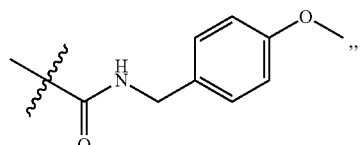
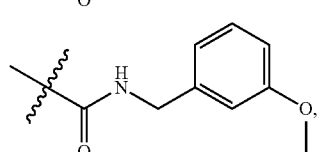
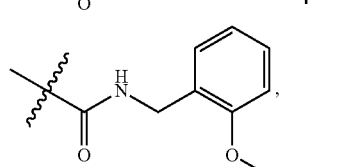
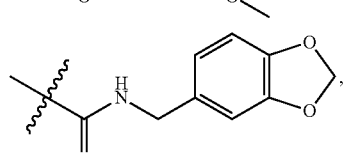
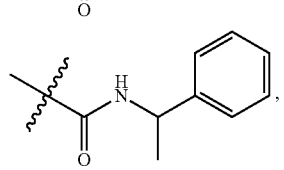
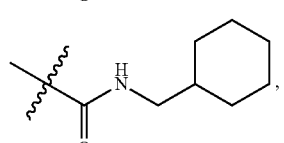
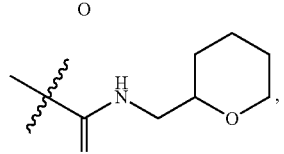
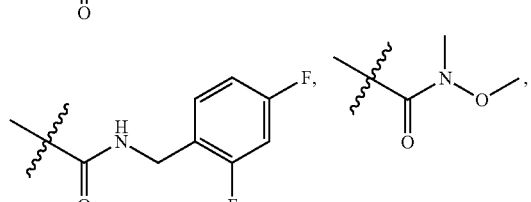
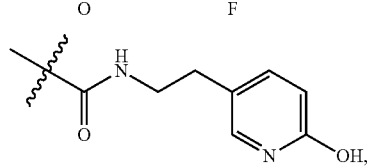
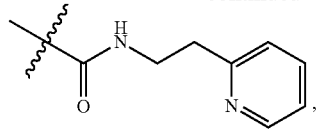
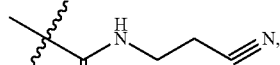
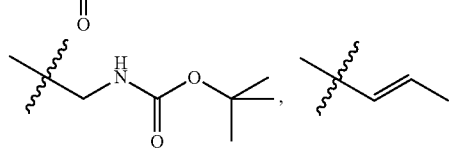
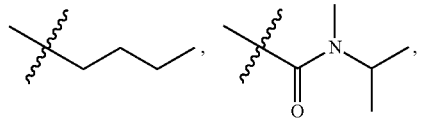
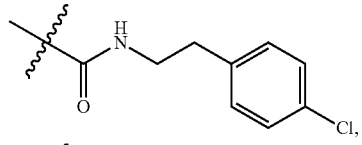
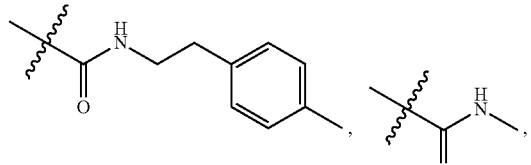
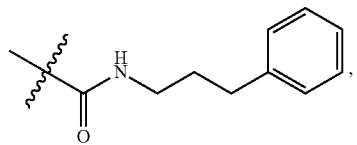
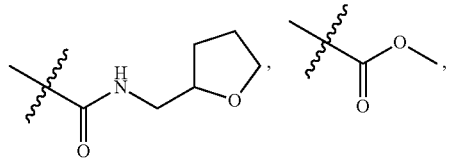
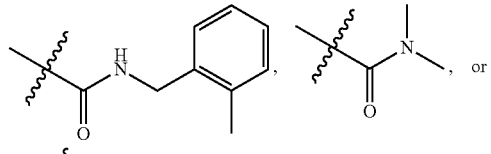
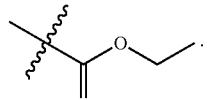
15. The compound of claim 12, wherein Y is —(C=O)—, —(C=O)O—, or —(C=O)NH—.
16. A compound which is:
1'-[9-ethyl-8-(1-propyl-1H-pyrazol-4-yl)-9H-purin-6-yl]spiro[indole-3,4'-piperidin]-2(1H)-one;
1'-{9-ethyl-8-[5-(1-methylethyl)-1,3,4-oxadiazol-2-yl]-9H-purin-6-yl}spiro[indole-3,4'-piperidin]-2(1H)-one;
1'-[8-(1,5-dimethyl-1H-pyrazol-4-yl)-9-ethyl-9H-purin-6-yl]spiro[indole-3,4'-piperidin]-2(1H)-one;
1'-{9-ethyl-8-[6-(trifluoromethyl)pyridin-3-yl]-9H-purin-6-yl}spiro[indole-3,4'-piperidin]-2(1H)-one;

1-(1-{9-ethyl-8-[6-(trifluoromethyl)pyridin-3-yl]-9H-purin-6-yl}piperidin-4-yl)-1,3-dihydro-2H-imidazo[4,5-b]pyridin-2-one;
1'-[9-ethyl-8-(1-methyl-1H-pyrazol-4-yl)-9H-purin-6-yl]spiro[indole-3,4'-piperidin]-2(1H)-one;
1'-[9-ethyl-8-(1H-pyrazol-4-yl)-9H-purin-6-yl]spiro[indole-3,4'-piperidin]-2(1H)-one;
1-{1-[8-(5-bromopyridin-3-yl)-9-methyl-9H-purin-6-yl]piperidin-4-yl}-1,3-dihydro-2H-benzimidazol-2-one;
1'-{9-methyl-8-[5-(1-methylethyl)-1,3,4-oxadiazol-2-yl]-9H-purin-6-yl}spiro[indole-3,4'-piperidin]-2(1H)-one;
1'-(9-ethyl-8-pyrimidin-5-yl-9H-purin-6-yl)spiro[indole-3,4'-piperidin]-2(1H)-one;
1-(1-{9-ethyl-8-[6-(trifluoromethyl)pyridin-3-yl]-9H-purin-6-yl}piperidin-4-yl)-1,3-dihydro-2H-benzimidazol-2-one;
1-{1-[9-ethyl-8-(1-propyl-1H-pyrazol-4-yl)-9H-purin-6-yl]piperidin-4-yl}-1,3-dihydro-2H-benzimidazol-2-one;
1-{1-[8-(1-ethyl-5-methyl-1H-pyrazol-4-yl)-9-methyl-9H-purin-6-yl]piperidin-4-yl}-4-fluoro-1,3-dihydro-2H-benzimidazol-2-one;
1'-[8-(5-cyclopropyl-1,3,4-oxadiazol-2-yl)-9-ethyl-9H-purin-6-yl]spiro[indole-3,4'-piperidin]-2(1H)-one;
1-{1-[8-(5-cyclopropyl-1H-pyrazol-4-yl)-9-methyl-9H-purin-6-yl]piperidin-4-yl}-1,3-dihydro-2H-benzimidazol-2-one;
1'-[9-methyl-8-(1H-pyrazol-4-yl)-9H-purin-6-yl]spiro[indole-3,4'-piperidin]-2(1H)-one;
1'-[9-ethyl-8-(1-ethyl-1H-pyrazol-4-yl)-9H-purin-6-yl]spiro[indole-3,4'-piperidin]-2(1H)-one;
9-ethyl-6-(2-oxo-1,2-dihydro-1'H-spiro[indole-3,4'-piperidin]-1'-yl)-N-(2,2,2-trifluoroethyl)-9H-purine-8-carboxamide;
1'-[9-methyl-8-(5-propyl-1,3,4-oxadiazol-2-yl)-9H-purin-6-yl]spiro[indole-3,4'-piperidin]-2(1H)-one;
1'-{9-methyl-8-[6-(trifluoromethyl)pyridin-3-yl]-9H-purin-6-yl}spiro[indole-3,4'-piperidin]-2(1H)-one;
1-(1-{9-methyl-8-[6-(methyloxy)pyridin-3-yl]-9H-purin-6-yl}piperidin-4-yl)-1,3-dihydro-2H-benzimidazol-2-one;
9-ethyl-N-(trans-4-hydroxycyclohexyl)-6-[4-(2-oxo-2,3-dihydro-1H-benzimidazol-1-yl)piperidin-1-yl]-9H-purine-8-carboxamide;
1'-[9-methyl-8-(1-propyl-1H-pyrazol-4-yl)-9H-purin-6-yl]spiro[indole-3,4'-piperidin]-2(1H)-one;
1-{1-[8-(1,2-dimethyl-1H-imidazol-5-yl)-9-methyl-9H-purin-6-yl]piperidin-4-yl}-1,3-dihydro-2H-benzimidazol-2-one;
1-{1-[9-ethyl-8-(2-methylpyrimidin-5-yl)-9H-purin-6-yl]piperidin-4-yl}-1,3-dihydro-2H-benzimidazol-2-one;
1-{1-[8-(1,5-dimethyl-1H-pyrazol-4-yl)-9-methyl-9H-purin-6-yl]piperidin-4-yl}-4-fluoro-1,3-dihydro-2H-benzimidazol-2-one;
1-(1-{9-methyl-8-[5-(2-methylpropyl)-1,3,4-oxadiazol-2-yl]-9H-purin-6-yl}piperidin-4-yl)-1,3-dihydro-2H-benzimidazol-2-one;
1-{1-[8-(1-ethyl-5-methyl-1H-pyrazol-4-yl)-9-methyl-9H-purin-6-yl]piperidin-4-yl}-1,3-dihydro-2H-benzimidazol-2-one;
1-{1-[8-(1-ethyl-5-methyl-1H-pyrazol-4-yl)-9-methyl-9H-purin-6-yl]piperidin-4-yl}-1,3-dihydro-2H-imidazo[4,5-b]pyridin-2-one;
1-[1-(9-ethyl-8-pyridin-3-yl-9H-purin-6-yl)piperidin-4-yl]-1,3-dihydro-2H-benzimidazol-2-one;
1'-(9-ethyl-8-pyridin-3-yl-9H-purin-6-yl)spiro[indole-3,4'-piperidin]-2(1H)-one;
9-ethyl-6-[4-(2-oxo-2,3-dihydro-1H-imidazo[4,5-b]pyridin-1-yl)piperidin-1-yl]-N-(2,2,2-trifluoroethyl)-9H-purine-8-carboxamide;
1'-[8-(1,5-dimethyl-1H-pyrazol-4-yl)-9-methyl-9H-purin-6-yl]spiro[indole-3,4'-piperidin]-2(1H)-one;
1'-[9-methyl-8-(5-methyl-1H-pyrazol-4-yl)-9H-purin-6-yl]spiro[indole-3,4'-piperidin]-2(1H)-one;
1-(1-{9-methyl-8-[6-(trifluoromethyl)pyridin-3-yl]-9H-purin-6-yl}piperidin-4-yl)-1,3-dihydro-2H-imidazo[4,5-b]pyridin-2-one;
1'-[8-(1-ethyl-1H-pyrazol-4-yl)-9-methyl-9H-purin-6-yl]spiro[indole-3,4'-piperidin]-2(1H)-one;
1-{1-[8-(1,2-dimethyl-1H-imidazol-5-yl)-9-methyl-9H-purin-6-yl]piperidin-4-yl}-1,3-dihydro-2H-imidazo[4,5-b]pyridin-2-one;
1-{1-[8-(2-aminopyrimidin-5-yl)-9-ethyl-9H-purin-6-yl]piperidin-4-yl}-1,3-dihydro-2H-benzimidazol-2-one;
9-ethyl-N-(trans-4-hydroxycyclohexyl)-6-(2-oxo-1,2-dihydro-1'H-spiro[indole-3,4'-piperidin]-1'-yl)-9H-purine-8-carboxamide;
N-(1-cyclopropylethyl)-9-ethyl-6-(2-oxo-1,2-dihydro-1'H-spiro[indole-3,4'-piperidin]-1'-yl)-9H-purine-8-carboxamide;
1-{1-[8-(6-chloropyridin-3-yl)-9-methyl-9H-purin-6-yl]piperidin-4-yl}-1,3-dihydro-2H-benzimidazol-2-one;
1-(1-{9-ethyl-8-[2-(methyloxy)pyrimidin-5-yl]-9H-purin-6-yl}piperidin-4-yl)-1,3-dihydro-2H-benzimidazol-2-one;
9-ethyl-N-oxetan-3-yl-6-[4-(2-oxo-2,3-dihydro-1H-benzimidazol-1-yl)piperidin-1-yl]-9H-purine-8-carboxamide;
9-ethyl-6-[4-(2-oxo-2,3-dihydro-1H-benzimidazol-1-yl)piperidin-1-yl]-N-(2,2,2-trifluoroethyl)-9H-purine-8-carboxamide;
1-{1-[9-ethyl-8-(1-ethyl-1H-pyrazol-4-yl)-9H-purin-6-yl]piperidin-4-yl}-1,3-dihydro-2H-imidazo[4,5-b]pyridin-2-one;
1-{1-[9-methyl-8-(1H-pyrrolo[2,3-b]pyridin-5-yl)-9H-purin-6-yl]piperidin-4-yl}-1,3-dihydro-2H-benzimidazol-2-one;
1-[1-(9-ethyl-8-pyrimidin-5-yl-9H-purin-6-yl)piperidin-4-yl]-1,3-dihydro-2H-benzimidazol-2-one;
9-ethyl-N-(trans-4-hydroxycyclohexyl)-6-[4-(2-oxo-2,3-dihydro-1H-imidazo[4,5-b]pyridin-1-yl)piperidin-1-yl]-9H-purine-8-carboxamide;
1'-[8-(5-cyclopropyl-1,3,4-oxadiazol-2-yl)-9-methyl-9H-purin-6-yl]spiro[indole-3,4'-piperidin]-2(1H)-one;
1-(1-{9-ethyl-8-[2-(methylamino)pyrimidin-5-yl]-9H-purin-6-yl}piperidin-4-yl)-1,3-dihydro-2H-benzimidazol-2-one;
1-{1-[8-(1,5-dimethyl-1H-pyrazol-4-yl)-9-ethyl-9H-purin-6-yl]piperidin-4-yl}-1,3-dihydro-2H-benzimidazol-2-one;
1-(1-{9-ethyl-8-[5-(1-methylethyl)-1,3,4-oxadiazol-2-yl]-9H-purin-6-yl}piperidin-4-yl)-1,3-dihydro-2H-benzimidazol-2-one;
1-{1-[9-methyl-8-(1-methyl-1H-imidazol-5-yl)-9H-purin-6-yl]piperidin-4-yl}-1,3-dihydro-2H-benzimidazol-2-one;
1-{1-[9-ethyl-8-(1-ethyl-1H-pyrazol-4-yl)-9H-purin-6-yl]piperidin-4-yl}-1,3-dihydro-2H-benzimidazol-2-one;
1-(1-{9-methyl-8-[5-(1-methylethyl)-1,3,4-oxadiazol-2-yl]-9H-purin-6-yl}piperidin-4-yl)-1,3-dihydro-2H-benzimidazol-2-one;

1-{1-[9-methyl-8-(5-methyl-1H-pyrazol-4-yl)-9H-purin-6-yl]piperidin-4-yl}-1,3-dihydro-2H-imidazo[4,5-b]pyridin-2-one;
1-[1-[9-ethyl-8-(1H-pyrazol-4-yl)-9H-purin-6-yl]piperidin-4-yl]-1,3-dihydro-2H-benzimidazol-2-one;
1'-(9-ethyl-8-pyridazin-4-yl-9H-purin-6-yl)spiro[indole-3,4'-piperidin]-2(1H)-one;
1-(1-{8-[6-(dimethylamino)pyridin-3-yl]-9-methyl-9H-purin-6-yl}piperidin-4-yl)-1,3-dihydro-2H-imidazo[4,5-b]pyridin-2-one;
1-{1-[8-(1,5-dimethyl-1H-pyrazol-4-yl)-9-methyl-9H-purin-6-yl]piperidin-4-yl}-1,3-dihydro-2H-imidazo[4,5-b]pyridin-2-one;
1-{1-[8-(1-ethyl-1H-pyrazol-4-yl)-9-methyl-9H-purin-6-yl]piperidin-4-yl}-4-fluoro-1,3-dihydro-2H-benzimidazol-2-one;
1'-[8-(5-ethyl-1,3,4-oxadiazol-2-yl)-9-methyl-9H-purin-6-yl]spiro[indole-3,4'-piperidin]-2(1H)-one;
1-(1-{9-methyl-8-[6-(trifluoromethyl)pyridin-3-yl]-9H-purin-6-yl}piperidin-4-yl)-1,3-dihydro-2H-benzimidazol-2-one;
1-{1-[8-(1,5-dimethyl-1H-pyrazol-4-yl)-9-methyl-9H-purin-6-yl]piperidin-4-yl}-1,3-dihydro-2H-benzimidazol-2-one;
1-{1-[9-methyl-8-(1-propyl-1H-pyrazol-4-yl)-9H-purin-6-yl]piperidin-4-yl}-1,3-dihydro-2H-benzimidazol-2-one;
1-{1-[9-methyl-8-(5-methyl-1H-pyrazol-4-yl)-9H-purin-6-yl]piperidin-4-yl}-1,3-dihydro-2H-benzimidazol-2-one;
1-(1-{9-methyl-8-[2-(methyloxy)pyrimidin-5-yl]-9H-purin-6-yl}piperidin-4-yl)-1,3-dihydro-2H-benzimidazol-2-one;
1-{1-[9-methyl-8-(5-methylpyridin-3-yl)-9H-purin-6-yl]piperidin-4-yl}-1,3-dihydro-2H-benzimidazol-2-one;
1-(1-{9-methyl-8-[6-(methylamino)pyridin-3-yl]-9H-purin-6-yl}piperidin-4-yl)-1,3dihydro-2H-imidazo[4,5-b]pyridin-2-one;
1-{1-[8-(1-ethyl-1H-pyrazol-4-yl)-9-methyl-9H-purin-6-yl]piperidin-4-yl}-1,3-dihydro-2H-benzimidazol-2-one;
N-(cyclopropylmethyl)-9-ethyl-6-[4(2-oxo-2,3-dihydro-1H-imidazo[4,5-b]pyridin-1-yl)piperidin-1-yl]-9H-purine-8-carboxamide;
1'-(9-ethyl-8{[(3R)-3-fluoropyrrolidin-1-yl]carbonyl}-9H-purin-6-yl)-spiro[indole-3-piperidin]-2(1H)-one;
1-{1-[8-(2-aminopyrimidin-5-yl)-9-methyl-9H-purin-6-yl]piperidin-4-yl}-1,3-dihydro-2H-benzimidazol-2-one;
1-{1-[9-methyl-8-(5-propyl-1,3,4-oxadiazol-2-yl)-9H-purin-6-yl]piperidin-4-yl}-1,3-dihydro-2H-benzimidazol-2-one;
9-ethyl-6-[4-(2-oxo-2,3-dihydro-1H-benzimidazol-1-yl)piperidin-1-yl]-N-(tetrahydro-2H-pyran-4-ylmethyl)-9H-purine-8-cearboxamide;
1-[1-[8-(1H-benzimidazol-1-yl)-9-methyl-9H-purin-6-yl]piperidin-4-yl}-1,3-dihydro-2H-benzimidazol-2-one;
1'-[9-ethyl-8-(5-propyl-1,3,4-oxadiazol-2-yl)-9H-purin-6-yl]spiro[indole-3,4'-piperidin]-2(1H)-one;
1-(1-{9-methyl-8-[6-(methylamino)pyridin-3-yl]-9H-purin-6-yl}piperidin-4-yl)-1,3-dihydro-2H-benzimidazol-2-one;
N-(1-cyclopropylethyl)-9-ethyl-6-[4-(2-oxo-2,3-dihydro-1H-benzimidazol-1-yl)piperidin-1-yl]-9H-purine-8-carboxamide;
1-(1-{9-methyl-8-[2-(methylamino)pyrimidin-5-yl]-9H-purin-6-yl}piperidin-4-yl)-1,3-dihydro-2H-benzimidazol-2-one;
9-ethyl-N-(2-methylpropyl)-6-(2-oxo-1,2-dihydro-1'H-spiro[indole-3,4'-piperidin]-1'-yl)-9H-purine-8-carboxamide;
1'-[9-ethyl-8-(5-ethyl-1,3,4-oxadiazol-2-yl)-9H-purin-6-yl]spiro[indole-3,4'-piperidin]-2(1H)-one;
1-{1-[8-(1-ethyl-1H-pyrazol-4-yl)-9-methyl-9H-purin-6-yl]piperidin-4-yl}-1,3-dihydro-2H-imidazo[4,5-b]pyridin-2-one;
1-{1-[9-methyl-8-(2-methylpyrimidin-5-yl)-9H-purin-6-yl]piperidin-4-yl}-1,3-dihydro-2H-benzimidazol-2-one;
9-ethyl-N-oxetan-3-yl-6-(2-oxo-1,2-dihydro-1'H-spiro[indole-3,4'-piperidin]-1'-yl)-9H-purine-8-carboxamide;
1'-{8-[(3,3-difluoroazetidin-1-yl)carbonyl]-9-ethyl-9H-purin-6-yl}spiro[indole-3,4'-piperidin]-2(1H)-one;
1-(1-{8-[2-(dimethylamino)pyrimidin-5-yl]-9-methyl-9H-purin-6-yl}piperidin-4-yl)-1,3-dihydro-2H-benzimidazol-2-one;
9-ethyl-6-[4-(2-oxo-2,3-dihydro-1H-benzimidazol-1-yl)piperidin-1-yl]-N-propyl-9H-purine-8-carboxamide;
1-(1-{9-methyl-8-[4-(1-methylethenyl)-1H-imidazol-1-yl]-9H-purin-6-yl}piperidin-4-yl)-1,3-dihydro-2H-benzimidazol-2-one;
N-(cyclopropylmethyl)-9-ethyl-6-[4-(2-oxo-2,3-dihydro-1H-benzimidazol-1-yl)piperidin-1-yl]-9H-purine-8-carboxamide;
1-(1-{9-methyl-8-[1-(2-methylpropyl)-1H-pyrazol-4-yl]-9H-purin-6-yl}piperidin-4-yl)-1,3-dihydro-2H-benzimidazol-2-one;
N-(trans-4-hydroxycyclohexyl)-9-methyl-6-(2-oxo-1,2-dihydro-1'H-spiro[indole-3,4'-piperidin]-1'-yl)-9H-purine-8-carboxamide;
1-(1-{8-[2-(dimethylamino)pyrimidin-5-yl]-9-ethyl-9H-purin-6-yl}piperidin-4-yl)-1,3-dihydro-2H-benzimidazol-2-one;
1-{1-[9-methyl-8-(1-methyl-1H-pyrazol-4-yl)-9H-purin-6-yl]piperidin-4-yl}-1,3-dihydro-2H-imidazo[4,5-b]pyridin-2-one;
1-{1-[9-methyl-8-(5-phenyl-1H-pyrazol-4-yl)-9H-purin-6-yl]piperidin-4-yl}-1,3-dihydro-2H-benzimidazol-2-one;
9-ethyl-N-(2-hydroxy-2-methylpropyl)-6-[4-(2-oxo-2,3-dihydro-1H-benzimidazol-1-yl)piperidin-1-yl]-9H-purine-8-carboxamide;
1-{1-[9-ethyl-8-(1-methyl-1H-pyrazol-4-yl)-9H-purin-6-yl]piperidin-4-yl}-1,3-dihydro-2H-imidazo[4,5-b]pyridin-2-one;
N-(cyclopropylmethyl)-9-ethyl-6-(2-oxo-1,2-dihydro-1'H-spiro[indole-3,4'-piperidin]-1'-yl)-9H-purine-8-carboxamide;
1-(1-{9-methyl-8-[1-(1-methylethyl)-1H-pyrazol-4-yl]-9H-purin-6-yl}piperidin-4-yl)-1,3-dihydro-2H-benzimidazol-2-one;
N-(trans-4-hydroxycyclohexyl)-9-methyl-6-[4-(2-oxo-2,3-dihydro-1H-benzimidazol-1-yl)piperidin-1-yl]-9H-purine-8-carboxamide;
4-fluoro-1-{1-[9-methyl-8-(1-methyl-1H-pyrazol-4-yl)-9H-purin-6-yl]piperidin-4-yl}-1,3-dihydro-2H-benzimidazol-2-one;
1-{1-[9-methyl-8-(1H-pyrazol-4-yl)-9H-purin-6-yl]piperidin-4-yl}-1,3-dihydro-2H-benzimidazol-2-one;

1-{1-[8-(6-aminopyridin-3-yl)-9-methyl-9H-purin-6-yl]piperidin-4-yl}-1,3-dihydro-2H-imidazo[4,5-b]pyridin-2-one;
N-(trans-4-hydroxycyclohexyl)-9-methyl-6-[4-(2-oxo-2,3-dihydro-1H-imidazo[4,5-b]pyridin-1-yl)piperidin-1-yl]-9H-purine-8-carboxamide;
9-ethyl-6-(2-oxo-1,2-dihydro-1'H-spiro[indole-3,4'-piperidin]-1'-yl)-N-propyl-9H-purine-8-carboxamide;
1-{1-[8-(6-aminopyridin-3-yl)-9-methyl-9H-purin-6-yl]piperidin-4-yl}-1,3-dihydro-2H-benzimidazol-2-one;
1-(1-{8-[6-(dimethylamino)pyridin-3-yl]-9-methyl-9H-purin-6-yl}piperidin-4-yl)-1,3-dihydro-2H-benzimidazol-2-one;
9-methyl-6-(2-oxo-1,2-dihydro-1'H-spiro[indole-3,4'-piperidin]-1'-yl)-N-(2,2,2-trifluoroethyl)-9H-purine-8-carboxamide;
9-methyl-6-[4-(2-oxo-2,3-dihydro-1H-imidazo[4,5-b]pyridin-1-yl)piperidin-1-yl]-N-(2,2,2-trifluoroethyl)-9H-purine-8-carboxamide;
9-ethyl-N-[(1-hydroxycyclopropyl)methyl]-6-[4-(2-oxo-2,3-dihydro-1H-benzimidazol-1-yl)piperidin-1-yl]-9H-purine-8-carboxamide;
N-(2,2-dimethylpropyl)-9-ethyl-6-[4-(2-oxo-2,3-dihydro-1H-benzimidazol-1-yl)piperidin-1-yl]-9H-purine-8-carboxamide;
9-methyl-6-[4-(2-oxo-2,3-dihydro-1H-benzimidazol-1-yl)piperidin-1-yl]-N-(2,2,2-trifluoroethyl)-9H-purine-8-carboxamide;
9-ethyl-6-(2-oxo-1,2-dihydro-1'H-spiro[indole-3,4'-piperidin]-1'-yl)-N-(tetrahydro-2H-pyran-4-ylmethyl)-9H-purine-8-carboxamide;
1'-[9-methyl-8-(1-methyl-1H-pyrazol-4-yl)-9H-purin-6-yl]spiro[indole-3,4'-piperidin]-2(1H)-one;
1-{1-[8-(5-butyl-1,3,4-oxadiazol-2-yl)-9-methyl-9H-purin-6-yl]piperidin-4-yl}-1,3-dihydro-2H-benzimidazol-2-one;
9-ethyl-N-(2-methylpropyl)-6-[4-(2-oxo-2,3-dihydro-1H-benzimidazol-1-yl)piperidin-1-yl]-9H-purine-8-carboxamide;
1-{1-[8-(5-cyclopropyl-1,3,4-oxadiazol-2-yl)-9-methyl-9H-purin-6-yl]piperidin-4-yl}-1,3-dihydro-2H-benzimidazol-2-one;
1'-(9-methyl-8-pyrimidin-5-yl-9H-purin-6-yl)spiro[indole-3,4'-piperidin]-2(1H)-one;
1-[1-(9-ethyl-8-{[(3R)-3-fluoropyrrolidin-1-yl]carbonyl}-9H-purin-6-yl)piperidin-4-yl]-1,3-dihydro-2H-benzimidazol-2-one;
1-{1-[9-ethyl-8-(1-methyl-1H-pyrazol-4-yl)-9H-purin-6-yl]piperidin-4-yl}-1,3-dihydro-2H-benzimidazol-2-one;
N-(cyclobutylmethyl)-9-ethyl-6-(2-oxo-1,2-dihydro-1'H-spiro[indole-3,4'-piperidin]-1'-yl)-9H-purine-8-carboxamide;
1-(1--{8-[(3,3-difluoroazetidin-1-yl)carbonyl]-9-ethyl-9H-purin-6-yl}piperidin-4-yl)-1,3-dihydro-2H-benzimidazol-2-one;
1-(1-{8-[(3,3-difluoropyrrolidin-1-yl)carbonyl]-9-ethyl-9H-purin-6-yl}piperidin-4-yl)-1,3-dihydro-2H-benzimidazol-2-one;
1-{1-[8-(5-ethyl-1,3,4-oxadiazol-2-yl)-9-methyl-9H-purin-6-yl]piperidin-4-yl}-1,3-dihydro-2H-benzimidazol-2-one;
9-ethyl-N-(1-methylethyl)-6-(2-oxo-1,2-dihydro-1'H-spiro[indole-3,4'-piperidin]-1'-yl)-9H-purine-8-carboxamide;
1'-{8-[(3,3-difluoropyrrolidin-1-yl)carbonyl]-9-ethyl-9H-purin-6-yl}spiro[indole-3,4'-piperidin]-2(1H)-one;
1-{1-[9-methyl-8-(1H-pyrrolo[2,3-b]pyridin-3-yl)-9H-purin-6-yl]piperidin-4-yl}-1,3-dihydro-2H-benzimidazol-2-one;
1'-(9-methyl-8-pyridin-3-yl-9H-purin-6-yl)spiro[indole-3,4'-piperidin]-2(1H)-one;
9-ethyl-N-(1-methylethyl)-6-[4-(2-oxo-2,3-dihydro-1H-benzimidazol-1-yl)piperidin-1-yl]-9H-purine-8-carboxamide;
1-{1-[8-(5-chloro-1-methyl-1H-pyrazol-4-yl)-9-methyl-9H-purin-6-yl]piperidin-4-yl}-1,3-dihydro-2H-benzimidazol-2-one;
6-(7-bromo-2-oxo-1,2-dihydro-1'H-spiro[indole-3,4'-piperidin]-1'-yl)-N-(cyclopropylmethyl)-9-methyl-9H-purine-8-carboxamide;
N-(2,2-dimethylpropyl)-9-ethyl-6-(2-oxo-1,2-dihydro-1'H-spiro[indole-3,4'-piperidin]-1'-yl)-9H-purine-8-carboxamide;
9-ethyl-N-[(1-hydroxycyclopropyl)methyl]-6-(2-oxo-1,2-dihydro-1'H-spiro[indole-3,4'-piperidin]-1'-yl)-9H-purine-8-carboxamide;
9-ethyl-N-(2-hydroxy-2-methylpropyl)-6-(2-oxo-1,2-dihydro-1'H-spiro[indole-3,4'-piperidin]-1'-yl)-9H-purine-8-carboxamide;
6-(7-chloro-2-oxo-1,2-dihydro-1'H-spiro[indole-3,4'-piperidin]-1'-yl)-N-(cyclopropylmethyl)-9-methyl-9H-purine-8-carboxamide;
N-(cyclobutylmethyl)-9-ethyl-6-[4-(2-oxo-2,3-dihydro-1H-benzimidazol-1-yl)piperidin-1-yl]-9H-purine-8-carboxamide;
1-(1-{8-[1-(cyclobutylmethyl)-1H-pyrazol-4-yl]-9-methyl-9H-purin-6-yl}piperidin-4-yl)-1,3-dihydro-2H-benzimidazol-2-one;
9-ethyl-N-(4-hydroxybutyl)-6-[4-(2-oxo-2,3-dihydro-1H-benzimidazol-1-yl)piperidin-1-yl]-9H-purine-8-carboxamide;
1-[1-(9-methyl-8-pyridin-3-yl-9H-purin-6-yl)piperidin-4-yl]-1,3-dihydro-2H-benzimidazol-2-one;
N-cyclobutyl-9-ethyl-6-(2-oxo-1,2-dihydro-1'H-spiro[indole-3,4'-piperidin]-1'-yl)-9H-purine-8-carboxamide;
1-[1-(9-methyl-8-pyrimidin-5-yl-9H-purin-6-yl)piperidin-4-yl]-1,3-dihydro-2H-benzimidazol-2-one;
N-butyl-9-ethyl-6-(2-oxo-1,2-dihydro-1'H-spiro[indole-3,4'-piperidin]-1'-yl)-9H-purine-8-carboxamide;
1-[1-(9-ethyl-8-pyridazin-4-yl-9H-purin-6-yl)piperidin-4-yl]-1,3-dihydro-2H-benzimidazol-2-one;
N-cyclobutyl-9-ethyl-6-[4-(2-oxo-2,3-dihydro-1H-benzimidazol-1-yl)piperidin-1-yl]-9H-purine-8-carboxamide;
N,9-diethyl-6-(2-oxo-1,2-dihydro-1'H-spiro[indole-3,4'-piperidin]-1'-yl)-9H-purine-8-carboxamide;
N-butyl-9-methyl-6-[4-(2-oxo-2,3-dihydro-1H-benzimidazol-1-yl)piperidin-1-yl]-9H-purine-8-carboxamide;
9-methyl-6-[4-(2-oxo-2,3-dihydro-1H-benzimidazol-1-yl)piperidin-1-yl]-N-(tetrahydro-2H-pyran-4-ylmethyl)-9H-purine-8-carboxamide;
methyl (3R,4R)-1-[9-methyl-8-(1-methyl-1H-pyrazol-4-yl)-9H-purin-6-yl]-4-(2-oxo-2,3-dihydro-1H-benzimidazol-1-yl)piperidine-3-carboxylate;
1-{1-[9-methyl-8-(1-methyl-1H-pyrazol-4-yl)-9H-purin-6-yl]piperidin-4-yl}-1,3-dihydro-2H-benzimidazol-2-one;
9-methyl-N-(2-methylpropyl)-6-(2-oxo-1,2-dihydro-1'H-spiro[indole-3,4'-piperidin]-1'-yl)-9H-purine-8-carboxamide;
9-methyl-N-(2-methylpropyl)-6-[4-(2-oxo-2,3-dihydro-1H-benzimidazol-1-yl)piperidin-1-yl]-9H-purine-8-carboxamide;

N-(2-hydroxy-2-methylpropyl)-9-methyl-6-[4-(2-oxo-2,3-dihydro-1H-benzimidazol-1-yl)piperidin-1-yl]-9H-purine-8-carboxamide;

N-(cyclopropylmethyl)-9-methyl-6-[4-(2-oxo-2,3-dihydro-1H-benzimidazol-1-yl)piperidin-1-yl]-9H-purine-8-carboxamide;

9-methyl-6-(2-oxo-1,2-dihydro-1'H-spiro[indole-3,4'-piperidin]-1'-yl)-N-propyl-9H-purine-8-carboxamide;

N-butyl-9-ethyl-6-[4-(2-oxo-2,3-dihydro-1H-benzimidazol-1-yl)piperidin-1-yl]-9H-purine-8-carboxamide;

1-[1-(8-{[(3R)-3-fluoropyrrolidin-1-yl]carbonyl}-9-methyl-9H-purin-6-yl)piperidin-4-yl]-1,3-dihydro-2H-benzimidazol-2-one;

1-(1-{8-[(3,3-difluoroazetidin-1-yl)carbonyl]-9-methyl-9H-purin-6-yl}piperidin-4-yl)-1,3-dihydro-2H-benzimidazol-2-one;

N-(cyclopropylmethyl)-6-[4-(4-fluoro-2-oxo-2,3-dihydro-1H-benzimidazol-1-yl)piperidin-1-yl]-9-methyl-9H-purine-8-carboxamide;

N,9-diethyl-6-[4-(2-oxo-2,3-dihydro-1H-benzimidazol-1-yl)piperidin-1-yl]-9H-purine-8-carboxamide;

N-(cyclopropylmethyl)-9-methyl-6-[3-methyl-4-(2-oxo-2,3-dihydro-1H-benzimidazol-1-yl)piperidin-1-yl]-9H-purine-8-carboxamide;

1-(1-{8-[1-(2-hydroxyethyl)-1H-pyrazol-4-yl]-9-methyl-9H-purin-6-yl}piperidin-4-yl)-1,3-dihydro-2H-benzimidazol-2-one;

N-(cyclobutylmethyl)-9-methyl-6-(2-oxo-1,2-dihydro-1'H-spiro[indole-3,4'-piperidin]-1'-yl)-9H-purine-8-carboxamide;

N-(cyclopropylmethyl)-9-methyl-6-[4-(2-thioxo-2,3-dihydro-1H-benzimidazol-1-yl)piperidin-1-yl]-9H-purine-8-carboxamide;

6-[4-(4-chloro-2-oxo-2,3-dihydro-1H-benzimidazol-1-yl)piperidin-1-yl]-N-(cyclopropylmethyl)-9-methyl-9H-purine-8-carboxamide;

N-(1-cyclopropylethyl)-9-methyl-6-(2-oxo-1,2-dihydro-1'H-spiro[indole-3,4'-piperidin]-1'-yl)-9H-purine-8-carboxamide;

1'-(8-{[(3R)-3-fluoropyrrolidin-1-yl]carbonyl}-9-methyl-9H-purin-6-yl)spiro[indole-3,4'-piperidin]-2(1H)-one;

N-[(1-hydroxycyclopropyl)methyl]-9-methyl-6-[4-(2-oxo-2,3-dihydro-1H-benzimidazol-1-yl)piperidin-1-yl]-9H-purine-8-carboxamide;

1-(1-{9-methyl-8-[4-(trifluoromethyl)-1H-imidazol-1-yl]-9H-purin-6-yl}piperidin-4-yl)-1,3-dihydro-2H-benzimidazol-2-one;

1-{1-[8-(4-bromo-1H-imidazol-1-yl)-9-methyl-9H-purin-6-yl]piperidin-4-yl}-1,3-dihydro-2H-benzimidazol-2-one;

9-methyl-6-(2-oxo-1,2-dihydro-1'H-spiro[indole-3,4'-piperidin]-1'-yl)-N-(tetrahydro-2H-pyran-4-ylmethyl)-9H-purine-8-carboxamide;

N-(cyclopropylmethyl)-9-methyl-6-[4-(2-oxo-2,3-dihydro-1H-imidazo[4,5-b]pyridin-1-yl)piperidin-1-yl]-9H-purine-8-carboxamide;

N-(cyclopropylmethyl)-9-methyl-6-(2-oxo-1,2-dihydro-1'H-spiro[indole-3,4'-piperidin]-1'-yl)-9H-purine-8-carboxamide;

1'-(9-methyl-8-pyridazin-4-yl-9H-purin-6-yl)spiro[indole-3,4'-piperidin]-2(1H)-one;

1-(1-{9-methyl-8-[1-(3-methylbutyl)-1H-pyrazol-4-yl]-9H-purin-6-yl}piperidin-4-yl)-1,3-dihydro-2H-benzimidazol-2-one;

1'-{8-[(3,3-difluoroazetidin-1-yl)carbonyl]-9-methyl-9H-purin-6-yl}spiro[indole-3,4'-piperidin]-2(1H)-one;

1-{(3R,4R)-3-(hydroxymethyl)-1-[9-methyl-8-(1-methyl-1H-pyrazol-4-yl)-9H-purin-6-yl]piperidin-4-yl}-1,3-dihydro-2H-benzimidazol-2-one;

N-(2,2-dimethylpropyl)-9-methyl-6-(2-oxo-1,2-dihydro-1'H-spiro[indole-3,4'-piperidin]-1'-yl)-9H-purine-8-carboxamide;

9-ethyl-N-(4-hydroxybutyl)-6-(2-oxo-1,2-dihydro-1'H-spiro[indole-3,4'-piperidin]-1'-yl)-9H-purine-8-carboxamide;

6-(4-{[5-chloro-2-(methyloxy)phenyl]sulfonyl}piperazin-1-yl)-9-methyl-8-(1-methyl-1H-pyrazol-4-yl)-9H-purine N-ethyl-9-methyl-6-[4-(2-oxo-2,3-dihydro-1H-benzimidazol-1-yl)piperidin-1-yl]-9H-purine-8-carboxamide;

9-methyl-6-[4-(2-oxo-2,3-dihydro-1H-benzimidazol-1-yl)piperidin-1-yl]-N-prop-2-yn-1-yl-9H-purine-8-carboxamide;

1-(1-{8-[(3,3-difluoropyrrolidin-1-yl)carbonyl]-9-methyl-9H-purin-6-yl}piperidin-4-yl)-1,3-dihydro-2H-benzimidazol-2-one;

9-methyl-6-[4-(2-oxo-2,3-dihydro-1H-benzimidazol-1-yl)piperidin-1-yl]-N-propyl-9H-purine-8-carboxamide;

1-[1-(8-furan-3-yl-9-methyl-9H-purin-6-yl)piperidin-4-yl]-1,3-dihydro-2H-benzimidazol-2-one;

1-[1-(9-methyl-8-pyridazin-4-yl-9H-purin-6-yl)piperidin-4-yl]-1,3-dihydro-2H-benzimidazol-2-one;

1'-{8-[(3,3-difluoropyrrolidin-1-yl)carbonyl]-9-methyl-9H-purin-6-yl}spiro[indole-3,4'-piperidin]-2(1H)-one;

9-methyl-6-[4-(2-oxo-2,3-dihydro-1H-benzimidazol-1-yl)piperidin-1-yl]-N-(pyridin-4-ylmethyl)-9H-purine-8-carboxamide;

N-(cyclopropylmethyl)-9-methyl-6-[4-(2-oxo-2,3-dihydro-1H-benzimidazol-1-yl)-3,6-dihydropyridin-1(2H)-yl]-9H-purine-8-carboxamide;

1-[9-methyl-8-(1-methyl-1H-pyrazol-4-yl)-9H-purin-6-yl]-4-phenylpiperidine-4-carbonitrile;

1-(1-{9-methyl-8-[5-(trifluoromethyl)-1H-pyrazol-4-yl]-9H-purin-6-yl}piperidin-4-yl)-1,3-dihydro-2H-benzimidazol-2-one;

9-methyl-6-(2-oxo-1,2-dihydro-1'H-spiro[indole-3,4'-piperidin]-1'-yl)-N-prop-2-yn-1-yl-9H-purine-8-carboxamide;

N-(4-hydroxybutyl)-9-methyl-6-[4-(2-oxo-2,3-dihydro-1H-benzimidazol-1-yl)piperidin-1-yl]-9H-purine-8-carboxamide;

1-[1-(9-methyl-8-pyridazin-3-yl-9H-purin-6-yl)piperidin-4-yl]-1,3-dihydro-2H-benzimidazol-2-one;

9-methyl-N-(1-methylethyl)-6-[4-(2-oxo-2,3-dihydro-1H-benzimidazol-1-yl)piperidin-1-yl]-9H-purine-8-carboxamide;

N-(cyclopropylmethyl)-9-methyl-6-(2-oxo-2,3-dihydro-1'H-spiro[indene-1,4'-piperidin]-1'-yl)-9H-purine-8-carboxamide;

N-(cyclopropylmethyl)-6-(4-hydroxy-4-phenylpiperidin-1-yl)-9-methyl-9H-purine-8-carboxamide;

N-(cyclopropylmethyl)-9-methyl-6-[4-(2-oxo-1,3-benzoxazol-3(2H)-yl)piperidin-1-yl]-9H-purine-8-carboxamide;

N-(2-hydroxy-2-methylpropyl)-9-methyl-6-(2-oxo-1,2-dihydro-1'H-spiro[indole-3,4'-piperidin]-1'-yl)-9H-purine-8-carboxamide;

1-[1-(8-butanoyl-9-methyl-9H-purin-6-yl)piperidin-4-yl]-1,3-dihydro-2H-benzimidazol-2-one;

9-methyl-N-(3-methylbutyl)-6-[4-(2-oxo-2,3-dihydro-1H-benzimidazol-1-yl)piperidin-1-yl]-9H-purine-8-carboxamide;

8-[9-methyl-8-(piperidin-1-ylcarbonyl)-9H-purin-6-yl]-1-phenyl-1,3,8-triazaspiro[4.5]decan-4-one;

1-{1-[8-(4,5-dimethyl-4H-1,2,4-triazol-3-yl)-9-methyl-9H-purin-6-yl]piperidin-4-yl}-1,3-dihydro-2H-benzimidazol-2-one;

1-[1-(9-methyl-8-pyridazin-3-yl-9H-purin-6-yl)piperidin-4-yl]-1,3-dihydro-2H-imidazo[4,5-b]pyridin-2-one;

9-ethyl-N-(3-methylbutyl)-6-[4-(2-oxo-2,3-dihydro-1H-benzimidazol-1-yl)piperidin-1-yl]-9H-purine-8-carboxamide;

N-(1,1-dimethylethyl)-9-methyl-6-(2-oxo-1,2-dihydro-1'H-spiro[indole-3,4'-piperidin]-1'-yl)-9H-purine-8-carboxamide;

N-(cyclopropylmethyl)-9-methyl-6-[4-(2-oxo-2,3-dihydro-1H-indol-1-yl)piperidin-1-yl]-9H-purine-8-carboxamide;

9-methyl-N-(1-methylethyl)-6-(2-oxo-1,2-dihydro-1'H-spiro[indole-3,4'-piperidin]-1'-yl)-9H-purine-8-carboxamide;

9-ethyl-N-(3-methylbutyl)-6-(2-oxo-1,2-dihydro-1'H-spiro[indole-3,4'-piperidin]-1'-yl)-9H-purine-8-carboxamide;

1-[1-(8-{[(3S)-3-fluoropyrrolidin-1-yl]carbonyl}-9-methyl-9H-purin-6-yl)piperidin-4-yl]-1,3-dihydro-2H-benzimidazol-2-one;

1-{1-[9-methyl-8-(5-methyl-1,3,4-oxadiazol-2-yl)-9H-purin-6-yl]piperidin-4-yl}-1,3-dihydro-2H-benzimidazol-2-one;

N-butyl-9-methyl-6-(2-oxo-1,2-dihydro-1'H-spiro[indole-3,4'-piperidin]-1'-yl)-9H-purine-8-carboxamide;

N-(cyclopropylmethyl)-9-methyl-6-{4-[4-(methyloxy)-2-oxo-2,3-dihydro-1H-benzimidazol-1-yl]piperidin-1-yl}-9H-purine-8-carboxamide;

N-(cyclopropylmethyl)-6-[4-(2,2-dioxido-2,1,3-benzothiadiazol-1(3H)-yl)piperidin-1-yl]-9-methyl-9H-purine-8-carboxamide;

1'-{8-[(3-hydroxyazetidin-1-yl)carbonyl]-9-methyl-9H-purin-6-yl}spiro[indole-3,4'-piperidin]-2(1H)-one;

1-{1-[8-(1H-imidazol-1-yl)-9-methyl-9H-purin-6-yl]piperidin-4-yl}-1,3-dihydro-2H-benzimidazol-2-one;

N-cyclopropyl-9-methyl-6-(2-oxo-1,2-dihydro-1'H-spiro[indole-3,4'-piperidin]-1'-yl)-9H-purine-8-carboxamide;

N-(2,3-dihydro-1H-inden-1-yl)-9-methyl-6-[4-(2-oxo-2,3-dihydro-1H-benzimidazol-1-yl)piperidin-1-yl]-9H-purine-8-carboxamide;

1-{1-[9-methyl-8-(1,3-oxazol-5-yl)-9H-purin-6-yl]piperidin-4-yl}-1,3-dihydro-2H-benzimidazol-2-one;

9-methyl-6-(2-oxo-1,2-dihydro-1'H-spiro[indole-3,4'-piperidin]-1'-yl)-N-(tetrahydro-2H-pyran-4-yl)-9H-purine-8-carboxamide;

6-(4-cyano-4-phenylpiperidin-1-yl)-N-(cyclopropylmethyl)-9-methyl-9H-purine-8-carboxamide;

1-(1-{8-[(3-hydroxyazetidin-1-yl)carbonyl]-9-methyl-9H-purin-6-yl}piperidin-4-yl)-1,3-dihydro-2H-benzimidazol-2-one;

9-methyl-8-(1-methyl-1H-pyrazol-4-yl)-6-(4-{[2-(trifluoromethyl)phenyl]sulfonyl}piperazin-1-yl)-9H-purine;

N-(cyclopropylmethyl)-9-methyl-6-[2-methyl-4-(2-oxo-2,3-dihydro-1H-benzimidazol-1-yl)piperidin-1-yl]-9H-purine-8-carboxamide;

N-cyclobutyl-9-methyl-6-(2-oxo-1,2-dihydro-1'H-spiro[indole-3,4'-piperidin]-1'-yl)-9H-purine-8-carboxamide;

9-cyclopropyl-N-(cyclopropylmethyl)-6-(2-oxo-1,2-dihydro-1'H-spiro[indole-3,4'-piperidin]-1'-yl)-9H-purine-8-carboxamide;

9-cyclopropyl-N-(2-methylpropyl)-6-(2-oxo-1,2-dihydro-1'H-spiro[indole-3,4'-piperidin]-1'-yl)-9H-purine-8-carboxamide;

N-(4,4-difluorocyclohexyl)-9-methyl-6-[4-(2-oxo-2,3-dihydro-1H-benzimidazol-1-yl)piperidin-1-yl]-9H-purine-8-carboxamide;

N-(4,4-difluorocyclohexyl)-9-methyl-6-(2-oxo-1,2-dihydro-1'H-spiro[indole-3,4'-piperidin]-1'-yl)-9H-purine-8-carboxamide;

9-methyl-6-[4-(2-oxo-2,3-dihydro-1H-benzimidazol-1-yl)piperidin-1-yl]-N-(2-thienylmethyl)-9H-purine-8-carboxamide;

6-[4-(1,1-dioxido-1,2-benzisothiazol-3-yl)piperazin-1-yl]-8-(1-ethyl-1H-pyrazol-4-yl)-9-methyl-9H-purine;

N-cyclopropyl-9-methyl-6-[4-(2-oxo-2,3-dihydro-1H-benzimidazol-1-yl)piperidin-1-yl]-9H-purine-8-carboxamide;

8-(1-ethyl-1H-pyrazol-4-yl)-9-methyl-6-[4-(phenylsulfonyl)piperazin-1-yl]-9H-purine;

1'-(8-{[(3S)-3-fluoropyrrolidin-1-yl]carbonyl}-9-methyl-9H-purin-6-yl)spiro[indole-3,4'-piperidin]-2(1H)-one;

9-cyclopropyl-N-(cyclopropylmethyl)-6-[4-(2-oxo-2,3-dihydro-1H-benzimidazol-1-yl)piperidin-1-yl]-9H-purine-8-carboxamide;

N-(furan-2-ylmethyl)-9-methyl-6-[4-(2-oxo-2,3-dihydro-1H-benzimidazol-1-yl)piperidin-1-yl]-9H-purine-8-carboxamide;

cyclopropylmethyl 9-methyl-6-[4-(2-oxo-2,3-dihydro-1H-benzimidazol-1-yl)piperidin-1-yl]-9H-purine-8-carboxylate;

N-[(3-fluorophenyl)methyl]-9-methyl-6-[4-(2-oxo-2,3-dihydro-1H-benzimidazol-1-yl)piperidin-1-yl]-9H-purine-8-carboxamide;

6-{4-[(3,4-dichlorophenyl)sulfonyl]piperazin-1-yl}-9-methyl-8-(1-methyl-1H-pyrazol-4-yl)-9H-purine;

N-(furan-2-ylmethyl)-9-methyl-6-(2-oxo-1,2-dihydro-1'H-spiro[indole-3,4'-piperidin]-1'-yl)-9H-purine-8-carboxamide;

N-ethyl-9-methyl-6-(2-oxo-1,2-dihydro-1'H-spiro[indole-3,4'-piperidin]-1'-yl)-9H-purine-8-carboxamide;

9-methyl-6-(2-oxo-1,2-dihydro-1'H-spiro[indole-3,4'-piperidin]-1'-yl)-N-(2-thienylmethyl)-9H-purine-8-carboxamide;

6-{4-[(2,5-dichlorophenyl)sulfonyl]piperazin-1-yl}-9-methyl-8-(1-methyl-1H-pyrazol-4-yl)-9H-purine;

N-(3-hydroxypropyl)-9-methyl-6-[4-(2-oxo-2,3-dihydro-1H-benzimidazol-1-yl)piperidin-1-yl]-9H-purine-8-carboxamide;

N-(cyclopropylmethyl)-9-methyl-6-{4-[4-(4-methylpiperazin-1-yl)-2-oxo-2,3-dihydro-1H-benzimidazol-1-yl]piperidin-1-yl}-9H-purine-8-carboxamide;

N-cyclobutyl-9-methyl-6-[4-(2-oxo-2,3-dihydro-1H-benzimidazol-1-yl)piperidin-1-yl]-9H-purine-8-carboxamide;

N-(3-hydroxypropyl)-9-methyl-6-(2-oxo-1,2-dihydro-1'H-spiro[indole-3,4'-piperidin]-1'-yl)-9H-purine-8-carboxamide;

N-(cyclopropylmethyl)-9-methyl-6-[3-(2-oxo-2,3-dihydro-1H-benzimidazol-1-yl)azetidin-1-yl]-9H-purine-8-carboxamide;

1-(1-{8-[2,4-bis(methyloxy)pyrimidin-5-yl]-9-methyl-9H-purin-6-yl}piperidin-4-yl)-1,3-dihydro-2H-benzimidazol-2-one;

N-(cyclopropylmethyl)-6-(2-hydroxy-2,3-dihydro-1'H-spiro[indene-1,4'-piperidin]-1'-yl)-9-methyl-9H-purine-8-carboxamide;
6-[4-(2-amino-1H-benzimidazol-1-yl)piperidin-1-yl]-N-(cyclopropylmethyl)-9-methyl-9H-purine-8-carboxamide;
9-methyl-N-(3-methylbutyl)-6-(2-oxo-1,2-dihydro-1'H-spiro[indole-3,4'-piperidin]-1'-yl)-9H-purine-8-carboxamide;
N-(cyclopropylmethyl)-6-[4-(5-fluoro-2-oxo-2,3-dihydro-1H-benzimidazol-1-yl)piperidin-1-yl]-9-methyl-9H-purine-8-carboxamide;
N-(4-hydroxybutyl)-9-methyl-6-(2-oxo-1,2-dihydro-1'H-spiro[indole-3,4'-piperidin]-1'-yl)-9H-purine-8-carboxamide;
6-[4-(1,1-dioxido-1,2-benzisothiazol-3-yl)piperazin-1-yl]-9-methyl-8-(1-methyl-1H-pyrazol-4-yl)-9H-purine;
N-(2-hydroxyethyl)-9-methyl-6-[4-(2-oxo-2,3-dihydro-1H-benzimidazol-1-yl)piperidin-1-yl]-9H-purine-8-carboxamide;
9-methyl-6-(2-oxo-1,2-dihydro-1'H-spiro[indole-3,4'-piperidin]-1'-yl)-N-(pyridin-4-ylmethyl)-9H-purine-8-carboxamide;
N-(cyclopropylmethyl)-9-methyl-6-[4-(2-oxo-2,3-dihydro-1H-indol-3-yl)piperidin-1-yl]-9H-purine-8-carboxamide;
6-{4-[(2-chlorophenyl)sulfonyl]piperazin-1-yl}-9-methyl-8-(1-methyl-1H-pyrazol-4-yl)-9H-purine;
9-methyl-8-(1-methyl-1H-pyrazol-4-yl)-6-{4-[(phenylmethyl)sulfonyl]piperazin-1-yl}-9H-purine;
1-{1-[9-methyl-8-(5-methylfuran-2-yl)-9H-purin-6-yl]piperidin-4-yl}-1,3-dihydro-2H-benzimidazol-2-one;
9-cyclopropyl-N-(2-methylpropyl)-6-[4-(2-oxo-2,3-dihydro-1H-benzimidazol-1-yl)piperidin-1-yl]-9H-purine-8-carboxamide;
1-{1-(8-furan-2-yl-9-methyl-9H-purin-6-yl)piperidin-4-yl}-1,3-dihydro-2H-benzimidazol-2-one;
9-methyl-6-[4-(2-oxo-2,3-dihydro-1H-benzimidazol-1-yl)piperidin-1-yl]-N-(tetrahydro-2H-pyran-3-ylmethyl)-9H-purine-8-carboxamide;
6-{4-[(2,6-dichlorophenyl)sulfonyl]piperazin-1-yl}-9-methyl-8-(1-methyl-1H-pyrazol-4-yl)-9H-purine;
9-methyl-8-(1-methyl-1H-pyrazol-4-yl)-6-[4-(phenylsulfonyl)piperazin-1-yl]-9H-purine;
3-({4-[9-methyl-8-(1-methyl-1H-pyrazol-4-yl)-9H-purin-6-yl]piperazin-1-yl}sulfonyl)benzonitrile;
9-methyl-6-[4-(2-oxo-2,3-dihydro-1H-benzimidazol-1-yl)piperidin-1-yl]-N-(2-phenylpropyl)-9H-purine-8-carboxamide;
2-({4-[9-methyl-8-(1-methyl-1H-pyrazol-4-yl)-9H-purin-6-yl]piperazin-1-yl}sulfonyl)benzonitrile;
3-methyl-N-[(2-{4-[9-methyl-8-(1-methyl-1H-pyrazol-4-yl)-9H-purin-6-yl]piperazin-1-yl}phenyl)methyl]benzamide;
1-{1-[9-methyl-8-(trifluoromethyl)-9H-purin-6-yl]piperidin-4-yl}-1,3-dihydro-2H-benzimidazol-2-one;
N-hexyl-9-methyl-6-[4-(2-oxo-2,3-dihydro-1H-benzimidazol-1-yl)piperidin-1-yl]-9H-purine-8-carboxamide;
6-(4-{[2,5-bis(methyloxy)phenyl]sulfonyl}piperazin-1-yl)-9-methyl-8-(1-methyl-1H-pyrazol-4-yl)-9H-purine;
N-(cyclopropylmethyl)-9-methyl-6-{4-[2-(trifluoromethyl)-1H-benzimidazol-1-yl]piperidin-1-yl}-9H-purine-8-carboxamide;
N-(cyclopropylmethyl)-9-methyl-6-(2-oxo-1'H-spiro[1-benzofuran-3,4'-piperidin]-1'-yl)-9H-purine-8-carboxamide;
N-(cyclopropylmethyl)-9-methyl-6-[4-(6-methyl-2-oxo-2,3-dihydro-1H-benzimidazol-1-yl)piperidin-1-yl]-9H-purine-8-carboxamide;
6-[4-(1H-indol-3-yl)piperidin-1-yl]-9-methyl-8-(1-methyl-1H-pyrazol-4-yl)-9H-purine;
N-(2-hydroxyethyl)-9-methyl-6-(2-oxo-1,2-dihydro-1'H-spiro[indole-3,4'-piperidin]-1'-yl)-9H-purine-8-carboxamide;
1-[1-(9-methyl-8-pyridin-4-yl-9H-purin-6-yl)piperidin-4-yl]-1,3-dihydro-2H-benzimidazol-2-one;
N-[(3-fluorophenyl)methyl]-9-methyl-6-(2-oxo-1,2-dihydro-1'H-spiro[indole-3-piperidin]-1'-yl)-9H-purine-8-carboxamide;
6-{4-[(2,3-dichlorophenyl)sulfonyl]piperazin-1-yl}-9-methyl-8-(1-methyl-1H-pyrazol-4-yl)-9H-purine;
8-[9-methyl-8-(pyrrolidin-1-ylcarbonyl)-9H-purin-6-yl]-1-phenyl-1,3,8-triazaspiro[4.5]decan-4-one;
N-(2,3-dihydro-1H-inden-1-yl)-9-methyl-6-(2-oxo-1'H-spiro[indole-3,4'-piperidin]-1'-yl)-9H-purine-8-carboxamide;
N-(cyclopropylmethyl)-6-[4-(4-{[2-(dimethylamino)ethyl]oxy}-2-oxo-2,3-dihydro-1H-benzimidazol-1-yl)piperidin-1-yl]-9-methyl-9H-purine-8-carboxamide;
6-{4-[(2-chloro-6-methylphenyl)sulfonyl]piperazin-1-yl}-9-methyl-8-(1-methyl-1H-pyrazol-4-yl)-9H-purine;
1-{1-[9-methyl-8-(3-methylfuran-2-yl)-9H-purin-6-yl]piperidin-4-yl}-1,3-dihydro-2H-benzimidazol-2-one;
1'-[8-(azetidin-1-ylcarbonyl)-9-methyl-9H-purin-6-yl]spiro[indole-3,4'-piperidin]-2(1H)-one;
9-methyl-N-[(2-methylphenyl)methyl]-6-[4-(2-oxo-2,3-dihydro-1H-benzimidazol-1-yl)piperidin-1-yl]-9H-purine-8-carboxamide;
1-[1-(9-methyl-8-pyrimidin-4-yl-9H-purin-6-yl)piperidin-4-yl]-1,3-dihydro-2H-benzimidazol-2-one;
9-ethyl-N-[(5-methyl-1,3,4-oxadiazol-2-yl)methyl]-6-(2-oxo-1,2-dihydro-1'H-spiro[indole-3,4'-piperidin]-1'-yl)-9H-purine-8-carboxamide;
N-(cyclopropylmethyl)-9-methyl-6-(4-oxo-4,5-dihydro-1'H,3H-spiro[1,5-benzoxazepine-2,4'-piperidin]-1'-yl)-9H-purine-8-carboxamide;
N-(cyclopropylmethyl)-9-methyl-6-[4-(2-oxo-3,4-dihydroquinazolin-1 (2H)-yl)piperidin-1-yl]-9H-purine-8-carboxamide;
N-(cyclopropylmethyl)-9-methyl-6-(1-phenyl-1,4,6,7-tetrahydro-5H-pyrazolo[4,3-c]pyridin-5-yl)-9H-purine-8-carboxamide;
ethyl (4-{9-methyl-6-[4-(2-oxo-2,3-dihydro-1H-benzimidazol-1-yl)piperidin-1-yl]-9H-purin-8-yl}-1H-pyrazol-1-yl)acetate;
N-(cyclopropylmethyl)-9-methyl-6-(3-oxo-2,3-dihydro-1'H-spiro[indene-1,4'-piperidin]-1'-yl)-9H-purine-8-carboxamide;
(3R,4R)-1-[9-methyl-8-(1-methyl-1H-pyrazol-4-yl)-9H-purin-6-yl]-4-phenylpiperidin-3-ol;
9-methyl-6-[4-(2-oxo-2,3-dihydro-1H-benzimidazol-1-yl)piperidin-1-yl]-N-pentyl-9H-purine-8-carboxamide;
9-methyl-8-(1-methyl-1H-pyrazol-4-yl)-6-(4-{[3-(trifluoromethyl)phenyl]sulfonyl}piperazin-1-yl)-9H-purine;
1-[1-(8-acetyl-9-methyl-9H-purin-6-yl)piperidin-4-yl]-1,3-dihydro-2H-benzimidazol-2-one;
6-(4-{3-[(2-azepan-1-yl-2-oxoethyl)oxy]phenyl}piperazin-1-yl)-9-methyl-8-(1-methyl-1H-pyrazol-4-yl)-9H-purine;

1-{1-[9-methyl-8-(pyrrolidin-1-ylcarbonyl)-9H-purin-6-yl]piperidin-4-yl}-1,3-dihydro-2H-benzimidazol-2-one;
8-(1-ethyl-1H-pyrazol-4-yl)-6-[4-(1H-indol-3-yl)piperidin-1-yl]-9-methyl-9H-purine;
9-methyl-N-{[4-(methyloxy)phenyl]methyl}-6-[4-(2-oxo-2,3-dihydro-1H-benzimidazol-1-yl)piperidin-1-yl]-9H-purine-8-carboxamide;
1-{1-[9-methyl-8-(1-methyl-1H-pyrazol-4-yl)-9H-purin-6-yl]piperidin-4-yl}-1,3-dihydro-2H-imidazo[4,5-c]pyridin-2-one;
N-(cyclopropylmethyl)-9-methyl-6-[3-(2-oxo-2,3-dihydro-1H-benzimidazol-1-yl)piperidin-1-yl]-9H-purine-8-carboxamide;
N-(cyclopropylmethyl)-9-methyl-6-{3-[2-oxo-5-(trifluoromethyl)-2,3-dihydro-1H-benzimidazol-1-yl]azetidin-1-yl}-9H-purine-8-carboxamide;
N-(2-methylpropyl)-6-[4-(2-oxo-2,3-dihydro-1H-benzimidazol-1-yl)piperidin-1-yl]-9-(2,2,2-trifluoroethyl)-9H-purine-8-carboxamide;
N-(1,3-benzodioxol-5-ylmethyl)-9-methyl-6-[4-(2-oxo-2,3-dihydro-1H-benzimidazol-1-yl)piperidin-1-yl]-9H-purine-8-carboxamide;
9-methyl-N-{[2-(methyloxy)phenyl]methyl}-6-[4-(2-oxo-2,3-dihydro-1H-benzimidazol-1-yl)piperidin-1-yl]-9H-purine-8-carboxamide;
N-[(2-{4-[9-methyl-8-(1-methyl-1H-pyrazol-4-yl)-9H-purin-6-yl]piperazin-1-yl}phenyl)methyl]cyclopropanecarboxamide;
N-cyclopentyl-2-[(3-{4-[9-methyl-8-(1-methyl-1H-pyrazol-4-yl)-9H-purin-6-yl]piperazin-1-yl}phenyl)oxy]acetamide;
6-{4-[(2-chloropyridin-3-yl)sulfonyl]piperazin-1-yl}-9-methyl-8-(1-methyl-1H-pyrazol-4-yl)-9H-purine;
9-methyl-6-[4-(2-oxo-2,3-dihydro-1H-benzimidazol-1-yl)piperidin-1-yl]-N-(1-phenylethyl)-9H-purine-8-carboxamide;
N-(cyclopropylmethyl)-9-methyl-6-[3-(2-oxo-2,3-dihydro-1H-benzimidazol-1-yl)pyrrolidin-1-yl]-9H-purine-8-carboxamide;
1-[1-(8,9-dimethyl-9H-purin-6-yl)piperidin-4-yl]-1,3-dihydro-2H-benzimidazol-2-one;
N-(cyclopropylmethyl)-9-methyl-6-(1-methyl-2-oxo-1,2-dihydro-1'H-spiro[indole-3,4'-piperidin]-1'-yl)-9H-purine-8-carboxamide;
N-(cyclopropylmethyl)-6-[4-(1,1-dioxido-1,2-benzisothiazol-3-yl)piperazin-1-yl]-9-methyl-9H-purine-8-carboxamide;
N-(cyclopropylmethyl)-6-[(3R,4R)-3-hydroxy-4-phenylpiperidin-1-yl]-9-methyl-9H-purine-8-carboxamide;
N-(cyclopropylmethyl)-9-methyl-6-(2-oxo-1,2-dihydro-1'H-spiro[indole-3,3'-pyrrolidin]-1'-yl)-9H-purine-8-carboxamide;
N-(cyclohexylmethyl)-9-methyl-6-(2-oxo-1,2-dihydro-1'H-spiro[indole-3,4'-piperidin]-1'-yl)-9H-purine-8-carboxamide;
Ethyl 9-methyl-6-[4-(2-oxo-2,3-dihydro-1H-benzimidazol-1-yl)piperidin-1-yl]-9H-purine-8-carboxylate;
N-(cyclopropylmethyl)-9-methyl-6-[1-(3-methylphenyl)-1,4,6,7-tetrahydro-5H-pyrazolo[4,3-c]pyridin-5-yl]-9H-purine-8-carboxamide;
9-methyl-8-(1-methyl-1H-pyrazol-4-yl)-6-(4-{3-[(2-oxo-2-piperidin-1-ylethyl)oxy]phenyl}piperazin-1-yl)-9H-purine;
8-(8-{[3-(dimethylamino)azetidin-1-yl]carbonyl}-9-methyl-9H-purin-6-yl)-1-phenyl-1,3,8-triazaspiro[4.5]decan-4-one;
N-(cyclopropylmethyl)-6-{1-[2-(dimethylamino)ethyl]-2-oxo-1,2-dihydro-1'H-spiro[indole-3,4'-piperidin]-1'-yl}-9-methyl-9H-purine-8-carboxamide;
9-methyl-N-[(2-methylphenyl)methyl]-6-(2-oxo-1,2-dihydro-1'H-spiro[indole-3,4'-piperidin]-1'-yl)-9H-purine-8-carboxamide;
9-methyl-6-(4-{[4-methyl-2-(methyloxy)phenyl]sulfonyl}piperazin-1-yl)-8-(1-methyl-1H-pyrazol-4-yl)-9H-purine;
N,N,9-trimethyl-6-(4-oxo-1-phenyl-1,3,8-triazaspiro[4.5]dec-8-yl)-9H-purine-8-carboxamide;
6-[4-(6-chloro-2-oxo-2,3-dihydro-1H-benzimidazol-1-yl)piperidin-1-yl]-N-(cyclopropylmethyl)-9-methyl-9H-purine-8-carboxamide;
6-{4-[(2,4-dichlorophenyl)sulfonyl]piperazin-1-yl}-9-methyl-8-(1-methyl-1H-pyrazol-4-yl)-9H-purine;
6-(4-{[3,4-bis(methyloxy)phenyl]sulfonyl}piperazin-1-yl)-9-methyl-8-(1-methyl-1H-pyrazol-4-yl)-9H-purine;
9-methyl-8-(1-methyl-1H-pyrazol-4-yl)-6-{4-[2-(methylsulfonyl)phenyl]piperazin-1-yl}-9H-purine;
6-{4-[(2,4-difluorophenyl)sulfonyl]piperazin-1-yl}-9-methyl-8-(1-methyl-1H-pyrazol-4-yl)-9H-purine;
9-methyl-6-(2-oxo-1,2-dihydro-1'H-spiro[indole-3,4'-piperidin]-1'-yl)-N-(2-phenylethyl)-9H-purine-8-carboxamide;
N,9-dimethyl-6-[4-(2-oxo-2,3-dihydro-1H-benzimidazol-1-yl)piperidin-1-yl]-9H-purine-8-carboxamide;
9-methyl-6-[4-(2-oxo-2,3-dihydro-1H-benzimidazol-1-yl)piperidin-1-yl]-N-(3-phenylpropyl)-9H-purine-8-carboxamide;
9-methyl-6-(2-oxo-1,2-dihydro-1'H-spiro[indole-3,4'-piperidin]-1'-yl)-N-(tetrahydrofuran-2-ylmethyl)-9H-purine-8-carboxamide;
N-(cyclopropylmethyl)-6-[4-(1H-indol-1-yl)piperidin-1-yl]-9-methyl-9H-purine-8-carboxamide;
9-methyl-N-{[4-(methyloxy)phenyl]methyl}-6-(2-oxo-1,2-dihydro-1'H-spiro[indole-3,4'-piperidin]-1'-yl)-9H-purine-8-carboxamide;
1-{1-[9-methyl-8-(1H-pyrrol-3-yl)-9H-purin-6-yl]piperidin-4-yl}-1,3-dihydro-2H-benzimidazol-2-one;
N-(cyclopropylmethyl)-9-methyl-6-(1'H,3H-spiro[2-benzofuran-1,4'-piperidin]-1'-yl)-9H-purine-8-carboxamide;
methyl 9-methyl-6-[4-(2-oxo-2,3-dihydro-1H-benzimidazol-1-yl)piperidin-1-yl]-9H-purine-8-carboxylate;
methyl 9-methyl-6-(2-oxo-1,2-dihydro-1'H-spiro[indole-3,4'-piperidin]-1'-yl)-9H-purine-8-carboxylate;
9-methyl-6-(2-oxo-1,2-dihydro-1'H-spiro[indole-3,4'-piperidin]-1'-yl)-N-(1-phenylethyl)-9H-purine-8-carboxamide;
N-(cyclopropylmethyl)-9-methyl-6-(3-oxo-1'H,3H-spiro[2-benzofuran-1,4'-piperidin]-1'-yl)-9H-purine-8-carboxamide;
9-methyl-N-[2-(4-methylphenyl)ethyl]-6-[4-(2-oxo-2,3-dihydro-1H-benzimidazol-1-yl)piperidin-1-yl]-9H-purine-8-carboxamide;
9-methyl-6-(2-oxo-1,2-dihydro-1'H-spiro[indole-3,4'-piperidin]-1'-yl)-N-(2-phenylpropyl)-9H-purine-8-carboxamide;
9-methyl-6-[4-(2-oxo-2,3-dihydro-1H-benzimidazol-1-yl)piperidin-1-yl]-N-(2-pyridin-2-ylethyl)-9H-purine-8-carboxamide;

N-(cyclopropylmethyl)-9-methyl-6-(3'-oxo-3',4'-dihydro-1H,1'H-spiro[piperidine-4,2'-quinoxalin]-1-yl)-9H-purine-8-carboxamide;
1-(1-{9-methyl-8-[2-methyl-6-(trifluoromethyl)pyridin-3-yl]-9H-purin-6-yl}piperidin-4-yl)-1,3-dihydro-2H-benzimidazol-2-one;
6-{4-[(4-fluorophenyl)sulfonyl]piperazin-1-yl}-9-methyl-8-(1-methyl-1H-pyrazol-4-yl)-9H-purine;
N-(cyclopropylmethyl)-9-methyl-6-(1-oxo-4-phenyl-2,8-diazaspiro[4.5]dec-8-yl)-9H-purine-8-carboxamide;
1-{1-[9-methyl-8-(1,3-oxazol-4-yl)-9H-purin-6-yl]piperidin-4-yl}-1,3-dihydro-2H-benzimidazol-2-one;
N-[2-(4-chlorophenyl)ethyl]-9-methyl-6-[4-(2-oxo-2,3-dihydro-1H-benzimidazol-1-yl)piperidin-1-yl]-9H-purine-8-carboxamide;
N-hexyl-9-methyl-6-(2-oxo-1,2-dihydro-1'H-spiro[indole-3,4'-piperidin]-1'-yl)-9H-purine-8-carboxamide;
N-[(2,4-difluorophenyl)methyl]-9-methyl-6-(2-oxo-1,2-dihydro-1'H-spiro[indole-3,4'-piperidin]-1'-yl)-9H-purine-8-carboxamide;
methyl 1-[9-methyl-8-(1-methyl-1H-pyrazol-4-yl)-9H-purin-6-yl]-4-phenylpiperidine-4-carboxylate;
6-{4-[(4-chlorophenyl)sulfonyl]piperazin-1-yl}-9-methyl-8-(1-methyl-1H-pyrazol-4-yl)-9H-purine;
1-{1-[9-methyl-8-(1H-pyrrol-1-yl)-9H-purin-6-yl]piperidin-4-yl}-1,3-dihydro-2H-benzimidazol-2-one;
N-(cyclopropylmethyl)-6-[4-(1H-indol-3-yl)piperidin-1-yl]-9-methyl-9H-purine-8-carboxamide;
N-(cyclopropylmethyl)-6-[1-(2,4-dimethylphenyl)-1,4,6,7-tetrahydro-5H-pyrazolo[4,3-c]pyridin-5-yl]-9-methyl-9H-purine-8-carboxamide;
9-methyl-N-{[2-(methyloxy)phenyl]methyl}-6-(2-oxo-1,2-dihydro-1'H-spiro[indole-3,4'-piperidin]-1'-yl)-9H-purine-8-carboxamide;
N,9-dimethyl-N-(1-methylethyl)-6-(2-oxo-1,2-dihydro-1'H-spiro[indole-3,4'-piperidin]-1'-yl)-9H-purine-8-carboxamide;
6-[4-(1H-1,2,3-benzotriazol-1-yl)piperidin-1-yl]-N-(cyclopropylmethyl)-9-methyl-9H-purine-8-carboxamide;
1-{1-[8-(6-hydroxypyridin-3-yl)-9-methyl-9H-purin-6-yl]piperidin-4-yl}-1,3-dihydro-2H-benzimidazol-2-one;
1-{1-[9-methyl-8-(1-methyl-1H-pyrazol-4-yl)-9H-purin-6-yl]-4-phenylpiperidin-4-yl}methanamine;
1'-[9-methyl-8-(pyrrolidin-1-ylcarbonyl)-9H-purin-6-yl]spiro[indole-3,4'-piperidin]-2(1H)-one;
8-(1-ethyl-1H-pyrazol-4-yl)-9-methyl-6-(4-phenylpiperazin-1-yl)-9H-purine;
1-[1-(9-methyl-8-phenyl-9H-purin-6-yl)piperidin-4-yl]-1,3-dihydro-2H-benzimidazol-2-one;
1,1-dimethylethyl({9-methyl-6-[4-(2-oxo-2,3-dihydro-1H-benzimidazol-1-yl)piperidin-1-yl]-9H-purin-8-yl}methyl)carbamate;
1-[1-(8-butyl-9-methyl-9H-purin-6-yl)piperidin-4-yl]-1,3-dihydro-2H-benzimidazol-2-one;
1-(1-{9-methyl-8-[(1E)-prop-1-en-1-yl]-9H-purin-6-yl}piperidin-4-yl)-1,3-dihydro-2H-benzimidazol-2-one;
9-methyl-6-{4-[(4-methylphenyl)sulfonyl]piperazin-1-yl}-8-(1-methyl-1H-pyrazol-4-yl)-9H-purine;
6-[4-(5-chloro-2-oxo-2,3-dihydro-1H-benzimidazol-1-yl)piperidin-1-yl]-N-(cyclopropylmethyl)-9-methyl-9H-purine-8-carboxamide;
9-methyl-6-(2-oxo-1,2-dihydro-1'H-spiro[indole-3,4'-piperidin]-1'-yl)-N-(2-pyridin-2-ylethyl)-9H-purine-8-carboxamide;
N-(cyclopropylmethyl)-9-methyl-6-[1-(2-methylphenyl)-1,4,6,7-tetrahydro-5H-pyrazolo[4,3-c]pyridin-5-yl]-9H-purine-8-carboxamide;
N-(2-cyanoethyl)-N,9-dimethyl-6-(2-oxo-1,2-dihydro-1'H-spiro[indole-3,4'-piperidin]-1'-yl)-9H-purine-8-carboxamide;
N-cyclohexyl-2-[(3-{4-[9-methyl-8-(1-methyl-1H-pyrazol-4-yl)-9H-purin-6-yl]piperazin-1-yl}phenyl)oxy]acetamide;
1-[1-(9-methyl-8-pyrrolidin-1-yl-9H-purin-6-yl)piperidin-4-yl]-1,3-dihydro-2H-benzimidazol-2-one;
9-methyl-6-(2-oxo-1,2-dihydro-1'H-spiro[indole-3,4'-piperidin]-1'-yl)-N-(tetrahydro-2H-pyran-2-ylmethyl)-9H-purine-8-carboxamide;
N-(cyclopropylmethyl)-6-[1-(2,6-dimethylphenyl)-1,4,6,7-tetrahydro-5H-pyrazolo[4,3-c]pyridin-5-yl]-9-methyl-9H-purine-8-carboxamide;
N-(cyclopropylmethyl)-9-methyl-6-[5-(1-methylethyl)-2-oxo-1,2-dihydro-1'H-spiro[indole-3,4'-piperidin]-1'-yl]-9H-purine-8-carboxamide;
N-(cyclopropylmethyl)-9-methyl-6-(3-oxo-2,3-dihydro-1'H-spiro[isoindole-1,4'-piperidin]-1'-yl)-9H-purine-8-carboxamide;
(3R,4R)-1-[9-methyl-8-(1-methyl-1H-pyrazol-4-yl)-9H-purin-6-yl]-4-(2-oxo-2,3-dihydro-1H-benzimidazol-1-yl)piperidine-3-carboxylic acid;
N-[(2,4-difluorophenyl)methyl]-9-methyl-6-[4-(2-oxo-2,3-dihydro-1H-benzimidazol-1-yl)piperidin-1-yl]-9H-purine-8-carboxamide;
methyl (3S,4R)-1-[9-methyl-8-(1-methyl-1H-pyrazol-4-yl)-9H-purin-6-yl]-4-(2-oxo-2,3-dihydro-1H-benzimidazol-1-yl)piperidine-3-carboxylate;
1-[1-(8-ethyl-9-methyl-9H-purin-6-yl)piperidin-4-yl]-1,3-dihydro-2H-benzimidazol-2-one;
N,9-dimethyl-N-(methyloxy)-6-[4-(2-oxo-2,3-dihydro-1H-benzimidazol-1-yl)piperidin-1-yl]-9H-purine-8-carboxamide;
1-(1-{8-[(3-hydroxypyrrolidin-1-yl)carbonyl]-9-methyl-9H-purin-6-yl}piperidin-4-yl)-1,3-dihydro-2H-benzimidazol-2-one;
1-(1-{8-[2,4-bis(methyloxy)pyrimidin-5-yl]-9-ethyl-9H-purin-6-yl}piperidin-4-yl)-1,3-dihydro-2H-benzimidazol-2-one;
N-[(2-{4-[9-methyl-8-(1-methyl-1H-pyrazol-4-yl)-9H-purin-6-yl]piperazin-1-yl}phenyl)methyl]naphthalene-2-sulfonamide;
9-methyl-6-(4-{[4-(methyloxy)phenyl]sulfonyl}piperazin-1-yl)-8-(1-methyl-1H-pyrazol-4-yl)-9H-purine;
1-[4-({4-[9-methyl-8-(1-methyl-1H-pyrazol-4-yl)-9H-purin-6-yl]piperazin-1-yl}sulfonyl)phenyl]ethanone;
6-(4-{4-[(cyclopropylmethyl)oxy]phenyl}piperazin-1-yl)-9-methyl-8-(1-methyl-1H-pyrazol-4-yl)-9H-purine;
2-{[(4-{4-[9-methyl-8-(1-methyl-1H-pyrazol-4-yl)-9H-purin-6-yl]piperazin-1-yl}phenyl)oxy]methyl}quinoline;
9-methyl-6-(2-oxo-1,2-dihydro-1'H-spiro[indole-3,4'-piperidin]-1'-yl)-N-(2-phenylethyl)-9H-purine-8-carboxamide.
1-[1-(8-{[(3S)-3-fluoropyrrolidin-1-yl]carbonyl}-9-methyl-9H-purin-6-yl)piperidin-4-yl]-1,3-dihydro-2H-benzimidazol-2-one;
N-(cyclopropylmethyl)-6-{1-[2-(dimethylamino)ethyl]-2-oxo-1,2-dihydro-1'H-spiro[indole-3,4'-piperidin]-1'-yl}-9-methyl-9H-purine-8-carboxamide;

6-(4-(((4,5-dimethyl-2-phenyl-1H-imidazol-1-yl)oxy)
methyl)piperidin-1-yl)-9-methyl-8-(1-methyl-1H-
pyrazol-4-yl)-9H-purine; or 1'-(8-(1,5-dimethyl-1H-pyrazol-4-yl)-9-methyl-9H-pu-
rin-6-yl)spiro[indoline-3,4'-piperidin]-2-one.

17. A pharmaceutical formulation comprising a compound of claim 1 admixed with a pharmaceutically acceptable carrier or excipient.

18. A method of inhibiting PI3K delta, comprising contacting the PI3K delta with an effective amount of a compound of claim 1.

19. A process for making a compound of claim 1, comprising:

(a) treating a compound of formula 1 with a base and $R^1X^1$ wherein $R^1$ is alkyl, haloalkyl, or optionally substituted cycloalkyl, to form a compound of formula 2, wherein X is halo, or OTf and $X^1$ is halo, O-Ms, or OTs and Rx is H or alkyl:

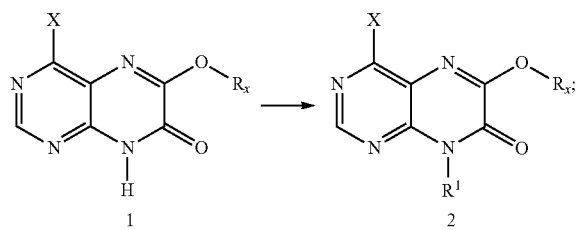

(b) heating a compound of formula 2 with a compound of formula 3 in the presence of base to form a compound of formula 4:

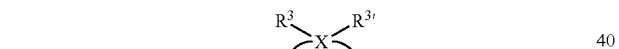

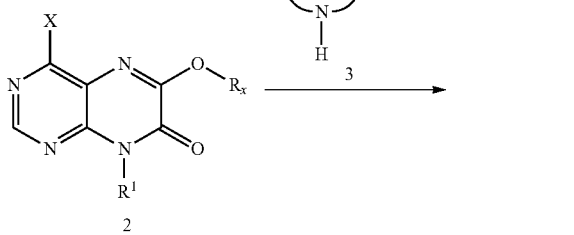

(c) heating a compound of formula 4 in a polar aprotic solvent in the presence of base to provide the carboxylic acid of formula 5:

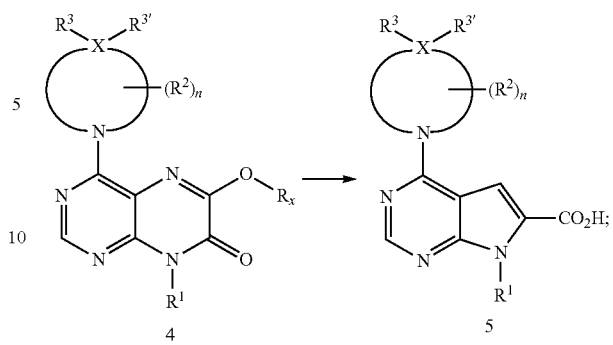

(d) amidating or esterifying the carboxylic acid of formula 5 with $R^aR^bNH$ or $R^cOH$ to form a compound of Formula I wherein $YR_4$ is $C(=O)-NR^aR^b$ or $C(=O)-OR^c$, wherein $R^a$ and $R^b$ are each independently H, $C_1$-$C_6$-alkyl, cycloalkyl, or alkylene-cylcoalkyl or one of $R^a$ and $R^b$ is H, $C_1$-$C_6$-alkyl, cycloalkyl, alkylene-cylcoalkyl and the other is $C_1$-$C_6$-alkyl or $NH^2$; and $R^c$ is $C_1$-$C_6$-alkyl:

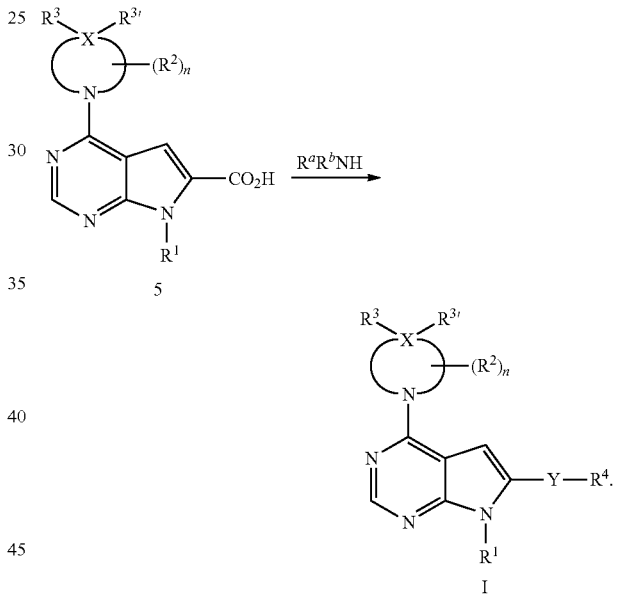

20. A process for making a compound of claim 1, comprising:

(a) treating a compound of formula 6 with a compound of formula 3 to form a compound of formula 7, wherein X is halo or OTf:

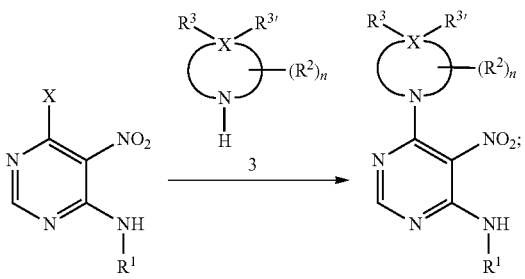

(b) reducing the compound of formula 7 to form the compound of formula 8:

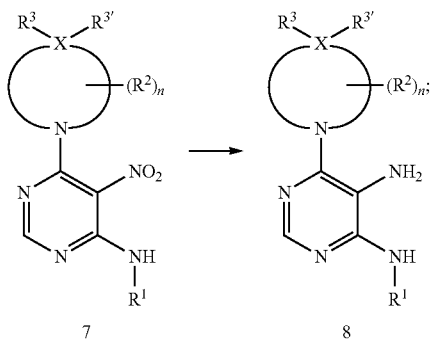

(c) treating a compound of formula 8 with an aldehyde of formula 9 to form a compound of Formula I, wherein Y is absent and $R^4$ is alkyl, cycloalkyl, heterocycloalkyl, aryl, or heteroaryl:

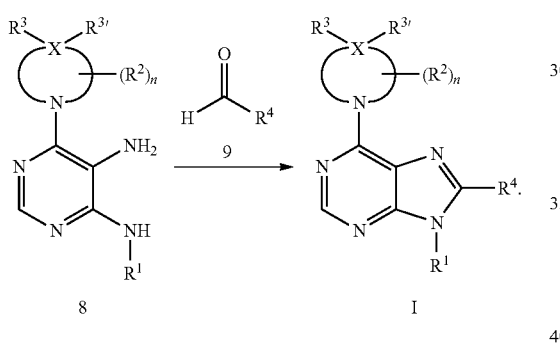

21. A process for making a compound of claim 1, comprising:

(a) treating a compound of formula 10 with a acetic anhydride to form a compound of formula 11, wherein X is chloro:

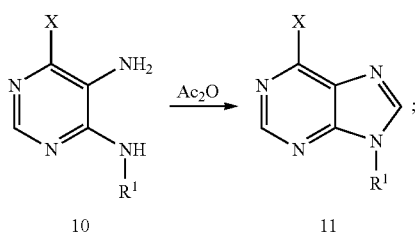

(b) treating the compound of formula 11 with a base and 1,2 dibromotetrachloroethane to form the compound of formula 12:

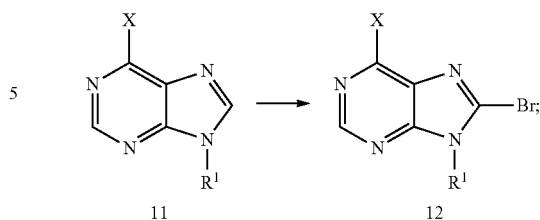

(c) treating a compound of formula 12 with a compound of formula 3 to form a compound of formula 13, wherein X is chloro:

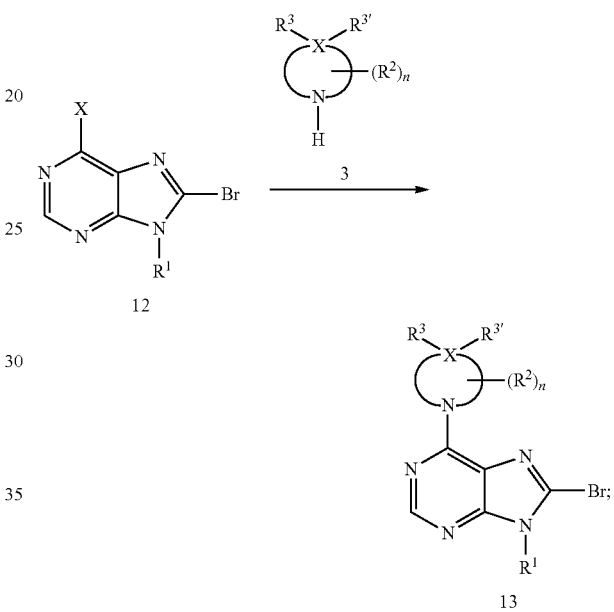

(d) treating a compound of formula 13 with $R^4$—H in the presence of base to form a compound of Formula I wherein Y is absent and $R^4$ is alkyl, cycloalkyl, heterocycloalkyl, aryl, or heteroaryl:

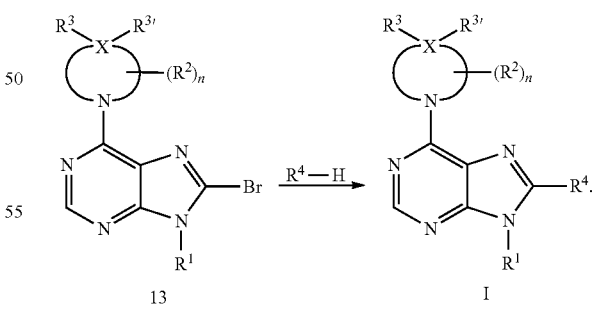

22. A compound which is 1-{1-[8-(1-ethyl-5-methyl-1H-pyrazol-4-yl)-9-methyl-9H-purin-6-yl]piperidin-4-yl}-1,3-dihydro-2H-imidazo[4,5-b]pyridine-2-one or a pharmaceutically acceptable salt thereof:

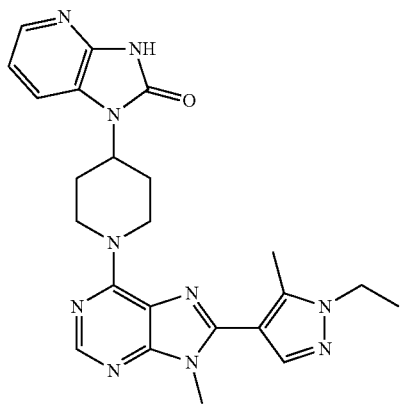

23. A method for treating inflammation, comprising administering to a mammal in need of such treatment a therapeutically effective amount of a compound of claim 1.

24. The method of claim 23, wherein the inflammation is mediated by PI3K delta.

25. The method of claim 24, wherein the compound is 1-{1-[8-ethyl-5-methyl-1H-pyrazol-4-yl)-9-methyl-9H-purin-6-yl]piperidin-4-yl}-1,3-dihydro-2H-imidazo[4,5-b]pyridine-2-one:

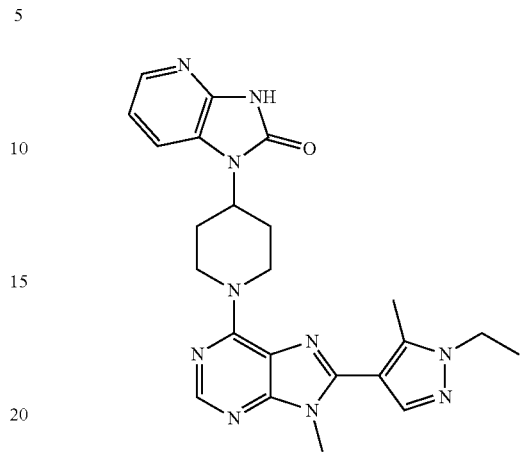

or a pharmaceutically acceptable salt thereof.

* * * * *